(12) United States Patent
Schafer et al.

(10) Patent No.: US 9,315,787 B2
(45) Date of Patent: Apr. 19, 2016

(54) MODIFIED DNA POLYMERASES FOR IMPROVED AMPLIFICATION

(75) Inventors: Wolfgang Schafer, Western Cape (ZA); Paul McEwan, Western Cape (ZA); Eric Van Der Walt, Western Cape (ZA); John Foskett, Western Cape (ZA); William Bourn, Western Cape (ZA)

(73) Assignee: KAPA BIOSYSTEMS, INC., Wilmington, MA (US)

( * ) Notice: Subject to any disclaimer, the term of this patent is extended or adjusted under 35 U.S.C. 154(b) by 62 days.

(21) Appl. No.: 13/979,509

(22) PCT Filed: Jan. 13, 2012

(86) PCT No.: PCT/US2012/021348
§ 371 (c)(1),
(2), (4) Date: Sep. 3, 2013

(87) PCT Pub. No.: WO2012/097318
PCT Pub. Date: Jul. 19, 2012

(65) Prior Publication Data
US 2014/0030765 A1    Jan. 30, 2014

Related U.S. Application Data

(60) Provisional application No. 61/432,936, filed on Jan. 14, 2011.

(51) Int. Cl.
*C12N 9/12* (2006.01)
*C12P 19/34* (2006.01)
*C12Q 1/68* (2006.01)

(52) U.S. Cl.
CPC ............... *C12N 9/1252* (2013.01); *C12P 19/34* (2013.01); *C12Q 1/686* (2013.01); *C12Y 207/07007* (2013.01); *Y02P 20/52* (2015.11)

(58) Field of Classification Search
None
See application file for complete search history.

(56) References Cited

U.S. PATENT DOCUMENTS

| 6,214,577 | B1 | 4/2001 | Yocum |
| 7,488,816 | B2 | 2/2009 | Jestin et al. |
| 2011/0027833 | A1 | 2/2011 | Hogrefe et al. |

FOREIGN PATENT DOCUMENTS

| WO | WO-2009/155464 A2 | 12/2009 |
| WO | WO-2010/062779 A2 | 6/2010 |

OTHER PUBLICATIONS

Vichier-Guerre, S. et al., A Population of Thermostable Reverse Transcriptases Evolved from Thermus aquaticus DNA Polymerase I by Phage Display, Agnew. Che. Int. Ed., 45: 6133-6137 (2006).
Davalieva, K. et al., Substitution of Ile(707) for Leu in Klentaq DNA polymerase reduces the amplification capacity of the enzyme, Prilozi, 30(2):57-69 (2009).
International Search Report for PCT/US12/21348, 5 pages (Aug. 29, 2012).
Patel, P.H. et al., A Single Highly Mutable Catalytic Site Amino Acid Is Critical for DNA Polymerase Fidelity, The Journal of Biological Chemistry, 276(7):5044-5051 (2000).
Suzuki, M. et al., *Thermus aquaticus* DNA Polymerase I Mutants with Altered Fidelity: Interacting mutations in the O-helix, The Journal of Biological Chemistry, 275(42):32786-32735 (2000).
Tosaka, A. et al., O-helix Mutant T664P of Thermus aquaticus DNA Polymerase I: altered catalytic properties for incorporation of incorrect nucleotides but not correct nucleotides, The Journal of Biological Chemistry, 275(29):27562-27567 (2001).
Written Opinion for PCT/US12/21348, 4 pages (Aug. 29, 2012).

*Primary Examiner* — Richard Hutson
(74) *Attorney, Agent, or Firm* — Brenda Herschbach Jarrell; Robert N. Sahr; Choate Hall & Stewart LLP

(57) ABSTRACT

The present invention provides improved DNA polymerases that may be better suited for applications in recombinant DNA technologies, in particular technologies involving plant-derived samples. Among other things, the present invention provides modified DNA polymerases derived from directed evolution experiments designed to select mutations that confer advantageous phenotypes under conditions used in industrial or research applications.

19 Claims, 11 Drawing Sheets

SEQUENCE LISTING

```
<160> NUMBER OF SEQ ID NOS: 54

<210> SEQ ID NO 1
<211> LENGTH: 832
<212> TYPE: PRT
<213> ORGANISM: Thermus aquaticus

<400> SEQUENCE: 1

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
        130                 135                 140
```

-continued

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser

```
            565                 570                 575
Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 2
<211> LENGTH: 834
<212> TYPE: PRT
<213> ORGANISM: Thermus thermophilus HB8

<400> SEQUENCE: 2

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
            85                  90                  95

Leu Ala Leu Ile Lys Glu Leu Val Asp Leu Leu Gly Phe Thr Arg Leu
            100                 105                 110
```

```
Glu Val Pro Gly Tyr Glu Ala Asp Val Leu Ala Thr Leu Ala Lys
            115                 120                 125
Lys Ala Glu Lys Glu Gly Tyr Glu Val Arg Ile Leu Thr Ala Asp Arg
130                 135                 140
Asp Leu Tyr Gln Leu Val Ser Asp Arg Val Ala Val Leu His Pro Glu
145                 150                 155                 160
Gly His Leu Ile Thr Pro Glu Trp Leu Trp Glu Lys Tyr Gly Leu Arg
                    165                 170                 175
Pro Glu Gln Trp Val Asp Phe Arg Ala Leu Val Gly Asp Pro Ser Asp
                180                 185                 190
Asn Leu Pro Gly Val Lys Gly Ile Gly Glu Lys Thr Ala Leu Lys Leu
            195                 200                 205
Leu Lys Glu Trp Gly Ser Leu Glu Asn Leu Leu Lys Asn Leu Asp Arg
210                 215                 220
Val Lys Pro Glu Asn Val Arg Glu Lys Ile Lys Ala His Leu Glu Asp
225                 230                 235                 240
Leu Arg Leu Ser Leu Glu Leu Ser Arg Val Arg Thr Asp Leu Pro Leu
                245                 250                 255
Glu Val Asp Leu Ala Gln Gly Arg Glu Pro Asp Arg Glu Gly Leu Arg
            260                 265                 270
Ala Phe Leu Glu Arg Leu Glu Phe Gly Ser Leu Leu His Glu Phe Gly
            275                 280                 285
Leu Leu Glu Ala Pro Ala Pro Leu Glu Glu Ala Pro Trp Pro Pro Pro
            290                 295                 300
Glu Gly Ala Phe Val Gly Phe Val Leu Ser Arg Pro Glu Pro Met Trp
305                 310                 315                 320
Ala Glu Leu Lys Ala Leu Ala Ala Cys Arg Asp Gly Arg Val His Arg
                325                 330                 335
Ala Ala Asp Pro Leu Ala Gly Leu Lys Asp Leu Lys Glu Val Arg Gly
                340                 345                 350
Leu Leu Ala Lys Asp Leu Ala Val Leu Ala Ser Arg Glu Gly Leu Asp
                355                 360                 365
Leu Val Pro Gly Asp Asp Pro Met Leu Leu Ala Tyr Leu Leu Asp Pro
            370                 375                 380
Ser Asn Thr Thr Pro Glu Gly Val Ala Arg Arg Tyr Gly Gly Glu Trp
385                 390                 395                 400
Thr Glu Asp Ala Ala His Arg Ala Leu Leu Ser Glu Arg Leu His Arg
                    405                 410                 415
Asn Leu Leu Lys Arg Leu Glu Gly Glu Glu Lys Leu Leu Trp Leu Tyr
                420                 425                 430
His Glu Val Glu Lys Pro Leu Ser Arg Val Leu Ala His Met Glu Ala
            435                 440                 445
Thr Gly Val Arg Leu Asp Val Ala Tyr Leu Gln Ala Leu Ser Leu Glu
450                 455                 460
Leu Ala Glu Glu Ile Arg Arg Leu Glu Glu Val Phe Arg Leu Ala
465                 470                 475                 480
Gly His Pro Phe Asn Leu Asn Ser Arg Asp Gln Leu Glu Arg Val Leu
                485                 490                 495
Phe Asp Glu Leu Arg Leu Pro Ala Leu Gly Lys Thr Gln Lys Thr Gly
            500                 505                 510
Lys Arg Ser Thr Ser Ala Ala Val Leu Glu Ala Leu Arg Glu Ala His
            515                 520                 525
Pro Ile Val Glu Lys Ile Leu Gln His Arg Glu Leu Thr Lys Leu Lys
```

```
            530                 535                 540
Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
                580                 585                 590

Gly Gln Arg Ile Arg Arg Ala Phe Val Ala Glu Ala Gly Trp Ala Leu
                595                 600                 605

Val Ala Leu Asp Tyr Ser Gln Ile Glu Leu Arg Val Leu Ala His Leu
610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
                660                 665                 670

Tyr Gly Met Ser Ala His Arg Leu Ser Gln Glu Leu Ala Ile Pro Tyr
                675                 680                 685

Glu Glu Ala Val Ala Phe Ile Glu Arg Tyr Phe Gln Ser Phe Pro Lys
690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
                755                 760                 765

Lys Leu Phe Pro Arg Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
                820                 825                 830

Lys Gly

<210> SEQ ID NO 3
<211> LENGTH: 834
<212> TYPE: PRT
<213> ORGANISM: Thermus caldophilus

<400> SEQUENCE: 3

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
                35                  40                  45

Lys Ser Leu Leu Lys Ala Leu Lys Glu Asp Gly Tyr Lys Ala Val Phe
                50                  55                  60

Val Val Phe Asp Ala Lys Ala Pro Ser Phe Arg His Glu Ala Tyr Glu
```

```
           65                  70                  75                  80
Ala Tyr Lys Ala Gly Arg Ala Pro Thr Pro Glu Asp Phe Pro Arg Gln
                85                  90                  95
Leu Ala Leu Ile Lys Glu Leu Val Asp Leu Gly Phe Thr Arg Leu
               100                 105                 110
Glu Val Pro Gly Tyr Glu Ala Asp Val Leu Ala Thr Leu Ala Lys
               115                 120                 125
Asn Pro Glu Lys Glu Gly Tyr Glu Val Arg Ile Leu Thr Ala Asp Arg
130                 135                 140
Asp Leu Asp Gln Leu Val Ser Asp Arg Val Ala Val Leu His Pro Glu
145                 150                 155                 160
Gly His Leu Ile Thr Pro Glu Trp Leu Trp Gln Lys Tyr Gly Leu Lys
                    165                 170                 175
Pro Glu Gln Trp Val Asp Phe Arg Ala Leu Val Gly Asp Pro Ser Asp
                180                 185                 190
Asn Leu Pro Gly Val Lys Gly Ile Gly Glu Lys Thr Ala Leu Lys Leu
                195                 200                 205
Leu Lys Glu Trp Gly Ser Leu Glu Asn Leu Leu Lys Asn Leu Asp Arg
    210                 215                 220
Val Lys Pro Glu Asn Val Arg Glu Lys Ile Lys Ala His Leu Glu Asp
225                 230                 235                 240
Leu Arg Leu Ser Leu Glu Leu Ser Arg Val Arg Thr Asp Leu Pro Leu
                    245                 250                 255
Glu Val Asp Leu Ala Gln Gly Arg Glu Pro Asp Arg Glu Gly Leu Arg
                260                 265                 270
Ala Phe Leu Glu Arg Leu Glu Phe Gly Ser Leu Leu His Glu Phe Gly
                275                 280                 285
Leu Leu Glu Ala Pro Ala Pro Leu Glu Glu Ala Pro Trp Pro Pro Pro
    290                 295                 300
Glu Gly Ala Phe Val Gly Phe Val Leu Ser Arg Pro Glu Pro Met Trp
305                 310                 315                 320
Ala Glu Leu Lys Ala Leu Ala Ala Cys Arg Asp Gly Arg Val His Arg
                325                 330                 335
Ala Ala Asp Pro Leu Ala Gly Leu Lys Asp Leu Lys Glu Val Arg Gly
                340                 345                 350
Leu Leu Ala Lys Asp Leu Ala Val Leu Ala Ser Arg Glu Gly Leu Asp
                355                 360                 365
Leu Val Pro Gly Asp Asp Pro Met Leu Leu Ala Tyr Leu Leu Asp Pro
    370                 375                 380
Ser Asn Thr Thr Pro Glu Gly Val Ala Arg Arg Tyr Gly Gly Glu Trp
385                 390                 395                 400
Thr Glu Asp Ala Ala His Arg Ala Leu Leu Ser Glu Arg Leu His Arg
                    405                 410                 415
Asn Leu Leu Lys Arg Leu Gln Gly Glu Glu Lys Leu Leu Trp Leu Tyr
                420                 425                 430
His Glu Val Glu Lys Pro Leu Ser Arg Val Leu Ala His Met Glu Ala
            435                 440                 445
Thr Gly Val Arg Leu Asp Val Ala Tyr Leu Gln Ala Leu Ser Leu Glu
            450                 455                 460
Leu Ala Glu Glu Ile Arg Arg Leu Glu Glu Val Phe Arg Leu Ala
465                 470                 475                 480
Gly His Pro Phe Asn Leu Asn Ser Arg Asp Gln Leu Glu Arg Val Leu
                485                 490                 495
```

```
Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Asn Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
    770                 775                 780

Val His Asp Glu Leu Leu Leu Glu Ala Pro Gln Ala Gly Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly

<210> SEQ ID NO 4
<211> LENGTH: 833
<212> TYPE: PRT
<213> ORGANISM: Thermus filiformis

<400> SEQUENCE: 4

Met Thr Pro Leu Phe Asp Leu Glu Glu Pro Pro Lys Arg Val Leu Leu
1               5                   10                  15

Val Asp Gly His His Leu Ala Tyr Arg Thr Phe Tyr Ala Leu Ser Leu
            20                  25                  30
```

-continued

```
Thr Thr Ser Arg Gly Glu Pro Val Gln Met Val Tyr Gly Phe Ala Arg
        35                  40                  45

Ser Leu Leu Lys Ala Leu Lys Glu Asp Gly Gln Ala Val Val Val
 50                  55                  60

Phe Asp Ala Lys Ala Pro Ser Phe Arg His Glu Ala Tyr Glu Ala Tyr
 65                  70                  75                  80

Lys Ala Gly Arg Ala Pro Thr Pro Glu Asp Phe Pro Arg Gln Leu Ala
                     85                  90                  95

Leu Val Lys Arg Leu Val Asp Leu Leu Gly Leu Val Arg Leu Glu Ala
                    100                 105                 110

Pro Gly Tyr Glu Ala Asp Asp Val Leu Gly Thr Leu Ala Lys Lys Ala
            115                 120                 125

Glu Arg Glu Gly Met Glu Val Arg Ile Leu Thr Gly Asp Arg Asp Phe
            130                 135                 140

Phe Gln Leu Leu Ser Glu Lys Val Ser Val Leu Leu Pro Asp Gly Thr
145                 150                 155                 160

Leu Val Thr Pro Lys Asp Val Gln Glu Lys Tyr Gly Val Pro Pro Glu
                    165                 170                 175

Arg Trp Val Asp Phe Arg Ala Leu Thr Gly Asp Arg Ser Asp Asn Ile
                180                 185                 190

Pro Gly Val Ala Gly Ile Gly Glu Lys Thr Ala Leu Arg Leu Leu Ala
            195                 200                 205

Glu Trp Gly Ser Val Glu Asn Leu Leu Lys Asn Leu Asp Arg Val Lys
            210                 215                 220

Pro Asp Ser Leu Arg Arg Lys Ile Glu Ala His Leu Glu Asp Leu His
225                 230                 235                 240

Leu Ser Leu Asp Leu Ala Arg Ile Arg Thr Asp Leu Pro Leu Glu Val
                    245                 250                 255

Asp Phe Lys Ala Leu Arg Arg Thr Pro Asp Leu Glu Gly Leu Arg
                260                 265                 270

Ala Phe Leu Glu Glu Leu Glu Phe Gly Ser Leu Leu His Glu Phe Gly
            275                 280                 285

Leu Leu Gly Gly Glu Lys Pro Arg Glu Glu Ala Pro Trp Pro Pro
            290                 295                 300

Glu Gly Ala Phe Val Gly Phe Leu Leu Ser Arg Lys Glu Pro Met Trp
305                 310                 315                 320

Ala Glu Leu Leu Ala Leu Ala Ala Ser Glu Gly Arg Val His Arg
                    325                 330                 335

Ala Thr Ser Pro Val Glu Ala Leu Ala Asp Leu Lys Glu Ala Arg Gly
                340                 345                 350

Phe Leu Ala Lys Asp Leu Ala Val Leu Ala Leu Arg Glu Gly Val Ala
            355                 360                 365

Leu Asp Pro Thr Asp Pro Leu Leu Val Ala Tyr Leu Leu Asp Pro
370                 375                 380

Ala Asn Thr His Pro Glu Gly Val Ala Arg Arg Tyr Gly Gly Glu Phe
385                 390                 395                 400

Thr Glu Asp Ala Ala Glu Arg Ala Leu Leu Ser Glu Arg Leu Phe Gln
                    405                 410                 415

Asn Leu Phe Pro Arg Leu Ser Glu Lys Leu Leu Trp Leu Tyr Gln Glu
                420                 425                 430

Val Glu Arg Pro Leu Ser Arg Val Leu Ala His Met Glu Ala Arg Gly
            435                 440                 445
```

Val Arg Leu Asp Val Pro Leu Leu Glu Ala Leu Ser Phe Glu Leu Glu
            450                 455                 460

Lys Glu Met Glu Arg Leu Glu Gly Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Thr Pro Val Gly Arg Thr Glu Lys Thr Gly Lys Arg
            500                 505                 510

Ser Thr Ala Gln Gly Ala Leu Glu Ala Leu Arg Gly Ala His Pro Ile
            515                 520                 525

Val Glu Leu Ile Leu Gln Tyr Arg Glu Leu Ser Lys Leu Lys Ser Thr
530                 535                 540

Tyr Leu Asp Pro Leu Pro Arg Leu Val His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Lys Ala Phe Val Ala Glu Glu Gly Trp Leu Leu Leu Ala
            595                 600                 605

Ala Asp Tyr Ser Gln Ile Glu Leu Arg Val Leu Ala His Leu Ser Gly
            610                 615                 620

Asp Glu Asn Leu Lys Arg Val Phe Arg Glu Gly Lys Asp Ile His Thr
625                 630                 635                 640

Glu Thr Ala Ala Trp Met Phe Gly Leu Asp Pro Ala Leu Val Asp Pro
                645                 650                 655

Lys Met Arg Arg Ala Ala Lys Thr Val Asn Phe Gly Val Leu Tyr Gly
                660                 665                 670

Met Ser Ala His Arg Leu Ser Gln Glu Leu Gly Ile Asp Tyr Lys Glu
            675                 680                 685

Ala Glu Ala Phe Ile Glu Arg Tyr Phe Gln Ser Phe Pro Lys Val Arg
            690                 695                 700

Ala Trp Ile Glu Arg Thr Leu Glu Glu Gly Arg Thr Arg Gly Tyr Val
705                 710                 715                 720

Glu Thr Leu Phe Gly Arg Arg Arg Tyr Val Pro Asp Leu Ala Ser Arg
                725                 730                 735

Val Arg Ser Val Arg Glu Ala Ala Glu Arg Met Ala Phe Asn Met Pro
            740                 745                 750

Val Gln Gly Thr Ala Ala Asp Leu Met Lys Ile Ala Met Val Lys Leu
            755                 760                 765

Phe Pro Arg Leu Lys Pro Leu Gly Ala His Leu Leu Leu Gln Val His
770                 775                 780

Asp Glu Leu Val Leu Glu Val Pro Glu Asp Arg Ala Glu Glu Ala Lys
785                 790                 795                 800

Ala Leu Val Lys Glu Val Met Glu Asn Ala Tyr Pro Leu Asp Val Pro
                805                 810                 815

Leu Glu Val Glu Val Gly Val Gly Arg Asp Trp Leu Glu Ala Lys Gln
            820                 825                 830

Asp

<210> SEQ ID NO 5
<211> LENGTH: 838
<212> TYPE: PRT
<213> ORGANISM: Thermodesulfovibrio yellowstonii DSM 11347

<400> SEQUENCE: 5

```
Met His Glu Ile Tyr Leu Val Asp Gly Ser Cys Phe Ile Tyr Arg Ala
1               5                   10                  15
Tyr His Ala Ile Lys Gly Leu Ser Thr Ser Arg Gly Ile Pro Thr Asn
            20                  25                  30
Ala Ile Tyr Gly Phe Thr Arg Met Leu Leu Lys Leu Leu Arg Glu Lys
        35                  40                  45
Asn Val Lys Tyr Ile Leu Cys Ala Phe Asp Ser Pro His Pro Thr Lys
    50                  55                  60
Arg His Lys Ile Tyr Glu Glu Tyr Lys Ile Thr Arg Pro Glu Thr Pro
65                  70                  75                  80
Lys Asp Leu Pro Val Gln Ile Asp Tyr Ile Lys Gln Ile Ile Asp Ala
            85                  90                  95
Leu Gly Ile Thr Arg Ile Glu Val Pro Gly Tyr Glu Ala Asp Asp Ile
            100                 105                 110
Ile Ala Thr Ala Val Gly Val Ile Asn Gln Phe Ala Pro Leu Asn Phe
        115                 120                 125
Ile Ile Ile Ser Ile Asp Lys Asp Met Leu Gln Leu Val Ser Asp Asn
130                 135                 140
Val Lys Ile Tyr Asp Pro Ile Asn Glu Leu Ile Ile Asp Arg Glu Tyr
145                 150                 155                 160
Val Ile Lys Lys Tyr Gly Val Pro Pro Glu Lys Leu Asn Asp Phe Met
            165                 170                 175
Ala Leu Val Gly Asp Ala Ile Asp Asn Ile Pro Gly Val Lys Gly Ile
        180                 185                 190
Gly Glu Lys Thr Ala Ala Asn Leu Ile Lys Arg Tyr Gly Ser Ile Glu
        195                 200                 205
Asn Ile Leu Lys Asn Leu Asp Ile Ile Lys Pro Leu Lys Val Ser Asp
    210                 215                 220
Ile Ile Lys Lys Asn Ile Lys Ser Leu Gln Leu Ser Lys Glu Leu Val
225                 230                 235                 240
Ile Leu Arg Lys Asp Thr Pro Ile Glu Ile Lys Leu Asp Asp Leu Lys
            245                 250                 255
Ile Lys Gln Gln Asp Arg Glu Lys Leu Val Gln Ile Phe Arg Glu Leu
        260                 265                 270
Glu Phe Asn Thr Leu Lys Gln Ile Ile Lys Asp Phe Pro Asn His
        275                 280                 285
Ser Ser Cys Ser Val Leu Gln Leu Asn Leu Ala Ser Glu Asn Arg Arg
    290                 295                 300
Asn Thr Ile Glu Leu Ile Glu Lys Ile Lys Glu Tyr Gly Lys Phe Ser
305                 310                 315                 320
Val Thr Phe Asn Lys Asp Ser Ile Ile Ala Gly Val Asn Gly Thr Leu
            325                 330                 335
Tyr Glu Ile Ala Phe Asn Asp Thr Arg Val Asn Glu Ile Leu Ser Ser
        340                 345                 350
Glu Ile Leu Lys Ile Ile Tyr Asn Ala Lys Glu Ala Leu Lys Lys Leu
        355                 360                 365
Lys Asn Ser Gly Leu Lys Leu Ser Pro Pro Tyr Phe Asp Leu Met Ile
    370                 375                 380
Val Ala Tyr Leu Ile Asn Pro Asn Arg Gly Lys Tyr Asn Ile Asp Glu
385                 390                 395                 400
Leu Ile Leu Glu Tyr Thr Gly Lys Phe Tyr Glu Asn Ala Glu Asn Ile
```

```
                    405                 410                 415
Asn Phe Tyr Met Phe Glu Leu Tyr Glu Lys Leu Asn Lys Glu Leu Lys
                420                 425                 430

Glu Lys Glu Leu Glu Asn Leu Tyr Phe Asp Ile Glu Met Pro Leu Ile
            435                 440                 445

Glu Val Leu Phe Asp Met Glu Thr Gly Ile Lys Val Asn Ile Glu
        450                 455                 460

Lys Leu Glu Thr Leu Thr Lys His Ile Ser Met Glu Leu Asp Lys Ile
465                 470                 475                 480

Lys Glu Lys Ile Tyr Thr Ile Ala Gly Thr Glu Phe Asn Ile Asn Ser
                485                 490                 495

Pro Lys Gln Leu Ala Glu Val Leu Tyr Asp Arg Leu Gly Leu Lys Thr
            500                 505                 510

Arg Lys Arg Gly Lys Lys Ala Arg Ser Thr Glu Met Glu Val Leu Glu
        515                 520                 525

Glu Leu Ala Ile Gln His Glu Leu Pro His Glu Val Ile Asn Tyr Arg
    530                 535                 540

Thr Leu Asn Lys Leu Leu Thr Gly Tyr Leu Ile Pro Leu Arg Asp Tyr
545                 550                 555                 560

Ile Asn Pro Glu Thr Lys Arg Ile His Thr Lys Trp Ser Gln Thr Val
                565                 570                 575

Ala Gly Thr Gly Arg Ile Val Ser Ser Glu Pro Asn Leu Gln Asn Ile
            580                 585                 590

Pro Val Lys Gly Glu Trp Ala Glu Phe Leu Arg Glu Val Phe Ile Pro
        595                 600                 605

Glu Asn Gly Tyr Met Phe Leu Ser Ala Asp Tyr Ser Gln Ile Glu Leu
    610                 615                 620

Arg Leu Leu Ala His Met Ser Glu Asp Pro Ala Leu Ile Lys Ala Phe
625                 630                 635                 640

Leu Asp Gly Lys Asp Ile His Thr Ala Thr Ala Ser Glu Ile Phe Ser
                645                 650                 655

Ile Pro Glu Asn Ala Val Thr Asp Glu His Arg Arg Ile Ala Lys Thr
            660                 665                 670

Val Asn Phe Gly Ile Ser Tyr Gly Ile Ser Pro Phe Gly Leu Ser Glu
        675                 680                 685

Ser Ile Lys Ile Pro Tyr Glu Lys Ala Glu Glu Leu Ile Glu Leu Tyr
    690                 695                 700

Phe Leu Arg Tyr Pro Met Val Arg Lys Phe Ile Glu Glu Thr Ile Ser
705                 710                 715                 720

Phe Ala Gln Lys Asn Gly Tyr Val Arg Thr Leu Phe Gly Arg Ile Arg
                725                 730                 735

Pro Leu Pro Glu Ile Asn Ser Pro Asn Gln Phe Leu Arg Met Gln Ser
            740                 745                 750

Glu Arg Met Ala Val Asn Ala Arg Val Gln Gly Thr Ala Ala Asp Ile
        755                 760                 765

Ile Lys Ile Ala Met Ile Arg Ile Tyr Asn Arg Leu Lys Lys Glu Lys
    770                 775                 780

Leu Asn Ala Lys Ile Ile Leu Gln Ile His Asp Glu Ile Val Leu Glu
785                 790                 795                 800

Val Glu Gln Lys Val Ile Glu Lys Val Ser Glu Ile Val Gln Asn Glu
                805                 810                 815

Met Lys Asp Phe Ser Leu Ser Val Pro Leu Glu Val Asn Val Phe Ser
            820                 825                 830
```

Gly Asn Ser Leu Asn Leu
        835

<210> SEQ ID NO 6
<211> LENGTH: 856
<212> TYPE: PRT
<213> ORGANISM: Dictyoglomus thermophilum

<400> SEQUENCE: 6

Met Glu Gln Lys Ser Leu Trp Asp Leu Phe Gln Glu Asn Thr Glu Lys
1               5                   10                  15

Glu Ser Lys Arg Lys Ile Leu Ile Ile Asp Gly Ser Ser Leu Ile Tyr
            20                  25                  30

Arg Val Tyr Tyr Ala Leu Pro Pro Leu Lys Thr Lys Asn Gly Glu Leu
        35                  40                  45

Thr Asn Ala Leu Tyr Gly Phe Ile Arg Ile Leu Leu Lys Ala Val Glu
    50                  55                  60

Asp Phe Asn Pro Asp Leu Val Gly Val Ala Phe Asp Arg Pro Glu Pro
65                  70                  75                  80

Thr Phe Arg His Val Ile Tyr Lys Glu Tyr Lys Ala Lys Arg Pro Pro
                85                  90                  95

Met Lys Asp Asp Leu Lys Ala Gln Ile Pro Trp Ile Arg Glu Phe Leu
            100                 105                 110

Arg Leu Asn Asp Ile Pro Leu Leu Glu Glu Pro Gly Tyr Glu Ala Asp
        115                 120                 125

Asp Ile Ile Ala Thr Ile Val Asn Lys Tyr Lys Asp Asp Leu Lys Tyr
    130                 135                 140

Ile Leu Ser Gly Asp Leu Asp Leu Leu Gln Leu Val Ser Asp Lys Thr
145                 150                 155                 160

Phe Leu Ile His Pro Gln Lys Gly Ile Thr Glu Phe Thr Ile Tyr Asp
                165                 170                 175

Pro Lys Ala Val Lys Asp Arg Phe Gly Val Glu Pro Tyr Lys Ile Pro
            180                 185                 190

Leu Tyr Lys Val Leu Val Gly Asp Glu Ser Asp Asn Ile Pro Gly Val
        195                 200                 205

Asn Gly Ile Gly Pro Lys Lys Ala Ser Lys Ile Leu Glu Lys Ile Ser
    210                 215                 220

Ser Val Asp Glu Phe Lys Ser Lys Ile Lys Val Leu Asp Ser Asp Leu
225                 230                 235                 240

Arg Glu Leu Ile Glu Lys Asn Trp Asn Ile Glu Arg Asn Leu Glu
                245                 250                 255

Leu Val Thr Leu Lys Asn Ile Asp Lys Asp Leu Ile Leu Lys Pro Phe
            260                 265                 270

Glu Ile Lys Arg Asp Glu Lys Val Ile Asp Phe Leu Lys Arg Tyr Glu
        275                 280                 285

Leu Lys Ser Ile Leu Gln Lys Leu Phe Pro Asp Leu Gln Glu Glu Glu
    290                 295                 300

Asn Ile Glu Ile Lys Asp Val Glu Glu Ile Asn Phe Asn Glu Val Glu
305                 310                 315                 320

Lys Glu Gly Tyr Phe Ala Phe Lys Cys Leu Gly Asp Arg Ala Phe Glu
                325                 330                 335

Gly Ile Ser Leu Ser Phe Lys Glu Gly Glu Gly Tyr Phe Ile Ser Pro
            340                 345                 350

Phe Asp Phe Asn Asn Glu Ile Arg Lys Lys Ile Glu Asn Ile Ile Ser

-continued

```
               355                 360                 365
Ser Glu Asn Val Lys Lys Ile Gly Ser Tyr Ile Gln Arg Asp Leu His
    370                 375                 380
Phe Leu Asn Cys Lys Ile Lys Gly Asp Val Phe Asp Val Ser Leu Ala
385                 390                 395                 400
Ser Tyr Leu Leu Asn Pro Glu Arg Gln Asn His Ser Leu Asp Ile Leu
                405                 410                 415
Ile Gly Glu Tyr Leu Asn Lys Thr Ser Phe Ile Pro Gln Lys Tyr Ala
            420                 425                 430
Gly Tyr Leu Phe Pro Leu Lys Ser Ile Leu Glu Glu Arg Ile Lys Asn
        435                 440                 445
Glu Gly Leu Glu Phe Val Leu Tyr Asn Ile Glu Ile Pro Leu Ile Pro
    450                 455                 460
Val Leu Tyr Ser Met Glu Lys Trp Gly Ile Lys Val Asp Lys Glu Tyr
465                 470                 475                 480
Leu Lys Gln Leu Ser Asp Glu Phe Cys Glu Arg Ile Lys Lys Leu Glu
                485                 490                 495
Glu Glu Ile Tyr Glu Leu Ala Gly Thr Arg Phe Asn Leu Asn Ser Pro
            500                 505                 510
Lys Gln Leu Ser Glu Val Leu Phe Glu Arg Leu Lys Leu Pro Ser Gly
        515                 520                 525
Lys Lys Gly Lys Thr Gly Tyr Ser Thr Ser Ser Val Leu Gln Asn
    530                 535                 540
Leu Ile Asn Ala His Pro Ile Val Arg Lys Ile Leu Gln Tyr Arg Glu
545                 550                 555                 560
Leu Tyr Lys Leu Lys Ser Thr Tyr Val Asp Ala Ile Pro Asn Leu Val
                565                 570                 575
Asn Pro Gln Thr Gly Arg Val His Thr Lys Phe Asn Pro Thr Gly Thr
            580                 585                 590
Ala Thr Gly Arg Ile Ser Ser Ser Glu Pro Asn Leu Gln Asn Ile Pro
        595                 600                 605
Ile Lys Ser Glu Glu Gly Arg Lys Ile Arg Arg Ala Phe Val Ser Glu
    610                 615                 620
Asp Gly Tyr Phe Leu Val Ser Leu Asp Tyr Ser Gln Ile Glu Leu Arg
625                 630                 635                 640
Ile Met Ala His Leu Ser Gln Glu Pro Lys Leu Ile Ser Ala Phe Gln
                645                 650                 655
Lys Gly Glu Asp Ile His Arg Thr Ala Ser Glu Ile Phe Gly Val
            660                 665                 670
Pro Glu Glu Glu Val Asp Asp Leu Leu Arg Ser Arg Ala Lys Ala Val
        675                 680                 685
Asn Phe Gly Ile Ile Tyr Gly Ile Ser Ser Phe Gly Leu Ser Glu Thr
    690                 695                 700
Val Ser Ile Thr Pro Glu Glu Ala Glu Lys Phe Ile Asp Ser Tyr Phe
705                 710                 715                 720
Lys His Tyr Pro Arg Val Lys Leu Phe Ile Asp Lys Thr Ile His Glu
                725                 730                 735
Ala Arg Glu Lys Leu Tyr Val Leu Thr Leu Phe Gly Lys Arg Tyr
            740                 745                 750
Ile Pro Glu Ile Lys Ser Ile Asn Lys Gln Val Arg Asn Ala Tyr Glu
        755                 760                 765
Arg Ile Ala Ile Asn Ala Pro Ile Gln Gly Thr Ala Ala Asp Ile Ile
    770                 775                 780
```

```
Lys Leu Ala Met Ile Glu Ile Tyr Lys Glu Ile Glu Asn Lys Asn Leu
785                 790                 795                 800

Lys Ser Arg Ile Leu Leu Gln Ile His Asp Glu Leu Ile Leu Glu Val
            805                 810                 815

Pro Glu Glu Glu Met Glu Phe Thr Pro Leu Met Ala Lys Glu Lys Met
        820                 825                 830

Glu Lys Val Val Glu Leu Ser Val Pro Leu Val Val Glu Ile Ser Val
            835                 840                 845

Gly Lys Asn Leu Ala Glu Leu Lys
        850                 855

<210> SEQ ID NO 7
<211> LENGTH: 930
<212> TYPE: PRT
<213> ORGANISM: Natranaerobius thermophilus

<400> SEQUENCE: 7

Met Asn Ser Asn Asp Tyr Gln Ala Asn Asp Lys Phe Val Val Ile Asp
1               5                   10                  15

Gly Asn Ser Leu Leu Asn Arg Ala Phe Tyr Ala Leu Pro Leu Leu Gln
            20                  25                  30

Thr Lys Gln Gly Phe Phe Thr Asn Ala Ile Tyr Gly Phe Thr Thr Met
        35                  40                  45

Leu Leu Lys Leu Val Gln Asp Glu Ser Pro Asn Tyr Leu Ala Val Val
    50                  55                  60

Phe Asp Thr Lys Ala Lys Thr Phe Arg His His Lys Phe Pro Glu Tyr
65                  70                  75                  80

Lys Gly His Arg Asp Lys Ala Pro Asp Glu Met Arg Pro Gln Met Pro
                85                  90                  95

Met Leu Lys Glu Leu Leu Glu Ala Met Asn Ile Asn Tyr Phe Glu Lys
            100                 105                 110

Asp Gly Tyr Glu Ala Asp Asp Leu Ile Gly Ala Phe Thr Lys Ile Ala
        115                 120                 125

Lys Gln Glu Asp Lys Glu Thr Met Val Val Thr Gly Asp Lys Asp Leu
    130                 135                 140

Leu Gln Leu Leu Asp Asp Lys Thr Thr Ile Leu Leu Thr Lys Lys Gly
145                 150                 155                 160

Ile Thr Gln Met Glu Ser Tyr Asp Gly Glu Lys Val Lys Glu Glu Phe
                165                 170                 175

Gly Val Asn Val Asp Lys Leu Ile Asp Leu Lys Ala Leu Thr Gly Asp
            180                 185                 190

Lys Ser Asp Asn Val Pro Gly Val Pro Gly Val Gly Lys Lys Thr Ala
        195                 200                 205

Leu Lys Leu Leu Asn Asn Tyr Gly Asp Leu Glu Lys Leu Tyr Lys Ser
    210                 215                 220

Leu Asp Gly Val Gly Gly Lys Leu Gln Ser Lys Leu Ala Asp Asn Lys
225                 230                 235                 240

Asp Lys Ala Phe Leu Ser Lys Glu Leu Val Thr Ile Asp Cys Glu Glu
                245                 250                 255

Ser Leu Ile Glu Asn Leu Asp Trp Asn Gln Leu Ser Lys Phe Glu Ile
            260                 265                 270

Ala Ser Pro Lys Ala Arg Glu Leu Leu Gln Glu Trp Glu Met Asn Ser
        275                 280                 285

Ile Leu Glu Arg Leu Pro Ala Ser Asp Glu Glu Gln Lys Lys Asp Gln
```

```
                290                 295                 300
Ser Pro Val Asn Glu Gly Lys Thr Ser Ser Phe Asn Trp Asp Asn Phe
305                 310                 315                 320

Tyr Tyr Ile Ser Glu Phe Pro His Glu Asn Ser Asp Asn Leu Glu Ser
                325                 330                 335

Glu Leu Glu Lys Phe Ile Gln Asp Gly Asn His Lys Met Ala Leu Tyr
                340                 345                 350

Arg His Leu Pro Lys Lys Leu Ser Thr Ala Lys Gln Lys Asp Ser Tyr
                355                 360                 365

Pro Glu Pro Glu Gly Gly Leu Val Val Ser Ile Asn Asp Leu Ile Phe
370                 375                 380

Tyr Val Pro Glu Lys Leu Leu Ser Gln Val Leu Ala Glu Thr Ile Ala
385                 390                 395                 400

Pro Lys Leu Ile Lys Gly Asn Asp Lys Gly Thr Glu Thr Glu Asp Ala
                405                 410                 415

Pro Lys Leu Lys Ile Ala Ser Tyr Asn Ile Lys Arg Ile Trp His Leu
                420                 425                 430

Phe Lys Asn Asn Thr Glu Leu Asp Leu Tyr Asp Leu Asp Thr Asn Lys
                435                 440                 445

Phe Leu Phe Tyr Asp Thr Glu Leu Met Ala Tyr Leu Leu Glu Pro Thr
450                 455                 460

Glu Ala Pro His Ser Ile Glu Asp Met Met Asn Arg Tyr Tyr Gly Gln
465                 470                 475                 480

Phe Asp Leu Thr Pro Tyr Gly Gln Asp Trp Gln Ala Val Cys Glu Arg
                485                 490                 495

Gly Ala Ile Leu Leu Asp Leu Ile Ser Pro Leu Glu Asp Ile Leu Gln
                500                 505                 510

Glu Arg Asn Gln Trp Gln Leu Tyr Lys Asn Ile Glu Leu Pro Leu Ala
                515                 520                 525

Phe Ile Leu Ala Arg Met Glu Phe Arg Gly Ile Lys Val Asp Ala Arg
530                 535                 540

Val Leu Thr Glu Met Glu Ala Asn Ile Asp His Arg Leu Ser Glu Ile
545                 550                 555                 560

Ser Thr Lys Ile Phe Glu Ile Ala Gly Glu Glu Phe Asn Leu Asn Ser
                565                 570                 575

Pro Lys Gln Leu Gly Tyr Ile Leu Phe Glu Lys Leu Gln Leu Pro Val
                580                 585                 590

Val Lys Lys Thr Lys Thr Gly Tyr Ser Thr Asp Ala Lys Thr Leu Glu
                595                 600                 605

Thr Leu Ser His Asp Tyr Glu Ile Cys Lys Leu Leu Leu Asp Tyr Arg
                610                 615                 620

Gln Leu His Lys Leu Lys Thr Thr Tyr Leu Val Gly Leu Lys Asp Leu
625                 630                 635                 640

Ile Ser Lys Thr Thr Gly Lys Ile His Thr Thr Tyr Asn Gln Thr Ile
                645                 650                 655

Thr Ala Thr Gly Arg Leu Ser Ser Thr Asp Pro Asn Leu Gln Asn Ile
                660                 665                 670

Pro Ile Lys Leu Glu Glu Gly Arg Lys Ile Arg Lys Gly Phe Val Ile
                675                 680                 685

Gln Asn Ser Asp Gln Leu Phe Leu Ala Ala Asp Tyr Ser Gln Ile Glu
                690                 695                 700

Leu Arg Ile Leu Ala His Val Ser Glu Asp Thr Asn Leu Ile Gln Ala
705                 710                 715                 720
```

```
Phe Gln Glu Gln Gln Asp Ile His Thr Gln Thr Ala Ala Gln Val Phe
                725                 730                 735

Glu Val Glu Ser Thr Gln Val Thr Arg Glu Met Arg Ser His Ala Lys
            740                 745                 750

Ala Val Asn Phe Gly Ile Val Tyr Gly Ile Ser Asp Tyr Gly Leu Ser
        755                 760                 765

Arg Gln Leu Gly Ile Ser Arg Lys Gln Ala Lys Thr Tyr Ile Asp Asn
    770                 775                 780

Tyr Leu Thr Arg Phe Ser Gly Val Lys Glu Tyr Met Asp Gln Ile Val
785                 790                 795                 800

Asn Gln Ala Lys Met Asn Gly Tyr Val Glu Thr Leu Tyr Asn Arg Arg
                805                 810                 815

Arg Asn Leu Pro Asp Ile Ser His Arg Asn Phe Asn Ile Arg Ser Ala
            820                 825                 830

Ala Glu Arg Thr Ala Ile Asn Thr Pro Ile Gln Gly Thr Ala Ala Asp
        835                 840                 845

Ile Ile Lys Asp Ala Met Val Lys Val Glu Lys Glu Leu Glu Lys Gln
    850                 855                 860

Asp Leu Leu Asp Lys Ala Ala Leu Leu Leu Gln Val His Asp Glu Leu
865                 870                 875                 880

Ile Leu Glu Ile Asn Lys Glu Val Leu Ser Asp Val Ala Thr Lys Val
                885                 890                 895

Lys Glu Ile Met Glu Asn Ile Ile Glu Leu Lys Val Pro Leu Thr Val
            900                 905                 910

Asp Leu Lys Thr Gly Pro Asn Trp Tyr Asp Leu Asn Pro Tyr Gln Ser
        915                 920                 925

Gly Glu
    930

<210> SEQ ID NO 8
<211> LENGTH: 928
<212> TYPE: PRT
<213> ORGANISM: Escherichia coli

<400> SEQUENCE: 8

Met Val Gln Ile Pro Gln Asn Pro Leu Ile Leu Val Asp Gly Ser Ser
1               5                   10                  15

Tyr Leu Tyr Arg Ala Tyr His Ala Phe Pro Pro Leu Thr Asn Ser Ala
            20                  25                  30

Gly Glu Pro Thr Gly Ala Met Tyr Gly Val Leu Asn Met Leu Arg Ser
        35                  40                  45

Leu Ile Met Gln Tyr Lys Pro Thr His Ala Ala Val Val Phe Asp Ala
    50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95

Ala Met Val Lys Ala Met Gly Leu Pro Leu Leu Ala Val Ser Gly Val
            100                 105                 110

Glu Ala Asp Asp Val Ile Gly Thr Leu Ala Arg Glu Ala Glu Lys Ala
        115                 120                 125

Gly Arg Pro Val Leu Ile Ser Thr Gly Asp Lys Asp Met Ala Gln Leu
    130                 135                 140

Val Thr Pro Asn Ile Thr Leu Ile Asn Thr Met Thr Asn Thr Ile Leu
```

```
             145                 150                 155                 160
Gly Pro Glu Glu Val Val Asn Lys Tyr Gly Val Pro Pro Glu Leu Ile
                    165                 170                 175

Ile Asp Phe Leu Ala Leu Met Gly Asp Ser Ser Asp Asn Ile Pro Gly
                    180                 185                 190

Val Pro Gly Val Gly Glu Lys Thr Ala Gln Ala Leu Leu Gln Gly Leu
                    195                 200                 205

Gly Gly Leu Asp Thr Leu Tyr Ala Glu Pro Glu Lys Ile Ala Gly Leu
        210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                    245                 250                 255

Glu Leu Glu Leu Thr Cys Glu Gln Leu Glu Val Gln Gln Pro Ala Ala
                    260                 265                 270

Glu Glu Leu Leu Gly Leu Phe Lys Lys Tyr Glu Phe Lys Arg Trp Thr
            275                 280                 285

Ala Asp Val Glu Ala Gly Lys Trp Leu Gln Ala Lys Gly Ala Lys Pro
        290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
                    325                 330                 335

Glu Thr Leu Lys Ala Trp Ile Ala Lys Leu Glu Lys Ala Pro Val Phe
                    340                 345                 350

Ala Phe Asp Thr Glu Thr Asp Ser Leu Asp Asn Ile Ser Ala Asn Leu
            355                 360                 365

Val Gly Leu Ser Phe Ala Ile Glu Pro Gly Val Ala Ala Tyr Ile Pro
        370                 375                 380

Val Ala His Asp Tyr Leu Asp Ala Pro Asp Gln Ile Ser Arg Glu Arg
385                 390                 395                 400

Ala Leu Glu Leu Leu Lys Pro Leu Leu Glu Asp Glu Lys Ala Leu Lys
                    405                 410                 415

Val Gly Gln Asn Leu Lys Tyr Asp Arg Gly Ile Leu Ala Asn Tyr Gly
                    420                 425                 430

Ile Glu Leu Arg Gly Ile Ala Phe Asp Thr Met Leu Glu Ser Tyr Ile
            435                 440                 445

Leu Asn Ser Val Ala Gly Arg His Asp Met Asp Ser Leu Ala Glu Arg
450                 455                 460

Trp Leu Lys His Lys Thr Ile Thr Phe Glu Glu Ile Ala Gly Lys Gly
465                 470                 475                 480

Lys Asn Gln Leu Thr Phe Asn Gln Ile Ala Leu Glu Glu Ala Gly Arg
                    485                 490                 495

Tyr Ala Ala Glu Asp Ala Asp Val Thr Leu Gln Leu His Leu Lys Met
            500                 505                 510

Trp Pro Asp Leu Gln Lys His Lys Gly Pro Leu Asn Val Phe Glu Asn
        515                 520                 525

Ile Glu Met Pro Leu Val Pro Val Leu Ser Arg Ile Glu Arg Asn Gly
        530                 535                 540

Val Lys Ile Asp Pro Lys Val Leu His Asn His Ser Glu Glu Leu Thr
545                 550                 555                 560

Leu Arg Leu Ala Glu Leu Glu Lys Lys Ala His Glu Ile Ala Gly Glu
                    565                 570                 575
```

```
Glu Phe Asn Leu Ser Ser Thr Lys Gln Leu Gln Thr Ile Leu Phe Glu
            580                 585                 590
Lys Gln Gly Ile Lys Pro Leu Lys Thr Pro Gly Ala Pro Ser
        595                 600                 605
Thr Ser Glu Glu Val Leu Glu Glu Leu Ala Leu Asp Tyr Pro Leu Pro
    610                 615                 620
Lys Val Ile Leu Glu Tyr Arg Gly Leu Ala Lys Leu Lys Ser Thr Tyr
625                 630                 635                 640
Thr Asp Lys Leu Pro Leu Met Ile Asn Pro Lys Thr Gly Arg Val His
                645                 650                 655
Thr Ser Tyr His Gln Ala Val Thr Ala Thr Gly Arg Leu Ser Ser Thr
            660                 665                 670
Asp Pro Asn Leu Gln Asn Ile Pro Val Arg Asn Glu Glu Gly Arg Arg
        675                 680                 685
Ile Arg Gln Ala Phe Ile Ala Pro Glu Asp Tyr Val Ile Val Ser Ala
    690                 695                 700
Asp Tyr Ser Gln Ile Glu Leu Arg Ile Met Ala His Leu Ser Arg Asp
705                 710                 715                 720
Lys Gly Leu Leu Thr Ala Phe Ala Glu Gly Lys Asp Ile His Arg Ala
                725                 730                 735
Thr Ala Ala Glu Val Phe Gly Leu Pro Leu Glu Thr Val Thr Ser Glu
            740                 745                 750
Gln Arg Arg Ser Ala Lys Ala Ile Asn Phe Gly Leu Ile Tyr Gly Met
        755                 760                 765
Ser Ala Phe Gly Leu Ala Arg Gln Leu Asn Ile Pro Arg Lys Glu Ala
    770                 775                 780
Gln Lys Tyr Met Asp Leu Tyr Phe Glu Arg Tyr Pro Gly Val Leu Gln
785                 790                 795                 800
Tyr Met Glu Arg Thr Arg Ala Gln Ala Lys Glu Gln Gly Tyr Val Glu
                805                 810                 815
Thr Leu Asp Gly Arg Arg Leu Tyr Leu Pro Asp Ile Lys Ser Ser Asn
            820                 825                 830
Gly Ala Arg Arg Ala Ala Ala Glu Arg Ala Ala Ile Asn Ala Pro Met
        835                 840                 845
Gln Gly Thr Ala Ala Asp Ile Ile Lys Arg Ala Met Ile Ala Val Asp
    850                 855                 860
Ala Trp Leu Gln Ala Glu Gln Pro Arg Val Arg Met Ile Met Gln Val
865                 870                 875                 880
His Asp Glu Leu Val Phe Glu Val His Lys Asp Val Asp Ala Val
                885                 890                 895
Ala Lys Gln Ile His Gln Leu Met Glu Asn Cys Thr Arg Leu Asp Val
                900                 905                 910
Pro Leu Leu Val Glu Val Gly Ser Gly Glu Asn Trp Asp Gln Ala His
            915                 920                 925

<210> SEQ ID NO 9
<211> LENGTH: 892
<212> TYPE: PRT
<213> ORGANISM: Thermotoga lettingae TMO

<400> SEQUENCE: 9

Met Ala Lys Leu Phe Leu Phe Asp Gly Thr Gly Leu Ala Tyr Arg Ala
1               5                   10                  15

Tyr Tyr Ala Leu Asp Gln Ser Leu Ser Thr Thr Ser Gly Ile Pro Thr
```

```
                 20                  25                  30
Asn Ala Thr Tyr Gly Val Leu Arg Met Leu Ile Arg Phe Leu Lys Asp
             35                  40                  45
Tyr Val Lys Ile Gly Asp Tyr Thr Ala Phe Ala Met Asp Thr Lys Thr
 50                  55                  60
Arg Thr Tyr Arg His Glu Leu Leu Glu Glu Tyr Lys Ala His Arg Pro
 65                  70                  75                  80
Gln Thr Pro Asp Ala Met Ile Gln Gln Leu Pro Tyr Ile Lys Arg Gly
                 85                  90                  95
Val Gln Ala Leu Gly Ile Lys Val Leu Glu Tyr Glu Gly Cys Glu Ala
             100                 105                 110
Asp Asp Val Ile Ala Thr Leu Ala Arg Met Gly Glu Lys Glu Phe Glu
             115                 120                 125
Asp Ile Phe Ile Ile Ser Gly Asp Lys Asp Met Phe Gln Leu Val Asn
             130                 135                 140
Asp Lys Ile Lys Val Trp Arg Pro Ser Lys Gly Ile Thr Asp Leu Glu
145                 150                 155                 160
Phe Tyr Asp Lys Lys Lys Ile Glu Lys Tyr Arg Val Glu Pro Ser
                 165                 170                 175
Lys Ile Val Asp Leu Leu Ala Leu Met Gly Asp Ser Val Asp Asn Val
             180                 185                 190
Pro Gly Val Lys Gly Ile Gly Met Lys Thr Ala Ala Glu Leu Ile Glu
             195                 200                 205
Lys Phe Gly Asn Leu Asp Glu Ile Tyr Gly Lys Ile Asp Glu Asn Ser
             210                 215                 220
Arg Ile Gly Lys Leu Leu Ser Arg Gly Lys Asp Asp Ala Phe Lys Ser
225                 230                 235                 240
Lys Gln Leu Val Thr Leu Met Thr Asp Leu Asp Leu Arg Leu Thr Trp
                 245                 250                 255
Asp Asp Leu Lys Tyr Ala Gly Tyr Lys Glu Lys Glu Leu Val Glu Phe
             260                 265                 270
Leu Arg Glu Met Glu Phe Ser Ser Ile Met Lys Glu Leu Gly Leu Tyr
             275                 280                 285
Thr Gln Gln Asp Gln Lys Thr Pro Tyr Ile Ala Val Lys Asp Asn Asn
             290                 295                 300
Ser Leu Asn Glu Leu Phe Glu Lys Ile Lys Lys Ser Gln Tyr Phe Val
305                 310                 315                 320
Leu Asp Leu Glu Thr Asp Ser Leu Ser Pro Ile Asp Ala Glu Ile Ile
                 325                 330                 335
Gly Phe Ser Ile Ser Leu Pro Ser Lys Glu Ser Tyr Tyr Val Pro Leu
             340                 345                 350
Ala His Lys Asn Gly Pro Asn Val Asp Lys Lys Ser Ala Leu Asn Asn
             355                 360                 365
Leu Lys Ser Ile Leu Glu Asn Gln Ser Ala Lys Ile Ile Gly Gln Asn
             370                 375                 380
Leu Lys Tyr Asp Tyr Ser Val Leu Lys Met His Gly Ile Glu Pro Val
385                 390                 395                 400
Arg Pro Ser Phe Asp Thr Met Ile Ala Ala Tyr Leu Leu Asn Pro Asp
             405                 410                 415
Glu Lys Arg Phe Asn Leu Asp Glu Leu Ala Met Lys Phe Leu Asn Tyr
             420                 425                 430
Lys Met Ile Ser Phe Glu Glu Leu Phe Lys Asp Thr Ser Pro Leu Phe
             435                 440                 445
```

```
Gly Ala Val Thr Phe Ala Asp Val Ser Val Glu Asp Ala Thr Lys Tyr
            450                 455                 460

Ser Ala Glu Asp Ala Asp Ile Thr Arg Arg Leu Tyr Glu Ile Leu Asn
465                 470                 475                 480

Ile Lys Leu His Glu Ala Asp Leu Leu Glu Val Leu Glu Lys Ile Glu
                485                 490                 495

Met Pro Leu Ile Pro Val Leu Val His Met Glu Leu Glu Gly Val Tyr
            500                 505                 510

Met Asn Ile Asp Tyr Leu Lys Asp Leu Ser Ser Lys Tyr Ala Ala Arg
            515                 520                 525

Met Asn Glu Leu Ser Gln Gln Ile Tyr Asn His Ala Gly Glu Ala Phe
            530                 535                 540

Asn Leu Asn Ser Pro Lys Gln Val Ala His Ile Leu Phe Asp Lys Leu
545                 550                 555                 560

Lys Ile Gln Pro Thr Lys Lys Thr Ser Thr Gly Glu Pro Ser Thr Arg
                565                 570                 575

Ala Asp Val Leu Glu Glu Leu Ser Glu His Pro Ile Val Arg Leu
            580                 585                 590

Ile Leu Glu Tyr Arg Lys Tyr Gln Lys Ile Lys Ser Thr Tyr Leu Asp
            595                 600                 605

Val Leu Pro Lys Leu Val His Pro Glu Thr Gly Arg Ile His Ser Ser
            610                 615                 620

Phe His Gln Thr Gly Thr Ala Thr Gly Arg Leu Ser Ser Ser Asp Pro
625                 630                 635                 640

Asn Leu Gln Asn Leu Pro Ser Lys Gln Glu Ser Arg Glu Ile Arg
                645                 650                 655

Lys Ala Val Val Pro Gln Arg Asp Ser Trp Lys Ile Leu Ser Ala Asp
                660                 665                 670

Tyr Ser Gln Ile Glu Leu Arg Val Leu Ala His Leu Ser Asn Asp Gln
            675                 680                 685

Asn Leu Ile Glu Ala Phe Lys Lys Asp Glu Asp Ile His Asn Phe Thr
            690                 695                 700

Ser Ser Arg Ile Phe Gln Val Pro Glu Asn Gln Val Thr Pro Gln Met
705                 710                 715                 720

Arg Ser Ile Gly Lys Met Val Asn Phe Ser Val Ile Tyr Gly Val Ser
                725                 730                 735

Pro Tyr Gly Leu Ser Gln Arg Thr Gly Leu Ser Tyr Asp Gln Ala Gln
            740                 745                 750

Lys Phe Ile Gly Glu Tyr Phe Ser Leu Tyr Pro Ser Val Lys Glu Tyr
            755                 760                 765

Phe Ala Lys Ile Val Ser Tyr Ala Lys Thr His Gly Tyr Val Arg Thr
            770                 775                 780

Met Phe Gly Arg Arg Glu Val Pro Gln Leu Arg Ser Lys Asn Ala
785                 790                 795                 800

Ser Val Arg Gln Glu Gly Glu Arg Ile Ala Ile Asn Thr Pro Ile Gln
                805                 810                 815

Gly Thr Ala Ala Asp Ile Met Lys Leu Ala Met Ile Asn Leu Tyr Asp
                820                 825                 830

Lys Ile Lys Gln Met Arg Leu Gln Ser Lys Met Ile Leu Gln Val His
            835                 840                 845

Asp Glu Leu Val Phe Glu Val Pro Asp Glu Val Glu Ile Val Lys
            850                 855                 860
```

Asn Leu Val Arg Asp Ser Met Glu Asn Val Val Arg Leu Ser Val Pro
865                 870                 875                 880

Leu Lys Val Asp Leu Lys Ile Ser Asp Ser Trp Glu
            885                 890

<210> SEQ ID NO 10
<211> LENGTH: 893
<212> TYPE: PRT
<213> ORGANISM: Thermotoga petrophila RKU-1

<400> SEQUENCE: 10

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ala Gly Ile Pro Thr
            20                  25                  30

Asn Ala Thr Tyr Gly Val Ala Arg Met Leu Val Arg Phe Ile Lys Asp
            35                  40                  45

His Ile Ile Val Gly Lys Asp Tyr Ala Ala Val Ala Phe Asp Lys Arg
    50                  55                  60

Ala Ala Thr Phe Arg His Lys Leu Leu Glu Thr Tyr Lys Ala Gln Arg
65                  70                  75                  80

Pro Lys Thr Pro Asp Leu Leu Ile Gln Gln Leu Pro Tyr Ile Lys Arg
                85                  90                  95

Leu Val Glu Ala Leu Gly Met Lys Val Leu Glu Ile Glu Gly Tyr Glu
            100                 105                 110

Ala Asp Asp Ile Ile Ala Thr Leu Ala Val Lys Gly Leu Ser Leu Phe
        115                 120                 125

Asp Glu Ile Phe Ile Val Thr Gly Asp Lys Asp Met Leu Gln Leu Val
    130                 135                 140

Asn Glu Lys Ile Lys Val Trp Arg Ile Val Lys Gly Ile Ser Asp Leu
145                 150                 155                 160

Glu Leu Tyr Asp Ala Gln Lys Val Lys Glu Lys Tyr Gly Val Glu Pro
                165                 170                 175

His Gln Ile Pro Asp Leu Leu Ala Leu Thr Gly Asp Glu Ile Asp Asn
            180                 185                 190

Ile Pro Gly Val Thr Gly Ile Gly Glu Lys Thr Ala Val Gln Leu Leu
        195                 200                 205

Glu Lys Tyr Arg Asp Leu Glu Asp Ile Leu Asn His Ile His Glu Leu
    210                 215                 220

Pro Gln Lys Thr Arg Lys Thr Met Leu Arg Asp Arg Glu Ser Ala Ile
225                 230                 235                 240

Leu Ser Lys Lys Leu Ala Ile Leu Glu Thr Asn Val Pro Ile Glu Ile
                245                 250                 255

Asn Trp Glu Glu Leu Arg Tyr Gln Gly His Asp Arg Glu Lys Leu Leu
            260                 265                 270

Ser Leu Leu Lys Glu Leu Glu Phe Ala Ser Ile Met Lys Glu Leu Gln
        275                 280                 285

Leu Tyr Glu Glu Ser Glu Pro Val Gly Tyr Arg Ile Val Lys Asp Pro
    290                 295                 300

Val Glu Phe Glu Lys Leu Val Glu Lys Leu Lys Glu Thr Pro Ser Phe
305                 310                 315                 320

Ala Ile Asp Leu Glu Thr Ser Ser Leu Asp Pro Phe Glu Cys Asp Ile
                325                 330                 335

Ala Gly Ile Ser Leu Ser Phe Lys Pro Lys Glu Ala Tyr Tyr Ile Pro
            340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Ile Glu Pro
385                 390                 395                 400

Val Pro Pro His Phe Asp Thr Met Ile Ala Ala Tyr Leu Ile Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Ser Pro Leu
            435                 440                 445

Phe Gly Phe Ser Phe Val Asp Val Pro Leu Glu Lys Ala Ala Asn Tyr
        450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Ser Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
            515                 520                 525

Leu Glu Glu Leu Ala Glu Glu Ile Tyr Arg Ile Ala Gly Glu Pro Phe
        530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
            595                 600                 605

Asp Ala Leu Pro Lys Met Val Asn Pro Lys Thr Gly Arg Ile His Ala
        610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
            675                 680                 685

Glu Asn Leu Leu Arg Ala Phe Glu Glu Gly Ile Asp Val His Thr Leu
        690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
            755                 760                 765

```
Tyr Ile Gln Arg Val Val Ser Glu Ala Lys Glu Lys Gly Tyr Val Arg
        770             775                 780

Thr Leu Phe Gly Arg Lys Arg Asp Ile Pro Gln Leu Met Ala Arg Asp
785             790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
                820             825                 830

Arg Glu Leu Lys Glu Arg Lys Met Arg Ser Lys Met Ile Ile Gln Val
            835                 840                 845

His Asp Glu Leu Val Phe Glu Val Pro Asn Glu Glu Lys Asp Ala Leu
850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890
```

<210> SEQ ID NO 11
<211> LENGTH: 893
<212> TYPE: PRT
<213> ORGANISM: Thermotoga maritima MSB8

<400> SEQUENCE: 11

```
Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30

Asn Ala Thr Tyr Gly Val Ala Arg Met Leu Val Arg Phe Ile Lys Asp
        35                  40                  45

His Ile Ile Val Gly Lys Asp Tyr Val Ala Val Ala Phe Asp Lys Lys
    50                  55                  60

Ala Ala Thr Phe Arg His Lys Leu Leu Glu Thr Tyr Lys Ala Gln Arg
65                  70                  75                  80

Pro Lys Thr Pro Asp Leu Leu Ile Gln Gln Leu Pro Tyr Ile Lys Lys
                85                  90                  95

Leu Val Glu Ala Leu Gly Met Lys Val Leu Glu Val Glu Gly Tyr Glu
            100                 105                 110

Ala Asp Asp Ile Ile Ala Thr Leu Ala Val Lys Gly Leu Pro Leu Phe
        115                 120                 125

Asp Glu Ile Phe Ile Val Thr Gly Asp Lys Asp Met Leu Gln Leu Val
    130                 135                 140

Asn Glu Lys Ile Lys Val Trp Arg Ile Val Lys Gly Ile Ser Asp Leu
145                 150                 155                 160

Glu Leu Tyr Asp Ala Gln Lys Val Lys Glu Lys Tyr Gly Val Glu Pro
                165                 170                 175

Gln Gln Ile Pro Asp Leu Leu Ala Leu Thr Gly Asp Glu Ile Asp Asn
            180                 185                 190

Ile Pro Gly Val Thr Gly Ile Gly Glu Lys Thr Ala Val Gln Leu Leu
        195                 200                 205

Glu Lys Tyr Lys Asp Leu Glu Asp Ile Leu Asn His Val Arg Glu Leu
    210                 215                 220

Pro Gln Lys Val Arg Lys Ala Leu Leu Arg Asp Arg Glu Asn Ala Ile
225                 230                 235                 240

Leu Ser Lys Lys Leu Ala Ile Leu Glu Thr Asn Val Pro Ile Glu Ile
                245                 250                 255
```

-continued

Asn Trp Glu Glu Leu Arg Tyr Gln Gly Tyr Asp Arg Glu Lys Leu Leu
            260                 265                 270

Pro Leu Leu Lys Glu Leu Glu Phe Ala Ser Ile Met Lys Glu Leu Gln
            275                 280                 285

Leu Tyr Glu Glu Ser Glu Pro Val Gly Tyr Arg Ile Val Lys Asp Leu
290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
            325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
            370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
            405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
            485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
            515                 520                 525

Leu Glu Glu Leu Ala Glu Glu Ile Tyr Arg Ile Ala Gly Glu Pro Phe
            530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
            565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
            595                 600                 605

Asp Ala Leu Pro Lys Met Val Asn Pro Lys Thr Gly Arg Ile His Ala
            610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
            645                 650                 655

Arg Lys Ala Ile Val Pro Gln Asp Pro Asn Trp Trp Ile Val Ser Ala
            660                 665                 670

-continued

```
Asp Tyr Ser Gln Ile Glu Leu Arg Ile Leu Ala His Leu Ser Gly Asp
            675                 680                 685

Glu Asn Leu Leu Arg Ala Phe Glu Gly Ile Asp Val His Thr Leu
690                 695                 700

Thr Ala Ser Arg Ile Phe Asn Val Lys Pro Glu Val Thr Glu Glu
705                 710                 715                 720

Met Arg Arg Ala Gly Lys Met Val Asn Phe Ser Ile Tyr Gly Val
                725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
            755                 760                 765

Tyr Ile Gln Arg Val Val Ser Glu Ala Lys Glu Lys Gly Tyr Val Arg
            770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
            835                 840                 845

His Asp Glu Leu Val Phe Glu Val Pro Asn Glu Glu Lys Asp Ala Leu
850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890

<210> SEQ ID NO 12
<211> LENGTH: 890
<212> TYPE: PRT
<213> ORGANISM: Thermosipho melanesiensis BI429

<400> SEQUENCE: 12

Met Arg Glu Leu Phe Leu Phe Asp Gly Thr Gly Leu Val Tyr Arg Ala
1               5                   10                  15

Phe Tyr Ala Ile Asp Gln Phe Leu Lys Thr Ser Thr Gly Met His Thr
                20                  25                  30

Asn Ala Leu Tyr Gly Ile Ala Lys Met Leu Ile Lys Phe Leu Lys Glu
            35                  40                  45

His Val Asn Met Glu Lys Asp Ala Cys Ala Phe Ile Leu Asp Ser Lys
50                  55                  60

Gly Gly Ser Lys Lys Arg Lys Glu Ile Leu Lys Asp Tyr Lys Ser Asn
65                  70                  75                  80

Arg Pro Glu Thr Pro Asp Leu Ile Leu Glu Gln Leu Pro Tyr Ile Glu
                85                  90                  95

Glu Phe Val Asp Ala Phe Gly Val Lys Val Leu Lys Leu Leu Gly Tyr
            100                 105                 110

Glu Ala Asp Asp Ile Ile Ala Thr Ile Ala Lys Arg Phe Cys Asn Ala
            115                 120                 125

Phe Glu Lys Val Asn Ile Ile Thr Gly Asp Lys Asp Leu Leu Gln Leu
            130                 135                 140

Val Asp Glu Lys Val Tyr Val Trp Arg Ile Glu Arg Gly Ile Thr Glu
145                 150                 155                 160
```

```
Leu Val Leu Tyr Asp Arg Lys Val Phe Glu Lys Tyr Gly Val Phe
            165                 170                 175

Pro Glu Gln Phe Gly Asp Tyr Leu Ser Leu Val Gly Asp Gln Ile Asp
            180                 185                 190

Asn Ile Pro Gly Val Lys Gly Ile Gly Lys Lys Thr Ala Val Ser Leu
            195                 200                 205

Leu Lys Lys Tyr Gly Thr Ile Asp Glu Val Leu Lys Asn Lys Lys Leu
            210                 215                 220

Leu Thr Glu Lys Leu Gln Lys Leu Leu Glu Asn Ala Thr Glu Ser Leu
225                 230                 235                 240

Glu Lys Ser Arg Gln Leu Val Gln Leu Ile Tyr Asp Val Pro Leu Asp
                245                 250                 255

Val Asn Ile Glu Asp Leu Ile Tyr Lys Gly Tyr Asp Ser Lys Lys Leu
                260                 265                 270

Leu Val Val Leu Lys Lys Tyr Glu Phe Ser Ile Ile Lys Glu Leu
            275                 280                 285

Gly Leu Lys Glu Glu Phe Glu Lys Lys Tyr Thr Ile Val Asn Ser Glu
            290                 295                 300

Lys Glu Leu Ser Lys Leu Arg Lys Arg Ile Asp Glu Val Lys Thr Phe
305                 310                 315                 320

Ser Ile Asp Thr Glu Thr Thr Ser Leu Asp Pro Phe Ser Ala Lys Leu
                325                 330                 335

Val Gly Val Ser Ile Ser Thr Asn Glu Gly Glu Ala Tyr Tyr Ile Pro
                340                 345                 350

Ile Ser His Val Ser Glu Asn Asn Leu Thr Lys Glu Ile Val Leu Lys
                355                 360                 365

Phe Leu Lys Glu Ile Leu Glu Cys Glu Arg Tyr Asn Ile Val Gly Gln
370                 375                 380

Asn Leu Lys Phe Asp Tyr Lys Val Phe Met Val Asn Gly Ile Glu Pro
385                 390                 395                 400

Gln Ile Pro His Phe Asp Thr Met Val Ala Ala Tyr Leu Ile Asn Pro
                405                 410                 415

Glu Glu Arg Arg Tyr Asn Leu Glu Glu Leu Ala Leu Lys Tyr Leu Gly
                420                 425                 430

Tyr Lys Met Ile Ser Phe Glu Glu Leu Val Asp Asn Asn Met Pro Leu
            435                 440                 445

Phe Gly Asn Asp Phe Ser Phe Ile Ser Ile Glu Lys Ala Ala Glu Tyr
450                 455                 460

Ser Cys Glu Asp Val Asp Ile Thr Phe Arg Leu Tyr Ser Tyr Leu Ser
465                 470                 475                 480

Lys Tyr Ile Gly Glu Met Lys Glu Leu Phe Tyr Asn Ile Glu Met Pro
            485                 490                 495

Leu Ile Asn Val Leu Ala Gln Met Glu Leu Asn Gly Val Tyr Phe Asp
            500                 505                 510

Val Asp Tyr Leu Lys Glu Leu Ser Lys Arg Tyr Glu Glu Met Lys
            515                 520                 525

Lys Leu Glu Glu Lys Ile Phe Glu Ile Ser Gly Glu Gln Phe Asn Ile
530                 535                 540

Asn Ser Ser Lys Gln Val Ala Glu Ile Leu Phe Glu Lys Leu Lys Leu
545                 550                 555                 560

Pro Ile Val Lys Lys Thr Ala Thr Gly Arg Asn Ser Thr Asn Ala Glu
                565                 570                 575
```

```
Val Leu Glu Glu Leu Ala Lys Asp Tyr Glu Ile Ala Arg Leu Ile Leu
            580                 585                 590

Glu Tyr Arg Lys Phe Gln Lys Leu Lys Ser Thr Tyr Val Asp Ser Ile
        595                 600                 605

Pro Ser Ser Val Asn Ile Thr Thr Asn Arg Val His Ser Ser Phe His
    610                 615                 620

Gln Thr Gly Thr Ser Thr Gly Arg Leu Ser Ser Ser Ala Pro Asn Leu
625                 630                 635                 640

Gln Asn Leu Pro Thr Arg Ser Glu Glu Gly Lys Glu Ile Arg His Ala
            645                 650                 655

Val Lys Pro Gln Phe Glu Asn Trp Tyr Ile Val Gly Ala Asp Tyr Ser
            660                 665                 670

Gln Ile Glu Leu Arg Val Leu Ala His Met Ser Glu Asp Glu Lys Leu
        675                 680                 685

Leu Asp Ala Phe Glu Asn Asp Tyr Asp Ile His Thr Ile Thr Ala Ser
690                 695                 700

Lys Ile Phe Asn Val Ser Glu Leu Met Val Thr Glu Asp Met Arg Arg
705                 710                 715                 720

Ile Gly Lys Met Ile Asn Phe Ala Ile Ile Tyr Gly Ile Ser Pro Tyr
                725                 730                 735

Gly Leu Ser Arg Arg Ile Gly Leu Asn Val Asn Glu Thr Lys Lys Ile
            740                 745                 750

Ile Asp Asn Tyr Phe Lys Tyr Tyr Gln Gly Val Phe Glu Phe Ile Lys
        755                 760                 765

Lys Thr Ile Asp Phe Ala Lys Lys Asn Gly Phe Val Lys Thr Leu Phe
    770                 775                 780

Gly Arg Lys Arg Phe Ile Pro Gln Leu Lys Leu Lys Asn Lys Asn Leu
785                 790                 795                 800

Ile Gln Glu Gly Glu Arg Ile Ala Ile Asn Thr Pro Val Gln Gly Thr
                805                 810                 815

Ala Ala Asp Ile Ile Lys Ile Ala Met Val Lys Val His Asn Glu Leu
            820                 825                 830

Lys Arg Asn Ser Leu Lys Thr Lys Leu Ile Leu Gln Val His Asp Glu
        835                 840                 845

Leu Val Phe Glu Val Pro Phe Asp Glu Leu Gln Ile Val Lys Glu Ile
    850                 855                 860

Ile Lys Asp Lys Met Glu Asn Ala Val Lys Leu Lys Val Pro Leu Lys
865                 870                 875                 880

Val Asp Leu Tyr Glu Gly Arg Glu Trp Glu
                885                 890

<210> SEQ ID NO 13
<211> LENGTH: 876
<212> TYPE: PRT
<213> ORGANISM: Geobacillus sp. MKK-2005

<400> SEQUENCE: 13

Met Lys Asn Lys Leu Val Leu Ile Asp Gly Asn Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Arg Pro Thr His Leu Leu Val Ala Phe Asp Ala Gly Lys Thr Thr
    50                  55                  60
```

-continued

```
Phe Arg His Glu Thr Phe Gln Glu Tyr Lys Gly Arg Gln Gln Thr
 65                  70                  75                  80

Pro Pro Glu Leu Ser Glu Gln Phe Pro Leu Arg Glu Leu Leu Asn
                 85                  90                  95

Ala Tyr Arg Ile Pro Ala Tyr Glu Leu Asp Arg Tyr Glu Ala Asp
            100                 105                 110

Ile Ile Gly Thr Leu Ala Ala Arg Ala Glu Gln Glu Gly Phe Glu Val
            115                 120                 125

Lys Val Ile Ser Gly Asp Arg Asp Leu Thr Gln Leu Ala Ser Pro His
130                 135                 140

Val Thr Val Asp Ile Thr Lys Lys Gly Ile Thr Asp Ile Glu Pro Tyr
145                 150                 155                 160

Thr Pro Glu Thr Val Glu Glu Lys Tyr Gly Leu Thr Pro Glu Gln Met
                165                 170                 175

Val Asp Leu Lys Gly Leu Met Gly Asp Lys Ser Asp Asn Ile Pro Gly
                180                 185                 190

Val Pro Gly Ile Gly Glu Lys Thr Ala Val Lys Leu Leu Lys Gln Phe
            195                 200                 205

Gly Thr Val Glu Asn Val Leu Ala Ser Ile Asp Glu Ile Lys Gly Glu
210                 215                 220

Lys Leu Lys Glu Asn Leu Arg Gln Tyr Arg Asp Leu Ala Leu Leu Ser
225                 230                 235                 240

Lys Gln Leu Ala Ala Ile Arg Arg Asp Ala Pro Val Glu Leu Ser Leu
                245                 250                 255

Asp Asp Ile Ile Tyr Glu Gly Gln Asp Arg Glu Lys Val Ile Ala Leu
            260                 265                 270

Phe Lys Glu Leu Gly Phe Gln Ser Phe Leu Glu Lys Met Asp Ala Pro
            275                 280                 285

Thr Ala Glu Asp Glu Thr Pro Leu Met Glu Met Glu Phe Val Ile Ala
290                 295                 300

Asp Gly Ile Thr Asp Glu Met Leu Ala Asp Lys Ala Ala Leu Val Val
305                 310                 315                 320

Glu Val Met Glu Glu Asn Tyr His Asp Ala Pro Ile Val Gly Ile Ala
                325                 330                 335

Leu Val Asn Glu His Gly Arg Phe Phe Leu Arg Ala Glu Met Ala Leu
                340                 345                 350

Ala Asp Ser Gln Phe Leu Ala Trp Leu Ala Asp Glu Thr Lys Lys Lys
            355                 360                 365

Ser Met Phe Asp Ala Lys Arg Ala Ala Val Ala Leu Lys Trp Lys Gly
            370                 375                 380

Ile Glu Leu Arg Gly Val Ala Phe Asp Leu Leu Leu Ala Ala Tyr Leu
385                 390                 395                 400

Leu Asn Pro Ala Gln Asp Ala Gly Asp Val Ala Ala Val Ala Lys Met
                405                 410                 415

Lys Gln Tyr Glu Ala Val Arg Pro Asp Glu Ala Val Tyr Gly Lys Gly
            420                 425                 430

Ala Lys Arg Ser Leu Pro Asp Glu Pro Thr Leu Ala Glu His Leu Val
            435                 440                 445

Arg Lys Ala Ala Ala Ile Trp Ala Leu Glu Arg Pro Phe Leu Asp Glu
            450                 455                 460

Leu Arg Ser Asn Glu Gln Asp Gly Leu Leu Ile Lys Leu Glu Gln Pro
465                 470                 475                 480
```

```
Leu Ala Thr Ile Leu Ala Glu Met Glu Phe Thr Gly Ile Lys Val Asp
                485                 490                 495
Thr Lys Arg Leu Glu Gln Met Gly Ser Glu Leu Ala Glu Gln Leu Arg
            500                 505                 510
Ala Val Glu Gln Arg Ile Tyr Glu Leu Ala Gly Gln Glu Phe Asn Ile
        515                 520                 525
Asn Ser Pro Lys Gln Leu Gly Ile Ile Leu Phe Glu Lys Leu Gln Leu
    530                 535                 540
Pro Val Leu Lys Lys Thr Lys Thr Gly Tyr Ser Thr Ser Ala Asp Val
545                 550                 555                 560
Leu Glu Lys Leu Ala Pro His His Glu Ile Val Glu Asn Ile Leu His
                565                 570                 575
Tyr Arg Gln Leu Gly Lys Leu Gln Ser Thr Tyr Ile Glu Gly Leu Leu
            580                 585                 590
Lys Val Val His Pro Asp Thr Gly Lys Val His Thr Met Phe Asn Gln
        595                 600                 605
Ala Leu Thr Gln Thr Gly Arg Leu Ser Ser Ala Glu Pro Asn Leu Gln
    610                 615                 620
Asn Ile Pro Ile Arg Leu Glu Glu Gly Arg Lys Ile Arg Gln Ala Phe
625                 630                 635                 640
Val Pro Ser Glu Pro Asp Trp Leu Ile Phe Ala Ala Asp Tyr Ser Gln
                645                 650                 655
Ile Glu Leu Arg Val Leu Ala His Ile Ala Asp Asp Asn Leu Ile
            660                 665                 670
Glu Ala Phe Arg Arg Asp Leu Asp Ile His Thr Lys Thr Ala Met Asp
        675                 680                 685
Ile Phe His Val Ser Glu Glu Val Thr Ala Thr Met Arg Arg Gln
    690                 695                 700
Ala Lys Ala Val Asn Phe Gly Ile Val Tyr Gly Ile Ser Asp Tyr Gly
705                 710                 715                 720
Leu Ala Gln Asn Leu Asn Ile Thr Arg Lys Glu Ala Ala Glu Phe Ile
                725                 730                 735
Glu Arg Tyr Phe Ala Ser Phe Pro Gly Val Lys Arg Tyr Met Glu Thr
            740                 745                 750
Ile Val Gln Glu Ala Lys Gln Lys Gly Tyr Val Thr Thr Leu Leu His
        755                 760                 765
Arg Arg Arg Tyr Leu Pro Asp Ile Thr Ser Arg Asn Phe Asn Val Arg
    770                 775                 780
Ser Phe Ala Glu Arg Thr Ala Met Asn Thr Pro Ile Gln Gly Ser Ala
785                 790                 795                 800
Ala Asp Ile Ile Lys Lys Ala Met Ile Asp Leu Ala Ala Arg Leu Lys
                805                 810                 815
Glu Glu Arg Leu Gln Ala Arg Leu Leu Leu Gln Val His Asp Glu Leu
            820                 825                 830
Ile Leu Glu Ala Pro Lys Glu Glu Met Glu Arg Leu Cys Gln Leu Val
        835                 840                 845
Pro Glu Val Met Glu Gln Ala Val Ala Leu Arg Val Pro Leu Lys Val
    850                 855                 860
Asp Tyr His Tyr Gly Pro Thr Trp Tyr Asp Ala Lys
865                 870                 875

<210> SEQ ID NO 14
<211> LENGTH: 877
<212> TYPE: PRT
```

<213> ORGANISM: Bacillus caldotenax

<400> SEQUENCE: 14

```
Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Glu Pro Thr His Met Leu Val Ala Phe Asp Ala Gly Lys Thr Thr
    50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
                85                  90                  95

Ala Tyr Arg Ile Pro Ala Tyr Glu Leu Glu Asn Tyr Glu Ala Asp Asp
            100                 105                 110

Ile Ile Gly Thr Leu Ala Ala Arg Ala Glu Gln Glu Gly Phe Glu Val
        115                 120                 125

Lys Val Ile Ser Gly Asp Arg Asp Leu Thr Gln Leu Ala Ser Pro His
130                 135                 140

Val Thr Val Asp Ile Thr Lys Lys Gly Ile Thr Asp Ile Glu Pro Tyr
145                 150                 155                 160

Thr Pro Glu Ala Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Arg Gln Phe
        195                 200                 205

Gly Thr Val Glu Asn Val Leu Ala Ser Ile Asp Glu Ile Lys Gly Glu
210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                245                 250                 255

Asp Asp Ile Ala Tyr Gln Gly Glu Asp Arg Glu Lys Val Val Ala Leu
            260                 265                 270

Phe Lys Glu Leu Gly Phe Gln Ser Phe Leu Glu Lys Met Glu Ser Pro
        275                 280                 285

Ser Ser Glu Glu Glu Lys Pro Leu Ala Lys Met Ala Phe Thr Leu Ala
290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                325                 330                 335

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
        355                 360                 365

Ser Met Phe Asp Ser Lys Arg Ala Ala Val Ala Leu Lys Trp Lys Gly
370                 375                 380

Ile Glu Leu Cys Gly Val Ser Phe Asp Leu Leu Leu Ala Ala Tyr Leu
385                 390                 395                 400
```

-continued

```
Leu Asp Pro Ala Gln Gly Val Asp Val Ala Ala Ala Lys Met
            405                 410                 415

Lys Gln Tyr Glu Ala Val Arg Pro Asp Glu Ala Val Tyr Gly Lys Gly
        420                 425                 430

Ala Lys Arg Ala Val Pro Asp Glu Pro Val Leu Ala Glu His Leu Val
        435                 440                 445

Arg Lys Ala Ala Ala Ile Trp Ala Leu Glu Arg Pro Phe Leu Asp Glu
    450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
            485                 490                 495

Thr Lys Arg Leu Glu Gln Met Gly Glu Glu Leu Ala Glu Gln Leu Arg
            500                 505                 510

Thr Val Glu Gln Arg Ile Tyr Glu Leu Ala Gly Gln Glu Phe Asn Ile
        515                 520                 525

Asn Ser Pro Lys Gln Leu Gly Val Ile Leu Phe Glu Lys Leu Gln Leu
    530                 535                 540

Pro Val Leu Lys Lys Ser Lys Thr Gly Tyr Ser Thr Ser Ala Asp Val
545                 550                 555                 560

Leu Glu Lys Leu Ala Pro Tyr His Glu Ile Val Glu Asn Ile Leu Gln
            565                 570                 575

His Tyr Arg Gln Leu Gly Lys Leu Gln Ser Thr Tyr Ile Glu Gly Leu
            580                 585                 590

Leu Lys Val Val Arg Pro Asp Thr Lys Lys Val His Thr Ile Phe Asn
        595                 600                 605

Gln Ala Leu Thr Gln Thr Gly Arg Leu Ser Ser Thr Glu Pro Asn Leu
    610                 615                 620

Gln Asn Ile Pro Ile Arg Leu Glu Glu Gly Arg Lys Ile Arg Gln Ala
625                 630                 635                 640

Phe Val Pro Ser Glu Ser Asp Trp Leu Ile Phe Ala Ala Asp Tyr Ser
            645                 650                 655

Gln Ile Glu Leu Arg Val Leu Ala His Ile Ala Glu Asp Asp Asn Leu
            660                 665                 670

Met Glu Ala Phe Arg Arg Asp Leu Asp Ile His Thr Lys Thr Ala Met
        675                 680                 685

Asp Ile Phe Gln Val Ser Glu Asp Glu Val Thr Pro Asn Met Arg Arg
    690                 695                 700

Gln Ala Lys Ala Val Asn Phe Gly Ile Val Tyr Gly Ile Ser Asp Tyr
705                 710                 715                 720

Gly Leu Ala Gln Asn Leu Asn Ile Ser Arg Lys Glu Ala Ala Glu Phe
            725                 730                 735

Ile Glu Arg Tyr Phe Glu Ser Phe Pro Gly Val Lys Arg Tyr Met Glu
            740                 745                 750

Asn Ile Val Gln Glu Ala Lys Gln Lys Gly Tyr Val Thr Thr Leu Leu
        755                 760                 765

His Arg Arg Arg Tyr Leu Pro Asp Ile Thr Ser Arg Asn Phe Asn Val
    770                 775                 780

Arg Ser Phe Ala Glu Arg Met Ala Met Asn Thr Pro Ile Gln Gly Ser
785                 790                 795                 800

Ala Ala Asp Ile Ile Lys Lys Ala Met Ile Asp Leu Asn Ala Arg Leu
            805                 810                 815

Lys Glu Glu Arg Leu Gln Ala Arg Leu Leu Leu Gln Val His Asp Glu
```

```
                     820                 825                 830
Leu Ile Leu Glu Ala Pro Lys Glu Glu Met Glu Arg Leu Cys Arg Leu
            835                 840                 845

Val Pro Glu Val Met Glu Gln Ala Val Thr Leu Arg Val Pro Leu Lys
    850                 855                 860

Val Asp Tyr His Tyr Gly Ser Thr Trp Tyr Asp Ala Lys
865                 870                 875

<210> SEQ ID NO 15
<211> LENGTH: 872
<212> TYPE: PRT
<213> ORGANISM: Bacillus caldontenax

<400> SEQUENCE: 15

Met Tyr Lys Phe Leu Ile Ile Asp Gly Ser Ser Leu Met Tyr Arg Ala
1               5                   10                  15

Tyr Tyr Ala Leu Pro Met Leu Thr Thr Ser Glu Gly Leu Pro Thr Asn
            20                  25                  30

Ala Leu Tyr Gly Phe Thr Met Met Leu Ile Lys Leu Ile Glu Glu Glu
        35                  40                  45

Lys Pro Asp Tyr Ile Ala Ile Ala Phe Asp Lys Lys Ala Pro Thr Phe
50                  55                  60

Arg His Lys Glu Tyr Gln Asp Tyr Lys Ala Thr Arg Gln Ala Met Pro
65                  70                  75                  80

Glu Glu Leu Ala Glu Gln Val Asp Tyr Leu Lys Glu Ile Ile Asp Gly
            85                  90                  95

Phe Asn Ile Lys Thr Leu Glu Leu Glu Gly Tyr Glu Ala Asp Asp Ile
        100                 105                 110

Ile Gly Thr Ile Ser Lys Leu Ala Glu Glu Lys Gly Met Glu Val Leu
    115                 120                 125

Val Val Thr Gly Asp Arg Asp Ala Leu Gln Leu Val Ser Asp Lys Val
130                 135                 140

Lys Ile Lys Ile Ser Lys Lys Gly Ile Thr Gln Met Glu Glu Phe Asp
145                 150                 155                 160

Glu Lys Ala Ile Leu Glu Arg Tyr Gly Ile Thr Pro Gln Gln Phe Ile
            165                 170                 175

Asp Leu Lys Gly Leu Met Gly Asp Lys Ser Asp Asn Ile Pro Gly Val
        180                 185                 190

Pro Asn Ile Gly Glu Lys Thr Ala Ile Lys Leu Leu Lys Asp Phe Gly
    195                 200                 205

Thr Ile Glu Asn Leu Ile Gln Asn Leu Ser Gln Leu Lys Gly Lys Ile
210                 215                 220

Lys Glu Asn Ile Glu Asn Asn Lys Glu Leu Ala Ile Met Ser Lys Arg
225                 230                 235                 240

Leu Ala Thr Ile Lys Arg Asp Ile Pro Ile Glu Ile Asp Phe Glu Glu
            245                 250                 255

Tyr Lys Val Lys Lys Phe Asn Glu Glu Lys Leu Leu Glu Leu Phe Asn
        260                 265                 270

Lys Leu Glu Phe Phe Ser Leu Ile Asp Asn Ile Lys Lys Glu Ser Ser
    275                 280                 285

Ile Glu Ile Val Asp Asn His Lys Val Glu Lys Trp Ser Lys Val Asp
290                 295                 300

Ile Lys Glu Leu Val Thr Leu Leu Gln Asp Asn Arg Asn Ile Ala Phe
305                 310                 315                 320
```

-continued

```
Tyr Pro Leu Ile Tyr Glu Gly Glu Ile Lys Lys Ile Ala Phe Ser Phe
                325                 330                 335

Gly Lys Asp Thr Val Tyr Ile Asp Val Phe Gln Thr Glu Asp Leu Lys
            340                 345                 350

Glu Ile Phe Glu Lys Glu Asp Phe Glu Phe Thr Thr His Glu Ile Lys
        355                 360                 365

Asp Phe Leu Val Arg Leu Ser Tyr Lys Gly Ile Glu Cys Lys Ser Lys
    370                 375                 380

Tyr Ile Asp Thr Ala Val Met Ala Tyr Leu Leu Asn Pro Ser Glu Ser
385                 390                 395                 400

Asn Tyr Asp Leu Asp Arg Val Leu Lys Lys Tyr Leu Lys Val Asp Val
                405                 410                 415

Pro Ser Tyr Glu Gly Ile Phe Gly Lys Gly Arg Asp Lys Lys Lys Ile
            420                 425                 430

Glu Glu Ile Asp Glu Asn Ile Leu Ala Asp Tyr Ile Cys Ser Arg Cys
        435                 440                 445

Val Tyr Leu Phe Asp Leu Lys Lys Leu Met Asn Phe Ile Glu Glu
    450                 455                 460

Met Asp Met Lys Lys Leu Leu Leu Glu Ile Glu Met Pro Leu Val Glu
465                 470                 475                 480

Val Leu Lys Ser Met Glu Val Ser Gly Phe Thr Leu Asp Lys Glu Val
                485                 490                 495

Leu Lys Glu Leu Ser Gln Lys Ile Asp Asp Arg Ile Gly Glu Ile Leu
            500                 505                 510

Asp Lys Ile Tyr Lys Glu Ala Gly Tyr Gln Phe Asn Val Asn Ser Pro
        515                 520                 525

Lys Gln Leu Ser Glu Phe Leu Phe Glu Lys Leu Asn Leu Pro Val Ile
    530                 535                 540

Lys Lys Thr Lys Thr Gly Tyr Ser Thr Asp Ser Glu Val Leu Glu Gln
545                 550                 555                 560

Leu Val Pro Tyr Asn Asp Ile Val Ser Asp Ile Ile Glu Tyr Arg Gln
                565                 570                 575

Leu Thr Lys Leu Lys Ser Thr Tyr Ile Asp Gly Phe Leu Pro Leu Met
            580                 585                 590

Asp Glu Asn Asn Arg Val His Ser Asn Phe Lys Gln Met Val Thr Ala
        595                 600                 605

Thr Gly Arg Ile Ser Ser Thr Glu Pro Asn Leu Gln Asn Ile Pro Ile
    610                 615                 620

Arg Glu Glu Phe Gly Arg Gln Ile Arg Arg Ala Phe Ile Pro Arg Ser
625                 630                 635                 640

Arg Asp Gly Tyr Ile Val Ser Ala Asp Tyr Ser Gln Ile Glu Leu Arg
                645                 650                 655

Val Leu Ala His Val Ser Gly Asp Glu Lys Leu Ile Glu Ser Phe Met
            660                 665                 670

Asn Asn Glu Asp Ile His Leu Arg Thr Ala Ser Glu Val Phe Lys Val
        675                 680                 685

Pro Met Glu Lys Val Thr Pro Glu Met Arg Arg Ala Ala Lys Ala Val
    690                 695                 700

Asn Phe Gly Ile Ile Tyr Gly Ile Ser Asp Tyr Gly Leu Ser Arg Asp
705                 710                 715                 720

Leu Lys Ile Ser Arg Lys Glu Ala Lys Glu Tyr Ile Asn Asn Tyr Phe
                725                 730                 735

Glu Arg Tyr Lys Gly Val Lys Asp Tyr Ile Glu Lys Ile Val Arg Phe
```

```
            740                 745                 750
Ala Lys Glu Asn Gly Tyr Val Thr Thr Ile Met Asn Arg Arg Arg Tyr
                755                 760                 765

Ile Pro Glu Ile Asn Ser Arg Asn Phe Thr Gln Arg Ser Gln Ala Glu
            770                 775                 780

Arg Leu Ala Met Asn Ala Pro Ile Gln Gly Ser Ala Ala Asp Ile Ile
785                 790                 795                 800

Lys Met Ala Met Val Lys Val Tyr Asn Asp Leu Lys Lys Leu Lys Leu
                805                 810                 815

Lys Ser Lys Leu Ile Leu Gln Val His Asp Glu Leu Val Val Asp Thr
                820                 825                 830

Tyr Lys Asp Glu Val Asp Ile Ile Lys Lys Ile Leu Lys Glu Asn Met
                835                 840                 845

Glu Asn Val Val Gln Leu Lys Val Pro Leu Val Val Glu Ile Gly Val
                850                 855                 860

Gly Pro Asn Trp Phe Leu Ala Lys
865                 870

<210> SEQ ID NO 16
<211> LENGTH: 872
<212> TYPE: PRT
<213> ORGANISM: Thermoanaerobacter pseudethanolicus ATCC 33223

<400> SEQUENCE: 16

Met Ser Lys Phe Leu Val Ile Asp Gly Ser Ser Leu Met Tyr Arg Ala
1               5                   10                  15

Tyr Tyr Ala Leu Pro Met Leu Thr Thr Ser Glu Gly Leu His Thr Asn
            20                  25                  30

Ala Leu Tyr Gly Phe Thr Met Met Leu Ile Lys Leu Ile Glu Glu Glu
        35                  40                  45

Lys Pro Asp Tyr Ile Ala Ile Ala Phe Asp Lys Lys Ala Pro Thr Phe
    50                  55                  60

Arg His Lys Glu Tyr Gln Asp Tyr Lys Ala Thr Arg Gln Ala Met Pro
65                  70                  75                  80

Glu Glu Leu Ala Glu Gln Val Asp Leu Leu Lys Glu Ile Ile Glu Gly
                85                  90                  95

Phe Asn Ile Lys Ile Leu Glu Leu Glu Gly Tyr Glu Ala Asp Asp Ile
            100                 105                 110

Ile Gly Thr Ile Ser Lys Leu Ala Glu Glu Lys Glu Met Glu Val Leu
        115                 120                 125

Val Val Thr Gly Asp Arg Asp Ala Leu Gln Leu Val Ser Asp Lys Val
    130                 135                 140

Lys Val Lys Ile Ser Lys Lys Gly Ile Thr Gln Met Glu Glu Phe Asp
145                 150                 155                 160

Glu Lys Ala Val Leu Glu Arg Tyr Glu Ile Thr Pro His Gln Phe Ile
                165                 170                 175

Asp Leu Lys Gly Leu Met Gly Asp Lys Ser Asp Asn Ile Pro Gly Ile
            180                 185                 190

Pro Asn Ile Gly Glu Lys Thr Ala Ile Lys Leu Leu Lys Asp Phe Gly
        195                 200                 205

Thr Ile Glu Asn Leu Leu Gln Asn Leu Ser Gln Leu Lys Gly Lys Ile
    210                 215                 220

Lys Glu Asn Ile Glu Asn Asn Lys Glu Leu Ala Ile Met Ser Lys Lys
225                 230                 235                 240
```

```
Leu Ala Thr Ile Lys Arg Asp Ile Pro Ile Glu Ile Asp Phe Glu Glu
                    245                 250                 255
Tyr Arg Val Lys Asp Phe Asn Glu Glu Lys Leu Leu Glu Leu Phe Asn
                260                 265                 270
Lys Leu Glu Phe Phe Ser Leu Ile Asp Ser Ile Lys Lys Lys Asn Asn
            275                 280                 285
Val Glu Ile Val Asn Asn His Lys Val Gln Lys Trp Ser Lys Val Asp
        290                 295                 300
Ile Lys Lys Leu Ile Ala Leu Leu Gln Asp Ser Lys Ser Ile Ala Phe
305                 310                 315                 320
Tyr Pro Leu Ile Tyr Glu Gly Glu Ile Lys Lys Ile Ala Phe Ser Phe
                325                 330                 335
Gly Asn Asp Thr Val Tyr Ile Asp Gly Phe Gln Ile Lys Asp Leu Lys
                340                 345                 350
Glu Ile Phe Glu Lys Glu Lys Phe Glu Phe Thr Thr His Glu Ile Lys
            355                 360                 365
Asp Phe Leu Val Lys Leu Ser Tyr Lys Gly Ile Glu Cys Lys Ser Lys
        370                 375                 380
Tyr Met Asp Thr Ala Ile Met Ala Tyr Leu Leu Asn Pro Ser Glu Ser
385                 390                 395                 400
Asn Tyr Asp Leu Asp Arg Val Leu Lys Lys Tyr Leu Lys Val Asp Val
                405                 410                 415
Pro Ser Tyr Glu Glu Val Phe Gly Lys Gly Arg Asp Lys Lys Lys Leu
                420                 425                 430
Glu Glu Ile Gly Glu Asp Ile Leu Ala Asp Tyr Ile Cys Ser Arg Cys
            435                 440                 445
Val His Leu Phe Asp Leu Arg Glu Lys Leu Met Asn Phe Ile Glu Glu
        450                 455                 460
Met Asp Met Lys Arg Leu Leu Glu Ile Glu Met Pro Leu Val Glu
465                 470                 475                 480
Val Leu Lys Ser Met Glu Val Ser Gly Phe Thr Leu Asp Lys Glu Val
                485                 490                 495
Leu Lys Glu Leu Ser Gln Lys Ile Asn Asp Arg Ile Ala Glu Ile Leu
                500                 505                 510
Asp Lys Ile Tyr Lys Glu Ala Gly Tyr Gln Phe Asn Val Asn Ser Pro
            515                 520                 525
Lys Gln Leu Ser Glu Phe Leu Phe Glu Lys Leu Asn Leu Pro Val Ile
        530                 535                 540
Lys Lys Thr Lys Thr Gly Tyr Ser Thr Asp Ser Glu Val Leu Glu Gln
545                 550                 555                 560
Leu Val Pro Tyr Asn Asn Ile Val Asn Asp Ile Ile Glu Tyr Arg Gln
                565                 570                 575
Leu Thr Lys Leu Lys Ser Thr Tyr Ile Asn Gly Phe Leu Pro Leu Met
                580                 585                 590
Asp Glu Asn Asn Arg Val His Ser Asn Phe Lys Gln Met Val Thr Ser
            595                 600                 605
Thr Gly Arg Ile Ser Ser Thr Glu Pro Asn Leu Gln Asn Ile Pro Ile
        610                 615                 620
Arg Glu Glu Phe Gly Arg Gln Ile Arg Arg Ala Phe Ile Pro Arg Thr
625                 630                 635                 640
Lys Asp Gly Tyr Ile Val Ser Ala Asp Tyr Ser Gln Ile Glu Leu Arg
                645                 650                 655
Val Leu Ala His Val Ser Gly Asp Glu Lys Leu Ile Glu Ser Phe Met
```

-continued

```
                660                 665                 670
Asn Asn Glu Asp Ile His Leu Arg Thr Ala Ser Glu Val Phe Lys Val
            675                 680                 685

Pro Met Glu Lys Val Thr Pro Glu Met Arg Arg Ala Ala Lys Ala Val
            690                 695                 700

Asn Phe Gly Ile Ile Tyr Gly Ile Ser Asp Tyr Gly Leu Ser Arg Asp
705                 710                 715                 720

Leu Lys Ile Ser Arg Lys Glu Ala Lys Glu Tyr Ile Asn Asn Tyr Phe
            725                 730                 735

Glu Arg Tyr Lys Gly Val Lys Glu Tyr Ile Glu Lys Ile Val Arg Phe
            740                 745                 750

Ala Lys Glu Asn Gly Tyr Val Ile Thr Ile Met Asn Arg Arg Arg Tyr
            755                 760                 765

Ile Pro Glu Ile Asn Ser Arg Asn Phe Thr Gln Arg Ser Gln Ala Glu
            770                 775                 780

Arg Leu Ala Met Asn Ala Pro Ile Gln Gly Ser Ala Ala Asp Ile Ile
785                 790                 795                 800

Lys Met Ala Met Val Arg Val Tyr Asn Asp Leu Glu Lys Leu Lys Leu
            805                 810                 815

Lys Ser Lys Leu Ile Leu Gln Val His Asp Glu Leu Val Val Asp Thr
            820                 825                 830

Tyr Lys Asp Glu Val Glu Ile Val Lys Lys Ile Leu Lys Asp Asn Met
            835                 840                 845

Glu Asn Val Val Gln Leu Lys Val Pro Leu Val Val Glu Ile Gly Val
            850                 855                 860

Gly Pro Asn Trp Phe Leu Ala Lys
865                 870

<210> SEQ ID NO 17
<211> LENGTH: 855
<212> TYPE: PRT
<213> ORGANISM: Enterobacteria phage T5

<400> SEQUENCE: 17

Met Lys Ile Ala Val Val Asp Lys Ala Leu Asn Asn Thr Arg Tyr Asp
1               5                   10                  15

Lys His Phe Gln Leu Tyr Gly Glu Glu Val Asp Val Phe His Met Cys
            20                  25                  30

Asn Glu Lys Leu Ser Gly Arg Leu Leu Lys Lys His Ile Thr Ile Gly
            35                  40                  45

Thr Pro Glu Asn Pro Phe Asp Pro Asn Asp Tyr Asp Phe Val Ile Leu
        50                  55                  60

Val Gly Ala Glu Pro Phe Leu Tyr Phe Ala Gly Lys Lys Gly Ile Gly
65                  70                  75                  80

Asp Tyr Thr Gly Lys Arg Val Glu Tyr Asn Gly Tyr Ala Asn Trp Ile
            85                  90                  95

Ala Ser Ile Ser Pro Ala Gln Leu His Phe Lys Pro Glu Met Lys Pro
            100                 105                 110

Val Phe Asp Ala Thr Val Glu Asn Ile His Asp Ile Ile Asn Gly Arg
            115                 120                 125

Glu Lys Ile Ala Lys Ala Gly Asp Tyr Arg Pro Ile Thr Asp Pro Asp
            130                 135                 140

Glu Ala Glu Glu Tyr Ile Lys Met Val Tyr Asn Met Val Ile Gly Pro
145                 150                 155                 160
```

```
Val Ala Phe Asp Ser Glu Thr Ser Ala Leu Tyr Cys Arg Asp Gly Tyr
                165                 170                 175

Leu Leu Gly Val Ser Ile Ser His Gln Glu Tyr Gln Gly Val Tyr Ile
            180                 185                 190

Asp Ser Asp Cys Leu Thr Glu Val Ala Val Tyr Tyr Leu Gln Lys Ile
            195                 200                 205

Leu Asp Ser Glu Asn His Thr Ile Val Phe His Asn Leu Lys Phe Asp
            210                 215                 220

Met His Phe Tyr Lys Tyr His Leu Gly Leu Thr Phe Asp Lys Ala His
225                 230                 235                 240

Lys Glu Arg Arg Leu His Asp Thr Met Leu Gln His Tyr Val Leu Asp
                245                 250                 255

Glu Arg Arg Gly Thr His Gly Leu Lys Ser Leu Ala Met Lys Tyr Thr
            260                 265                 270

Asp Met Gly Asp Tyr Asp Phe Glu Leu Asp Lys Phe Lys Asp Asp Tyr
            275                 280                 285

Cys Lys Ala His Lys Ile Lys Lys Glu Asp Phe Thr Tyr Asp Leu Ile
            290                 295                 300

Pro Phe Asp Ile Met Trp Pro Tyr Ala Ala Lys Asp Thr Asp Ala Thr
305                 310                 315                 320

Ile Arg Leu His Asn Phe Phe Leu Pro Lys Ile Glu Lys Asn Glu Lys
                325                 330                 335

Leu Cys Ser Leu Tyr Tyr Asp Val Leu Met Pro Gly Cys Val Phe Leu
            340                 345                 350

Gln Arg Val Glu Asp Arg Gly Val Pro Ile Ser Ile Asp Arg Leu Lys
            355                 360                 365

Glu Ala Gln Tyr Gln Leu Thr His Asn Leu Asn Lys Ala Arg Glu Lys
            370                 375                 380

Leu Tyr Thr Tyr Pro Glu Val Lys Gln Leu Glu Gln Asp Gln Asn Glu
385                 390                 395                 400

Ala Phe Asn Pro Asn Ser Val Lys Gln Leu Arg Val Leu Leu Phe Asp
                405                 410                 415

Tyr Val Gly Leu Thr Pro Thr Gly Lys Leu Thr Asp Thr Gly Ala Asp
            420                 425                 430

Ser Thr Asp Ala Glu Ala Leu Asn Glu Leu Ala Thr Gln His Pro Ile
            435                 440                 445

Ala Lys Thr Leu Leu Glu Ile Arg Lys Leu Thr Lys Leu Ile Ser Thr
450                 455                 460

Tyr Val Glu Lys Ile Leu Leu Ser Ile Asp Ala Asp Gly Cys Ile Arg
465                 470                 475                 480

Thr Gly Phe His Glu His Met Thr Thr Ser Gly Arg Leu Ser Ser Ser
                485                 490                 495

Gly Lys Leu Asn Leu Gln Gln Leu Pro Arg Asp Glu Ser Ile Ile Lys
            500                 505                 510

Gly Cys Val Val Ala Pro Pro Gly Tyr Arg Val Ile Ala Trp Asp Leu
            515                 520                 525

Thr Thr Ala Glu Val Tyr Tyr Ala Ala Val Leu Ser Gly Asp Arg Asn
530                 535                 540

Met Gln Gln Val Phe Ile Asn Met Arg Asn Glu Pro Asp Lys Tyr Pro
545                 550                 555                 560

Asp Phe His Ser Asn Ile Ala His Met Val Phe Lys Leu Gln Cys Glu
                565                 570                 575

Pro Arg Asp Val Lys Lys Leu Phe Pro Ala Leu Arg Gln Ala Ala Lys
```

```
                    580                 585                 590
Ala Ile Thr Phe Gly Ile Leu Tyr Gly Ser Gly Pro Ala Lys Val Ala
                595                 600                 605

His Ser Val Asn Glu Ala Leu Leu Glu Gln Ala Ala Lys Thr Gly Glu
        610                 615                 620

Pro Phe Val Glu Cys Thr Val Ala Asp Ala Lys Glu Tyr Ile Glu Thr
625                 630                 635                 640

Tyr Phe Gly Gln Phe Pro Gln Leu Lys Arg Trp Ile Asp Lys Cys His
                645                 650                 655

Asp Gln Ile Lys Asn His Gly Phe Ile Tyr Ser His Phe Gly Arg Lys
            660                 665                 670

Arg Arg Leu His Asn Ile His Ser Glu Asp Arg Gly Val Gln Gly Glu
        675                 680                 685

Glu Ile Arg Ser Gly Phe Asn Ala Ile Ile Gln Ser Ala Ser Ser Asp
            690                 695                 700

Ser Leu Leu Leu Gly Ala Val Asp Ala Asp Asn Glu Ile Ile Ser Leu
705                 710                 715                 720

Gly Leu Glu Gln Glu Met Lys Ile Val Met Leu Val His Asp Ser Val
                725                 730                 735

Val Ala Ile Val Arg Glu Asp Leu Ile Asp Gln Tyr Asn Glu Ile Leu
            740                 745                 750

Ile Arg Asn Ile Gln Lys Asp Arg Gly Ile Ser Ile Pro Gly Cys Pro
            755                 760                 765

Ile Gly Ile Asp Ser Asp Ser Glu Ala Gly Gly Ser Arg Asp Tyr Ser
770                 775                 780

Cys Gly Lys Met Lys Lys Gln His Pro Ser Ile Ala Cys Ile Asp Asp
785                 790                 795                 800

Asp Glu Tyr Thr Arg Tyr Val Lys Gly Val Leu Leu Asp Ala Glu Phe
                805                 810                 815

Glu Tyr Lys Lys Leu Ala Ala Met Asp Lys Glu His Pro Asp His Ser
            820                 825                 830

Lys Tyr Lys Asp Asp Lys Phe Ile Ala Val Cys Lys Asp Leu Asp Asn
        835                 840                 845

Val Lys Arg Ile Leu Gly Ala
    850                 855

<210> SEQ ID NO 18
<211> LENGTH: 704
<212> TYPE: PRT
<213> ORGANISM: Enterobacteria phage T7

<400> SEQUENCE: 18

Met Ile Val Ser Asp Ile Glu Ala Asn Ala Leu Leu Glu Ser Val Thr
1               5                   10                  15

Lys Phe His Cys Gly Val Ile Tyr Asp Tyr Ser Thr Ala Glu Tyr Val
            20                  25                  30

Ser Tyr Arg Pro Ser Asp Phe Gly Ala Tyr Leu Asp Ala Leu Glu Ala
        35                  40                  45

Glu Val Ala Arg Gly Gly Leu Ile Val Phe His Asn Gly His Lys Tyr
    50                  55                  60

Asp Val Pro Ala Leu Thr Lys Leu Ala Lys Leu Gln Leu Asn Arg Glu
65                  70                  75                  80

Phe His Leu Pro Arg Glu Asn Cys Ile Asp Thr Leu Val Leu Ser Arg
                85                  90                  95
```

```
Leu Ile His Ser Asn Leu Lys Asp Thr Asp Met Gly Leu Leu Arg Ser
                100                 105                 110

Gly Lys Leu Pro Gly Lys Arg Phe Gly Ser His Ala Leu Glu Ala Trp
            115                 120                 125

Gly Tyr Arg Leu Gly Glu Met Lys Gly Glu Tyr Lys Asp Asp Phe Lys
        130                 135                 140

Arg Met Leu Glu Glu Gln Gly Glu Glu Tyr Val Asp Gly Met Glu Trp
145                 150                 155                 160

Trp Asn Phe Asn Glu Met Met Asp Tyr Asn Val Gln Asp Val Val
                165                 170                 175

Val Thr Lys Ala Leu Leu Glu Lys Leu Leu Ser Asp Lys His Tyr Phe
                180                 185                 190

Pro Pro Glu Ile Asp Phe Thr Asp Val Gly Tyr Thr Thr Phe Trp Ser
            195                 200                 205

Glu Ser Leu Glu Ala Val Asp Ile Glu His Arg Ala Ala Trp Leu Leu
        210                 215                 220

Ala Lys Gln Glu Arg Asn Gly Phe Pro Phe Asp Thr Lys Ala Ile Glu
225                 230                 235                 240

Glu Leu Tyr Val Glu Leu Ala Ala Arg Ser Glu Leu Leu Arg Lys
                245                 250                 255

Leu Thr Glu Thr Phe Gly Ser Trp Tyr Gln Pro Lys Gly Gly Thr Glu
            260                 265                 270

Met Phe Cys His Pro Arg Thr Gly Lys Pro Leu Pro Lys Tyr Pro Arg
        275                 280                 285

Ile Lys Thr Pro Lys Val Gly Gly Ile Phe Lys Lys Pro Lys Asn Lys
                290                 295                 300

Ala Gln Arg Glu Gly Arg Glu Pro Cys Glu Leu Asp Thr Arg Glu Tyr
305                 310                 315                 320

Val Ala Gly Ala Pro Tyr Thr Pro Val Glu His Val Phe Asn Pro
                325                 330                 335

Ser Ser Arg Asp His Ile Gln Lys Lys Leu Gln Glu Ala Gly Trp Val
            340                 345                 350

Pro Thr Lys Tyr Thr Asp Lys Gly Ala Pro Val Val Asp Asp Glu Val
        355                 360                 365

Leu Glu Gly Val Arg Val Asp Asp Pro Glu Lys Gln Ala Ala Ile Asp
370                 375                 380

Leu Ile Lys Glu Tyr Leu Met Ile Gln Lys Arg Ile Gly Gln Ser Ala
385                 390                 395                 400

Glu Gly Asp Lys Ala Trp Leu Arg Tyr Val Ala Glu Asp Gly Lys Ile
            405                 410                 415

His Gly Ser Val Asn Pro Asn Gly Ala Val Thr Gly Arg Ala Thr His
        420                 425                 430

Ala Phe Pro Asn Leu Ala Gln Ile Pro Gly Val Arg Ser Pro Tyr Gly
            435                 440                 445

Glu Gln Cys Arg Ala Ala Phe Gly Ala Glu His Leu Asp Gly Ile
        450                 455                 460

Thr Gly Lys Pro Trp Val Gln Ala Gly Ile Asp Ala Ser Gly Leu Glu
465                 470                 475                 480

Leu Arg Cys Leu Ala His Phe Met Ala Arg Phe Asp Asn Gly Glu Tyr
                485                 490                 495

Ala His Glu Ile Leu Asn Gly Asp Ile His Thr Lys Asn Gln Ile Ala
            500                 505                 510

Ala Glu Leu Pro Thr Arg Asp Asn Ala Lys Thr Phe Ile Tyr Gly Phe
```

```
                515                 520                 525
Leu Tyr Gly Ala Gly Asp Glu Lys Ile Gly Gln Ile Val Gly Ala Gly
        530                 535                 540

Lys Glu Arg Gly Lys Glu Leu Lys Lys Lys Phe Leu Glu Asn Thr Pro
545                 550                 555                 560

Ala Ile Ala Ala Leu Arg Glu Ser Ile Gln Gln Thr Leu Val Glu Ser
                565                 570                 575

Ser Gln Trp Val Ala Gly Glu Gln Gln Val Lys Trp Lys Arg Arg Trp
        580                 585                 590

Ile Lys Gly Leu Asp Gly Arg Lys Val His Val Arg Ser Pro His Ala
                595                 600                 605

Ala Leu Asn Thr Leu Leu Gln Ser Ala Gly Ala Leu Ile Cys Lys Leu
        610                 615                 620

Trp Ile Ile Lys Thr Glu Glu Met Leu Val Glu Lys Gly Leu Lys His
625                 630                 635                 640

Gly Trp Asp Gly Asp Phe Ala Tyr Met Ala Trp Val His Asp Glu Ile
                645                 650                 655

Gln Val Gly Cys Arg Thr Glu Glu Ile Ala Gln Val Val Ile Glu Thr
        660                 665                 670

Ala Gln Glu Ala Met Arg Trp Val Gly Asp His Trp Asn Phe Arg Cys
                675                 680                 685

Leu Leu Asp Thr Glu Gly Lys Met Gly Pro Asn Trp Ala Ile Cys His
        690                 695                 700

<210> SEQ ID NO 19
<211> LENGTH: 1090
<212> TYPE: PRT
<213> ORGANISM: artificial sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X= is M
<220> FEATURE:
<221> NAME/KEY: MISC_FEATURE
<222> LOCATION: (2)..(2)
<223> OTHER INFORMATION: X= is E
<220> FEATURE:
<221> NAME/KEY: MISC_FEATURE
<222> LOCATION: (3)..(3)
<223> OTHER INFORMATION: X= is Q
<220> FEATURE:
<221> NAME/KEY: MISC_FEATURE
<222> LOCATION: (4)..(4)
<223> OTHER INFORMATION: X= is K
<220> FEATURE:
<221> NAME/KEY: MISC_FEATURE
<222> LOCATION: (5)..(5)
<223> OTHER INFORMATION: X= is S
<220> FEATURE:
<221> NAME/KEY: MISC_FEATURE
<222> LOCATION: (6)..(6)
<223> OTHER INFORMATION: X= is L
<220> FEATURE:
<221> NAME/KEY: MISC_FEATURE
<222> LOCATION: (7)..(7)
<223> OTHER INFORMATION: X= is W
<220> FEATURE:
<221> NAME/KEY: MISC_FEATURE
<222> LOCATION: (8)..(8)
<223> OTHER INFORMATION: X= is D
<220> FEATURE:
<221> NAME/KEY: MISC_FEATURE
<222> LOCATION: (9)..(9)
<223> OTHER INFORMATION: X= is M or L
<220> FEATURE:
```

-continued

```
<221> NAME/KEY: MISC_FEATURE
<222> LOCATION: (10)..(10)
<223> OTHER INFORMATION: X= is R, E, T or F
<220> FEATURE:
<221> NAME/KEY: MISC_FEATURE
<222> LOCATION: (11)..(11)
<223> OTHER INFORMATION: X= is G, A, P, Q or M
<220> FEATURE:
<221> NAME/KEY: MISC_FEATURE
<222> LOCATION: (12)..(12)
<223> OTHER INFORMATION: X= is M, L, E or N
<220> FEATURE:
<221> NAME/KEY: MISC_FEATURE
<222> LOCATION: (13)..(13)
<223> OTHER INFORMATION: X= is L, F, N or S
<220> FEATURE:
<221> NAME/KEY: MISC_FEATURE
<222> LOCATION: (14)..(14)
<223> OTHER INFORMATION: X= is P, D, T, N or M
<220> FEATURE:
<221> NAME/KEY: MISC_FEATURE
<222> LOCATION: (15)..(15)
<223> OTHER INFORMATION: X= is L, E, D or V
<220> FEATURE:
<221> NAME/KEY: MISC_FEATURE
<222> LOCATION: (16)..(16)
<223> OTHER INFORMATION: X= is F, E, K, Y or Q
<220> FEATURE:
<221> NAME/KEY: MISC_FEATURE
<222> LOCATION: (17)..(17)
<223> OTHER INFORMATION: X= is E, Q or I
<220> FEATURE:
<221> NAME/KEY: MISC_FEATURE
<222> LOCATION: (18)..(18)
<223> OTHER INFORMATION: X= is P, S or A
<220> FEATURE:
<221> NAME/KEY: MISC_FEATURE
<222> LOCATION: (19)..(19)
<223> OTHER INFORMATION: X= is K, P, M, N or Q
<220> FEATURE:
<221> NAME/KEY: MISC_FEATURE
<222> LOCATION: (20)..(20)
<223> OTHER INFORMATION: X= is G, K, H, R, D, N, A, Y or S
<220> FEATURE:
<221> NAME/KEY: MISC_FEATURE
<222> LOCATION: (21)..(21)
<223> OTHER INFORMATION: X= is  R, E, K or P
<220> FEATURE:
<221> NAME/KEY: MISC_FEATURE
<222> LOCATION: (22)..(22)
<223> OTHER INFORMATION: X= is  V, I, F or L
<220> FEATURE:
<221> NAME/KEY: MISC_FEATURE
<222> LOCATION: (23)..(23)
<223> OTHER INFORMATION: X= is  L, Y, V, I or F
<220> FEATURE:
<221> NAME/KEY: MISC_FEATURE
<222> LOCATION: (24)..(24)
<223> OTHER INFORMATION: X= is  L
<220> FEATURE:
<221> NAME/KEY: MISC_FEATURE
<222> LOCATION: (25)..(25)
<223> OTHER INFORMATION: X= is V, I or F
<220> FEATURE:
<221> NAME/KEY: MISC_FEATURE
<222> LOCATION: (26)..(26)
<223> OTHER INFORMATION: X= is  D
<220> FEATURE:
<221> NAME/KEY: MISC_FEATURE
<222> LOCATION: (27)..(27)
<223> OTHER INFORMATION: X= is  G
<220> FEATURE:
<221> NAME/KEY: MISC_FEATURE
<222> LOCATION: (28)..(28)
<223> OTHER INFORMATION: X= is  H, S, N or T
<220> FEATURE:
<221> NAME/KEY: MISC_FEATURE
<222> LOCATION: (29)..(29)
<223> OTHER INFORMATION: X= is  H, C, S, G or A
```

-continued

```
<220> FEATURE:
<221> NAME/KEY: MISC_FEATURE
<222> LOCATION: (30)..(30)
<223> OTHER INFORMATION: X= is  L
<220> FEATURE:
<221> NAME/KEY: MISC_FEATURE
<222> LOCATION: (31)..(31)
<223> OTHER INFORMATION: X= is A, I, L, V or M
<220> FEATURE:
<221> NAME/KEY: MISC_FEATURE
<222> LOCATION: (32)..(32)
<223> OTHER INFORMATION: X= is Y
<220> FEATURE:
<221> NAME/KEY: MISC_FEATURE
<222> LOCATION: (33)..(33)
<223> OTHER INFORMATION: X= is R
<220> FEATURE:
<221> NAME/KEY: MISC_FEATURE
<222> LOCATION: (34)..(34)
<223> OTHER INFORMATION: X= is A
<220> FEATURE:
<221> NAME/KEY: MISC_FEATURE
<222> LOCATION: (35)..(35)
<223> OTHER INFORMATION: X= is F or Y
<220> FEATURE:
<221> NAME/KEY: MISC_FEATURE
<222> LOCATION: (36)..(36)
<223> OTHER INFORMATION: X= is H, F or Y
<220> FEATURE:
<221> NAME/KEY: MISC_FEATURE
<222> LOCATION: (37)..(37)
<223> OTHER INFORMATION: X= is A
<220> FEATURE:
<221> NAME/KEY: MISC_FEATURE
<222> LOCATION: (38)..(38)
<223> OTHER INFORMATION: X= is L
<220> FEATURE:
<221> NAME/KEY: MISC_FEATURE
<222> LOCATION: (39)..(39)
<223> OTHER INFORMATION: X= is K, S, P or D
<220> FEATURE:
<221> NAME/KEY: MISC_FEATURE
<222> LOCATION: (40)..(40)
<223> OTHER INFORMATION: X= is Q or R
<220> FEATURE:
<221> NAME/KEY: MISC_FEATURE
<222> LOCATION: (41)..(41)
<223> OTHER INFORMATION: X= is G, P, L, S, F or M
<220> FEATURE:
<221> NAME/KEY: MISC_FEATURE
<222> LOCATION: (42)..(42)
<223> OTHER INFORMATION: X= is L
<220> FEATURE:
<221> NAME/KEY: MISC_FEATURE
<222> LOCATION: (43)..(43)
<223> OTHER INFORMATION: X= is K, T, S, Q or H
<220> FEATURE:
<221> NAME/KEY: MISC_FEATURE
<222> LOCATION: (44)..(44)
<223> OTHER INFORMATION: X= is T
<220> FEATURE:
<221> NAME/KEY: MISC_FEATURE
<222> LOCATION: (45)..(45)
<223> OTHER INFORMATION: X= is S
<220> FEATURE:
<221> NAME/KEY: MISC_FEATURE
<222> LOCATION: (46)..(46)
<223> OTHER INFORMATION: X= is R, N, Q, A, S, T, K or E
<220> FEATURE:
<221> NAME/KEY: MISC_FEATURE
<222> LOCATION: (47)..(47)
<223> OTHER INFORMATION: X= is G
<220> FEATURE:
<221> NAME/KEY: MISC_FEATURE
<222> LOCATION: (48)..(48)
<223> OTHER INFORMATION: X= is E, I, F, M or L
<220> FEATURE:
<221> NAME/KEY: MISC_FEATURE
<222> LOCATION: (49)..(49)
```

```
<223> OTHER INFORMATION: X= is P, L, F or H
<220> FEATURE:
<221> NAME/KEY: MISC_FEATURE
<222> LOCATION: (50)..(50)
<223> OTHER INFORMATION: X= is T
<220> FEATURE:
<221> NAME/KEY: MISC_FEATURE
<222> LOCATION: (51)..(51)
<223> OTHER INFORMATION: X= is N
<220> FEATURE:
<221> NAME/KEY: MISC_FEATURE
<222> LOCATION: (52)..(52)
<223> OTHER INFORMATION: X= is A
<220> FEATURE:
<221> NAME/KEY: MISC_FEATURE
<222> LOCATION: (53)..(53)
<223> OTHER INFORMATION: X= is V, I, L, M or T
<220> FEATURE:
<221> NAME/KEY: MISC_FEATURE
<222> LOCATION: (54)..(54)
<223> OTHER INFORMATION: X= is Y
<220> FEATURE:
<221> NAME/KEY: MISC_FEATURE
<222> LOCATION: (55)..(55)
<223> OTHER INFORMATION: X= is G
<220> FEATURE:
<221> NAME/KEY: MISC_FEATURE
<222> LOCATION: (56)..(56)
<223> OTHER INFORMATION: X= is F
<220> FEATURE:
<221> NAME/KEY: MISC_FEATURE
<222> LOCATION: (57)..(57)
<223> OTHER INFORMATION: X= is A, T, I or L
<220> FEATURE:
<221> NAME/KEY: MISC_FEATURE
<222> LOCATION: (58)..(58)
<223> OTHER INFORMATION: X= is K, R, T, N or M
<220> FEATURE:
<221> NAME/KEY: MISC_FEATURE
<222> LOCATION: (59)..(59)
<223> OTHER INFORMATION: X= is M
<220> FEATURE:
<221> NAME/KEY: MISC_FEATURE
<222> LOCATION: (60)..(60)
<223> OTHER INFORMATION: X= is L
<220> FEATURE:
<221> NAME/KEY: MISC_FEATURE
<222> LOCATION: (61)..(61)
<223> OTHER INFORMATION: X= is V, I, N, R or L
<220> FEATURE:
<221> NAME/KEY: MISC_FEATURE
<222> LOCATION: (62)..(62)
<223> OTHER INFORMATION: X= is K
<220> FEATURE:
<221> NAME/KEY: MISC_FEATURE
<222> LOCATION: (63)..(63)
<223> OTHER INFORMATION: X= is A, L, F or I
<220> FEATURE:
<221> NAME/KEY: MISC_FEATURE
<222> LOCATION: (64)..(64)
<223> OTHER INFORMATION: X= is L, V or I
<220> FEATURE:
<221> NAME/KEY: MISC_FEATURE
<222> LOCATION: (65)..(65)
<223> OTHER INFORMATION: X= is K, R, E, Q, M or A
<220> FEATURE:
<221> NAME/KEY: MISC_FEATURE
<222> LOCATION: (66)..(66)
<223> OTHER INFORMATION: X= is E, D or Q
<220> FEATURE:
<221> NAME/KEY: MISC_FEATURE
<222> LOCATION: (67)..(67)
<223> OTHER INFORMATION: X= is D, K, F, E, Y or H
<220> FEATURE:
<221> NAME/KEY: MISC_FEATURE
<222> LOCATION: (68)..(68)
<223> OTHER INFORMATION: X= is V or I
<220> FEATURE:
<221> NAME/KEY: MISC_FEATURE
```

```
<222> LOCATION: (69)..(69)
<223> OTHER INFORMATION: X= is K, N or I
<220> FEATURE:
<221> NAME/KEY: MISC_FEATURE
<222> LOCATION: (70)..(70)
<223> OTHER INFORMATION: X= is V, M or I
<220> FEATURE:
<221> NAME/KEY: MISC_FEATURE
<222> LOCATION: (71)..(71)
<223> OTHER INFORMATION: X= is G, N, S, K, E or R
<220> FEATURE:
<221> NAME/KEY: MISC_FEATURE
<222> LOCATION: (72)..(72)
<223> OTHER INFORMATION: X= is Y, V, P or K
<220> FEATURE:
<221> NAME/KEY: MISC_FEATURE
<222> LOCATION: (73)..(73)
<223> OTHER INFORMATION: X= is D, Q, N, T or K
<220> FEATURE:
<221> NAME/KEY: MISC_FEATURE
<222> LOCATION: (74)..(74)
<223> OTHER INFORMATION: X= is A, Y, L or H
<220> FEATURE:
<221> NAME/KEY: MISC_FEATURE
<222> LOCATION: (75)..(75)
<223> OTHER INFORMATION: X= is V, I, L, A, T, C or M
<220> FEATURE:
<221> NAME/KEY: MISC_FEATURE
<222> LOCATION: (76)..(76)
<223> OTHER INFORMATION: X= is I, F, V, L, G or A
<220> FEATURE:
<221> NAME/KEY: MISC_FEATURE
<222> LOCATION: (77)..(77)
<223> OTHER INFORMATION: X= is V
<220> FEATURE:
<221> NAME/KEY: MISC_FEATURE
<222> LOCATION: (78)..(78)
<223> OTHER INFORMATION: X= is A, V or I
<220> FEATURE:
<221> NAME/KEY: MISC_FEATURE
<222> LOCATION: (79)..(79)
<223> OTHER INFORMATION: X= is F
<220> FEATURE:
<221> NAME/KEY: MISC_FEATURE
<222> LOCATION: (80)..(80)
<223> OTHER INFORMATION: X= is D
<220> FEATURE:
<221> NAME/KEY: MISC_FEATURE
<222> LOCATION: (81)..(81)
<223> OTHER INFORMATION: X= is A, S, R, T or K
<220> FEATURE:
<221> NAME/KEY: MISC_FEATURE
<222> LOCATION: (82)..(82)
<223> OTHER INFORMATION: X= is K
<220> FEATURE:
<221> NAME/KEY: MISC_FEATURE
<222> LOCATION: (83)..(83)
<223> OTHER INFORMATION: X= is A, H, E, G, T or K
<220> FEATURE:
<221> NAME/KEY: MISC_FEATURE
<222> LOCATION: (84)..(84)
<223> OTHER INFORMATION: X= is P, A, R, G, T or K
<220> FEATURE:
<221> NAME/KEY: MISC_FEATURE
<222> LOCATION: (85)..(85)
<223> OTHER INFORMATION: X= is T
<220> FEATURE:
<221> NAME/KEY: MISC_FEATURE
<222> LOCATION: (86)..(86)
<223> OTHER INFORMATION: X= is F
<220> FEATURE:
<221> NAME/KEY: MISC_FEATURE
<222> LOCATION: (87)..(87)
<223> OTHER INFORMATION: X= is K
<220> FEATURE:
<221> NAME/KEY: MISC_FEATURE
<222> LOCATION: (88)..(88)
<223> OTHER INFORMATION: X= is R
<220> FEATURE:
```

```
<221> NAME/KEY: MISC_FEATURE
<222> LOCATION: (89)..(89)
<223> OTHER INFORMATION: X= is H
<220> FEATURE:
<221> NAME/KEY: MISC_FEATURE
<222> LOCATION: (90)..(90)
<223> OTHER INFORMATION: X= is E, K, V or H
<220> FEATURE:
<221> NAME/KEY: MISC_FEATURE
<222> LOCATION: (91)..(91)
<223> OTHER INFORMATION: X= is E, A, I, K, T or L
<220> FEATURE:
<221> NAME/KEY: MISC_FEATURE
<222> LOCATION: (92)..(92)
<223> OTHER INFORMATION: X= is Y, F or L
<220> FEATURE:
<221> NAME/KEY: MISC_FEATURE
<222> LOCATION: (93)..(93)
<223> OTHER INFORMATION: X= is G, E, K, P or Q
<220> FEATURE:
<221> NAME/KEY: MISC_FEATURE
<222> LOCATION: (94)..(94)
<223> OTHER INFORMATION: X= is G, E, A, H, T or D
<220> FEATURE:
<221> NAME/KEY: MISC_FEATURE
<222> LOCATION: (95)..(95)
<223> OTHER INFORMATION: X= is Y
<220> FEATURE:
<221> NAME/KEY: MISC_FEATURE
<222> LOCATION: (96)..(96)
<223> OTHER INFORMATION: X= is K
<220> FEATURE:
<221> NAME/KEY: MISC_FEATURE
<222> LOCATION: (97)..(97)
<223> OTHER INFORMATION: X= is A, I, G or S
<220> FEATURE:
<221> NAME/KEY: MISC_FEATURE
<222> LOCATION: (98)..(98)
<223> OTHER INFORMATION: X= is G, T, Q, H, K or N
<220> FEATURE:
<221> NAME/KEY: MISC_FEATURE
<222> LOCATION: (99)..(99)
<223> OTHER INFORMATION: X= is R
<220> FEATURE:
<221> NAME/KEY: MISC_FEATURE
<222> LOCATION: (100)..(100)
<223> OTHER INFORMATION: X= is A, P, D or Q
<220> FEATURE:
<221> NAME/KEY: MISC_FEATURE
<222> LOCATION: (101)..(101)
<223> OTHER INFORMATION: X= is P, E, K, A or Q
<220> FEATURE:
<221> NAME/KEY: MISC_FEATURE
<222> LOCATION: (102)..(102)
<223> OTHER INFORMATION: X= is T, M or A
<220> FEATURE:
<221> NAME/KEY: MISC_FEATURE
<222> LOCATION: (103)..(103)
<223> OTHER INFORMATION: X= is P
<220> FEATURE:
<221> NAME/KEY: MISC_FEATURE
<222> LOCATION: (104)..(104)
<223> OTHER INFORMATION: X= is P, E, K or D
<220> FEATURE:
<221> NAME/KEY: MISC_FEATURE
<222> LOCATION: (105)..(105)
<223> OTHER INFORMATION: X= is A, E, L or D
<220> FEATURE:
<221> NAME/KEY: MISC_FEATURE
<222> LOCATION: (106)..(106)
<223> OTHER INFORMATION: X= is F, M, L or I
<220> FEATURE:
<221> NAME/KEY: MISC_FEATURE
<222> LOCATION: (107)..(107)
<223> OTHER INFORMATION: X= is P, K, R, I, L, S or A
<220> FEATURE:
<221> NAME/KEY: MISC_FEATURE
<222> LOCATION: (108)..(108)
<223> OTHER INFORMATION: X= is R, V, A, P, Q or E
```

-continued

```
<220> FEATURE:
<221> NAME/KEY: MISC_FEATURE
<222> LOCATION: (109)..(109)
<223> OTHER INFORMATION: X= is Q
<220> FEATURE:
<221> NAME/KEY: MISC_FEATURE
<222> LOCATION: (110)..(110)
<223> OTHER INFORMATION: X= is L, I, M, F or V
<220> FEATURE:
<221> NAME/KEY: MISC_FEATURE
<222> LOCATION: (111)..(111)
<223> OTHER INFORMATION: X= is A, D, P or E
<220> FEATURE:
<221> NAME/KEY: MISC_FEATURE
<222> LOCATION: (112)..(112)
<223> OTHER INFORMATION: X= is L, Y, W, M or P
<220> FEATURE:
<221> NAME/KEY: MISC_FEATURE
<222> LOCATION: (113)..(113)
<223> OTHER INFORMATION: X= is I, V or L
<220> FEATURE:
<221> NAME/KEY: MISC_FEATURE
<222> LOCATION: (114)..(114)
<223> OTHER INFORMATION: X= is K, R, H or E
<220> FEATURE:
<221> NAME/KEY: MISC_FEATURE
<222> LOCATION: (115)..(115)
<223> OTHER INFORMATION: X= is E, R, Q, A or K
<220> FEATURE:
<221> NAME/KEY: MISC_FEATURE
<222> LOCATION: (116)..(116)
<223> OTHER INFORMATION: X= is L, I, F, M or G
<220> FEATURE:
<221> NAME/KEY: MISC_FEATURE
<222> LOCATION: (117)..(117)
<223> OTHER INFORMATION: X= is V, I or L
<220> FEATURE:
<221> NAME/KEY: MISC_FEATURE
<222> LOCATION: (118)..(118)
<223> OTHER INFORMATION: X= is D, R, E, K, Q or N
<220> FEATURE:
<221> NAME/KEY: MISC_FEATURE
<222> LOCATION: (119)..(119)
<223> OTHER INFORMATION: X= is L, A or G
<220> FEATURE:
<221> NAME/KEY: MISC_FEATURE
<222> LOCATION: (120)..(120)
<223> OTHER INFORMATION: X= is L, N, M, F or Y
<220> FEATURE:
<221> NAME/KEY: MISC_FEATURE
<222> LOCATION: (121)..(121)
<223> OTHER INFORMATION: X= is G, D, N or R
<220> FEATURE:
<221> NAME/KEY: MISC_FEATURE
<222> LOCATION: (122)..(122)
<223> OTHER INFORMATION: X= is L, F, I, M or V
<220> FEATURE:
<221> NAME/KEY: MISC_FEATURE
<222> LOCATION: (123)..(123)
<223> OTHER INFORMATION: X= is A, T, V, P, N or K
<220> FEATURE:
<221> NAME/KEY: MISC_FEATURE
<222> LOCATION: (124)..(124)
<223> OTHER INFORMATION: X= is R, L, Y, V, A, T or I
<220> FEATURE:
<221> NAME/KEY: MISC_FEATURE
<222> LOCATION: (125)..(125)
<223> OTHER INFORMATION: X= is L
<220> FEATURE:
<221> NAME/KEY: MISC_FEATURE
<222> LOCATION: (126)..(126)
<223> OTHER INFORMATION: X= is E
<220> FEATURE:
<221> NAME/KEY: MISC_FEATURE
<222> LOCATION: (127)..(127)
<223> OTHER INFORMATION: X= is V, A, E, K, Y, I or L
<220> FEATURE:
<221> NAME/KEY: MISC_FEATURE
<222> LOCATION: (128)..(128)
```

```
<223> OTHER INFORMATION: X= is P, D, S, E or L
<220> FEATURE:
<221> NAME/KEY: MISC_FEATURE
<222> LOCATION: (129)..(129)
<223> OTHER INFORMATION: X= is G
<220> FEATURE:
<221> NAME/KEY: MISC_FEATURE
<222> LOCATION: (130)..(130)
<223> OTHER INFORMATION: X= is Y
<220> FEATURE:
<221> NAME/KEY: MISC_FEATURE
<222> LOCATION: (131)..(131)
<223> OTHER INFORMATION: X= is E
<220> FEATURE:
<221> NAME/KEY: MISC_FEATURE
<222> LOCATION: (132)..(132)
<223> OTHER INFORMATION: X= is A
<220> FEATURE:
<221> NAME/KEY: MISC_FEATURE
<222> LOCATION: (133)..(133)
<223> OTHER INFORMATION: X= is D
<220> FEATURE:
<221> NAME/KEY: MISC_FEATURE
<222> LOCATION: (134)..(134)
<223> OTHER INFORMATION: X= is D
<220> FEATURE:
<221> NAME/KEY: MISC_FEATURE
<222> LOCATION: (135)..(135)
<223> OTHER INFORMATION: X= is I
<220> FEATURE:
<221> NAME/KEY: MISC_FEATURE
<222> LOCATION: (136)..(136)
<223> OTHER INFORMATION: X= is I
<220> FEATURE:
<221> NAME/KEY: MISC_FEATURE
<222> LOCATION: (137)..(137)
<223> OTHER INFORMATION: X= is A, G or V
<220> FEATURE:
<221> NAME/KEY: MISC_FEATURE
<222> LOCATION: (138)..(138)
<223> OTHER INFORMATION: X= is T
<220> FEATURE:
<221> NAME/KEY: MISC_FEATURE
<222> LOCATION: (139)..(139)
<223> OTHER INFORMATION: X= is L, A, F, I or D
<220> FEATURE:
<221> NAME/KEY: MISC_FEATURE
<222> LOCATION: (140)..(140)
<223> OTHER INFORMATION: X= is A, V, T, S or K
<220> FEATURE:
<221> NAME/KEY: MISC_FEATURE
<222> LOCATION: (141)..(141)
<223> OTHER INFORMATION: X= is K, G, R, V or A
<220> FEATURE:
<221> NAME/KEY: MISC_FEATURE
<222> LOCATION: (142)..(142)
<223> OTHER INFORMATION: X= is K, N, V, I, E, M, R or L
<220> FEATURE:
<221> NAME/KEY: MISC_FEATURE
<222> LOCATION: (143)..(143)
<223> OTHER INFORMATION: X= is A, P, I, V, G, F or N
<220> FEATURE:
<221> NAME/KEY: MISC_FEATURE
<222> LOCATION: (144)..(144)
<223> OTHER INFORMATION: X= is E, N, K, L or C
<220> FEATURE:
<221> NAME/KEY: MISC_FEATURE
<222> LOCATION: (145)..(145)
<223> OTHER INFORMATION: X= is K, R, Q, S, P, N, E or T
<220> FEATURE:
<221> NAME/KEY: MISC_FEATURE
<222> LOCATION: (146)..(146)
<223> OTHER INFORMATION: X= is E, F, Y, A, L, K or R
<220> FEATURE:
<221> NAME/KEY: MISC_FEATURE
<222> LOCATION: (147)..(147)
<223> OTHER INFORMATION: X= is G, A, K, D, F or Y
<220> FEATURE:
<221> NAME/KEY: MISC_FEATURE
```

-continued

```
<222> LOCATION: (148)..(148)
<223> OTHER INFORMATION: X= is Y, M, P, D, K, R, E or F
<220> FEATURE:
<221> NAME/KEY: MISC_FEATURE
<222> LOCATION: (149)..(149)
<223> OTHER INFORMATION: X= is E, L, D, P or K
<220> FEATURE:
<221> NAME/KEY: MISC_FEATURE
<222> LOCATION: (150)..(150)
<223> OTHER INFORMATION: X= is V, N, L, T, I or H
<220> FEATURE:
<221> NAME/KEY: MISC_FEATURE
<222> LOCATION: (151)..(151)
<223> OTHER INFORMATION: X= is R, F, K, M or L
<220> FEATURE:
<221> NAME/KEY: MISC_FEATURE
<222> LOCATION: (152)..(152)
<223> OTHER INFORMATION: X= is I, Y or Q
<220> FEATURE:
<221> NAME/KEY: MISC_FEATURE
<222> LOCATION: (153)..(153)
<223> OTHER INFORMATION: X= is I
<220> FEATURE:
<221> NAME/KEY: MISC_FEATURE
<222> LOCATION: (154)..(154)
<223> OTHER INFORMATION: X= is L, I, V, S or Y
<220> FEATURE:
<221> NAME/KEY: MISC_FEATURE
<222> LOCATION: (155)..(155)
<223> OTHER INFORMATION: X= is T, S or G
<220> FEATURE:
<221> NAME/KEY: MISC_FEATURE
<222> LOCATION: (156)..(156)
<223> OTHER INFORMATION: X= is G
<220> FEATURE:
<221> NAME/KEY: MISC_FEATURE
<222> LOCATION: (157)..(157)
<223> OTHER INFORMATION: X= is D
<220> FEATURE:
<221> NAME/KEY: MISC_FEATURE
<222> LOCATION: (158)..(158)
<223> OTHER INFORMATION: X= is K, R, L or V
<220> FEATURE:
<221> NAME/KEY: MISC_FEATURE
<222> LOCATION: (159)..(159)
<223> OTHER INFORMATION: X= is D
<220> FEATURE:
<221> NAME/KEY: MISC_FEATURE
<222> LOCATION: (160)..(160)
<223> OTHER INFORMATION: X= is L, F, M, A or V
<220> FEATURE:
<221> NAME/KEY: MISC_FEATURE
<222> LOCATION: (161)..(161)
<223> OTHER INFORMATION: X= is Y, D, F, L, R or T
<220> FEATURE:
<221> NAME/KEY: MISC_FEATURE
<222> LOCATION: (162)..(162)
<223> OTHER INFORMATION: X= is Q
<220> FEATURE:
<221> NAME/KEY: MISC_FEATURE
<222> LOCATION: (163)..(163)
<223> OTHER INFORMATION: X= is L
<220> FEATURE:
<221> NAME/KEY: MISC_FEATURE
<222> LOCATION: (164)..(164)
<223> OTHER INFORMATION: X= is V
<220> FEATURE:
<221> NAME/KEY: MISC_FEATURE
<222> LOCATION: (165)..(165)
<223> OTHER INFORMATION: X= is S, D, T or N
<220> FEATURE:
<221> NAME/KEY: MISC_FEATURE
<222> LOCATION: (166)..(166)
<223> OTHER INFORMATION: X= is D, E or P
<220> FEATURE:
<221> NAME/KEY: MISC_FEATURE
<222> LOCATION: (167)..(167)
<223> OTHER INFORMATION: X= is K
<220> FEATURE:
```

-continued

```
<221> NAME/KEY: MISC_FEATURE
<222> LOCATION: (168)..(168)
<223> OTHER INFORMATION: X= is I, V, T or L
<220> FEATURE:
<221> NAME/KEY: MISC_FEATURE
<222> LOCATION: (169)..(169)
<223> OTHER INFORMATION: X= is H, A, S, K, F, T or Y
<220> FEATURE:
<221> NAME/KEY: MISC_FEATURE
<222> LOCATION: (170)..(170)
<223> OTHER INFORMATION: X= is V, I , L or G
<220> FEATURE:
<221> NAME/KEY: MISC_FEATURE
<222> LOCATION: (171)..(171)
<223> OTHER INFORMATION: X= is L, Y, I , W, D, K or R
<220> FEATURE:
<221> NAME/KEY: MISC_FEATURE
<222> LOCATION: (172)..(172)
<223> OTHER INFORMATION: X= is H, L, D, N, R or I
<220> FEATURE:
<221> NAME/KEY: MISC_FEATURE
<222> LOCATION: (173)..(173)
<223> OTHER INFORMATION: X= is P, T, I, S or L
<220> FEATURE:
<221> NAME/KEY: MISC_FEATURE
<222> LOCATION: (174)..(174)
<223> OTHER INFORMATION: X= is E, D, I, Q, K, M, S or V
<220> FEATURE:
<221> NAME/KEY: MISC_FEATURE
<222> LOCATION: (175)..(175)
<223> OTHER INFORMATION: X= is K
<220> FEATURE:
<221> NAME/KEY: MISC_FEATURE
<222> LOCATION: (176)..(176)
<223> OTHER INFORMATION: X= is Y, H, T, E, G or N
<220> FEATURE:
<221> NAME/KEY: MISC_FEATURE
<222> LOCATION: (177)..(177)
<223> OTHER INFORMATION: X= is I
<220> FEATURE:
<221> NAME/KEY: MISC_FEATURE
<222> LOCATION: (178)..(178)
<223> OTHER INFORMATION: X= is T
<220> FEATURE:
<221> NAME/KEY: MISC_FEATURE
<222> LOCATION: (179)..(179)
<223> OTHER INFORMATION: X= is E, Q or D
<220> FEATURE:
<221> NAME/KEY: MISC_FEATURE
<222> LOCATION: (180)..(180)
<223> OTHER INFORMATION: X= is F, M, L or I
<220> FEATURE:
<221> NAME/KEY: MISC_FEATURE
<222> LOCATION: (181)..(181)
<223> OTHER INFORMATION: X= is T or E
<220> FEATURE:
<221> NAME/KEY: MISC_FEATURE
<222> LOCATION: (182)..(182)
<223> OTHER INFORMATION: X= is I, S, F, L, P or E
<220> FEATURE:
<221> NAME/KEY: MISC_FEATURE
<222> LOCATION: (183)..(183)
<223> OTHER INFORMATION: X= is I, V, Y, L or F
<220> FEATURE:
<221> NAME/KEY: MISC_FEATURE
<222> LOCATION: (184)..(184)
<223> OTHER INFORMATION: X= is T, D or G
<220> FEATURE:
<221> NAME/KEY: MISC_FEATURE
<222> LOCATION: (185)..(185)
<223> OTHER INFORMATION: X= is P, R, G, K, A or E
<220> FEATURE:
<221> NAME/KEY: MISC_FEATURE
<222> LOCATION: (186)..(186)
<223> OTHER INFORMATION: X= is A, E, K or Q
<220> FEATURE:
<221> NAME/KEY: MISC_FEATURE
<222> LOCATION: (187)..(187)
<223> OTHER INFORMATION: X= is W, D, Y, A, K, E, T or I
```

```
-continued

<220> FEATURE:
<221> NAME/KEY: MISC_FEATURE
<222> LOCATION: (188)..(188)
<223> OTHER INFORMATION: X= is V
<220> FEATURE:
<221> NAME/KEY: MISC_FEATURE
<222> LOCATION: (189)..(189)
<223> OTHER INFORMATION: X= is W, Q, I, K, V, E, R, L or T
<220> FEATURE:
<221> NAME/KEY: MISC_FEATURE
<222> LOCATION: (190)..(190)
<223> OTHER INFORMATION: X= is E
<220> FEATURE:
<221> NAME/KEY: MISC_FEATURE
<222> LOCATION: (191)..(191)
<223> OTHER INFORMATION: X= is K
<220> FEATURE:
<221> NAME/KEY: MISC_FEATURE
<222> LOCATION: (192)..(192)
<223> OTHER INFORMATION: X= is Y
<220> FEATURE:
<221> NAME/KEY: MISC_FEATURE
<222> LOCATION: (193)..(193)
<223> OTHER INFORMATION: X= is G
<220> FEATURE:
<221> NAME/KEY: MISC_FEATURE
<222> LOCATION: (194)..(194)
<223> OTHER INFORMATION: X= is V
<220> FEATURE:
<221> NAME/KEY: MISC_FEATURE
<222> LOCATION: (195)..(195)
<223> OTHER INFORMATION: X= is R, K, P, E, N, F, T or D
<220> FEATURE:
<221> NAME/KEY: MISC_FEATURE
<222> LOCATION: (196)..(196)
<223> OTHER INFORMATION: X= is P
<220> FEATURE:
<221> NAME/KEY: MISC_FEATURE
<222> LOCATION: (197)..(197)
<223> OTHER INFORMATION: X= is D, E, Y, S, H, Q or N
<220> FEATURE:
<221> NAME/KEY: MISC_FEATURE
<222> LOCATION: (198)..(198)
<223> OTHER INFORMATION: X= is Q, R, K, L or D
<220> FEATURE:
<221> NAME/KEY: MISC_FEATURE
<222> LOCATION: (199)..(199)
<223> OTHER INFORMATION: X= is W, L, I, F, M or Y
<220> FEATURE:
<221> NAME/KEY: MISC_FEATURE
<222> LOCATION: (200)..(200)
<223> OTHER INFORMATION: X= is A, V, N, P, I, G or D
<220> FEATURE:
<221> NAME/KEY: MISC_FEATURE
<222> LOCATION: (201)..(201)
<223> OTHER INFORMATION: X= is D
<220> FEATURE:
<221> NAME/KEY: MISC_FEATURE
<222> LOCATION: (202)..(202)
<223> OTHER INFORMATION: X= is Y, F, L or V
<220> FEATURE:
<221> NAME/KEY: MISC_FEATURE
<222> LOCATION: (203)..(203)
<223> OTHER INFORMATION: X= is R, M, K, L or I
<220> FEATURE:
<221> NAME/KEY: MISC_FEATURE
<222> LOCATION: (204)..(204)
<223> OTHER INFORMATION: X= is A, V, S, G, L or M
<220> FEATURE:
<221> NAME/KEY: MISC_FEATURE
<222> LOCATION: (205)..(205)
<223> OTHER INFORMATION: X= is L
<220> FEATURE:
<221> NAME/KEY: MISC_FEATURE
<222> LOCATION: (206)..(206)
<223> OTHER INFORMATION: X= is T, V, M or G
<220> FEATURE:
<221> NAME/KEY: MISC_FEATURE
<222> LOCATION: (207)..(207)
```

```
-continued

<223> OTHER INFORMATION: X= is G
<220> FEATURE:
<221> NAME/KEY: MISC_FEATURE
<222> LOCATION: (208)..(208)
<223> OTHER INFORMATION: X= is D or E
<220> FEATURE:
<221> NAME/KEY: MISC_FEATURE
<222> LOCATION: (209)..(209)
<223> OTHER INFORMATION: X=is E, P, R, A, K, S, Q or I
<220> FEATURE:
<221> NAME/KEY: MISC_FEATURE
<222> LOCATION: (210)..(210)
<223> OTHER INFORMATION: X= is S
<220> FEATURE:
<221> NAME/KEY: MISC_FEATURE
<222> LOCATION: (211)..(211)
<223> OTHER INFORMATION: X= is D
<220> FEATURE:
<221> NAME/KEY: MISC_FEATURE
<222> LOCATION: (212)..(212)
<223> OTHER INFORMATION: X= is N
<220> FEATURE:
<221> NAME/KEY: MISC_FEATURE
<222> LOCATION: (213)..(213)
<223> OTHER INFORMATION: X= is I
<220> FEATURE:
<221> NAME/KEY: MISC_FEATURE
<222> LOCATION: (214)..(214)
<223> OTHER INFORMATION: X= is P
<220> FEATURE:
<221> NAME/KEY: MISC_FEATURE
<222> LOCATION: (215)..(215)
<223> OTHER INFORMATION: X= is G
<220> FEATURE:
<221> NAME/KEY: MISC_FEATURE
<222> LOCATION: (216)..(216)
<223> OTHER INFORMATION: X= is V
<220> FEATURE:
<221> NAME/KEY: MISC_FEATURE
<222> LOCATION: (217)..(217)
<223> OTHER INFORMATION: X= is K, A, N, P, T or L
<220> FEATURE:
<221> NAME/KEY: MISC_FEATURE
<222> LOCATION: (218)..(218)
<223> OTHER INFORMATION: X= is G
<220> FEATURE:
<221> NAME/KEY: MISC_FEATURE
<222> LOCATION: (219)..(219)
<223> OTHER INFORMATION: X= is I
<220> FEATURE:
<221> NAME/KEY: MISC_FEATURE
<222> LOCATION: (220)..(220)
<223> OTHER INFORMATION: X= is G
<220> FEATURE:
<221> NAME/KEY: MISC_FEATURE
<222> LOCATION: (221)..(221)
<223> OTHER INFORMATION: X= is E
<220> FEATURE:
<221> NAME/KEY: MISC_FEATURE
<222> LOCATION: (222)..(222)
<223> OTHER INFORMATION: X= is K
<220> FEATURE:
<221> NAME/KEY: MISC_FEATURE
<222> LOCATION: (223)..(223)
<223> OTHER INFORMATION: X= is T
<220> FEATURE:
<221> NAME/KEY: MISC_FEATURE
<222> LOCATION: (224)..(224)
<223> OTHER INFORMATION: X= is A
<220> FEATURE:
<221> NAME/KEY: MISC_FEATURE
<222> LOCATION: (225)..(225)
<223> OTHER INFORMATION: X= is R, L, A, S, Q, V, I, K or C
<220> FEATURE:
<221> NAME/KEY: MISC_FEATURE
<222> LOCATION: (226)..(226)
<223> OTHER INFORMATION: X= is K, R, N, E, Q, S or G
<220> FEATURE:
<221> NAME/KEY: MISC_FEATURE
```

```
<222> LOCATION: (227)..(227)
<223> OTHER INFORMATION: X= is L
<220> FEATURE:
<221> NAME/KEY: MISC_FEATURE
<222> LOCATION: (228)..(228)
<223> OTHER INFORMATION: X= is L
<220> FEATURE:
<221> NAME/KEY: MISC_FEATURE
<222> LOCATION: (229)..(229)
<223> OTHER INFORMATION: X= is E, K, A, N, Q, R or Y
<220> FEATURE:
<221> NAME/KEY: MISC_FEATURE
<222> LOCATION: (230)..(230)
<223> OTHER INFORMATION: X= is E, R, K, N, G, Q or D
<220> FEATURE:
<221> NAME/KEY: MISC_FEATURE
<222> LOCATION: (231)..(231)
<223> OTHER INFORMATION: X= is W, Y, I, L or F
<220> FEATURE:
<221> NAME/KEY: MISC_FEATURE
<222> LOCATION: (232)..(232)
<223> OTHER INFORMATION: X= is G
<220> FEATURE:
<221> NAME/KEY: MISC_FEATURE
<222> LOCATION: (233)..(233)
<223> OTHER INFORMATION: X= is S, D, G, N or T
<220> FEATURE:
<221> NAME/KEY: MISC_FEATURE
<222> LOCATION: (234)..(234)
<223> OTHER INFORMATION: X= is L, V, I, Y or A
<220> FEATURE:
<221> NAME/KEY: MISC_FEATURE
<222> LOCATION: (235)..(235)
<223> OTHER INFORMATION: X= is E
<220> FEATURE:
<221> NAME/KEY: MISC_FEATURE
<222> LOCATION: (236)..(236)
<223> OTHER INFORMATION: X= is A, N, E, K, T, D or Y
<220> FEATURE:
<221> NAME/KEY: MISC_FEATURE
<222> LOCATION: (237)..(237)
<223> OTHER INFORMATION: X= is L, I, F, V or W
<220> FEATURE:
<221> NAME/KEY: MISC_FEATURE
<222> LOCATION: (238)..(238)
<223> OTHER INFORMATION: X= is L, K, Y, I or S
<220> FEATURE:
<221> NAME/KEY: MISC_FEATURE
<222> LOCATION: (239)..(239)
<223> OTHER INFORMATION: X= is K, S, A, G, N, Q or Y
<220> FEATURE:
<221> NAME/KEY: MISC_FEATURE
<222> LOCATION: (240)..(240)
<223> OTHER INFORMATION: X= is N, K, S, E, H or R
<220> FEATURE:
<221> NAME/KEY: MISC_FEATURE
<222> LOCATION: (241)..(241)
<223> OTHER INFORMATION: X= is L, I , P, V or K
<220> FEATURE:
<221> NAME/KEY: MISC_FEATURE
<222> LOCATION: (242)..(242)
<223> OTHER INFORMATION: X= is D, K, E, H, R or S
<220> FEATURE:
<221> NAME/KEY: MISC_FEATURE
<222> LOCATION: (243)..(243)
<223> OTHER INFORMATION: X= is R, I, V, G, K, E, L, Q or D
<220> FEATURE:
<221> NAME/KEY: MISC_FEATURE
<222> LOCATION: (244)..(244)
<223> OTHER INFORMATION: X= is L, V, I or F
<220> FEATURE:
<221> NAME/KEY: MISC_FEATURE
<222> LOCATION: (245)..(245)
<223> OTHER INFORMATION: X= is K, D, G, A, N, P or T
<220> FEATURE:
<221> NAME/KEY: MISC_FEATURE
<222> LOCATION: (246)..(246)
<223> OTHER INFORMATION: X= is P, S, G, Q, E or A
<220> FEATURE:
```

```
<221> NAME/KEY: MISC_FEATURE
<222> LOCATION: (247)..(247)
<223> OTHER INFORMATION: X= is L
<220> FEATURE:
<221> NAME/KEY: MISC_FEATURE
<222> LOCATION: (248)..(248)
<223> OTHER INFORMATION: X= is S
<220> FEATURE:
<221> NAME/KEY: MISC_FEATURE
<222> LOCATION: (249)..(249)
<223> OTHER INFORMATION: X= is S
<220> FEATURE:
<221> NAME/KEY: MISC_FEATURE
<222> LOCATION: (250)..(250)
<223> OTHER INFORMATION: X= is R
<220> FEATURE:
<221> NAME/KEY: MISC_FEATURE
<222> LOCATION: (251)..(251)
<223> OTHER INFORMATION: X= is G
<220> FEATURE:
<221> NAME/KEY: MISC_FEATURE
<222> LOCATION: (252)..(252)
<223> OTHER INFORMATION: X= is A
<220> FEATURE:
<221> NAME/KEY: MISC_FEATURE
<222> LOCATION: (253)..(253)
<223> OTHER INFORMATION: X= is A, E, D, L or K
<220> FEATURE:
<221> NAME/KEY: MISC_FEATURE
<222> LOCATION: (254)..(254)
<223> OTHER INFORMATION: X= is N, S, K, D, T or R
<220> FEATURE:
<221> NAME/KEY: MISC_FEATURE
<222> LOCATION: (255)..(255)
<223> OTHER INFORMATION: X= is I, V, L, M, T or Y
<220> FEATURE:
<221> NAME/KEY: MISC_FEATURE
<222> LOCATION: (256)..(256)
<223> OTHER INFORMATION: X= is R, S, Q, A, G, K, P or L
<220> FEATURE:
<221> NAME/KEY: MISC_FEATURE
<222> LOCATION: (257)..(257)
<223> OTHER INFORMATION: X= is E, R, D, S, A or K
<220> FEATURE:
<221> NAME/KEY: MISC_FEATURE
<222> LOCATION: (258)..(258)
<223> OTHER INFORMATION: X= is K, I, L, T, A, N or Q
<220> FEATURE:
<221> NAME/KEY: MISC_FEATURE
<222> LOCATION: (259)..(259)
<223> OTHER INFORMATION: X= is L
<220> FEATURE:
<221> NAME/KEY: MISC_FEATURE
<222> LOCATION: (260)..(260)
<223> OTHER INFORMATION: X= is L, K, E, A, S, R or H
<220> FEATURE:
<221> NAME/KEY: MISC_FEATURE
<222> LOCATION: (261)..(261)
<223> OTHER INFORMATION: X= is A, K, D, Q, R, N or F
<220> FEATURE:
<221> NAME/KEY: MISC_FEATURE
<222> LOCATION: (262)..(262)
<223> OTHER INFORMATION: X= is H, N, G, D, A, Y, K or E
<220> FEATURE:
<221> NAME/KEY: MISC_FEATURE
<222> LOCATION: (263)..(263)
<223> OTHER INFORMATION: X=is M, L, I, W, K, R, T, P or V
<220> FEATURE:
<221> NAME/KEY: MISC_FEATURE
<222> LOCATION: (264)..(264)
<223> OTHER INFORMATION: X= is E
<220> FEATURE:
<221> NAME/KEY: MISC_FEATURE
<222> LOCATION: (265)..(265)
<223> OTHER INFORMATION: X= is D, S, I, K, V, N, L, M or R
<220> FEATURE:
<221> NAME/KEY: MISC_FEATURE
<222> LOCATION: (266)..(266)
<223> OTHER INFORMATION: X= is L, I, A, K or G
```

-continued

```
<220> FEATURE:
<221> NAME/KEY: MISC_FEATURE
<222> LOCATION: (267)..(267)
<223> OTHER INFORMATION: X=is K, R, H, Q, E, F, Y, I, L, P or G
<220> FEATURE:
<221> NAME/KEY: MISC_FEATURE
<222> LOCATION: (268)..(268)
<223> OTHER INFORMATION: X= is L
<220> FEATURE:
<221> NAME/KEY: MISC_FEATURE
<222> LOCATION: (269)..(269)
<223> OTHER INFORMATION: X= is S
<220> FEATURE:
<221> NAME/KEY: MISC_FEATURE
<222> LOCATION: (270)..(270)
<223> OTHER INFORMATION: X= is W, L, K, Y, R, D or V
<220> FEATURE:
<221> NAME/KEY: MISC_FEATURE
<222> LOCATION: (271)..(271)
<223> OTHER INFORMATION: X= is D, E, Q, K, R, A or F
<220> FEATURE:
<221> NAME/KEY: MISC_FEATURE
<222> LOCATION: (272)..(272)
<223> OTHER INFORMATION: X= is L
<220> FEATURE:
<221> NAME/KEY: MISC_FEATURE
<222> LOCATION: (273)..(273)
<223> OTHER INFORMATION: X= is A, S, V or N
<220> FEATURE:
<221> NAME/KEY: MISC_FEATURE
<222> LOCATION: (274)..(274)
<223> OTHER INFORMATION: X= is K, R, I, T, Q, A, E or G
<220> FEATURE:
<221> NAME/KEY: MISC_FEATURE
<222> LOCATION: (275)..(275)
<223> OTHER INFORMATION: X= is V, I , L, N or H
<220> FEATURE:
<221> NAME/KEY: MISC_FEATURE
<222> LOCATION: (276)..(276)
<223> OTHER INFORMATION: X= is R, D, K, M, E or I
<220> FEATURE:
<221> NAME/KEY: MISC_FEATURE
<222> LOCATION: (277)..(277)
<223> OTHER INFORMATION: X= is T, K, C, Y, R or H
<220> FEATURE:
<221> NAME/KEY: MISC_FEATURE
<222> LOCATION: (278)..(278)
<223> OTHER INFORMATION: X= is D, N or E
<220> FEATURE:
<221> NAME/KEY: MISC_FEATURE
<222> LOCATION: (279)..(279)
<223> OTHER INFORMATION: X= is L, T, I, E, V or A
<220> FEATURE:
<221> NAME/KEY: MISC_FEATURE
<222> LOCATION: (280)..(280)
<223> OTHER INFORMATION: X= is P
<220> FEATURE:
<221> NAME/KEY: MISC_FEATURE
<222> LOCATION: (281)..(281)
<223> OTHER INFORMATION: X= is L, I, K, V, N or A
<220> FEATURE:
<221> NAME/KEY: MISC_FEATURE
<222> LOCATION: (282)..(282)
<223> OTHER INFORMATION: X= is I or G
<220> FEATURE:
<221> NAME/KEY: MISC_FEATURE
<222> LOCATION: (283)..(283)
<223> OTHER INFORMATION: X= is E or R
<220> FEATURE:
<221> NAME/KEY: MISC_FEATURE
<222> LOCATION: (284)..(284)
<223> OTHER INFORMATION: X= is E
<220> FEATURE:
<221> NAME/KEY: MISC_FEATURE
<222> LOCATION: (285)..(285)
<223> OTHER INFORMATION: X= is V, I, L, K or T
<220> FEATURE:
<221> NAME/KEY: MISC_FEATURE
<222> LOCATION: (286)..(286)
```

```
<223> OTHER INFORMATION: X= is D, K, I, T, N or S
<220> FEATURE:
<221> NAME/KEY: MISC_FEATURE
<222> LOCATION: (287)..(287)
<223> OTHER INFORMATION: X= is F, L, W, C, I or A
<220> FEATURE:
<221> NAME/KEY: MISC_FEATURE
<222> LOCATION: (288)..(288)
<223> OTHER INFORMATION: X= is A, K, D, N or E
<220> FEATURE:
<221> NAME/KEY: MISC_FEATURE
<222> LOCATION: (289)..(289)
<223> OTHER INFORMATION: X is A, D, P, Q or K
<220> FEATURE:
<221> NAME/KEY: MISC_FEATURE
<222> LOCATION: (290)..(290)
<223> OTHER INFORMATION: X= is L
<220> FEATURE:
<221> NAME/KEY: MISC_FEATURE
<222> LOCATION: (291)..(291)
<223> OTHER INFORMATION: X= is K, Q, R, E, I, A or D
<220> FEATURE:
<221> NAME/KEY: MISC_FEATURE
<222> LOCATION: (292)..(292)
<223> OTHER INFORMATION: X= is R, G, I, K, V, Y or L
<220> FEATURE:
<221> NAME/KEY: MISC_FEATURE
<222> LOCATION: (293)..(293)
<223> OTHER INFORMATION: X= is R, K, F, Q, A, E or N
<220> FEATURE:
<221> NAME/KEY: MISC_FEATURE
<222> LOCATION: (294)..(294)
<223> OTHER INFORMATION: X= is E, T, Q, R, G, K, D or P
<220> FEATURE:
<221> NAME/KEY: MISC_FEATURE
<222> LOCATION: (295)..(295)
<223> OTHER INFORMATION: X= is P, Q, D, I, Y, H, E or F
<220> FEATURE:
<221> NAME/KEY: MISC_FEATURE
<222> LOCATION: (296)..(296)
<223> OTHER INFORMATION: X= is D, A, K, N, T or F
<220> FEATURE:
<221> NAME/KEY: MISC_FEATURE
<222> LOCATION: (297)..(297)
<223> OTHER INFORMATION: X= is R, L, S, A, E, D or H
<220> FEATURE:
<221> NAME/KEY: MISC_FEATURE
<222> LOCATION: (298)..(298)
<223> OTHER INFORMATION: X= is E
<220> FEATURE:
<221> NAME/KEY: MISC_FEATURE
<222> LOCATION: (299)..(299)
<223> OTHER INFORMATION: X= is K
<220> FEATURE:
<221> NAME/KEY: MISC_FEATURE
<222> LOCATION: (300)..(300)
<223> OTHER INFORMATION: X= is L
<220> FEATURE:
<221> NAME/KEY: MISC_FEATURE
<222> LOCATION: (301)..(301)
<223> OTHER INFORMATION: X= is R, V, I , L, A or E
<220> FEATURE:
<221> NAME/KEY: MISC_FEATURE
<222> LOCATION: (302)..(302)
<223> OTHER INFORMATION: X= is A, Q, D, E, G, S, P, V or N
<220> FEATURE:
<221> NAME/KEY: MISC_FEATURE
<222> LOCATION: (303)..(303)
<223> OTHER INFORMATION: X= is F, I, L, V, E or C
<220> FEATURE:
<221> NAME/KEY: MISC_FEATURE
<222> LOCATION: (304)..(304)
<223> OTHER INFORMATION: X= is L, F, Y or I
<220> FEATURE:
<221> NAME/KEY: MISC_FEATURE
<222> LOCATION: (305)..(305)
<223> OTHER INFORMATION: X= is E, R, K, Q, N, I or D
<220> FEATURE:
<221> NAME/KEY: MISC_FEATURE
```

```
-continued

<222> LOCATION: (306)..(306)
<223> OTHER INFORMATION: X= is R, E, K or T
<220> FEATURE:
<221> NAME/KEY: MISC_FEATURE
<222> LOCATION: (307)..(307)
<223> OTHER INFORMATION: X= is L
<220> FEATURE:
<221> NAME/KEY: MISC_FEATURE
<222> LOCATION: (308)..(308)
<223> OTHER INFORMATION: X= is E
<220> FEATURE:
<221> NAME/KEY: MISC_FEATURE
<222> LOCATION: (309)..(309)
<223> OTHER INFORMATION: X= is F
<220> FEATURE:
<221> NAME/KEY: MISC_FEATURE
<222> LOCATION: (310)..(310)
<223> OTHER INFORMATION: X= is G, N, K, S, A, Q or F
<220> FEATURE:
<221> NAME/KEY: MISC_FEATURE
<222> LOCATION: (311)..(311)
<223> OTHER INFORMATION: X= is S
<220> FEATURE:
<221> NAME/KEY: MISC_FEATURE
<222> LOCATION: (312)..(312)
<223> OTHER INFORMATION: X= is L, I, W, F or V
<220> FEATURE:
<221> NAME/KEY: MISC_FEATURE
<222> LOCATION: (313)..(313)
<223> OTHER INFORMATION: X= is L,T, M or I
<220> FEATURE:
<221> NAME/KEY: MISC_FEATURE
<222> LOCATION: (314)..(314)
<223> OTHER INFORMATION: X= is H, K, Q, E, A, D or G
<220> FEATURE:
<221> NAME/KEY: MISC_FEATURE
<222> LOCATION: (315)..(315)
<223> OTHER INFORMATION: X= is E, Q, K, R, D, N, S or P
<220> FEATURE:
<221> NAME/KEY: MISC_FEATURE
<222> LOCATION: (316)..(316)
<223> OTHER INFORMATION: X= is F, I, L, V, M or N
<220> FEATURE:
<221> NAME/KEY: MISC_FEATURE
<222> LOCATION: (317)..(317)
<223> OTHER INFORMATION: X= is I, F, P, E, G, Q, D, K , A or L
<220> FEATURE:
<221> NAME/KEY: MISC_FEATURE
<222> LOCATION: (318)..(318)
<223> OTHER INFORMATION: X= is K, P, A, L or F
<220> FEATURE:
<221> NAME/KEY: MISC_FEATURE
<222> LOCATION: (319)..(319)
<223> OTHER INFORMATION: X= is D, S, G or Y
<220> FEATURE:
<221> NAME/KEY: MISC_FEATURE
<222> LOCATION: (320)..(320)
<223> OTHER INFORMATION: X= is F, L, D, K, T or S
<220> FEATURE:
<221> NAME/KEY: MISC_FEATURE
<222> LOCATION: (321)..(321)
<223> OTHER INFORMATION: X=is P, Q, E, W, K, A, S or D
<220> FEATURE:
<221> NAME/KEY: MISC_FEATURE
<222> LOCATION: (322)..(322)
<223> OTHER INFORMATION: X= is N, E, L, Q, P, K, T or M
<220> FEATURE:
<221> NAME/KEY: MISC_FEATURE
<222> LOCATION: (323)..(323)
<223> OTHER INFORMATION: X= is G, H, E, Q, D, S, T or N
<220> FEATURE:
<221> NAME/KEY: MISC_FEATURE
<222> LOCATION: (324)..(324)
<223> OTHER INFORMATION: X= is L, S, E, K, A, Q or N
<220> FEATURE:
<221> NAME/KEY: MISC_FEATURE
<222> LOCATION: (325)..(325)
<223> OTHER INFORMATION: X= is L, S, N, K, P, E or V
<220> FEATURE:
```

```
<221> NAME/KEY: MISC_FEATURE
<222> LOCATION: (326)..(326)
<223> OTHER INFORMATION: X= is E, G, C, I, D, T, V, K or R
<220> FEATURE:
<221> NAME/KEY: MISC_FEATURE
<222> LOCATION: (327)..(327)
<223> OTHER INFORMATION: X= is S, A, G, E, Q, P, K or I
<220> FEATURE:
<221> NAME/KEY: MISC_FEATURE
<222> LOCATION: (328)..(328)
<223> OTHER INFORMATION: X= is S, K, Y, T, V or G
<220> FEATURE:
<221> NAME/KEY: MISC_FEATURE
<222> LOCATION: (329)..(329)
<223> OTHER INFORMATION: X= is P, I, R, T, D, N or K
<220> FEATURE:
<221> NAME/KEY: MISC_FEATURE
<222> LOCATION: (330)..(330)
<223> OTHER INFORMATION: X= is V, A, I , L or N
<220> FEATURE:
<221> NAME/KEY: MISC_FEATURE
<222> LOCATION: (331)..(331)
<223> OTHER INFORMATION: X= is N, A, V, M, H or P
<220> FEATURE:
<221> NAME/KEY: MISC_FEATURE
<222> LOCATION: (332)..(332)
<223> OTHER INFORMATION: X= is E, K, N or G
<220> FEATURE:
<221> NAME/KEY: MISC_FEATURE
<222> LOCATION: (333)..(333)
<223> OTHER INFORMATION: X= is G, P or K
<220> FEATURE:
<221> NAME/KEY: MISC_FEATURE
<222> LOCATION: (334)..(334)
<223> OTHER INFORMATION: X= is K, Q or R
<220> FEATURE:
<221> NAME/KEY: MISC_FEATURE
<222> LOCATION: (335)..(335)
<223> OTHER INFORMATION: X= is T or E
<220> FEATURE:
<221> NAME/KEY: MISC_FEATURE
<222> LOCATION: (336)..(336)
<223> OTHER INFORMATION: X= is S or T
<220> FEATURE:
<221> NAME/KEY: MISC_FEATURE
<222> LOCATION: (337)..(337)
<223> OTHER INFORMATION: X= is S
<220> FEATURE:
<221> NAME/KEY: MISC_FEATURE
<222> LOCATION: (338)..(338)
<223> OTHER INFORMATION: X= is F or V
<220> FEATURE:
<221> NAME/KEY: MISC_FEATURE
<222> LOCATION: (339)..(339)
<223> OTHER INFORMATION: X= is N or A
<220> FEATURE:
<221> NAME/KEY: MISC_FEATURE
<222> LOCATION: (340)..(340)
<223> OTHER INFORMATION: X= is W or D
<220> FEATURE:
<221> NAME/KEY: MISC_FEATURE
<222> LOCATION: (341)..(341)
<223> OTHER INFORMATION: X= is D or E
<220> FEATURE:
<221> NAME/KEY: MISC_FEATURE
<222> LOCATION: (342)..(342)
<223> OTHER INFORMATION: X= is N or A
<220> FEATURE:
<221> NAME/KEY: MISC_FEATURE
<222> LOCATION: (343)..(343)
<223> OTHER INFORMATION: X= is P
<220> FEATURE:
<221> NAME/KEY: MISC_FEATURE
<222> LOCATION: (344)..(344)
<223> OTHER INFORMATION: X= is E
<220> FEATURE:
<221> NAME/KEY: MISC_FEATURE
<222> LOCATION: (345)..(345)
<223> OTHER INFORMATION: X= is V
```

```
<220> FEATURE:
<221> NAME/KEY: MISC_FEATURE
<222> LOCATION: (346)..(346)
<223> OTHER INFORMATION: X= is T
<220> FEATURE:
<221> NAME/KEY: MISC_FEATURE
<222> LOCATION: (347)..(347)
<223> OTHER INFORMATION: X= is A
<220> FEATURE:
<221> NAME/KEY: MISC_FEATURE
<222> LOCATION: (348)..(348)
<223> OTHER INFORMATION: X= is T
<220> FEATURE:
<221> NAME/KEY: MISC_FEATURE
<222> LOCATION: (349)..(349)
<223> OTHER INFORMATION: X= is V
<220> FEATURE:
<221> NAME/KEY: MISC_FEATURE
<222> LOCATION: (350)..(350)
<223> OTHER INFORMATION: X= is F or I
<220> FEATURE:
<221> NAME/KEY: MISC_FEATURE
<222> LOCATION: (351)..(351)
<223> OTHER INFORMATION: X= is S or Y
<220> FEATURE:
<221> NAME/KEY: MISC_FEATURE
<222> LOCATION: (352)..(352)
<223> OTHER INFORMATION: X= is Y
<220> FEATURE:
<221> NAME/KEY: MISC_FEATURE
<222> LOCATION: (353)..(353)
<223> OTHER INFORMATION: X= is I or D
<220> FEATURE:
<221> NAME/KEY: MISC_FEATURE
<222> LOCATION: (354)..(354)
<223> OTHER INFORMATION: X= is S or N
<220> FEATURE:
<221> NAME/KEY: MISC_FEATURE
<222> LOCATION: (355)..(355)
<223> OTHER INFORMATION: X= is E or Y
<220> FEATURE:
<221> NAME/KEY: MISC_FEATURE
<222> LOCATION: (356)..(356)
<223> OTHER INFORMATION: X= is F or V
<220> FEATURE:
<221> NAME/KEY: MISC_FEATURE
<222> LOCATION: (357)..(357)
<223> OTHER INFORMATION: X= is P or T
<220> FEATURE:
<221> NAME/KEY: MISC_FEATURE
<222> LOCATION: (358)..(358)
<223> OTHER INFORMATION: X= is H or I
<220> FEATURE:
<221> NAME/KEY: MISC_FEATURE
<222> LOCATION: (359)..(359)
<223> OTHER INFORMATION: X= is E, L or F
<220> FEATURE:
<221> NAME/KEY: MISC_FEATURE
<222> LOCATION: (360)..(360)
<223> OTHER INFORMATION: X= is N, D, S, M, V or G
<220> FEATURE:
<221> NAME/KEY: MISC_FEATURE
<222> LOCATION: (361)..(361)
<223> OTHER INFORMATION: X= is P, E, V, I, S, N, L, A or Q
<220> FEATURE:
<221> NAME/KEY: MISC_FEATURE
<222> LOCATION: (362)..(362)
<223> OTHER INFORMATION: X= is K, A, L, D, E, N, V, F, Y or H
<220> FEATURE:
<221> NAME/KEY: MISC_FEATURE
<222> LOCATION: (363)..(363)
<223> OTHER INFORMATION: X= is A, P, Q, D, N, T, S, E, V, W, C or A
<220> FEATURE:
<221> NAME/KEY: MISC_FEATURE
<222> LOCATION: (364)..(364)
<223> OTHER INFORMATION: X= is L
<220> FEATURE:
<221> NAME/KEY: MISC_FEATURE
<222> LOCATION: (365)..(365)
```

-continued

```
<223> OTHER INFORMATION: X= is E, N , K, S, A or D
<220> FEATURE:
<221> NAME/KEY: MISC_FEATURE
<222> LOCATION: (366)..(366)
<223> OTHER INFORMATION: X= is E, L, S, A, K, D, V or G
<220> FEATURE:
<221> NAME/KEY: MISC_FEATURE
<222> LOCATION: (367)..(367)
<223> OTHER INFORMATION: X= is A, I, E, W, L, G, R, D or Y
<220> FEATURE:
<221> NAME/KEY: MISC_FEATURE
<222> LOCATION: (368)..(368)
<223> OTHER INFORMATION: X= is P, S, N, L, I, F, V, R or G
<220> FEATURE:
<221> NAME/KEY: MISC_FEATURE
<222> LOCATION: (369)..(369)
<223> OTHER INFORMATION: X= is W, E, F, A, K, T, L or Y
<220> FEATURE:
<221> NAME/KEY: MISC_FEATURE
<222> LOCATION: (370)..(370)
<223> OTHER INFORMATION: X= is P, N, K , R, D, E or G
<220> FEATURE:
<221> NAME/KEY: MISC_FEATURE
<222> LOCATION: (371)..(371)
<223> OTHER INFORMATION: X= is P, R, E, F, L, I or V
<220> FEATURE:
<221> NAME/KEY: MISC_FEATURE
<222> LOCATION: (372)..(372)
<223> OTHER INFORMATION: X= is P, R, V, I, E, K, R, D, M, S or G
<220> FEATURE:
<221> NAME/KEY: MISC_FEATURE
<222> LOCATION: (373)..(373)
<223> OTHER INFORMATION: X= is E, N, Q, K, L, T or I
<220> FEATURE:
<221> NAME/KEY: MISC_FEATURE
<222> LOCATION: (374)..(374)
<223> OTHER INFORMATION: X= is G, T, K, D, A, S, V, L or M
<220> FEATURE:
<221> NAME/KEY: MISC_FEATURE
<222> LOCATION: (375)..(375)
<223> OTHER INFORMATION: X= is I, G, P, Q, K, D, L or H
<220> FEATURE:
<221> NAME/KEY: MISC_FEATURE
<222> LOCATION: (376)..(376)
<223> OTHER INFORMATION: X= is E, N, V, Y, S, T, K, Q or G
<220> FEATURE:
<221> NAME/KEY: MISC_FEATURE
<222> LOCATION: (377)..(377)
<223> OTHER INFORMATION: X= is A, L , G, H, F, D or E
<220> FEATURE:
<221> NAME/KEY: MISC_FEATURE
<222> LOCATION: (378)..(378)
<223> OTHER INFORMATION: X= is F, I , Y, K, A, V, S or N
<220> FEATURE:
<221> NAME/KEY: MISC_FEATURE
<222> LOCATION: (379)..(379)
<223> OTHER INFORMATION: X= is V, E, F, M, L, I, R, K or Q
<220> FEATURE:
<221> NAME/KEY: MISC_FEATURE
<222> LOCATION: (380)..(380)
<223> OTHER INFORMATION: X= is G, K, A, D, V, N or S
<220> FEATURE:
<221> NAME/KEY: MISC_FEATURE
<222> LOCATION: (381)..(381)
<223> OTHER INFORMATION: X= is F, I , L, T, V or D
<220> FEATURE:
<221> NAME/KEY: MISC_FEATURE
<222> LOCATION: (382)..(382)
<223> OTHER INFORMATION: X= is V, L, K, Y, E, A or F
<220> FEATURE:
<221> NAME/KEY: MISC_FEATURE
<222> LOCATION: (383)..(383)
<223> OTHER INFORMATION: X= is L, E, C, R, T, V, F, I or K
<220> FEATURE:
<221> NAME/KEY: MISC_FEATURE
<222> LOCATION: (384)..(384)
<223> OTHER INFORMATION: X= is S, Y , L, H, T, M, V or R
<220> FEATURE:
<221> NAME/KEY: MISC_FEATURE
```

```
-continued

<222> LOCATION: (385)..(385)
<223> OTHER INFORMATION: X= is R, G, L, S, E, P or M
<220> FEATURE:
<221> NAME/KEY: MISC_FEATURE
<222> LOCATION: (386)..(386)
<223> OTHER INFORMATION: X= is K, P, D, L or E
<220> FEATURE:
<221> NAME/KEY: MISC_FEATURE
<222> LOCATION: (387)..(387)
<223> OTHER INFORMATION: X= is E, F, R, K, D, S, N, I or C
<220> FEATURE:
<221> NAME/KEY: MISC_FEATURE
<222> LOCATION: (388)..(388)
<223> OTHER INFORMATION: X= is P, S, A, K, N, Y, L or E
<220> FEATURE:
<221> NAME/KEY: MISC_FEATURE
<222> LOCATION: (389)..(389)
<223> OTHER INFORMATION: X= is M, V, F, L, I, H, T or G
<220> FEATURE:
<221> NAME/KEY: MISC_FEATURE
<222> LOCATION: (390)..(390)
<223> OTHER INFORMATION: X= is W, T, E, S, D or G
<220> FEATURE:
<221> NAME/KEY: MISC_FEATURE
<222> LOCATION: (391)..(391)
<223> OTHER INFORMATION: X= is A, F, G, T, C, V or E
<220> FEATURE:
<221> NAME/KEY: MISC_FEATURE
<222> LOCATION: (392)..(392)
<223> OTHER INFORMATION: X= is D, E, N, I, A, K or P
<220> FEATURE:
<221> NAME/KEY: MISC_FEATURE
<222> LOCATION: (393)..(393)
<223> OTHER INFORMATION: X= is L, K, S, I, V or Y
<220> FEATURE:
<221> NAME/KEY: MISC_FEATURE
<222> LOCATION: (394)..(394)
<223> OTHER INFORMATION: X= is L, K, D, Q, V, I, A or Y
<220> FEATURE:
<221> NAME/KEY: MISC_FEATURE
<222> LOCATION: (395)..(395)
<223> OTHER INFORMATION: X= is A, S, K, G, Y or D
<220> FEATURE:
<221> NAME/KEY: MISC_FEATURE
<222> LOCATION: (396)..(396)
<223> OTHER INFORMATION: X= is L, I, F, D, V or G
<220> FEATURE:
<221> NAME/KEY: MISC_FEATURE
<222> LOCATION: (397)..(397)
<223> OTHER INFORMATION: X= is A, I, K, S, Q or M
<220> FEATURE:
<221> NAME/KEY: MISC_FEATURE
<222> LOCATION: (398)..(398)
<223> OTHER INFORMATION: X= is A, E, Y, F, I, L, V or K
<220> FEATURE:
<221> NAME/KEY: MISC_FEATURE
<222> LOCATION: (399)..(399)
<223> OTHER INFORMATION: X= is A, C, G, P, S, V, I or W
<220> FEATURE:
<221> NAME/KEY: MISC_FEATURE
<222> LOCATION: (400)..(400)
<223> OTHER INFORMATION: X= is R, S, V, E, I, L, F, T, N or W
<220> FEATURE:
<221> NAME/KEY: MISC_FEATURE
<222> LOCATION: (401)..(401)
<223> OTHER INFORMATION: X= is G, D, E, N, P or K
<220> FEATURE:
<221> NAME/KEY: MISC_FEATURE
<222> LOCATION: (402)..(402)
<223> OTHER INFORMATION: X= is G, Y, P, S, E, H, K, N or F
<220> FEATURE:
<221> NAME/KEY: MISC_FEATURE
<222> LOCATION: (403)..(403)
<223> OTHER INFORMATION: X= is R, T, F, E, G, K, D or N
<220> FEATURE:
<221> NAME/KEY: MISC_FEATURE
<222> LOCATION: (404)..(404)
<223> OTHER INFORMATION: X= is V, L, I, G, E, R, T or N
<220> FEATURE:
```

```
<221> NAME/KEY: MISC_FEATURE
<222> LOCATION: (405)..(405)
<223> OTHER INFORMATION: X= is H, S, G, A, F, V or E
<220> FEATURE:
<221> NAME/KEY: MISC_FEATURE
<222> LOCATION: (406)..(406)
<223> OTHER INFORMATION: X= is L, A, Y, F, T or M
<220> FEATURE:
<221> NAME/KEY: MISC_FEATURE
<222> LOCATION: (407)..(407)
<223> OTHER INFORMATION: X= is V, Y, L, I or M
<220> FEATURE:
<221> NAME/KEY: MISC_FEATURE
<222> LOCATION: (408)..(408)
<223> OTHER INFORMATION: X= is V or I
<220> FEATURE:
<221> NAME/KEY: MISC_FEATURE
<222> LOCATION: (409)..(409)
<223> OTHER INFORMATION: X= is S or P
<220> FEATURE:
<221> NAME/KEY: MISC_FEATURE
<222> LOCATION: (410)..(410)
<223> OTHER INFORMATION: X= is I, V or L
<220> FEATURE:
<221> NAME/KEY: MISC_FEATURE
<222> LOCATION: (411)..(411)
<223> OTHER INFORMATION: X= is N, A, H or S
<220> FEATURE:
<221> NAME/KEY: MISC_FEATURE
<222> LOCATION: (412)..(412)
<223> OTHER INFORMATION: X= is D or H
<220> FEATURE:
<221> NAME/KEY: MISC_FEATURE
<222> LOCATION: (413)..(413)
<223> OTHER INFORMATION: X= is L, D, K, R or V
<220> FEATURE:
<221> NAME/KEY: MISC_FEATURE
<222> LOCATION: (414)..(414)
<223> OTHER INFORMATION: X= is I or Y
<220> FEATURE:
<221> NAME/KEY: MISC_FEATURE
<222> LOCATION: (415)..(415)
<223> OTHER INFORMATION: X= is F or L
<220> FEATURE:
<221> NAME/KEY: MISC_FEATURE
<222> LOCATION: (416)..(416)
<223> OTHER INFORMATION: X= is Y or D
<220> FEATURE:
<221> NAME/KEY: MISC_FEATURE
<222> LOCATION: (417)..(417)
<223> OTHER INFORMATION: X= is V, A, N or S
<220> FEATURE:
<221> NAME/KEY: MISC_FEATURE
<222> LOCATION: (418)..(418)
<223> OTHER INFORMATION: X= is P, G, A, E or D
<220> FEATURE:
<221> NAME/KEY: MISC_FEATURE
<222> LOCATION: (419)..(419)
<223> OTHER INFORMATION: X= is E, D, P, Q, N or Y
<220> FEATURE:
<221> NAME/KEY: MISC_FEATURE
<222> LOCATION: (420)..(420)
<223> OTHER INFORMATION: X= is R, E, P, K, Q, N or D
<220> FEATURE:
<221> NAME/KEY: MISC_FEATURE
<222> LOCATION: (421)..(421)
<223> OTHER INFORMATION: X= is A, I, F, L, V or P
<220> FEATURE:
<221> NAME/KEY: MISC_FEATURE
<222> LOCATION: (422)..(422)
<223> OTHER INFORMATION: X= is P, A, T, D, L, S, E, H or Q
<220> FEATURE:
<221> NAME/KEY: MISC_FEATURE
<222> LOCATION: (423)..(423)
<223> OTHER INFORMATION: X= is E, D, S, F, R, K, M, T or N
<220> FEATURE:
<221> NAME/KEY: MISC_FEATURE
<222> LOCATION: (424)..(424)
<223> OTHER INFORMATION: X= is P, N, Q, E, K, A, V, G or L
```

-continued

```
<220> FEATURE:
<221> NAME/KEY: MISC_FEATURE
<222> LOCATION: (425)..(425)
<223> OTHER INFORMATION: X= is Y, L, V, D, N, R, S, E, I, F or K
<220> FEATURE:
<221> NAME/KEY: MISC_FEATURE
<222> LOCATION: (426)..(426)
<223> OTHER INFORMATION: X= is K, A, E, T, L, V, Q or F
<220> FEATURE:
<221> NAME/KEY: MISC_FEATURE
<222> LOCATION: (427)..(427)
<223> OTHER INFORMATION: X= is I, A, L, D or T
<220> FEATURE:
<221> NAME/KEY: MISC_FEATURE
<222> LOCATION: (428)..(428)
<223> OTHER INFORMATION: X= is R, E, N, K, S, P or M
<220> FEATURE:
<221> NAME/KEY: MISC_FEATURE
<222> LOCATION: (429)..(429)
<223> OTHER INFORMATION: X= is K, T, L, N, F, Q, D, H or A
<220> FEATURE:
<221> NAME/KEY: MISC_FEATURE
<222> LOCATION: (430)..(430)
<223> OTHER INFORMATION: X= is A, G, R, K, I, L or F
<220> FEATURE:
<221> NAME/KEY: MISC_FEATURE
<222> LOCATION: (431)..(431)
<223> OTHER INFORMATION: X= is L, V, I, A, K or Y
<220> FEATURE:
<221> NAME/KEY: MISC_FEATURE
<222> LOCATION: (432)..(432)
<223> OTHER INFORMATION: X= is R, K, A, N, E, P or S
<220> FEATURE:
<221> NAME/KEY: MISC_FEATURE
<222> LOCATION: (433)..(433)
<223> OTHER INFORMATION: X= is D, E, N, K, L, I, W or Y
<220> FEATURE:
<221> NAME/KEY: MISC_FEATURE
<222> LOCATION: (434)..(434)
<223> OTHER INFORMATION: X= is L
<220> FEATURE:
<221> NAME/KEY: MISC_FEATURE
<222> LOCATION: (435)..(435)
<223> OTHER INFORMATION: X= is K, L, I, E, A or G
<220> FEATURE:
<221> NAME/KEY: MISC_FEATURE
<222> LOCATION: (436)..(436)
<223> OTHER INFORMATION: X= is E, S, K, D, N, C or G
<220> FEATURE:
<221> NAME/KEY: MISC_FEATURE
<222> LOCATION: (437)..(437)
<223> OTHER INFORMATION: X= is A, V, S, G, E, Q, P, L or D
<220> FEATURE:
<221> NAME/KEY: MISC_FEATURE
<222> LOCATION: (438)..(438)
<223> OTHER INFORMATION: X= is R, E, N, K, S, G, T or D
<220> FEATURE:
<221> NAME/KEY: MISC_FEATURE
<222> LOCATION: (439)..(439)
<223> OTHER INFORMATION: X= is G, I, N, D, A, Y, K, F or H
<220> FEATURE:
<221> NAME/KEY: MISC_FEATURE
<222> LOCATION: (440)..(440)
<223> OTHER INFORMATION: X= is L, F, V, K, E, D or Y
<220> FEATURE:
<221> NAME/KEY: MISC_FEATURE
<222> LOCATION: (441)..(441)
<223> OTHER INFORMATION: X= is L, K, I or F
<220> FEATURE:
<221> NAME/KEY: MISC_FEATURE
<222> LOCATION: (442)..(442)
<223> OTHER INFORMATION: X= is A, I, K, G, V, S, T or P
<220> FEATURE:
<221> NAME/KEY: MISC_FEATURE
<222> LOCATION: (443)..(443)
<223> OTHER INFORMATION: X= is K, I, T, G, M, H or P
<220> FEATURE:
<221> NAME/KEY: MISC_FEATURE
<222> LOCATION: (444)..(444)
```

```
<223> OTHER INFORMATION: X= is D, Y, G, E, Q, F, H or K
<220> FEATURE:
<221> NAME/KEY: MISC_FEATURE
<222> LOCATION: (445)..(445)
<223> OTHER INFORMATION: X= is L, N, S, T, D, E or I
<220> FEATURE:
<221> NAME/KEY: MISC_FEATURE
<222> LOCATION: (446)..(446)
<223> OTHER INFORMATION: X= is S, A, Y, E, L, I, R or D
<220> FEATURE:
<221> NAME/KEY: MISC_FEATURE
<222> LOCATION: (447)..(447)
<223> OTHER INFORMATION: X= is V, K, I, D, R or F
<220> FEATURE:
<221> NAME/KEY: MISC_FEATURE
<222> LOCATION: (448)..(448)
<223> OTHER INFORMATION: X= is L, E, Q, A, Y, F, R, D or T
<220> FEATURE:
<221> NAME/KEY: MISC_FEATURE
<222> LOCATION: (449)..(449)
<223> OTHER INFORMATION: X= is A, P, D, F or H
<220> FEATURE:
<221> NAME/KEY: MISC_FEATURE
<222> LOCATION: (450)..(450)
<223> OTHER INFORMATION: X= is L, S, K, R, Y, A, D or V
<220> FEATURE:
<221> NAME/KEY: MISC_FEATURE
<222> LOCATION: (451)..(451)
<223> OTHER INFORMATION: X= is R, K, L, G, S, V or T
<220> FEATURE:
<221> NAME/KEY: MISC_FEATURE
<222> LOCATION: (452)..(452)
<223> OTHER INFORMATION: X= is E, K, D, I, V, A, R, M or Y
<220> FEATURE:
<221> NAME/KEY: MISC_FEATURE
<222> LOCATION: (453)..(453)
<223> OTHER INFORMATION: X= is L
<220> FEATURE:
<221> NAME/KEY: MISC_FEATURE
<222> LOCATION: (454)..(454)
<223> OTHER INFORMATION: X= is K, H, A, M, S, Q or T
<220> FEATURE:
<221> NAME/KEY: MISC_FEATURE
<222> LOCATION: (455)..(455)
<223> OTHER INFORMATION: X= is N, F, S, M, V, W, Y or H
<220> FEATURE:
<221> NAME/KEY: MISC_FEATURE
<222> LOCATION: (456)..(456)
<223> OTHER INFORMATION: X= is S, L, Y, H, K, N or W
<220> FEATURE:
<221> NAME/KEY: MISC_FEATURE
<222> LOCATION: (457)..(457)
<223> OTHER INFORMATION: X= is G
<220> FEATURE:
<221> NAME/KEY: MISC_FEATURE
<222> LOCATION: (458)..(458)
<223> OTHER INFORMATION: X= is L, V, C, I or E
<220> FEATURE:
<221> NAME/KEY: MISC_FEATURE
<222> LOCATION: (459)..(459)
<223> OTHER INFORMATION: X= is G, D, A, K, E or S
<220> FEATURE:
<221> NAME/KEY: MISC_FEATURE
<222> LOCATION: (460)..(460)
<223> OTHER INFORMATION: X= is L
<220> FEATURE:
<221> NAME/KEY: MISC_FEATURE
<222> LOCATION: (461)..(461)
<223> OTHER INFORMATION: X= is S, K, I, R, V, Q, C or E
<220> FEATURE:
<221> NAME/KEY: MISC_FEATURE
<222> LOCATION: (462)..(462)
<223> OTHER INFORMATION: X= is P, V, D, G, W, R, I, S or A
<220> FEATURE:
<221> NAME/KEY: MISC_FEATURE
<222> LOCATION: (463)..(463)
<223> OTHER INFORMATION: X= is P, D, H, I, V, K or G
<220> FEATURE:
<221> NAME/KEY: MISC_FEATURE
```

-continued

```
<222> LOCATION: (464)..(464)
<223> OTHER INFORMATION: X= is G, T, Y , V,  L,  A, S, H or D
<220> FEATURE:
<221> NAME/KEY: MISC_FEATURE
<222> LOCATION: (465)..(465)
<223> OTHER INFORMATION: X= is F
<220> FEATURE:
<221> NAME/KEY: MISC_FEATURE
<222> LOCATION: (466)..(466)
<223> OTHER INFORMATION: X= is K or G
<220> FEATURE:
<221> NAME/KEY: MISC_FEATURE
<222> LOCATION: (467)..(467)
<223> OTHER INFORMATION: X= is N or L
<220> FEATURE:
<221> NAME/KEY: MISC_FEATURE
<222> LOCATION: (468)..(468)
<223> OTHER INFORMATION: X= is D
<220> FEATURE:
<221> NAME/KEY: MISC_FEATURE
<222> LOCATION: (469)..(469)
<223> OTHER INFORMATION: X= is P, L, V, T, S or H
<220> FEATURE:
<221> NAME/KEY: MISC_FEATURE
<222> LOCATION: (470)..(470)
<223> OTHER INFORMATION: X= is M, L, S, E, A or R
<220> FEATURE:
<221> NAME/KEY: MISC_FEATURE
<222> LOCATION: (471)..(471)
<223> OTHER INFORMATION: X= is L, I, V or A
<220> FEATURE:
<221> NAME/KEY: MISC_FEATURE
<222> LOCATION: (472)..(472)
<223> OTHER INFORMATION: X= is L, V, R, D, E, A or M
<220> FEATURE:
<221> NAME/KEY: MISC_FEATURE
<222> LOCATION: (473)..(473)
<223> OTHER INFORMATION: X= is A
<220> FEATURE:
<221> NAME/KEY: MISC_FEATURE
<222> LOCATION: (474)..(474)
<223> OTHER INFORMATION: X= is Y
<220> FEATURE:
<221> NAME/KEY: MISC_FEATURE
<222> LOCATION: (475)..(475)
<223> OTHER INFORMATION: X= is L
<220> FEATURE:
<221> NAME/KEY: MISC_FEATURE
<222> LOCATION: (476)..(476)
<223> OTHER INFORMATION: X= is L
<220> FEATURE:
<221> NAME/KEY: MISC_FEATURE
<222> LOCATION: (477)..(477)
<223> OTHER INFORMATION: X= is D, N, E or K
<220> FEATURE:
<221> NAME/KEY: MISC_FEATURE
<222> LOCATION: (478)..(478)
<223> OTHER INFORMATION: X= is P
<220> FEATURE:
<221> NAME/KEY: MISC_FEATURE
<222> LOCATION: (479)..(479)
<223> OTHER INFORMATION: X= is S, A, N, E, V, D or G
<220> FEATURE:
<221> NAME/KEY: MISC_FEATURE
<222> LOCATION: (480)..(480)
<223> OTHER INFORMATION: X= is R, K, A, E, Q or D
<220> FEATURE:
<221> NAME/KEY: MISC_FEATURE
<222> LOCATION: (481)..(481)
<223> OTHER INFORMATION: X= is G, Q, F, K, R, D, S, Y or N
<220> FEATURE:
<221> NAME/KEY: MISC_FEATURE
<222> LOCATION: (482)..(482)
<223> OTHER INFORMATION: X= is N, K, L, R, A, V, D or G
<220> FEATURE:
<221> NAME/KEY: MISC_FEATURE
<222> LOCATION: (483)..(483)
<223> OTHER INFORMATION: X= is T, Y, H, F, G or D
<220> FEATURE:
```

```
<221> NAME/KEY: MISC_FEATURE
<222> LOCATION: (484)..(484)
<223> OTHER INFORMATION: X= is T, H, N, S, Y, D, E or P
<220> FEATURE:
<221> NAME/KEY: MISC_FEATURE
<222> LOCATION: (485)..(485)
<223> OTHER INFORMATION: X= is P, I, L, D, M, V or F
<220> FEATURE:
<221> NAME/KEY: MISC_FEATURE
<222> LOCATION: (486)..(486)
<223> OTHER INFORMATION: X= is D
<220> FEATURE:
<221> NAME/KEY: MISC_FEATURE
<222> LOCATION: (487)..(487)
<223> OTHER INFORMATION: X= is G, E, I, S, D, A, R, K or T
<220> FEATURE:
<221> NAME/KEY: MISC_FEATURE
<222> LOCATION: (488)..(488)
<223> OTHER INFORMATION: X= is V, L , A, F or K
<220> FEATURE:
<221> NAME/KEY: MISC_FEATURE
<222> LOCATION: (489)..(489)
<223> OTHER INFORMATION: X= is A
<220> FEATURE:
<221> NAME/KEY: MISC_FEATURE
<222> LOCATION: (490)..(490)
<223> OTHER INFORMATION: X= is R, L, G, A, E, M, K, D or I
<220> FEATURE:
<221> NAME/KEY: MISC_FEATURE
<222> LOCATION: (491)..(491)
<223> OTHER INFORMATION: X= is R, E, Y, K, M or D
<220> FEATURE:
<221> NAME/KEY: MISC_FEATURE
<222> LOCATION: (492)..(492)
<223> OTHER INFORMATION: X= is Y
<220> FEATURE:
<221> NAME/KEY: MISC_FEATURE
<222> LOCATION: (493)..(493)
<223> OTHER INFORMATION: X= is L
<220> FEATURE:
<221> NAME/KEY: MISC_FEATURE
<222> LOCATION: (494)..(494)
<223> OTHER INFORMATION: X= is G, N, E, K or Y
<220> FEATURE:
<221> NAME/KEY: MISC_FEATURE
<222> LOCATION: (495)..(495)
<223> OTHER INFORMATION: X= is P, H, Y, E, V or A
<220> FEATURE:
<221> NAME/KEY: MISC_FEATURE
<222> LOCATION: (496)..(496)
<223> OTHER INFORMATION: X= is T, K, A, D or H
<220> FEATURE:
<221> NAME/KEY: MISC_FEATURE
<222> LOCATION: (497)..(497)
<223> OTHER INFORMATION: X= is E, T, M, V or K
<220> FEATURE:
<221> NAME/KEY: MISC_FEATURE
<222> LOCATION: (498)..(498)
<223> OTHER INFORMATION: X= is A, I , T, R or P
<220> FEATURE:
<221> NAME/KEY: MISC_FEATURE
<222> LOCATION: (499)..(499)
<223> OTHER INFORMATION: X= is P, T, S or K
<220> FEATURE:
<221> NAME/KEY: MISC_FEATURE
<222> LOCATION: (500)..(500)
<223> OTHER INFORMATION: X= is H, F, Y, D or K
<220> FEATURE:
<221> NAME/KEY: MISC_FEATURE
<222> LOCATION: (501)..(501)
<223> OTHER INFORMATION: X= is S, E or Q
<220> FEATURE:
<221> NAME/KEY: MISC_FEATURE
<222> LOCATION: (502)..(502)
<223> OTHER INFORMATION: X= is I, E, A, G or D
<220> FEATURE:
<221> NAME/KEY: MISC_FEATURE
<222> LOCATION: (503)..(503)
<223> OTHER INFORMATION: X= is E, I , L, V or F
```

-continued

```
<220> FEATURE:
<221> NAME/KEY: MISC_FEATURE
<222> LOCATION: (504)..(504)
<223> OTHER INFORMATION: X= is D, A, F, M, V or Y
<220> FEATURE:
<221> NAME/KEY: MISC_FEATURE
<222> LOCATION: (505)..(505)
<223> OTHER INFORMATION: X= is M, G, K, S or D
<220> FEATURE:
<221> NAME/KEY: MISC_FEATURE
<222> LOCATION: (506)..(506)
<223> OTHER INFORMATION: X= is M, K, D, F or M
<220> FEATURE:
<221> NAME/KEY: MISC_FEATURE
<222> LOCATION: (507)..(507)
<223> OTHER INFORMATION: X= is N, G, T or S
<220> FEATURE:
<221> NAME/KEY: MISC_FEATURE
<222> LOCATION: (508)..(508)
<223> OTHER INFORMATION: X= is R, K, S, F, M or A
<220> FEATURE:
<221> NAME/KEY: MISC_FEATURE
<222> LOCATION: (509)..(509)
<223> OTHER INFORMATION: X= is Y, N, P or D
<220> FEATURE:
<221> NAME/KEY: MISC_FEATURE
<222> LOCATION: (510)..(510)
<223> OTHER INFORMATION: X= is Y, Q, L or K
<220> FEATURE:
<221> NAME/KEY: MISC_FEATURE
<222> LOCATION: (511)..(511)
<223> OTHER INFORMATION: X= is F
<220> FEATURE:
<221> NAME/KEY: MISC_FEATURE
<222> LOCATION: (512)..(512)
<223> OTHER INFORMATION: X= is G
<220> FEATURE:
<221> NAME/KEY: MISC_FEATURE
<222> LOCATION: (513)..(513)
<223> OTHER INFORMATION: X= is A
<220> FEATURE:
<221> NAME/KEY: MISC_FEATURE
<222> LOCATION: (514)..(514)
<223> OTHER INFORMATION: X= is G, L, V, F, N or K
<220> FEATURE:
<221> NAME/KEY: MISC_FEATURE
<222> LOCATION: (515)..(515)
<223> OTHER INFORMATION: X= is Q, T, S, D or K
<220> FEATURE:
<221> NAME/KEY: MISC_FEATURE
<222> LOCATION: (516)..(516)
<223> OTHER INFORMATION: X= is F, R, I, L or Y
<220> FEATURE:
<221> NAME/KEY: MISC_FEATURE
<222> LOCATION: (517)..(517)
<223> OTHER INFORMATION: X= is D, N, A, V, S or E
<220> FEATURE:
<221> NAME/KEY: MISC_FEATURE
<222> LOCATION: (518)..(518)
<223> OTHER INFORMATION: X= is L, Q, D, F, V or E
<220> FEATURE:
<221> NAME/KEY: MISC_FEATURE
<222> LOCATION: (519)..(519)
<223> OTHER INFORMATION: X= is T, I , V or P
<220> FEATURE:
<221> NAME/KEY: MISC_FEATURE
<222> LOCATION: (520)..(520)
<223> OTHER INFORMATION: X= is P, A, S, D or G
<220> FEATURE:
<221> NAME/KEY: MISC_FEATURE
<222> LOCATION: (521)..(521)
<223> OTHER INFORMATION: X= is Y, L, V, I, E or F
<220> FEATURE:
<221> NAME/KEY: MISC_FEATURE
<222> LOCATION: (522)..(522)
<223> OTHER INFORMATION: X= is G, E, P, N or D
<220> FEATURE:
<221> NAME/KEY: MISC_FEATURE
<222> LOCATION: (523)..(523)
```

```
-continued

<223> OTHER INFORMATION: X= is E, K, Q, D, T, V or I
<220> FEATURE:
<221> NAME/KEY: MISC_FEATURE
<222> LOCATION: (524)..(524)
<223> OTHER INFORMATION: X= is W, F, T, D, A, L, M or Y
<220> FEATURE:
<221> NAME/KEY: MISC_FEATURE
<222> LOCATION: (525)..(525)
<223> OTHER INFORMATION: X= is T, Y, S, W, G, A or V
<220> FEATURE:
<221> NAME/KEY: MISC_FEATURE
<222> LOCATION: (526)..(526)
<223> OTHER INFORMATION: X= is E, F, Q, R, K, N, D or P
<220> FEATURE:
<221> NAME/KEY: MISC_FEATURE
<222> LOCATION: (527)..(527)
<223> OTHER INFORMATION: X= is E, D, N, I, A, Y, H or L
<220> FEATURE:
<221> NAME/KEY: MISC_FEATURE
<222> LOCATION: (528)..(528)
<223> OTHER INFORMATION: X= is A
<220> FEATURE:
<221> NAME/KEY: MISC_FEATURE
<222> LOCATION: (529)..(529)
<223> OTHER INFORMATION: X= is G, A, E, Q, C, R or V
<220> FEATURE:
<221> NAME/KEY: MISC_FEATURE
<222> LOCATION: (530)..(530)
<223> OTHER INFORMATION: X= is E, H, N, K, R or S
<220> FEATURE:
<221> NAME/KEY: MISC_FEATURE
<222> LOCATION: (531)..(531)
<223> OTHER INFORMATION: X= is R, I, Y, D or K
<220> FEATURE:
<221> NAME/KEY: MISC_FEATURE
<222> LOCATION: (532)..(532)
<223> OTHER INFORMATION: X= is A
<220> FEATURE:
<221> NAME/KEY: MISC_FEATURE
<222> LOCATION: (533)..(533)
<223> OTHER INFORMATION: X= is A, L, F, G, D, V or E
<220> FEATURE:
<221> NAME/KEY: MISC_FEATURE
<222> LOCATION: (534)..(534)
<223> OTHER INFORMATION: X= is L, Y, I, V, A or H
<220> FEATURE:
<221> NAME/KEY: MISC_FEATURE
<222> LOCATION: (535)..(535)
<223> OTHER INFORMATION: X= is S, M, L, T or I
<220> FEATURE:
<221> NAME/KEY: MISC_FEATURE
<222> LOCATION: (536)..(536)
<223> OTHER INFORMATION: X= is E, F, L, R, Y, W or I
<220> FEATURE:
<221> NAME/KEY: MISC_FEATURE
<222> LOCATION: (537)..(537)
<223> OTHER INFORMATION: X= is R, E, P, D, Q, A or K
<220> FEATURE:
<221> NAME/KEY: MISC_FEATURE
<222> LOCATION: (538)..(538)
<223> OTHER INFORMATION: X= is L
<220> FEATURE:
<221> NAME/KEY: MISC_FEATURE
<222> LOCATION: (539)..(539)
<223> OTHER INFORMATION: X= is F, H, Y, K or T
<220> FEATURE:
<221> NAME/KEY: MISC_FEATURE
<222> LOCATION: (540)..(540)
<223> OTHER INFORMATION: X= is A, R, Q, E, S, I, L, Y, K or N
<220> FEATURE:
<221> NAME/KEY: MISC_FEATURE
<222> LOCATION: (541)..(541)
<223> OTHER INFORMATION: X= is N, K, I, S, E, R, F or T
<220> FEATURE:
<221> NAME/KEY: MISC_FEATURE
<222> LOCATION: (542)..(542)
<223> OTHER INFORMATION: X= is L, P, M, I, T, Y, K or F
<220> FEATURE:
<221> NAME/KEY: MISC_FEATURE
```

```
<222> LOCATION: (543)..(543)
<223> OTHER INFORMATION: X= is W, L, F, N, E or G
<220> FEATURE:
<221> NAME/KEY: MISC_FEATURE
<222> LOCATION: (544)..(544)
<223> OTHER INFORMATION: X= is G, K, P, E, N, S, L or M
<220> FEATURE:
<221> NAME/KEY: MISC_FEATURE
<222> LOCATION: (545)..(545)
<223> OTHER INFORMATION: X= is R, E, D, I, L, K, N or W
<220> FEATURE:
<221> NAME/KEY: MISC_FEATURE
<222> LOCATION: (546)..(546)
<223> OTHER INFORMATION: X= is L, I, K, Y, E or F
<220> FEATURE:
<221> NAME/KEY: MISC_FEATURE
<222> LOCATION: (547)..(547)
<223> OTHER INFORMATION: X= is E, Q, S, K, L or I
<220> FEATURE:
<221> NAME/KEY: MISC_FEATURE
<222> LOCATION: (548)..(548)
<223> OTHER INFORMATION: X= is G, Q, K, H, R, E or P
<220> FEATURE:
<221> NAME/KEY: MISC_FEATURE
<222> LOCATION: (549)..(549)
<223> OTHER INFORMATION: X= is E
<220> FEATURE:
<221> NAME/KEY: MISC_FEATURE
<222> LOCATION: (550)..(550)
<223> OTHER INFORMATION: X= is E, K, R, A, N, M or G
<220> FEATURE:
<221> NAME/KEY: MISC_FEATURE
<222> LOCATION: (551)..(551)
<223> OTHER INFORMATION: X= is R, K E, G, N or D
<220> FEATURE:
<221> NAME/KEY: MISC_FEATURE
<222> LOCATION: (552)..(552)
<223> OTHER INFORMATION: X= is L
<220> FEATURE:
<221> NAME/KEY: MISC_FEATURE
<222> LOCATION: (553)..(553)
<223> OTHER INFORMATION: X= is L, E, W, K, D or C
<220> FEATURE:
<221> NAME/KEY: MISC_FEATURE
<222> LOCATION: (554)..(554)
<223> OTHER INFORMATION: X= is W, N, F, Q, E, G, R, K, S or M
<220> FEATURE:
<221> NAME/KEY: MISC_FEATURE
<222> LOCATION: (555)..(555)
<223> OTHER INFORMATION: X= is L
<220> FEATURE:
<221> NAME/KEY: MISC_FEATURE
<222> LOCATION: (556)..(556)
<223> OTHER INFORMATION: X= is Y, L , F or C
<220> FEATURE:
<221> NAME/KEY: MISC_FEATURE
<222> LOCATION: (557)..(557)
<223> OTHER INFORMATION: X= is R, H, Q, F, Y, K, E, I, V or L
<220> FEATURE:
<221> NAME/KEY: MISC_FEATURE
<222> LOCATION: (558)..(558)
<223> OTHER INFORMATION: X= is E, D, N, K or P
<220> FEATURE:
<221> NAME/KEY: MISC_FEATURE
<222> LOCATION: (559)..(559)
<223> OTHER INFORMATION: X= is I
<220> FEATURE:
<221> NAME/KEY: MISC_FEATURE
<222> LOCATION: (560)..(560)
<223> OTHER INFORMATION: X= is E
<220> FEATURE:
<221> NAME/KEY: MISC_FEATURE
<222> LOCATION: (561)..(561)
<223> OTHER INFORMATION: X= is R, K, M, I, L, Q or G
<220> FEATURE:
<221> NAME/KEY: MISC_FEATURE
<222> LOCATION: (562)..(562)
<223> OTHER INFORMATION: X= is P
<220> FEATURE:
```

-continued

```
<221> NAME/KEY: MISC_FEATURE
<222> LOCATION: (563)..(563)
<223> OTHER INFORMATION: X= is L
<220> FEATURE:
<221> NAME/KEY: MISC_FEATURE
<222> LOCATION: (564)..(564)
<223> OTHER INFORMATION: X= is S, I, A, V, C or L
<220> FEATURE:
<221> NAME/KEY: MISC_FEATURE
<222> LOCATION: (565)..(565)
<223> OTHER INFORMATION: X= is A, R, E, P, F, S, N, T or V
<220> FEATURE:
<221> NAME/KEY: MISC_FEATURE
<222> LOCATION: (566)..(566)
<223> OTHER INFORMATION: X= is V
<220> FEATURE:
<221> NAME/KEY: MISC_FEATURE
<222> LOCATION: (567)..(567)
<223> OTHER INFORMATION: X= is L
<220> FEATURE:
<221> NAME/KEY: MISC_FEATURE
<222> LOCATION: (568)..(568)
<223> OTHER INFORMATION: X= is A, F, Y, S, V, K, Q or P
<220> FEATURE:
<221> NAME/KEY: MISC_FEATURE
<222> LOCATION: (569)..(569)
<223> OTHER INFORMATION: X= is H, D, S, R, Q or E
<220> FEATURE:
<221> NAME/KEY: MISC_FEATURE
<222> LOCATION: (570)..(570)
<223> OTHER INFORMATION: X= is M
<220> FEATURE:
<221> NAME/KEY: MISC_FEATURE
<222> LOCATION: (571)..(571)
<223> OTHER INFORMATION: X= is E
<220> FEATURE:
<221> NAME/KEY: MISC_FEATURE
<222> LOCATION: (572)..(572)
<223> OTHER INFORMATION: X= is A, E, K, F, R, L, V, D or T
<220> FEATURE:
<221> NAME/KEY: MISC_FEATURE
<222> LOCATION: (573)..(573)
<223> OTHER INFORMATION: X= is T, R, W, N, E, A, S or P
<220> FEATURE:
<221> NAME/KEY: MISC_FEATURE
<222> LOCATION: (574)..(574)
<223> OTHER INFORMATION: X= is G
<220> FEATURE:
<221> NAME/KEY: MISC_FEATURE
<222> LOCATION: (575)..(575)
<223> OTHER INFORMATION: X= is V, I or F
<220> FEATURE:
<221> NAME/KEY: MISC_FEATURE
<222> LOCATION: (576)..(576)
<223> OTHER INFORMATION: X= is R, K, Y, T, P or G
<220> FEATURE:
<221> NAME/KEY: MISC_FEATURE
<222> LOCATION: (577)..(577)
<223> OTHER INFORMATION: X= is L, V, I, M, F or G
<220> FEATURE:
<221> NAME/KEY: MISC_FEATURE
<222> LOCATION: (578)..(578)
<223> OTHER INFORMATION: X= is D
<220> FEATURE:
<221> NAME/KEY: MISC_FEATURE
<222> LOCATION: (579)..(579)
<223> OTHER INFORMATION: X= is V, I, K, A, P, T or F
<220> FEATURE:
<221> NAME/KEY: MISC_FEATURE
<222> LOCATION: (580)..(580)
<223> OTHER INFORMATION: X= is A, P, E, R, K or D
<220> FEATURE:
<221> NAME/KEY: MISC_FEATURE
<222> LOCATION: (581)..(581)
<223> OTHER INFORMATION: X= is Y, L, K, V, F or R
<220> FEATURE:
<221> NAME/KEY: MISC_FEATURE
<222> LOCATION: (582)..(582)
<223> OTHER INFORMATION: X= is L
```

```
<220> FEATURE:
<221> NAME/KEY: MISC_FEATURE
<222> LOCATION: (583)..(583)
<223> OTHER INFORMATION: X= is K
<220> FEATURE:
<221> NAME/KEY: MISC_FEATURE
<222> LOCATION: (584)..(584)
<223> OTHER INFORMATION: X= is A, T, Q, E, N, D or K
<220> FEATURE:
<221> NAME/KEY: MISC_FEATURE
<222> LOCATION: (585)..(585)
<223> OTHER INFORMATION: X= is L
<220> FEATURE:
<221> NAME/KEY: MISC_FEATURE
<222> LOCATION: (586)..(586)
<223> OTHER INFORMATION: X= is S
<220> FEATURE:
<221> NAME/KEY: MISC_FEATURE
<222> LOCATION: (587)..(587)
<223> OTHER INFORMATION: X= is L, F, K, D, A, E, S, Q or Y
<220> FEATURE:
<221> NAME/KEY: MISC_FEATURE
<222> LOCATION: (588)..(588)
<223> OTHER INFORMATION: X= is E, H, N, K, R or Q
<220> FEATURE:
<221> NAME/KEY: MISC_FEATURE
<222> LOCATION: (589)..(589)
<223> OTHER INFORMATION: X= is V, L, I, F, Y or E
<220> FEATURE:
<221> NAME/KEY: MISC_FEATURE
<222> LOCATION: (590)..(590)
<223> OTHER INFORMATION: X= is A, E, S, C, D, T, G or N
<220> FEATURE:
<221> NAME/KEY: MISC_FEATURE
<222> LOCATION: (591)..(591)
<223> OTHER INFORMATION: X= is E, K, M, H, L, A, D or R
<220> FEATURE:
<221> NAME/KEY: MISC_FEATURE
<222> LOCATION: (592)..(592)
<223> OTHER INFORMATION: X= is E, R, K, Q or N
<220> FEATURE:
<221> NAME/KEY: MISC_FEATURE
<222> LOCATION: (593)..(593)
<223> OTHER INFORMATION: X= is I, M, L or P
<220> FEATURE:
<221> NAME/KEY: MISC_FEATURE
<222> LOCATION: (594)..(594)
<223> OTHER INFORMATION: X= is A, R, E, D, K, S, N, G or C
<220> FEATURE:
<221> NAME/KEY: MISC_FEATURE
<222> LOCATION: (595)..(595)
<223> OTHER INFORMATION: X= is  R, K, E, A or T
<220> FEATURE:
<221> NAME/KEY: MISC_FEATURE
<222> LOCATION: (596)..(596)
<223> OTHER INFORMATION: X= is  L
<220> FEATURE:
<221> NAME/KEY: MISC_FEATURE
<222> LOCATION: (597)..(597)
<223> OTHER INFORMATION: X= is  E, K, S, A, L, R or D
<220> FEATURE:
<221> NAME/KEY: MISC_FEATURE
<222> LOCATION: (598)..(598)
<223> OTHER INFORMATION: X= is  A, E, G, T, K or Q
<220> FEATURE:
<221> NAME/KEY: MISC_FEATURE
<222> LOCATION: (599)..(599)
<223> OTHER INFORMATION: X= is E, K, Q or R
<220> FEATURE:
<221> NAME/KEY: MISC_FEATURE
<222> LOCATION: (600)..(600)
<223> OTHER INFORMATION: X= is I
<220> FEATURE:
<221> NAME/KEY: MISC_FEATURE
<222> LOCATION: (601)..(601)
<223> OTHER INFORMATION: X= is F, Y or H
<220> FEATURE:
<221> NAME/KEY: MISC_FEATURE
<222> LOCATION: (602)..(602)
```

-continued

```
<223> OTHER INFORMATION: X= is R, T, E, N, K or V
<220> FEATURE:
<221> NAME/KEY: MISC_FEATURE
<222> LOCATION: (603)..(603)
<223> OTHER INFORMATION: X= is L, I, H, E, Y or A
<220> FEATURE:
<221> NAME/KEY: MISC_FEATURE
<222> LOCATION: (604)..(604)
<223> OTHER INFORMATION: X= is P or G
<220> FEATURE:
<221> NAME/KEY: MISC_FEATURE
<222> LOCATION: (605)..(605)
<223> OTHER INFORMATION: X= is E or A
<220> FEATURE:
<221> NAME/KEY: MISC_FEATURE
<222> LOCATION: (606)..(606)
<223> OTHER INFORMATION: X= is V
<220> FEATURE:
<221> NAME/KEY: MISC_FEATURE
<222> LOCATION: (607)..(607)
<223> OTHER INFORMATION: X= is K
<220> FEATURE:
<221> NAME/KEY: MISC_FEATURE
<222> LOCATION: (608)..(608)
<223> OTHER INFORMATION: X= is Q or P
<220> FEATURE:
<221> NAME/KEY: MISC_FEATURE
<222> LOCATION: (609)..(609)
<223> OTHER INFORMATION: X= is L or Y
<220> FEATURE:
<221> NAME/KEY: MISC_FEATURE
<222> LOCATION: (610)..(610)
<223> OTHER INFORMATION: X= is E or T
<220> FEATURE:
<221> NAME/KEY: MISC_FEATURE
<222> LOCATION: (611)..(611)
<223> OTHER INFORMATION: X= is Q or P
<220> FEATURE:
<221> NAME/KEY: MISC_FEATURE
<222> LOCATION: (612)..(612)
<223> OTHER INFORMATION: X= is D or V
<220> FEATURE:
<221> NAME/KEY: MISC_FEATURE
<222> LOCATION: (613)..(613)
<223> OTHER INFORMATION: X= is A
<220> FEATURE:
<221> NAME/KEY: MISC_FEATURE
<222> LOCATION: (614)..(614)
<223> OTHER INFORMATION: X= is G
<220> FEATURE:
<221> NAME/KEY: MISC_FEATURE
<222> LOCATION: (615)..(615)
<223> OTHER INFORMATION: X= is H, T, E, Q, Y or V
<220> FEATURE:
<221> NAME/KEY: MISC_FEATURE
<222> LOCATION: (616)..(616)
<223> OTHER INFORMATION: X= is P, E, R, A, Q or V
<220> FEATURE:
<221> NAME/KEY: MISC_FEATURE
<222> LOCATION: (617)..(617)
<223> OTHER INFORMATION: X= is F
<220> FEATURE:
<221> NAME/KEY: MISC_FEATURE
<222> LOCATION: (618)..(618)
<223> OTHER INFORMATION: X= is N
<220> FEATURE:
<221> NAME/KEY: MISC_FEATURE
<222> LOCATION: (619)..(619)
<223> OTHER INFORMATION: X= is L, I, V or P
<220> FEATURE:
<221> NAME/KEY: MISC_FEATURE
<222> LOCATION: (620)..(620)
<223> OTHER INFORMATION: X= is N
<220> FEATURE:
<221> NAME/KEY: MISC_FEATURE
<222> LOCATION: (621)..(621)
<223> OTHER INFORMATION: X= is S
<220> FEATURE:
<221> NAME/KEY: MISC_FEATURE
```

```
<222> LOCATION: (622)..(622)
<223> OTHER INFORMATION: X= is R, P, T, S or V
<220> FEATURE:
<221> NAME/KEY: MISC_FEATURE
<222> LOCATION: (623)..(623)
<223> OTHER INFORMATION: X= is K
<220> FEATURE:
<221> NAME/KEY: MISC_FEATURE
<222> LOCATION: (624)..(624)
<223> OTHER INFORMATION: X= is Q
<220> FEATURE:
<221> NAME/KEY: MISC_FEATURE
<222> LOCATION: (625)..(625)
<223> OTHER INFORMATION: X= is L
<220> FEATURE:
<221> NAME/KEY: MISC_FEATURE
<222> LOCATION: (626)..(626)
<223> OTHER INFORMATION: X= is E, A, S, G, Q or R
<220> FEATURE:
<221> NAME/KEY: MISC_FEATURE
<222> LOCATION: (627)..(627)
<223> OTHER INFORMATION: X= is R, E, Y, T, H, V or K
<220> FEATURE:
<221> NAME/KEY: MISC_FEATURE
<222> LOCATION: (628)..(628)
<223> OTHER INFORMATION: X= is V, I, F, L or K
<220> FEATURE:
<221> NAME/KEY: MISC_FEATURE
<222> LOCATION: (629)..(629)
<223> OTHER INFORMATION: X= is L
<220> FEATURE:
<221> NAME/KEY: MISC_FEATURE
<222> LOCATION: (630)..(630)
<223> OTHER INFORMATION: X= is F
<220> FEATURE:
<221> NAME/KEY: MISC_FEATURE
<222> LOCATION: (631)..(631)
<223> OTHER INFORMATION: X= is D or E
<220> FEATURE:
<221> NAME/KEY: MISC_FEATURE
<222> LOCATION: (632)..(632)
<223> OTHER INFORMATION: X= is E, R, K, Y or A
<220> FEATURE:
<221> NAME/KEY: MISC_FEATURE
<222> LOCATION: (633)..(633)
<223> OTHER INFORMATION: X= is L
<220> FEATURE:
<221> NAME/KEY: MISC_FEATURE
<222> LOCATION: (634)..(634)
<223> OTHER INFORMATION: X= is G, R, K, Q, N or W
<220> FEATURE:
<221> NAME/KEY: MISC_FEATURE
<222> LOCATION: (635)..(635)
<223> OTHER INFORMATION: X= is L
<220> FEATURE:
<221> NAME/KEY: MISC_FEATURE
<222> LOCATION: (636)..(636)
<223> OTHER INFORMATION: X= is P
<220> FEATURE:
<221> NAME/KEY: MISC_FEATURE
<222> LOCATION: (637)..(637)
<223> OTHER INFORMATION: X= is A, P, T, S, V or I
<220> FEATURE:
<221> NAME/KEY: MISC_FEATURE
<222> LOCATION: (638)..(638)
<223> OTHER INFORMATION: X= is I, L, V, T or R
<220> FEATURE:
<221> NAME/KEY: MISC_FEATURE
<222> LOCATION: (639)..(639)
<223> OTHER INFORMATION: X= is G, R or K
<220> FEATURE:
<221> NAME/KEY: MISC_FEATURE
<222> LOCATION: (640)..(640)
<223> OTHER INFORMATION: X= is K
<220> FEATURE:
<221> NAME/KEY: MISC_FEATURE
<222> LOCATION: (641)..(641)
<223> OTHER INFORMATION: X= is T
<220> FEATURE:
```

```
<221> NAME/KEY: MISC_FEATURE
<222> LOCATION: (642)..(642)
<223> OTHER INFORMATION: X= is E, Q, G, K, P, S, T or A
<220> FEATURE:
<221> NAME/KEY: MISC_FEATURE
<222> LOCATION: (643)..(643)
<223> OTHER INFORMATION: X= is K or D
<220> FEATURE:
<221> NAME/KEY: MISC_FEATURE
<222> LOCATION: (644)..(644)
<223> OTHER INFORMATION: X= is T
<220> FEATURE:
<221> NAME/KEY: MISC_FEATURE
<222> LOCATION: (645)..(645)
<223> OTHER INFORMATION: X= is G
<220> FEATURE:
<221> NAME/KEY: MISC_FEATURE
<222> LOCATION: (646)..(646)
<223> OTHER INFORMATION: X= is K, Y, A, E, D or R
<220> FEATURE:
<221> NAME/KEY: MISC_FEATURE
<222> LOCATION: (647)..(647)
<223> OTHER INFORMATION: X= is R, Y, P, N or D
<220> FEATURE:
<221> NAME/KEY: MISC_FEATURE
<222> LOCATION: (648)..(648)
<223> OTHER INFORMATION: X= is S
<220> FEATURE:
<221> NAME/KEY: MISC_FEATURE
<222> LOCATION: (649)..(649)
<223> OTHER INFORMATION: X= is T
<220> FEATURE:
<221> NAME/KEY: MISC_FEATURE
<222> LOCATION: (650)..(650)
<223> OTHER INFORMATION: X= is S, A, E, D, R or N
<220> FEATURE:
<221> NAME/KEY: MISC_FEATURE
<222> LOCATION: (651)..(651)
<223> OTHER INFORMATION: X= is A, Q, M, S, E, I or D
<220> FEATURE:
<221> NAME/KEY: MISC_FEATURE
<222> LOCATION: (652)..(652)
<223> OTHER INFORMATION: X= is E
<220> FEATURE:
<221> NAME/KEY: MISC_FEATURE
<222> LOCATION: (653)..(653)
<223> OTHER INFORMATION: X= is V
<220> FEATURE:
<221> NAME/KEY: MISC_FEATURE
<222> LOCATION: (654)..(654)
<223> OTHER INFORMATION: X= is L
<220> FEATURE:
<221> NAME/KEY: MISC_FEATURE
<222> LOCATION: (655)..(655)
<223> OTHER INFORMATION: X= is E, Q or N
<220> FEATURE:
<221> NAME/KEY: MISC_FEATURE
<222> LOCATION: (656)..(656)
<223> OTHER INFORMATION: X= is A, E, N, T, K, Q or G
<220> FEATURE:
<221> NAME/KEY: MISC_FEATURE
<222> LOCATION: (657)..(657)
<223> OTHER INFORMATION: X= is L
<220> FEATURE:
<221> NAME/KEY: MISC_FEATURE
<222> LOCATION: (658)..(658)
<223> OTHER INFORMATION: X= is R, A, I, S or V
<220> FEATURE:
<221> NAME/KEY: MISC_FEATURE
<222> LOCATION: (659)..(659)
<223> OTHER INFORMATION: X= is E, G, I, N, H, L, K, P, T or V
<220> FEATURE:
<221> NAME/KEY: MISC_FEATURE
<222> LOCATION: (660)..(660)
<223> OTHER INFORMATION: X= is A, Q, D, E, H or Y
<220> FEATURE:
<221> NAME/KEY: MISC_FEATURE
<222> LOCATION: (661)..(661)
<223> OTHER INFORMATION: X= is H
```

-continued

```
<220> FEATURE:
<221> NAME/KEY: MISC_FEATURE
<222> LOCATION: (662)..(662)
<223> OTHER INFORMATION: X= is P
<220> FEATURE:
<221> NAME/KEY: MISC_FEATURE
<222> LOCATION: (663)..(663)
<223> OTHER INFORMATION: X= is E
<220> FEATURE:
<221> NAME/KEY: MISC_FEATURE
<222> LOCATION: (664)..(664)
<223> OTHER INFORMATION: X= is K
<220> FEATURE:
<221> NAME/KEY: MISC_FEATURE
<222> LOCATION: (665)..(665)
<223> OTHER INFORMATION: X= is Q
<220> FEATURE:
<221> NAME/KEY: MISC_FEATURE
<222> LOCATION: (666)..(666)
<223> OTHER INFORMATION: X= is I
<220> FEATURE:
<221> NAME/KEY: MISC_FEATURE
<222> LOCATION: (667)..(667)
<223> OTHER INFORMATION: X= is V, P, C, I or A
<220> FEATURE:
<221> NAME/KEY: MISC_FEATURE
<222> LOCATION: (668)..(668)
<223> OTHER INFORMATION: X= is E, H, R, K, P, S, N or I
<220> FEATURE:
<221> NAME/KEY: MISC_FEATURE
<222> LOCATION: (669)..(669)
<223> OTHER INFORMATION: X= is K, L, E, V, N, D or T
<220> FEATURE:
<221> NAME/KEY: MISC_FEATURE
<222> LOCATION: (670)..(670)
<223> OTHER INFORMATION: X= is I
<220> FEATURE:
<221> NAME/KEY: MISC_FEATURE
<222> LOCATION: (671)..(671)
<223> OTHER INFORMATION: X= is L
<220> FEATURE:
<221> NAME/KEY: MISC_FEATURE
<222> LOCATION: (672)..(672)
<223> OTHER INFORMATION: X= is Q or K
<220> FEATURE:
<221> NAME/KEY: MISC_FEATURE
<222> LOCATION: (673)..(673)
<223> OTHER INFORMATION: X= is Q, N, D, E or H
<220> FEATURE:
<221> NAME/KEY: MISC_FEATURE
<222> LOCATION: (674)..(674)
<223> OTHER INFORMATION: X= is Y
<220> FEATURE:
<221> NAME/KEY: MISC_FEATURE
<222> LOCATION: (675)..(675)
<223> OTHER INFORMATION: X= is R
<220> FEATURE:
<221> NAME/KEY: MISC_FEATURE
<222> LOCATION: (676)..(676)
<223> OTHER INFORMATION: X= is E, T, Q, G, K or M
<220> FEATURE:
<221> NAME/KEY: MISC_FEATURE
<222> LOCATION: (677)..(677)
<223> OTHER INFORMATION: X= is L
<220> FEATURE:
<221> NAME/KEY: MISC_FEATURE
<222> LOCATION: (678)..(678)
<223> OTHER INFORMATION: X= is T, S, N, Y, H, A, Q or G
<220> FEATURE:
<221> NAME/KEY: MISC_FEATURE
<222> LOCATION: (679)..(679)
<223> OTHER INFORMATION: X= is K
<220> FEATURE:
<221> NAME/KEY: MISC_FEATURE
<222> LOCATION: (680)..(680)
<223> OTHER INFORMATION: X= is L
<220> FEATURE:
<221> NAME/KEY: MISC_FEATURE
<222> LOCATION: (681)..(681)
```

```
<223> OTHER INFORMATION: X= is K
<220> FEATURE:
<221> NAME/KEY: MISC_FEATURE
<222> LOCATION: (682)..(682)
<223> OTHER INFORMATION: X= is S
<220> FEATURE:
<221> NAME/KEY: MISC_FEATURE
<222> LOCATION: (683)..(683)
<223> OTHER INFORMATION: X= is T
<220> FEATURE:
<221> NAME/KEY: MISC_FEATURE
<222> LOCATION: (684)..(684)
<223> OTHER INFORMATION: X= is Y
<220> FEATURE:
<221> NAME/KEY: MISC_FEATURE
<222> LOCATION: (685)..(685)
<223> OTHER INFORMATION: X= is I, V, L, T or A
<220> FEATURE:
<221> NAME/KEY: MISC_FEATURE
<222> LOCATION: (686)..(686)
<223> OTHER INFORMATION: X= is D
<220> FEATURE:
<221> NAME/KEY: MISC_FEATURE
<222> LOCATION: (687)..(687)
<223> OTHER INFORMATION: X= is P, A, G, K , V, S or G
<220> FEATURE:
<221> NAME/KEY: MISC_FEATURE
<222> LOCATION: (688)..(688)
<223> OTHER INFORMATION: X= is L
<220> FEATURE:
<221> NAME/KEY: MISC_FEATURE
<222> LOCATION: (689)..(689)
<223> OTHER INFORMATION: X= is P, R, K or L
<220> FEATURE:
<221> NAME/KEY: MISC_FEATURE
<222> LOCATION: (690)..(690)
<223> OTHER INFORMATION: X= is D, S, R, N, K, P or A
<220> FEATURE:
<221> NAME/KEY: MISC_FEATURE
<222> LOCATION: (691)..(691)
<223> OTHER INFORMATION: X= is L, Y, M, S, V or W
<220> FEATURE:
<221> NAME/KEY: MISC_FEATURE
<222> LOCATION: (692)..(692)
<223> OTHER INFORMATION: X= is I, V, M or L
<220> FEATURE:
<221> NAME/KEY: MISC_FEATURE
<222> LOCATION: (693)..(693)
<223> OTHER INFORMATION: X= is H, S, N, R or D
<220> FEATURE:
<221> NAME/KEY: MISC_FEATURE
<222> LOCATION: (694)..(694)
<223> OTHER INFORMATION: X= is Y
<220> FEATURE:
<221> NAME/KEY: MISC_FEATURE
<222> LOCATION: (695)..(695)
<223> OTHER INFORMATION: X= is V
<220> FEATURE:
<221> NAME/KEY: MISC_FEATURE
<222> LOCATION: (696)..(696)
<223> OTHER INFORMATION: X= is P
<220> FEATURE:
<221> NAME/KEY: MISC_FEATURE
<222> LOCATION: (697)..(697)
<223> OTHER INFORMATION: X= is R, N, E, Q, T, K or D
<220> FEATURE:
<221> NAME/KEY: MISC_FEATURE
<222> LOCATION: (698)..(698)
<223> OTHER INFORMATION: X= is T
<220> FEATURE:
<221> NAME/KEY: MISC_FEATURE
<222> LOCATION: (699)..(699)
<223> OTHER INFORMATION: X= is G
<220> FEATURE:
<221> NAME/KEY: MISC_FEATURE
<222> LOCATION: (700)..(700)
<223> OTHER INFORMATION: X= is R
<220> FEATURE:
<221> NAME/KEY: MISC_FEATURE
```

```
<222> LOCATION: (701)..(701)
<223> OTHER INFORMATION: X= is L, I or V
<220> FEATURE:
<221> NAME/KEY: MISC_FEATURE
<222> LOCATION: (702)..(702)
<223> OTHER INFORMATION: X= is H
<220> FEATURE:
<221> NAME/KEY: MISC_FEATURE
<222> LOCATION: (703)..(703)
<223> OTHER INFORMATION: X= is T
<220> FEATURE:
<221> NAME/KEY: MISC_FEATURE
<222> LOCATION: (704)..(704)
<223> OTHER INFORMATION: X= is R, K, T, S, M, I, N or G
<220> FEATURE:
<221> NAME/KEY: MISC_FEATURE
<222> LOCATION: (705)..(705)
<223> OTHER INFORMATION: X= is F
<220> FEATURE:
<221> NAME/KEY: MISC_FEATURE
<222> LOCATION: (706)..(706)
<223> OTHER INFORMATION: X= is N
<220> FEATURE:
<221> NAME/KEY: MISC_FEATURE
<222> LOCATION: (707)..(707)
<223> OTHER INFORMATION: X= is Q
<220> FEATURE:
<221> NAME/KEY: MISC_FEATURE
<222> LOCATION: (708)..(708)
<223> OTHER INFORMATION: X= is T
<220> FEATURE:
<221> NAME/KEY: MISC_FEATURE
<222> LOCATION: (709)..(709)
<223> OTHER INFORMATION: X= is A, V, G, I, L or M
<220> FEATURE:
<221> NAME/KEY: MISC_FEATURE
<222> LOCATION: (710)..(710)
<223> OTHER INFORMATION: X= is T
<220> FEATURE:
<221> NAME/KEY: MISC_FEATURE
<222> LOCATION: (711)..(711)
<223> OTHER INFORMATION: X= is A
<220> FEATURE:
<221> NAME/KEY: MISC_FEATURE
<222> LOCATION: (712)..(712)
<223> OTHER INFORMATION: X= is T
<220> FEATURE:
<221> NAME/KEY: MISC_FEATURE
<222> LOCATION: (713)..(713)
<223> OTHER INFORMATION: X= is G
<220> FEATURE:
<221> NAME/KEY: MISC_FEATURE
<222> LOCATION: (714)..(714)
<223> OTHER INFORMATION: X= is R
<220> FEATURE:
<221> NAME/KEY: MISC_FEATURE
<222> LOCATION: (715)..(715)
<223> OTHER INFORMATION: X= is L
<220> FEATURE:
<221> NAME/KEY: MISC_FEATURE
<222> LOCATION: (716)..(716)
<223> OTHER INFORMATION: X= is S
<220> FEATURE:
<221> NAME/KEY: MISC_FEATURE
<222> LOCATION: (717)..(717)
<223> OTHER INFORMATION: X= is S
<220> FEATURE:
<221> NAME/KEY: MISC_FEATURE
<222> LOCATION: (718)..(718)
<223> OTHER INFORMATION: X= is S
<220> FEATURE:
<221> NAME/KEY: MISC_FEATURE
<222> LOCATION: (719)..(719)
<223> OTHER INFORMATION: X= is D, E, A, G or F
<220> FEATURE:
<221> NAME/KEY: MISC_FEATURE
<222> LOCATION: (720)..(720)
<223> OTHER INFORMATION: X= is P
<220> FEATURE:
```

```
<221> NAME/KEY: MISC_FEATURE
<222> LOCATION: (721)..(721)
<223> OTHER INFORMATION: X= is L
<220> FEATURE:
<221> NAME/KEY: MISC_FEATURE
<222> LOCATION: (722)..(722)
<223> OTHER INFORMATION: X= is N
<220> FEATURE:
<221> NAME/KEY: MISC_FEATURE
<222> LOCATION: (723)..(723)
<223> OTHER INFORMATION: X= is L
<220> FEATURE:
<221> NAME/KEY: MISC_FEATURE
<222> LOCATION: (724)..(724)
<223> OTHER INFORMATION: X= is Q
<220> FEATURE:
<221> NAME/KEY: MISC_FEATURE
<222> LOCATION: (725)..(725)
<223> OTHER INFORMATION: X= is N or Q
<220> FEATURE:
<221> NAME/KEY: MISC_FEATURE
<222> LOCATION: (726)..(726)
<223> OTHER INFORMATION: X= is I
<220> FEATURE:
<221> NAME/KEY: MISC_FEATURE
<222> LOCATION: (727)..(727)
<223> OTHER INFORMATION: X= is P
<220> FEATURE:
<221> NAME/KEY: MISC_FEATURE
<222> LOCATION: (728)..(728)
<223> OTHER INFORMATION: X= is G
<220> FEATURE:
<221> NAME/KEY: MISC_FEATURE
<222> LOCATION: (729)..(729)
<223> OTHER INFORMATION: X= is V, I, S or T
<220> FEATURE:
<221> NAME/KEY: MISC_FEATURE
<222> LOCATION: (730)..(730)
<223> OTHER INFORMATION: X= is R
<220> FEATURE:
<221> NAME/KEY: MISC_FEATURE
<222> LOCATION: (731)..(731)
<223> OTHER INFORMATION: X= is T, G, S, L, N or Q
<220> FEATURE:
<221> NAME/KEY: MISC_FEATURE
<222> LOCATION: (732)..(732)
<223> OTHER INFORMATION: X= is E
<220> FEATURE:
<221> NAME/KEY: MISC_FEATURE
<222> LOCATION: (733)..(733)
<223> OTHER INFORMATION: X= is L, W, E, F, R or Y
<220> FEATURE:
<221> NAME/KEY: MISC_FEATURE
<222> LOCATION: (734)..(734)
<223> OTHER INFORMATION: X= is G
<220> FEATURE:
<221> NAME/KEY: MISC_FEATURE
<222> LOCATION: (735)..(735)
<223> OTHER INFORMATION: X= is Q, E, R or K
<220> FEATURE:
<221> NAME/KEY: MISC_FEATURE
<222> LOCATION: (736)..(736)
<223> OTHER INFORMATION: X= is R, F, K, E, Q or S
<220> FEATURE:
<221> NAME/KEY: MISC_FEATURE
<222> LOCATION: (737)..(737)
<223> OTHER INFORMATION: X= is I
<220> FEATURE:
<221> NAME/KEY: MISC_FEATURE
<222> LOCATION: (738)..(738)
<223> OTHER INFORMATION: X= is R
<220> FEATURE:
<221> NAME/KEY: MISC_FEATURE
<222> LOCATION: (739)..(739)
<223> OTHER INFORMATION: X= is R, K, E, Q, H or A
<220> FEATURE:
<221> NAME/KEY: MISC_FEATURE
<222> LOCATION: (740)..(740)
<223> OTHER INFORMATION: X= is A
```

```
<220> FEATURE:
<221> NAME/KEY: MISC_FEATURE
<222> LOCATION: (741)..(741)
<223> OTHER INFORMATION: X= is F
<220> FEATURE:
<221> NAME/KEY: MISC_FEATURE
<222> LOCATION: (742)..(742)
<223> OTHER INFORMATION: X= is V
<220> FEATURE:
<221> NAME/KEY: MISC_FEATURE
<222> LOCATION: (743)..(743)
<223> OTHER INFORMATION: X= is A, P, S, I or V
<220> FEATURE:
<221> NAME/KEY: MISC_FEATURE
<222> LOCATION: (744)..(744)
<223> OTHER INFORMATION: X= is E, Q, P, S, R or A
<220> FEATURE:
<221> NAME/KEY: MISC_FEATURE
<222> LOCATION: (745)..(745)
<223> OTHER INFORMATION: X= is E, A, N, D, R, F, S, T, H or P
<220> FEATURE:
<221> NAME/KEY: MISC_FEATURE
<222> LOCATION: (746)..(746)
<223> OTHER INFORMATION: X= is S, D, P, E, R, K or H
<220> FEATURE:
<221> NAME/KEY: MISC_FEATURE
<222> LOCATION: (747)..(747)
<223> OTHER INFORMATION: X= is G, D, S, N or L
<220> FEATURE:
<221> NAME/KEY: MISC_FEATURE
<222> LOCATION: (748)..(748)
<223> OTHER INFORMATION: X= is W, Y, Q, G or D
<220> FEATURE:
<221> NAME/KEY: MISC_FEATURE
<222> LOCATION: (749)..(749)
<223> OTHER INFORMATION: X= is L, A, M, F, V, K, W, Y, R or G
<220> FEATURE:
<221> NAME/KEY: MISC_FEATURE
<222> LOCATION: (750)..(750)
<223> OTHER INFORMATION: X= is I
<220> FEATURE:
<221> NAME/KEY: MISC_FEATURE
<222> LOCATION: (751)..(751)
<223> OTHER INFORMATION: X= is V, L, F, I or T
<220> FEATURE:
<221> NAME/KEY: MISC_FEATURE
<222> LOCATION: (752)..(752)
<223> OTHER INFORMATION: X= is A, S or G
<220> FEATURE:
<221> NAME/KEY: MISC_FEATURE
<222> LOCATION: (753)..(753)
<223> OTHER INFORMATION: X= is A
<220> FEATURE:
<221> NAME/KEY: MISC_FEATURE
<222> LOCATION: (754)..(754)
<223> OTHER INFORMATION: X= is D
<220> FEATURE:
<221> NAME/KEY: MISC_FEATURE
<222> LOCATION: (755)..(755)
<223> OTHER INFORMATION: X= is Y
<220> FEATURE:
<221> NAME/KEY: MISC_FEATURE
<222> LOCATION: (756)..(756)
<223> OTHER INFORMATION: X= is S
<220> FEATURE:
<221> NAME/KEY: MISC_FEATURE
<222> LOCATION: (757)..(757)
<223> OTHER INFORMATION: X= is Q
<220> FEATURE:
<221> NAME/KEY: MISC_FEATURE
<222> LOCATION: (758)..(758)
<223> OTHER INFORMATION: X= is I
<220> FEATURE:
<221> NAME/KEY: MISC_FEATURE
<222> LOCATION: (759)..(759)
<223> OTHER INFORMATION: X= is E
<220> FEATURE:
<221> NAME/KEY: MISC_FEATURE
<222> LOCATION: (760)..(760)
```

```
<223> OTHER INFORMATION: X= is L
<220> FEATURE:
<221> NAME/KEY: MISC_FEATURE
<222> LOCATION: (761)..(761)
<223> OTHER INFORMATION: X= is R
<220> FEATURE:
<221> NAME/KEY: MISC_FEATURE
<222> LOCATION: (762)..(762)
<223> OTHER INFORMATION: X= is V, L, I, Y or A
<220> FEATURE:
<221> NAME/KEY: MISC_FEATURE
<222> LOCATION: (763)..(763)
<223> OTHER INFORMATION: X= is L
<220> FEATURE:
<221> NAME/KEY: MISC_FEATURE
<222> LOCATION: (764)..(764)
<223> OTHER INFORMATION: X= is A
<220> FEATURE:
<221> NAME/KEY: MISC_FEATURE
<222> LOCATION: (765)..(765)
<223> OTHER INFORMATION: X= is L
<220> FEATURE:
<221> NAME/KEY: MISC_FEATURE
<222> LOCATION: (766)..(766)
<223> OTHER INFORMATION: X= is H
<220> FEATURE:
<221> NAME/KEY: MISC_FEATURE
<222> LOCATION: (767)..(767)
<223> OTHER INFORMATION: X= is L
<220> FEATURE:
<221> NAME/KEY: MISC_FEATURE
<222> LOCATION: (768)..(768)
<223> OTHER INFORMATION: X= is S
<220> FEATURE:
<221> NAME/KEY: MISC_FEATURE
<222> LOCATION: (769)..(769)
<223> OTHER INFORMATION: X= is G, E, Q, R, N, D or C
<220> FEATURE:
<221> NAME/KEY: MISC_FEATURE
<222> LOCATION: (770)..(770)
<223> OTHER INFORMATION: X= is D
<220> FEATURE:
<221> NAME/KEY: MISC_FEATURE
<222> LOCATION: (771)..(771)
<223> OTHER INFORMATION: X= is E, P, T, K, Q, R or A
<220> FEATURE:
<221> NAME/KEY: MISC_FEATURE
<222> LOCATION: (772)..(772)
<223> OTHER INFORMATION: X= is N
<220> FEATURE:
<221> NAME/KEY: MISC_FEATURE
<222> LOCATION: (773)..(773)
<223> OTHER INFORMATION: X= is L
<220> FEATURE:
<221> NAME/KEY: MISC_FEATURE
<222> LOCATION: (774)..(774)
<223> OTHER INFORMATION: X= is I
<220> FEATURE:
<221> NAME/KEY: MISC_FEATURE
<222> LOCATION: (775)..(775)
<223> OTHER INFORMATION: X= is R, K, S, Q, T, E, D or A
<220> FEATURE:
<221> NAME/KEY: MISC_FEATURE
<222> LOCATION: (776)..(776)
<223> OTHER INFORMATION: X= is A
<220> FEATURE:
<221> NAME/KEY: MISC_FEATURE
<222> LOCATION: (777)..(777)
<223> OTHER INFORMATION: X= is F
<220> FEATURE:
<221> NAME/KEY: MISC_FEATURE
<222> LOCATION: (778)..(778)
<223> OTHER INFORMATION: X= is Q, R, L, A, K, E, M, I or D
<220> FEATURE:
<221> NAME/KEY: MISC_FEATURE
<222> LOCATION: (779)..(779)
<223> OTHER INFORMATION: X= is E, D, K, N or R
<220> FEATURE:
<221> NAME/KEY: MISC_FEATURE
```

```
<222> LOCATION: (780)..(780)
<223> OTHER INFORMATION: X= is G
<220> FEATURE:
<221> NAME/KEY: MISC_FEATURE
<222> LOCATION: (781)..(781)
<223> OTHER INFORMATION: X= is R, K, E, Q, Y, I or L
<220> FEATURE:
<221> NAME/KEY: MISC_FEATURE
<222> LOCATION: (782)..(782)
<223> OTHER INFORMATION: X= is N
<220> FEATURE:
<221> NAME/KEY: MISC_FEATURE
<222> LOCATION: (783)..(783)
<223> OTHER INFORMATION: X= is E
<220> FEATURE:
<221> NAME/KEY: MISC_FEATURE
<222> LOCATION: (784)..(784)
<223> OTHER INFORMATION: X= is P
<220> FEATURE:
<221> NAME/KEY: MISC_FEATURE
<222> LOCATION: (785)..(785)
<223> OTHER INFORMATION: X= is D
<220> FEATURE:
<221> NAME/KEY: MISC_FEATURE
<222> LOCATION: (786)..(786)
<223> OTHER INFORMATION: X= is K
<220> FEATURE:
<221> NAME/KEY: MISC_FEATURE
<222> LOCATION: (787)..(787)
<223> OTHER INFORMATION: X= is Y
<220> FEATURE:
<221> NAME/KEY: MISC_FEATURE
<222> LOCATION: (788)..(788)
<223> OTHER INFORMATION: X= is P
<220> FEATURE:
<221> NAME/KEY: MISC_FEATURE
<222> LOCATION: (789)..(789)
<223> OTHER INFORMATION: X= is D
<220> FEATURE:
<221> NAME/KEY: MISC_FEATURE
<222> LOCATION: (790)..(790)
<223> OTHER INFORMATION: X= is I
<220> FEATURE:
<221> NAME/KEY: MISC_FEATURE
<222> LOCATION: (791)..(791)
<223> OTHER INFORMATION: X= is H
<220> FEATURE:
<221> NAME/KEY: MISC_FEATURE
<222> LOCATION: (792)..(792)
<223> OTHER INFORMATION: X= is T
<220> FEATURE:
<221> NAME/KEY: MISC_FEATURE
<222> LOCATION: (793)..(793)
<223> OTHER INFORMATION: X= is E, Q, A, R, F, L, I, K or N
<220> FEATURE:
<221> NAME/KEY: MISC_FEATURE
<222> LOCATION: (794)..(794)
<223> OTHER INFORMATION: X= is T
<220> FEATURE:
<221> NAME/KEY: MISC_FEATURE
<222> LOCATION: (795)..(795)
<223> OTHER INFORMATION: X=is A
<220> FEATURE:
<221> NAME/KEY: MISC_FEATURE
<222> LOCATION: (796)..(796)
<223> OTHER INFORMATION: X= is S
<220> FEATURE:
<221> NAME/KEY: MISC_FEATURE
<222> LOCATION: (797)..(797)
<223> OTHER INFORMATION: X= is W, E, Q, R, K, D or M
<220> FEATURE:
<221> NAME/KEY: MISC_FEATURE
<222> LOCATION: (798)..(798)
<223> OTHER INFORMATION: X= is I
<220> FEATURE:
<221> NAME/KEY: MISC_FEATURE
<222> LOCATION: (799)..(799)
<223> OTHER INFORMATION: X= is F
<220> FEATURE:
```

```
<221> NAME/KEY: MISC_FEATURE
<222> LOCATION: (800)..(800)
<223> OTHER INFORMATION: X= is G, S, E, Q, N, H, K or T
<220> FEATURE:
<221> NAME/KEY: MISC_FEATURE
<222> LOCATION: (801)..(801)
<223> OTHER INFORMATION: X= is V
<220> FEATURE:
<221> NAME/KEY: MISC_FEATURE
<222> LOCATION: (802)..(802)
<223> OTHER INFORMATION: X= is P, D, E, K, S, Q or N
<220> FEATURE:
<221> NAME/KEY: MISC_FEATURE
<222> LOCATION: (803)..(803)
<223> OTHER INFORMATION: X= is R, P, E, S, L, M, C or Q
<220> FEATURE:
<221> NAME/KEY: MISC_FEATURE
<222> LOCATION: (804)..(804)
<223> OTHER INFORMATION: X= is E
<220> FEATURE:
<221> NAME/KEY: MISC_FEATURE
<222> LOCATION: (805)..(805)
<223> OTHER INFORMATION: X= is P
<220> FEATURE:
<221> NAME/KEY: MISC_FEATURE
<222> LOCATION: (806)..(806)
<223> OTHER INFORMATION: X= is R
<220> FEATURE:
<221> NAME/KEY: MISC_FEATURE
<222> LOCATION: (807)..(807)
<223> OTHER INFORMATION: X= is D
<220> FEATURE:
<221> NAME/KEY: MISC_FEATURE
<222> LOCATION: (808)..(808)
<223> OTHER INFORMATION: X= is V
<220> FEATURE:
<221> NAME/KEY: MISC_FEATURE
<222> LOCATION: (809)..(809)
<223> OTHER INFORMATION: X= is K
<220> FEATURE:
<221> NAME/KEY: MISC_FEATURE
<222> LOCATION: (810)..(810)
<223> OTHER INFORMATION: X= is A, L , E, Q, T, M or K
<220> FEATURE:
<221> NAME/KEY: MISC_FEATURE
<222> LOCATION: (811)..(811)
<223> OTHER INFORMATION: X= is V
<220> FEATURE:
<221> NAME/KEY: MISC_FEATURE
<222> LOCATION: (812)..(812)
<223> OTHER INFORMATION: X= is T
<220> FEATURE:
<221> NAME/KEY: MISC_FEATURE
<222> LOCATION: (813)..(813)
<223> OTHER INFORMATION: X= is P, D, R, S, E, A or L
<220> FEATURE:
<221> NAME/KEY: MISC_FEATURE
<222> LOCATION: (814)..(814)
<223> OTHER INFORMATION: X= is L, K, E, Q, D, T, N, A or P
<220> FEATURE:
<221> NAME/KEY: MISC_FEATURE
<222> LOCATION: (815)..(815)
<223> OTHER INFORMATION: X= is M
<220> FEATURE:
<221> NAME/KEY: MISC_FEATURE
<222> LOCATION: (816)..(816)
<223> OTHER INFORMATION: X= is R
<220> FEATURE:
<221> NAME/KEY: MISC_FEATURE
<222> LOCATION: (817)..(817)
<223> OTHER INFORMATION: X= is R
<220> FEATURE:
<221> NAME/KEY: MISC_FEATURE
<222> LOCATION: (818)..(818)
<223> OTHER INFORMATION: X= is A, I , R, H, S, Q or N
<220> FEATURE:
<221> NAME/KEY: MISC_FEATURE
<222> LOCATION: (819)..(819)
<223> OTHER INFORMATION: X= is A
```

```
<220> FEATURE:
<221> NAME/KEY: MISC_FEATURE
<222> LOCATION: (820)..(820)
<223> OTHER INFORMATION: X= is K
<220> FEATURE:
<221> NAME/KEY: MISC_FEATURE
<222> LOCATION: (821)..(821)
<223> OTHER INFORMATION: X=is T, A or M
<220> FEATURE:
<221> NAME/KEY: MISC_FEATURE
<222> LOCATION: (822)..(822)
<223> OTHER INFORMATION: X= is V
<220> FEATURE:
<221> NAME/KEY: MISC_FEATURE
<222> LOCATION: (823)..(823)
<223> OTHER INFORMATION: X= is N
<220> FEATURE:
<221> NAME/KEY: MISC_FEATURE
<222> LOCATION: (824)..(824)
<223> OTHER INFORMATION: X= is F or Y
<220> FEATURE:
<221> NAME/KEY: MISC_FEATURE
<222> LOCATION: (825)..(825)
<223> OTHER INFORMATION: X= is G
<220> FEATURE:
<221> NAME/KEY: MISC_FEATURE
<222> LOCATION: (826)..(826)
<223> OTHER INFORMATION: X= is I
<220> FEATURE:
<221> NAME/KEY: MISC_FEATURE
<222> LOCATION: (827)..(827)
<223> OTHER INFORMATION: X= is L, S, I or V
<220> FEATURE:
<221> NAME/KEY: MISC_FEATURE
<222> LOCATION: (828)..(828)
<223> OTHER INFORMATION: X= is Y
<220> FEATURE:
<221> NAME/KEY: MISC_FEATURE
<222> LOCATION: (829)..(829)
<223> OTHER INFORMATION: X= is G
<220> FEATURE:
<221> NAME/KEY: MISC_FEATURE
<222> LOCATION: (830)..(830)
<223> OTHER INFORMATION: X= is M, I, V, S or A
<220> FEATURE:
<221> NAME/KEY: MISC_FEATURE
<222> LOCATION: (831)..(831)
<223> OTHER INFORMATION: X= is S
<220> FEATURE:
<221> NAME/KEY: MISC_FEATURE
<222> LOCATION: (832)..(832)
<223> OTHER INFORMATION: X= is A, P, S or D
<220> FEATURE:
<221> NAME/KEY: MISC_FEATURE
<222> LOCATION: (833)..(833)
<223> OTHER INFORMATION: X= is H, F, Y, A or E
<220> FEATURE:
<221> NAME/KEY: MISC_FEATURE
<222> LOCATION: (834)..(834)
<223> OTHER INFORMATION: X= is G
<220> FEATURE:
<221> NAME/KEY: MISC_FEATURE
<222> LOCATION: (835)..(835)
<223> OTHER INFORMATION: X= is L
<220> FEATURE:
<221> NAME/KEY: MISC_FEATURE
<222> LOCATION: (836)..(836)
<223> OTHER INFORMATION: X= is S
<220> FEATURE:
<221> NAME/KEY: MISC_FEATURE
<222> LOCATION: (837)..(837)
<223> OTHER INFORMATION: X= is Q, E, R, V or H
<220> FEATURE:
<221> NAME/KEY: MISC_FEATURE
<222> LOCATION: (838)..(838)
<223> OTHER INFORMATION: X= is E, S, T, Q, R, N, D or I
<220> FEATURE:
<221> NAME/KEY: MISC_FEATURE
<222> LOCATION: (839)..(839)
```

```
<223> OTHER INFORMATION: X= is L
<220> FEATURE:
<221> NAME/KEY: MISC_FEATURE
<222> LOCATION: (840)..(840)
<223> OTHER INFORMATION: X= is A, G, K, S or N
<220> FEATURE:
<221> NAME/KEY: MISC_FEATURE
<222> LOCATION: (841)..(841)
<223> OTHER INFORMATION: X= is E or A
<220> FEATURE:
<221> NAME/KEY: MISC_FEATURE
<222> LOCATION: (842)..(842)
<223> OTHER INFORMATION: X= is A or G
<220> FEATURE:
<221> NAME/KEY: MISC_FEATURE
<222> LOCATION: (843)..(843)
<223> OTHER INFORMATION: X= is L or K
<220> FEATURE:
<221> NAME/KEY: MISC_FEATURE
<222> LOCATION: (844)..(844)
<223> OTHER INFORMATION: X= is L
<220> FEATURE:
<221> NAME/KEY: MISC_FEATURE
<222> LOCATION: (845)..(845)
<223> OTHER INFORMATION: X= is E
<220> FEATURE:
<221> NAME/KEY: MISC_FEATURE
<222> LOCATION: (846)..(846)
<223> OTHER INFORMATION: X= is Q
<220> FEATURE:
<221> NAME/KEY: MISC_FEATURE
<222> LOCATION: (847)..(847)
<223> OTHER INFORMATION: X= is A
<220> FEATURE:
<221> NAME/KEY: MISC_FEATURE
<222> LOCATION: (848)..(848)
<223> OTHER INFORMATION: X= is A
<220> FEATURE:
<221> NAME/KEY: MISC_FEATURE
<222> LOCATION: (849)..(849)
<223> OTHER INFORMATION: X= is K
<220> FEATURE:
<221> NAME/KEY: MISC_FEATURE
<222> LOCATION: (850)..(850)
<223> OTHER INFORMATION: X= is T
<220> FEATURE:
<221> NAME/KEY: MISC_FEATURE
<222> LOCATION: (851)..(851)
<223> OTHER INFORMATION: X= is G
<220> FEATURE:
<221> NAME/KEY: MISC_FEATURE
<222> LOCATION: (852)..(852)
<223> OTHER INFORMATION: X= is E
<220> FEATURE:
<221> NAME/KEY: MISC_FEATURE
<222> LOCATION: (853)..(853)
<223> OTHER INFORMATION: X= is P
<220> FEATURE:
<221> NAME/KEY: MISC_FEATURE
<222> LOCATION: (854)..(854)
<223> OTHER INFORMATION: X= is F
<220> FEATURE:
<221> NAME/KEY: MISC_FEATURE
<222> LOCATION: (855)..(855)
<223> OTHER INFORMATION: X= is V
<220> FEATURE:
<221> NAME/KEY: MISC_FEATURE
<222> LOCATION: (856)..(856)
<223> OTHER INFORMATION: X= is E
<220> FEATURE:
<221> NAME/KEY: MISC_FEATURE
<222> LOCATION: (857)..(857)
<223> OTHER INFORMATION: X= is I
<220> FEATURE:
<221> NAME/KEY: MISC_FEATURE
<222> LOCATION: (858)..(858)
<223> OTHER INFORMATION: X= is P, D, T, S, N or G
<220> FEATURE:
<221> NAME/KEY: MISC_FEATURE
```

```
<222> LOCATION: (859)..(859)
<223> OTHER INFORMATION: X= is Y, P, R, V or K
<220> FEATURE:
<221> NAME/KEY: MISC_FEATURE
<222> LOCATION: (860)..(860)
<223> OTHER INFORMATION: X= is E, K, D, N or A
<220> FEATURE:
<221> NAME/KEY: MISC_FEATURE
<222> LOCATION: (861)..(861)
<223> OTHER INFORMATION: X= is E
<220> FEATURE:
<221> NAME/KEY: MISC_FEATURE
<222> LOCATION: (862)..(862)
<223> OTHER INFORMATION: X= is A
<220> FEATURE:
<221> NAME/KEY: MISC_FEATURE
<222> LOCATION: (863)..(863)
<223> OTHER INFORMATION: X= is Q, V, E or K
<220> FEATURE:
<221> NAME/KEY: MISC_FEATURE
<222> LOCATION: (864)..(864)
<223> OTHER INFORMATION: X= is A, E, K or T
<220> FEATURE:
<221> NAME/KEY: MISC_FEATURE
<222> LOCATION: (865)..(865)
<223> OTHER INFORMATION: X= is F, L, Y, M or I
<220> FEATURE:
<221> NAME/KEY: MISC_FEATURE
<222> LOCATION: (866)..(866)
<223> OTHER INFORMATION: X= is I
<220> FEATURE:
<221> NAME/KEY: MISC_FEATURE
<222> LOCATION: (867)..(867)
<223> OTHER INFORMATION: X= is E
<220> FEATURE:
<221> NAME/KEY: MISC_FEATURE
<222> LOCATION: (868)..(868)
<223> OTHER INFORMATION: X= is R, L, S, N, E or T
<220> FEATURE:
<221> NAME/KEY: MISC_FEATURE
<222> LOCATION: (869)..(869)
<223> OTHER INFORMATION: X= is Y
<220> FEATURE:
<221> NAME/KEY: MISC_FEATURE
<222> LOCATION: (870)..(870)
<223> OTHER INFORMATION: X= is F
<220> FEATURE:
<221> NAME/KEY: MISC_FEATURE
<222> LOCATION: (871)..(871)
<223> OTHER INFORMATION: X= is Q, L, K, T, E, S, V, A or G
<220> FEATURE:
<221> NAME/KEY: MISC_FEATURE
<222> LOCATION: (872)..(872)
<223> OTHER INFORMATION: X= is S, R, H, L, Y, Q or I
<220> FEATURE:
<221> NAME/KEY: MISC_FEATURE
<222> LOCATION: (873)..(873)
<223> OTHER INFORMATION: X= is F, Y or A
<220> FEATURE:
<221> NAME/KEY: MISC_FEATURE
<222> LOCATION: (874)..(874)
<223> OTHER INFORMATION: X= is P
<220> FEATURE:
<221> NAME/KEY: MISC_FEATURE
<222> LOCATION: (875)..(875)
<223> OTHER INFORMATION: X= is K, M, R, G, S, Q or L
<220> FEATURE:
<221> NAME/KEY: MISC_FEATURE
<222> LOCATION: (876)..(876)
<223> OTHER INFORMATION: X= is V
<220> FEATURE:
<221> NAME/KEY: MISC_FEATURE
<222> LOCATION: (877)..(877)
<223> OTHER INFORMATION: X= is R, K, L, F or E
<220> FEATURE:
<221> NAME/KEY: MISC_FEATURE
<222> LOCATION: (878)..(878)
<223> OTHER INFORMATION: X= is A, K, L, E, Q, D, R or S
<220> FEATURE:
```

```
<221> NAME/KEY: MISC_FEATURE
<222> LOCATION: (879)..(879)
<223> OTHER INFORMATION: X= is W, F, Y or I
<220> FEATURE:
<221> NAME/KEY: MISC_FEATURE
<222> LOCATION: (880)..(880)
<223> OTHER INFORMATION: X= is I
<220> FEATURE:
<221> NAME/KEY: MISC_FEATURE
<222> LOCATION: (881)..(881)
<223> OTHER INFORMATION: X= is E, D, A, Q or K
<220> FEATURE:
<221> NAME/KEY: MISC_FEATURE
<222> LOCATION: (882)..(882)
<223> OTHER INFORMATION: X= is K, R, E, Q, T or N
<220> FEATURE:
<221> NAME/KEY: MISC_FEATURE
<222> LOCATION: (883)..(883)
<223> OTHER INFORMATION: X= is T, I, V, C or L
<220> FEATURE:
<221> NAME/KEY: MISC_FEATURE
<222> LOCATION: (884)..(884)
<223> OTHER INFORMATION: X is L, I, V, R or H
<220> FEATURE:
<221> NAME/KEY: MISC_FEATURE
<222> LOCATION: (885)..(885)
<223> OTHER INFORMATION: X= is E, S, H, N, A, D, Q or R
<220> FEATURE:
<221> NAME/KEY: MISC_FEATURE
<222> LOCATION: (886)..(886)
<223> OTHER INFORMATION: X= is E, F, Q, Y or S
<220> FEATURE:
<221> NAME/KEY: MISC_FEATURE
<222> LOCATION: (887)..(887)
<223> OTHER INFORMATION: X= is A
<220> FEATURE:
<221> NAME/KEY: MISC_FEATURE
<222> LOCATION: (888)..(888)
<223> OTHER INFORMATION: X= is K
<220> FEATURE:
<221> NAME/KEY: MISC_FEATURE
<222> LOCATION: (889)..(889)
<223> OTHER INFORMATION: X= is R, K, T, E, M, Q, N or W
<220> FEATURE:
<221> NAME/KEY: MISC_FEATURE
<222> LOCATION: (890)..(890)
<223> OTHER INFORMATION: X= is R, N, K, Q, H or V
<220> FEATURE:
<221> NAME/KEY: MISC_FEATURE
<222> LOCATION: (891)..(891)
<223> OTHER INFORMATION: X= is G
<220> FEATURE:
<221> NAME/KEY: MISC_FEATURE
<222> LOCATION: (892)..(892)
<223> OTHER INFORMATION: X= is Y
<220> FEATURE:
<221> NAME/KEY: MISC_FEATURE
<222> LOCATION: (893)..(893)
<223> OTHER INFORMATION: X= is V
<220> FEATURE:
<221> NAME/KEY: MISC_FEATURE
<222> LOCATION: (894)..(894)
<223> OTHER INFORMATION: X= is E, R, K, T, Y or Q
<220> FEATURE:
<221> NAME/KEY: MISC_FEATURE
<222> LOCATION: (895)..(895)
<223> OTHER INFORMATION: X= is T
<220> FEATURE:
<221> NAME/KEY: MISC_FEATURE
<222> LOCATION: (896)..(896)
<223> OTHER INFORMATION: X= is L
<220> FEATURE:
<221> NAME/KEY: MISC_FEATURE
<222> LOCATION: (897)..(897)
<223> OTHER INFORMATION: X= is F
<220> FEATURE:
<221> NAME/KEY: MISC_FEATURE
<222> LOCATION: (898)..(898)
<223> OTHER INFORMATION: X= is G
```

-continued

```
<220> FEATURE:
<221> NAME/KEY: MISC_FEATURE
<222> LOCATION: (899)..(899)
<223> OTHER INFORMATION: X= is R
<220> FEATURE:
<221> NAME/KEY: MISC_FEATURE
<222> LOCATION: (900)..(900)
<223> OTHER INFORMATION: X= is R
<220> FEATURE:
<221> NAME/KEY: MISC_FEATURE
<222> LOCATION: (901)..(901)
<223> OTHER INFORMATION: X= is R
<220> FEATURE:
<221> NAME/KEY: MISC_FEATURE
<222> LOCATION: (902)..(902)
<223> OTHER INFORMATION: X= is Y, P, N, E, D, F, R or W
<220> FEATURE:
<221> NAME/KEY: MISC_FEATURE
<222> LOCATION: (903)..(903)
<223> OTHER INFORMATION: X= is V, L or I
<220> FEATURE:
<221> NAME/KEY: MISC_FEATURE
<222> LOCATION: (904)..(904)
<223> OTHER INFORMATION: X= is P
<220> FEATURE:
<221> NAME/KEY: MISC_FEATURE
<222> LOCATION: (905)..(905)
<223> OTHER INFORMATION: X= is D, E, Q, N or G
<220> FEATURE:
<221> NAME/KEY: MISC_FEATURE
<222> LOCATION: (906)..(906)
<223> OTHER INFORMATION: X= is I
<220> FEATURE:
<221> NAME/KEY: MISC_FEATURE
<222> LOCATION: (907)..(907)
<223> OTHER INFORMATION: X= is E, N, A, K, S, R, M, T, H or D
<220> FEATURE:
<221> NAME/KEY: MISC_FEATURE
<222> LOCATION: (908)..(908)
<223> OTHER INFORMATION: X= is S
<220> FEATURE:
<221> NAME/KEY: MISC_FEATURE
<222> LOCATION: (909)..(909)
<223> OTHER INFORMATION: X= is R
<220> FEATURE:
<221> NAME/KEY: MISC_FEATURE
<222> LOCATION: (910)..(910)
<223> OTHER INFORMATION: X= is N
<220> FEATURE:
<221> NAME/KEY: MISC_FEATURE
<222> LOCATION: (911)..(911)
<223> OTHER INFORMATION: X= is K, R, Q, F, G, A or V
<220> FEATURE:
<221> NAME/KEY: MISC_FEATURE
<222> LOCATION: (912)..(912)
<223> OTHER INFORMATION: X= is S, F, Q, N, A, T, G or H
<220> FEATURE:
<221> NAME/KEY: MISC_FEATURE
<222> LOCATION: (913)..(913)
<223> OTHER INFORMATION: X= is V
<220> FEATURE:
<221> NAME/KEY: MISC_FEATURE
<222> LOCATION: (914)..(914)
<223> OTHER INFORMATION: X= is R
<220> FEATURE:
<221> NAME/KEY: MISC_FEATURE
<222> LOCATION: (915)..(915)
<223> OTHER INFORMATION: X= is E, M, N, S, A, Q or G
<220> FEATURE:
<221> NAME/KEY: MISC_FEATURE
<222> LOCATION: (916)..(916)
<223> OTHER INFORMATION: X= is A, Q, E or F
<220> FEATURE:
<221> NAME/KEY: MISC_FEATURE
<222> LOCATION: (917)..(917)
<223> OTHER INFORMATION: X= is A, S, Y, G or E
<220> FEATURE:
<221> NAME/KEY: MISC_FEATURE
<222> LOCATION: (918)..(918)
```

-continued

```
<223> OTHER INFORMATION: X= is E
<220> FEATURE:
<221> NAME/KEY: MISC_FEATURE
<222> LOCATION: (919)..(919)
<223> OTHER INFORMATION: X= is R
<220> FEATURE:
<221> NAME/KEY: MISC_FEATURE
<222> LOCATION: (920)..(920)
<223> OTHER INFORMATION: X= is M, I, T, A, L or S
<220> FEATURE:
<221> NAME/KEY: MISC_FEATURE
<222> LOCATION: (921)..(921)
<223> OTHER INFORMATION: X= is A
<220> FEATURE:
<221> NAME/KEY: MISC_FEATURE
<222> LOCATION: (922)..(922)
<223> OTHER INFORMATION: X= is F, V, I, M or L
<220> FEATURE:
<221> NAME/KEY: MISC_FEATURE
<222> LOCATION: (923)..(923)
<223> OTHER INFORMATION: X= is N
<220> FEATURE:
<221> NAME/KEY: MISC_FEATURE
<222> LOCATION: (924)..(924)
<223> OTHER INFORMATION: X= is M, A or T
<220> FEATURE:
<221> NAME/KEY: MISC_FEATURE
<222> LOCATION: (925)..(925)
<223> OTHER INFORMATION: X= is P
<220> FEATURE:
<221> NAME/KEY: MISC_FEATURE
<222> LOCATION: (926)..(926)
<223> OTHER INFORMATION: X= is I
<220> FEATURE:
<221> NAME/KEY: MISC_FEATURE
<222> LOCATION: (927)..(927)
<223> OTHER INFORMATION: X= is Q
<220> FEATURE:
<221> NAME/KEY: MISC_FEATURE
<222> LOCATION: (928)..(928)
<223> OTHER INFORMATION: X= is G
<220> FEATURE:
<221> NAME/KEY: MISC_FEATURE
<222> LOCATION: (929)..(929)
<223> OTHER INFORMATION: X= is T
<220> FEATURE:
<221> NAME/KEY: MISC_FEATURE
<222> LOCATION: (930)..(930)
<223> OTHER INFORMATION: X= is A
<220> FEATURE:
<221> NAME/KEY: MISC_FEATURE
<222> LOCATION: (931)..(931)
<223> OTHER INFORMATION: X= is A
<220> FEATURE:
<221> NAME/KEY: MISC_FEATURE
<222> LOCATION: (932)..(932)
<223> OTHER INFORMATION: X= is D
<220> FEATURE:
<221> NAME/KEY: MISC_FEATURE
<222> LOCATION: (933)..(933)
<223> OTHER INFORMATION: X= is I
<220> FEATURE:
<221> NAME/KEY: MISC_FEATURE
<222> LOCATION: (934)..(934)
<223> OTHER INFORMATION: X= is I
<220> FEATURE:
<221> NAME/KEY: MISC_FEATURE
<222> LOCATION: (935)..(935)
<223> OTHER INFORMATION: X= is K
<220> FEATURE:
<221> NAME/KEY: MISC_FEATURE
<222> LOCATION: (936)..(936)
<223> OTHER INFORMATION: X= is L
<220> FEATURE:
<221> NAME/KEY: MISC_FEATURE
<222> LOCATION: (937)..(937)
<223> OTHER INFORMATION: X= is A
<220> FEATURE:
<221> NAME/KEY: MISC_FEATURE
```

```
<222> LOCATION: (938)..(938)
<223> OTHER INFORMATION: X= is M
<220> FEATURE:
<221> NAME/KEY: MISC_FEATURE
<222> LOCATION: (939)..(939)
<223> OTHER INFORMATION: X= is V or I
<220> FEATURE:
<221> NAME/KEY: MISC_FEATURE
<222> LOCATION: (940)..(940)
<223> OTHER INFORMATION: X= is K, R, E, A, N or D
<220> FEATURE:
<221> NAME/KEY: MISC_FEATURE
<222> LOCATION: (941)..(941)
<223> OTHER INFORMATION: X= is L, I, V, A or T
<220> FEATURE:
<221> NAME/KEY: MISC_FEATURE
<222> LOCATION: (942)..(942)
<223> OTHER INFORMATION: X= is F, Y, E, D, H, A, N
<220> FEATURE:
<221> NAME/KEY: MISC_FEATURE
<222> LOCATION: (943)..(943)
<223> OTHER INFORMATION: X= is P, N, K, A, D, R or E
<220> FEATURE:
<221> NAME/KEY: MISC_FEATURE
<222> LOCATION: (944)..(944)
<223> OTHER INFORMATION: X= is R, E, W, K, D or M
<220> FEATURE:
<221> NAME/KEY: MISC_FEATURE
<222> LOCATION: (945)..(945)
<223> OTHER INFORMATION: X= is L
<220> FEATURE:
<221> NAME/KEY: MISC_FEATURE
<222> LOCATION: (946)..(946)
<223> OTHER INFORMATION: X= is E, R, K, Q, I or V
<220> FEATURE:
<221> NAME/KEY: MISC_FEATURE
<222> LOCATION: (947)..(947)
<223> OTHER INFORMATION: X= is E, P, K, N, A, Q, R or S
<220> FEATURE:
<221> NAME/KEY: MISC_FEATURE
<222> LOCATION: (948)..(948)
<223> OTHER INFORMATION: X= is E, K, Q, M, R, N or L
<220> FEATURE:
<221> NAME/KEY: MISC_FEATURE
<222> LOCATION: (949)..(949)
<223> OTHER INFORMATION: X= is K, N, D, Q, R, S or G
<220> FEATURE:
<221> NAME/KEY: MISC_FEATURE
<222> LOCATION: (950)..(950)
<223> OTHER INFORMATION: X= is M or L
<220> FEATURE:
<221> NAME/KEY: MISC_FEATURE
<222> LOCATION: (951)..(951)
<223> OTHER INFORMATION: X= is I, E or K
<220> FEATURE:
<221> NAME/KEY: MISC_FEATURE
<222> LOCATION: (952)..(952)
<223> OTHER INFORMATION: X= is D, P, Q or H
<220> FEATURE:
<221> NAME/KEY: MISC_FEATURE
<222> LOCATION: (953)..(953)
<223> OTHER INFORMATION: X= is G, N, K, R, Q or E
<220> FEATURE:
<221> NAME/KEY: MISC_FEATURE
<222> LOCATION: (954)..(954)
<223> OTHER INFORMATION: X= is W
<220> FEATURE:
<221> NAME/KEY: MISC_FEATURE
<222> LOCATION: (955)..(955)
<223> OTHER INFORMATION: X= is D
<220> FEATURE:
<221> NAME/KEY: MISC_FEATURE
<222> LOCATION: (956)..(956)
<223> OTHER INFORMATION: X= is G
<220> FEATURE:
<221> NAME/KEY: MISC_FEATURE
<222> LOCATION: (957)..(957)
<223> OTHER INFORMATION: X= is D
<220> FEATURE:
```

-continued

```
<221> NAME/KEY: MISC_FEATURE
<222> LOCATION: (958)..(958)
<223> OTHER INFORMATION: X= is A, S, V, T, M or F
<220> FEATURE:
<221> NAME/KEY: MISC_FEATURE
<222> LOCATION: (959)..(959)
<223> OTHER INFORMATION: X= is R, H, K or A
<220> FEATURE:
<221> NAME/KEY: MISC_FEATURE
<222> LOCATION: (960)..(960)
<223> OTHER INFORMATION: X=is M, L, I or Y
<220> FEATURE:
<221> NAME/KEY: MISC_FEATURE
<222> LOCATION: (961)..(961)
<223> OTHER INFORMATION: X= is L, I, V or M
<220> FEATURE:
<221> NAME/KEY: MISC_FEATURE
<222> LOCATION: (962)..(962)
<223> OTHER INFORMATION: X= is L
<220> FEATURE:
<221> NAME/KEY: MISC_FEATURE
<222> LOCATION: (963)..(963)
<223> OTHER INFORMATION: X= is Q
<220> FEATURE:
<221> NAME/KEY: MISC_FEATURE
<222> LOCATION: (964)..(964)
<223> OTHER INFORMATION: X= is V or I
<220> FEATURE:
<221> NAME/KEY: MISC_FEATURE
<222> LOCATION: (965)..(965)
<223> OTHER INFORMATION: X= is H
<220> FEATURE:
<221> NAME/KEY: MISC_FEATURE
<222> LOCATION: (966)..(966)
<223> OTHER INFORMATION: X= is D
<220> FEATURE:
<221> NAME/KEY: MISC_FEATURE
<222> LOCATION: (967)..(967)
<223> OTHER INFORMATION: X= is E
<220> FEATURE:
<221> NAME/KEY: MISC_FEATURE
<222> LOCATION: (968)..(968)
<223> OTHER INFORMATION: X= is L
<220> FEATURE:
<221> NAME/KEY: MISC_FEATURE
<222> LOCATION: (969)..(969)
<223> OTHER INFORMATION: X= is V
<220> FEATURE:
<221> NAME/KEY: MISC_FEATURE
<222> LOCATION: (970)..(970)
<223> OTHER INFORMATION: X= is L, F, V or A
<220> FEATURE:
<221> NAME/KEY: MISC_FEATURE
<222> LOCATION: (971)..(971)
<223> OTHER INFORMATION: X= is E
<220> FEATURE:
<221> NAME/KEY: MISC_FEATURE
<222> LOCATION: (972)..(972)
<223> OTHER INFORMATION: X= is V
<220> FEATURE:
<221> NAME/KEY: MISC_FEATURE
<222> LOCATION: (973)..(973)
<223> OTHER INFORMATION: X= is P, E, N, H, Y or R
<220> FEATURE:
<221> NAME/KEY: MISC_FEATURE
<222> LOCATION: (974)..(974)
<223> OTHER INFORMATION: X= is K, Q, E, D, N, F or T
<220> FEATURE:
<221> NAME/KEY: MISC_FEATURE
<222> LOCATION: (975)..(975)
<223> OTHER INFORMATION: X= is E
<220> FEATURE:
<221> NAME/KEY: MISC_FEATURE
<222> LOCATION: (976)..(976)
<223> OTHER INFORMATION: X= is E
<220> FEATURE:
<221> NAME/KEY: MISC_FEATURE
<222> LOCATION: (977)..(977)
<223> OTHER INFORMATION: X= is A, I , M, L, V or K
```

```
<220> FEATURE:
<221> NAME/KEY: MISC_FEATURE
<222> LOCATION: (978)..(978)
<223> OTHER INFORMATION: X= is E, S, D, Q or A
<220> FEATURE:
<221> NAME/KEY: MISC_FEATURE
<222> LOCATION: (979)..(979)
<223> OTHER INFORMATION: X= is A, E, K, F, D, I, R or Q
<220> FEATURE:
<221> NAME/KEY: MISC_FEATURE
<222> LOCATION: (980)..(980)
<223> OTHER INFORMATION: X= is V
<220> FEATURE:
<221> NAME/KEY: MISC_FEATURE
<222> LOCATION: (981)..(981)
<223> OTHER INFORMATION: X= is A, K, S, P, V or C
<220> FEATURE:
<221> NAME/KEY: MISC_FEATURE
<222> LOCATION: (982)..(982)
<223> OTHER INFORMATION: X= is R, A, E, L, T, K, N, Q or I
<220> FEATURE:
<221> NAME/KEY: MISC_FEATURE
<222> LOCATION: (983)..(983)
<223> OTHER INFORMATION: X= is L, I, M, K, Q or E
<220> FEATURE:
<221> NAME/KEY: MISC_FEATURE
<222> LOCATION: (984)..(984)
<223> OTHER INFORMATION: X= is A, V, I, L or T
<220> FEATURE:
<221> NAME/KEY: MISC_FEATURE
<222> LOCATION: (985)..(985)
<223> OTHER INFORMATION: X= is K
<220> FEATURE:
<221> NAME/KEY: MISC_FEATURE
<222> LOCATION: (986)..(986)
<223> OTHER INFORMATION: X= is E, N, Q, D or R
<220> FEATURE:
<221> NAME/KEY: MISC_FEATURE
<222> LOCATION: (987)..(987)
<223> OTHER INFORMATION: X= is V, A, E, K, I, L, S, R or N
<220> FEATURE:
<221> NAME/KEY: MISC_FEATURE
<222> LOCATION: (988)..(988)
<223> OTHER INFORMATION: X= is M
<220> FEATURE:
<221> NAME/KEY: MISC_FEATURE
<222> LOCATION: (989)..(989)
<223> OTHER INFORMATION: X= is E
<220> FEATURE:
<221> NAME/KEY: MISC_FEATURE
<222> LOCATION: (990)..(990)
<223> OTHER INFORMATION: X= is G, K, N, Q or R
<220> FEATURE:
<221> NAME/KEY: MISC_FEATURE
<222> LOCATION: (991)..(991)
<223> OTHER INFORMATION: X= is V, A, D, I, C or W
<220> FEATURE:
<221> NAME/KEY: MISC_FEATURE
<222> LOCATION: (992)..(992)
<223> OTHER INFORMATION: X= is V
<220> FEATURE:
<221> NAME/KEY: MISC_FEATURE
<222> LOCATION: (993)..(993)
<223> OTHER INFORMATION: X= is P, S, E, R, K, A, T, Q or G
<220> FEATURE:
<221> NAME/KEY: MISC_FEATURE
<222> LOCATION: (994)..(994)
<223> OTHER INFORMATION: X= is L
<220> FEATURE:
<221> NAME/KEY: MISC_FEATURE
<222> LOCATION: (995)..(995)
<223> OTHER INFORMATION: X= is R, D, S, K or H
<220> FEATURE:
<221> NAME/KEY: MISC_FEATURE
<222> LOCATION: (996)..(996)
<223> OTHER INFORMATION: X= is V
<220> FEATURE:
<221> NAME/KEY: MISC_FEATURE
<222> LOCATION: (997)..(997)
```

```
<223> OTHER INFORMATION: X= is P
<220> FEATURE:
<221> NAME/KEY: MISC_FEATURE
<222> LOCATION: (998)..(998)
<223> OTHER INFORMATION: X= is G or F
<220> FEATURE:
<221> NAME/KEY: MISC_FEATURE
<222> LOCATION: (999)..(999)
<223> OTHER INFORMATION: X= is R
<220> FEATURE:
<221> NAME/KEY: MISC_FEATURE
<222> LOCATION: (1000)..(1000)
<223> OTHER INFORMATION: X= is C
<220> FEATURE:
<221> NAME/KEY: MISC_FEATURE
<222> LOCATION: (1001)..(1001)
<223> OTHER INFORMATION: X= is L
<220> FEATURE:
<221> NAME/KEY: MISC_FEATURE
<222> LOCATION: (1002)..(1002)
<223> OTHER INFORMATION: X= is L
<220> FEATURE:
<221> NAME/KEY: MISC_FEATURE
<222> LOCATION: (1003)..(1003)
<223> OTHER INFORMATION: X= is E, V, T, L, K, P or D
<220> FEATURE:
<221> NAME/KEY: MISC_FEATURE
<222> LOCATION: (1004)..(1004)
<223> OTHER INFORMATION: X= is V
<220> FEATURE:
<221> NAME/KEY: MISC_FEATURE
<222> LOCATION: (1005)..(1005)
<223> OTHER INFORMATION: X= is E, N, D or G
<220> FEATURE:
<221> NAME/KEY: MISC_FEATURE
<222> LOCATION: (1006)..(1006)
<223> OTHER INFORMATION: X= is V, I, L, Y or G
<220> FEATURE:
<221> NAME/KEY: MISC_FEATURE
<222> LOCATION: (1007)..(1007)
<223> OTHER INFORMATION: X= is G, F, S, K, T, Y, H or D
<220> FEATURE:
<221> NAME/KEY: MISC_FEATURE
<222> LOCATION: (1008)..(1008)
<223> OTHER INFORMATION: X= is I, M, V, S, T, I, E or Y
<220> FEATURE:
<221> NAME/KEY: MISC_FEATURE
<222> LOCATION: (1009)..(1009)
<223> OTHER INFORMATION: X= is G
<220> FEATURE:
<221> NAME/KEY: MISC_FEATURE
<222> LOCATION: (1010)..(1010)
<223> OTHER INFORMATION: X= is E, R, N, K, P, D or S
<220> FEATURE:
<221> NAME/KEY: MISC_FEATURE
<222> LOCATION: (1011)..(1011)
<223> OTHER INFORMATION: X= is D, S, N, T or E
<220> FEATURE:
<221> NAME/KEY: MISC_FEATURE
<222> LOCATION: (1012)..(1012)
<223> OTHER INFORMATION: X= is W
<220> FEATURE:
<221> NAME/KEY: MISC_FEATURE
<222> LOCATION: (1013)..(1013)
<223> OTHER INFORMATION: X= is L, N, A, Y, D, E, S, F or G
<220> FEATURE:
<221> NAME/KEY: MISC_FEATURE
<222> LOCATION: (1014)..(1014)
<223> OTHER INFORMATION: X= is S, E, I, L, D, Q or G
<220> FEATURE:
<221> NAME/KEY: MISC_FEATURE
<222> LOCATION: (1015)..(1015)
<223> OTHER INFORMATION: X= is A, L, S or C
<220> FEATURE:
<221> NAME/KEY: MISC_FEATURE
<222> LOCATION: (1016)..(1016)
<223> OTHER INFORMATION: X= is K, N, H or R
<220> FEATURE:
<221> NAME/KEY: MISC_FEATURE
```

```
<222> LOCATION: (1017)..(1017)
<223> OTHER INFORMATION: X= is E, G, Q, P or D
<220> FEATURE:
<221> NAME/KEY: MISC_FEATURE
<222> LOCATION: (1018)..(1018)
<223> OTHER INFORMATION: X= is D or Y
<220> FEATURE:
<221> NAME/KEY: MISC_FEATURE
<222> LOCATION: (1019)..(1019)
<223> OTHER INFORMATION: X= is Q or S
<220> FEATURE:
<221> NAME/KEY: MISC_FEATURE
<222> LOCATION: (1020)..(1020)
<223> OTHER INFORMATION: X= is S or C
<220> FEATURE:
<221> NAME/KEY: MISC_FEATURE
<222> LOCATION: (1021)..(1021)
<223> OTHER INFORMATION: X= is G
<220> FEATURE:
<221> NAME/KEY: MISC_FEATURE
<222> LOCATION: (1022)..(1022)
<223> OTHER INFORMATION: X= is E or K
<220> FEATURE:
<221> NAME/KEY: MISC_FEATURE
<222> LOCATION: (1023)..(1023)
<223> OTHER INFORMATION: X= is M
<220> FEATURE:
<221> NAME/KEY: MISC_FEATURE
<222> LOCATION: (1024)..(1024)
<223> OTHER INFORMATION: X= is K
<220> FEATURE:
<221> NAME/KEY: MISC_FEATURE
<222> LOCATION: (1025)..(1025)
<223> OTHER INFORMATION: X= is K
<220> FEATURE:
<221> NAME/KEY: MISC_FEATURE
<222> LOCATION: (1026)..(1026)
<223> OTHER INFORMATION: X= is Q
<220> FEATURE:
<221> NAME/KEY: MISC_FEATURE
<222> LOCATION: (1027)..(1027)
<223> OTHER INFORMATION: X= is H
<220> FEATURE:
<221> NAME/KEY: MISC_FEATURE
<222> LOCATION: (1028)..(1028)
<223> OTHER INFORMATION: X= is P
<220> FEATURE:
<221> NAME/KEY: MISC_FEATURE
<222> LOCATION: (1029)..(1029)
<223> OTHER INFORMATION: X= is S
<220> FEATURE:
<221> NAME/KEY: MISC_FEATURE
<222> LOCATION: (1030)..(1030)
<223> OTHER INFORMATION: X= is I
<220> FEATURE:
<221> NAME/KEY: MISC_FEATURE
<222> LOCATION: (1031)..(1031)
<223> OTHER INFORMATION: X= is A
<220> FEATURE:
<221> NAME/KEY: MISC_FEATURE
<222> LOCATION: (1032)..(1032)
<223> OTHER INFORMATION: X= is C
<220> FEATURE:
<221> NAME/KEY: MISC_FEATURE
<222> LOCATION: (1033)..(1033)
<223> OTHER INFORMATION: X= is I
<220> FEATURE:
<221> NAME/KEY: MISC_FEATURE
<222> LOCATION: (1034)..(1034)
<223> OTHER INFORMATION: X= is D
<220> FEATURE:
<221> NAME/KEY: MISC_FEATURE
<222> LOCATION: (1035)..(1035)
<223> OTHER INFORMATION: X= is D
<220> FEATURE:
<221> NAME/KEY: MISC_FEATURE
<222> LOCATION: (1036)..(1036)
<223> OTHER INFORMATION: X= is D
<220> FEATURE:
```

```
<221> NAME/KEY: MISC_FEATURE
<222> LOCATION: (1037)..(1037)
<223> OTHER INFORMATION: X= is E
<220> FEATURE:
<221> NAME/KEY: MISC_FEATURE
<222> LOCATION: (1038)..(1038)
<223> OTHER INFORMATION: X= is Y
<220> FEATURE:
<221> NAME/KEY: MISC_FEATURE
<222> LOCATION: (1039)..(1039)
<223> OTHER INFORMATION: X= is T
<220> FEATURE:
<221> NAME/KEY: MISC_FEATURE
<222> LOCATION: (1040)..(1040)
<223> OTHER INFORMATION: X= is R
<220> FEATURE:
<221> NAME/KEY: MISC_FEATURE
<222> LOCATION: (1041)..(1041)
<223> OTHER INFORMATION: X= is Y
<220> FEATURE:
<221> NAME/KEY: MISC_FEATURE
<222> LOCATION: (1042)..(1042)
<223> OTHER INFORMATION: X= is V
<220> FEATURE:
<221> NAME/KEY: MISC_FEATURE
<222> LOCATION: (1043)..(1043)
<223> OTHER INFORMATION: X= is K
<220> FEATURE:
<221> NAME/KEY: MISC_FEATURE
<222> LOCATION: (1044)..(1044)
<223> OTHER INFORMATION: X= is G
<220> FEATURE:
<221> NAME/KEY: MISC_FEATURE
<222> LOCATION: (1045)..(1045)
<223> OTHER INFORMATION: X= is V
<220> FEATURE:
<221> NAME/KEY: MISC_FEATURE
<222> LOCATION: (1046)..(1046)
<223> OTHER INFORMATION: X= is L
<220> FEATURE:
<221> NAME/KEY: MISC_FEATURE
<222> LOCATION: (1047)..(1047)
<223> OTHER INFORMATION: X= is L
<220> FEATURE:
<221> NAME/KEY: MISC_FEATURE
<222> LOCATION: (1048)..(1048)
<223> OTHER INFORMATION: X= is D
<220> FEATURE:
<221> NAME/KEY: MISC_FEATURE
<222> LOCATION: (1049)..(1049)
<223> OTHER INFORMATION: X= is A
<220> FEATURE:
<221> NAME/KEY: MISC_FEATURE
<222> LOCATION: (1050)..(1050)
<223> OTHER INFORMATION: X= is E
<220> FEATURE:
<221> NAME/KEY: MISC_FEATURE
<222> LOCATION: (1051)..(1051)
<223> OTHER INFORMATION: X= is F
<220> FEATURE:
<221> NAME/KEY: MISC_FEATURE
<222> LOCATION: (1052)..(1052)
<223> OTHER INFORMATION: X= is E
<220> FEATURE:
<221> NAME/KEY: MISC_FEATURE
<222> LOCATION: (1053)..(1053)
<223> OTHER INFORMATION: X= is Y
<220> FEATURE:
<221> NAME/KEY: MISC_FEATURE
<222> LOCATION: (1054)..(1054)
<223> OTHER INFORMATION: X= is K
<220> FEATURE:
<221> NAME/KEY: MISC_FEATURE
<222> LOCATION: (1055)..(1055)
<223> OTHER INFORMATION: X= is K
<220> FEATURE:
<221> NAME/KEY: MISC_FEATURE
<222> LOCATION: (1056)..(1056)
<223> OTHER INFORMATION: X= is L
```

```
<220> FEATURE:
<221> NAME/KEY: MISC_FEATURE
<222> LOCATION: (1057)..(1057)
<223> OTHER INFORMATION: X= is A
<220> FEATURE:
<221> NAME/KEY: MISC_FEATURE
<222> LOCATION: (1058)..(1058)
<223> OTHER INFORMATION: X= is A
<220> FEATURE:
<221> NAME/KEY: MISC_FEATURE
<222> LOCATION: (1059)..(1059)
<223> OTHER INFORMATION: X= is M
<220> FEATURE:
<221> NAME/KEY: MISC_FEATURE
<222> LOCATION: (1060)..(1060)
<223> OTHER INFORMATION: X= is D
<220> FEATURE:
<221> NAME/KEY: MISC_FEATURE
<222> LOCATION: (1061)..(1061)
<223> OTHER INFORMATION: X= is K
<220> FEATURE:
<221> NAME/KEY: MISC_FEATURE
<222> LOCATION: (1062)..(1062)
<223> OTHER INFORMATION: X= is E
<220> FEATURE:
<221> NAME/KEY: MISC_FEATURE
<222> LOCATION: (1063)..(1063)
<223> OTHER INFORMATION: X= is H
<220> FEATURE:
<221> NAME/KEY: MISC_FEATURE
<222> LOCATION: (1064)..(1064)
<223> OTHER INFORMATION: X=is P
<220> FEATURE:
<221> NAME/KEY: MISC_FEATURE
<222> LOCATION: (1065)..(1065)
<223> OTHER INFORMATION: X= is D
<220> FEATURE:
<221> NAME/KEY: MISC_FEATURE
<222> LOCATION: (1066)..(1066)
<223> OTHER INFORMATION: X= is H
<220> FEATURE:
<221> NAME/KEY: MISC_FEATURE
<222> LOCATION: (1067)..(1067)
<223> OTHER INFORMATION: X= is S
<220> FEATURE:
<221> NAME/KEY: MISC_FEATURE
<222> LOCATION: (1068)..(1068)
<223> OTHER INFORMATION: X= is K
<220> FEATURE:
<221> NAME/KEY: MISC_FEATURE
<222> LOCATION: (1069)..(1069)
<223> OTHER INFORMATION: X= is Y
<220> FEATURE:
<221> NAME/KEY: MISC_FEATURE
<222> LOCATION: (1070)..(1070)
<223> OTHER INFORMATION: X= is K
<220> FEATURE:
<221> NAME/KEY: MISC_FEATURE
<222> LOCATION: (1071)..(1071)
<223> OTHER INFORMATION: X= is D
<220> FEATURE:
<221> NAME/KEY: MISC_FEATURE
<222> LOCATION: (1072)..(1072)
<223> OTHER INFORMATION: X= is D
<220> FEATURE:
<221> NAME/KEY: MISC_FEATURE
<222> LOCATION: (1073)..(1073)
<223> OTHER INFORMATION: X= is K
<220> FEATURE:
<221> NAME/KEY: MISC_FEATURE
<222> LOCATION: (1074)..(1074)
<223> OTHER INFORMATION: X= is F
<220> FEATURE:
<221> NAME/KEY: MISC_FEATURE
<222> LOCATION: (1075)..(1075)
<223> OTHER INFORMATION: X= is I
<220> FEATURE:
<221> NAME/KEY: MISC_FEATURE
<222> LOCATION: (1076)..(1076)
```

```
<223> OTHER INFORMATION: X= is A
<220> FEATURE:
<221> NAME/KEY: MISC_FEATURE
<222> LOCATION: (1077)..(1077)
<223> OTHER INFORMATION: X= is V
<220> FEATURE:
<221> NAME/KEY: MISC_FEATURE
<222> LOCATION: (1078)..(1078)
<223> OTHER INFORMATION: X= is C
<220> FEATURE:
<221> NAME/KEY: MISC_FEATURE
<222> LOCATION: (1079)..(1079)
<223> OTHER INFORMATION: X= is K
<220> FEATURE:
<221> NAME/KEY: MISC_FEATURE
<222> LOCATION: (1080)..(1080)
<223> OTHER INFORMATION: X= is D
<220> FEATURE:
<221> NAME/KEY: MISC_FEATURE
<222> LOCATION: (1081)..(1081)
<223> OTHER INFORMATION: X= is L
<220> FEATURE:
<221> NAME/KEY: MISC_FEATURE
<222> LOCATION: (1082)..(1082)
<223> OTHER INFORMATION: X= is D
<220> FEATURE:
<221> NAME/KEY: MISC_FEATURE
<222> LOCATION: (1083)..(1083)
<223> OTHER INFORMATION: X= is N
<220> FEATURE:
<221> NAME/KEY: MISC_FEATURE
<222> LOCATION: (1084)..(1084)
<223> OTHER INFORMATION: X= is V
<220> FEATURE:
<221> NAME/KEY: MISC_FEATURE
<222> LOCATION: (1085)..(1085)
<223> OTHER INFORMATION: X= is K
<220> FEATURE:
<221> NAME/KEY: MISC_FEATURE
<222> LOCATION: (1086)..(1086)
<223> OTHER INFORMATION: X=is R
<220> FEATURE:
<221> NAME/KEY: MISC_FEATURE
<222> LOCATION: (1087)..(1087)
<223> OTHER INFORMATION: X= is I
<220> FEATURE:
<221> NAME/KEY: MISC_FEATURE
<222> LOCATION: (1088)..(1088)
<223> OTHER INFORMATION: X= is L
<220> FEATURE:
<221> NAME/KEY: MISC_FEATURE
<222> LOCATION: (1089)..(1089)
<223> OTHER INFORMATION: X= is G
<220> FEATURE:
<221> NAME/KEY: MISC_FEATURE
<222> LOCATION: (1090)..(1090)
<223> OTHER INFORMATION: X= is A

<400> SEQUENCE: 19

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Leu Xaa Asp Gly Xaa Xaa Leu Xaa Tyr
            20                  25                  30

Arg Ala Xaa Xaa Ala Leu Xaa Xaa Xaa Leu Xaa Thr Ser Xaa Gly Xaa
        35                  40                  45

Xaa Thr Asn Ala Xaa Tyr Gly Phe Xaa Xaa Met Leu Xaa Lys Xaa Xaa
    50                  55                  60

Xaa Xaa Xaa Xaa Xaa Xaa Xaa Xaa Xaa Xaa Xaa Val Xaa Phe Asp
65                  70                  75                  80

Xaa Lys Xaa Xaa Thr Phe Xaa Arg His Xaa Xaa Xaa Xaa Xaa Tyr Lys
            85                  90                  95

Xaa Xaa Arg Xaa Xaa Xaa Pro Xaa Xaa Xaa Xaa Xaa Gln Xaa Xaa Xaa
```

```
                100                 105                 110
Xaa Xaa Xaa Xaa Xaa Xaa Xaa Xaa Xaa Xaa Xaa Leu Glu Xaa Xaa
            115                 120                 125
Gly Tyr Glu Ala Asp Asp Ile Ile Xaa Thr Xaa Xaa Xaa Xaa Xaa
            130                 135                 140
Xaa Xaa Xaa Xaa Xaa Xaa Xaa Ile Xaa Xaa Gly Asp Xaa Asp Xaa
145                 150                 155                 160
Xaa Gln Leu Val Xaa Xaa Lys Xaa Xaa Xaa Xaa Xaa Xaa Lys Xaa
                165                 170                 175
Ile Thr Xaa Xaa Xaa Xaa Xaa Xaa Xaa Xaa Val Xaa Glu Lys Tyr
                180                 185                 190
Gly Val Xaa Pro Xaa Xaa Xaa Asp Xaa Xaa Xaa Leu Xaa Gly Xaa
            195                 200                 205
Xaa Ser Asp Asn Ile Pro Gly Val Xaa Gly Ile Gly Glu Lys Thr Ala
            210                 215                 220
Xaa Xaa Leu Leu Xaa Xaa Xaa Gly Xaa Xaa Glu Xaa Xaa Xaa Xaa
225                 230                 235                 240
Xaa Xaa Xaa Xaa Xaa Xaa Xaa Xaa Xaa Xaa Xaa Xaa Xaa Xaa Xaa
            245                 250                 255
Xaa Xaa Leu Xaa Xaa Xaa Xaa Glu Xaa Xaa Xaa Leu Ser Xaa Xaa Leu
            260                 265                 270
Xaa Xaa Xaa Xaa Xaa Xaa Xaa Pro Xaa Xaa Xaa Glu Xaa Xaa Xaa Xaa
            275                 280                 285
Xaa Leu Xaa Xaa Xaa Xaa Xaa Xaa Xaa Glu Lys Leu Xaa Xaa Xaa Xaa
            290                 295                 300
Xaa Xaa Leu Glu Phe Xaa Ser Xaa Xaa Xaa Xaa Xaa Xaa Xaa Xaa
305                 310                 315                 320
Xaa Xaa Xaa Xaa Xaa Xaa Xaa Xaa Xaa Xaa Xaa Xaa Xaa Xaa Xaa
            325                 330                 335
Xaa Xaa Xaa Xaa Xaa Xaa Xaa Xaa Xaa Xaa Xaa Xaa Xaa Xaa Xaa
            340                 345                 350
Xaa Xaa Xaa Xaa Xaa Xaa Xaa Xaa Xaa Xaa Leu Xaa Xaa Xaa Xaa
            355                 360                 365
Xaa Xaa Xaa Xaa Xaa Xaa Xaa Xaa Xaa Xaa Xaa Xaa Xaa Xaa Xaa
            370                 375                 380
Xaa Xaa Xaa Xaa Xaa Xaa Xaa Xaa Xaa Xaa Xaa Xaa Xaa Xaa Xaa
385                 390                 395                 400
Xaa Xaa Xaa Xaa Xaa Xaa Xaa Xaa Xaa Xaa Xaa Xaa Xaa Xaa Xaa
            405                 410                 415
Xaa Xaa Xaa Xaa Xaa Xaa Xaa Xaa Xaa Xaa Xaa Xaa Xaa Xaa Xaa
            420                 425                 430
Xaa Leu Xaa Xaa Xaa Xaa Xaa Xaa Xaa Xaa Xaa Xaa Xaa Xaa Xaa
            435                 440                 445
Xaa Xaa Xaa Xaa Leu Xaa Xaa Xaa Gly Xaa Xaa Leu Xaa Xaa Xaa Xaa
            450                 455                 460
Phe Xaa Xaa Asp Xaa Xaa Xaa Xaa Ala Tyr Leu Leu Xaa Pro Xaa Xaa
465                 470                 475                 480
Xaa Xaa Xaa Xaa Xaa Asp Xaa Xaa Ala Xaa Xaa Tyr Leu Xaa Xaa Xaa
            485                 490                 495
Xaa Xaa Xaa Xaa Xaa Xaa Xaa Xaa Xaa Xaa Xaa Xaa Xaa Xaa Xaa
            500                 505                 510
Xaa Xaa Xaa Xaa Xaa Xaa Xaa Xaa Xaa Xaa Xaa Xaa Xaa Xaa Ala
            515                 520                 525
```

```
Xaa Xaa Xaa Ala Xaa Xaa Xaa Xaa Leu Xaa Xaa Xaa Xaa Xaa Xaa
    530                 535                 540
Xaa Xaa Xaa Xaa Glu Xaa Xaa Leu Xaa Xaa Leu Xaa Xaa Xaa Ile Glu
545                 550                 555                 560
Xaa Pro Leu Xaa Xaa Val Leu Xaa Xaa Met Glu Xaa Xaa Gly Xaa Xaa
                565                 570                 575
Xaa Asp Xaa Xaa Xaa Leu Lys Xaa Leu Ser Xaa Xaa Xaa Xaa Xaa
            580                 585                 590
Xaa Xaa Xaa Leu Xaa Xaa Xaa Ile Xaa Xaa Xaa Xaa Xaa Xaa Xaa
        595                 600                 605
Xaa Xaa Xaa Xaa Ala Gly Xaa Xaa Phe Asn Xaa Asn Ser Xaa Lys Gln
610                 615                 620
Leu Xaa Xaa Xaa Leu Phe Xaa Xaa Leu Xaa Leu Pro Xaa Xaa Xaa Lys
625                 630                 635                 640
Thr Xaa Xaa Thr Gly Xaa Xaa Ser Thr Xaa Xaa Glu Val Leu Xaa Xaa
                645                 650                 655
Leu Xaa Xaa Xaa His Pro Xaa Xaa Xaa Ile Xaa Xaa Xaa Ile Leu Xaa
            660                 665                 670
Xaa Tyr Arg Xaa Leu Xaa Lys Leu Lys Ser Thr Tyr Xaa Asp Xaa Leu
        675                 680                 685
Xaa Xaa Xaa Xaa Xaa Xaa Xaa Pro Xaa Thr Gly Arg Xaa His Thr Xaa
690                 695                 700
Phe Asn Gln Thr Xaa Thr Ala Thr Gly Arg Leu Ser Ser Ser Xaa Pro
705                 710                 715                 720
Xaa Asn Leu Gln Xaa Ile Pro Xaa Xaa Arg Xaa Glu Xaa Gly Xaa Xaa
                725                 730                 735
Ile Arg Xaa Ala Phe Val Xaa Xaa Xaa Xaa Xaa Xaa Ile Xaa Xaa
            740                 745                 750
Ala Asp Tyr Ser Gln Ile Glu Leu Arg Xaa Leu Ala Xaa His Leu Ser
            755                 760                 765
Xaa Asp Xaa Asn Leu Ile Xaa Ala Phe Xaa Gly Xaa Xaa Xaa Xaa
770                 775                 780
Xaa Xaa Xaa Xaa Asp Ile His Thr Xaa Thr Ala Ser Xaa Ile Phe Xaa
785                 790                 795                 800
Val Xaa Xaa Glu Xaa Xaa Xaa Xaa Xaa Val Thr Xaa Xaa Met Arg
            805                 810                 815
Arg Xaa Ala Lys Xaa Val Asn Xaa Gly Ile Xaa Tyr Gly Xaa Ser Xaa
        820                 825                 830
Xaa Gly Leu Ser Xaa Xaa Leu Xaa Xaa Xaa Xaa Xaa Xaa Xaa Xaa
        835                 840                 845
Xaa Xaa Xaa Xaa Xaa Xaa Xaa Ile Xaa Xaa Xaa Glu Ala Xaa Xaa
850                 855                 860
Xaa Ile Glu Xaa Tyr Phe Xaa Xaa Xaa Pro Xaa Val Xaa Xaa Xaa Ile
865                 870                 875                 880
Xaa Xaa Xaa Xaa Xaa Xaa Ala Lys Xaa Xaa Gly Tyr Val Xaa Thr Leu
            885                 890                 895
Phe Gly Arg Arg Arg Xaa Xaa Pro Xaa Ile Xaa Ser Arg Asn Xaa Xaa
                900                 905                 910
Val Arg Xaa Xaa Xaa Glu Arg Xaa Ala Xaa Asn Xaa Pro Ile Gln Gly
        915                 920                 925
Thr Ala Ala Asp Ile Ile Lys Leu Ala Met Xaa Xaa Xaa Xaa Xaa Xaa
930                 935                 940
```

```
Leu Xaa Xaa Xaa Xaa Xaa Xaa Xaa Xaa Xaa Xaa Xaa Xaa Xaa Xaa Xaa
945                 950                 955                 960

Xaa Leu Gln Xaa His Asp Glu Leu Val Xaa Glu Val Xaa Xaa Glu Glu
            965                 970                 975

Xaa Xaa Xaa Val Xaa Xaa Xaa Xaa Lys Xaa Xaa Met Glu Xaa Xaa Val
        980                 985                 990

Xaa Leu Xaa Val Pro Xaa Xaa Xaa  Xaa Leu Xaa Val Xaa  Xaa Xaa Xaa
        995                 1000                1005

Gly Xaa  Xaa Trp Xaa Xaa Xaa  Xaa Xaa Xaa Xaa  Xaa Xaa Xaa
    1010             1015                 1020

Xaa Xaa  Xaa Xaa Xaa Xaa Xaa  Xaa Xaa Xaa Xaa  Xaa Xaa Xaa
    1025             1030                 1035

Xaa Xaa  Xaa Xaa Xaa Xaa Xaa  Xaa Xaa Xaa Xaa  Xaa Xaa Xaa
    1040             1045                 1050

Xaa Xaa  Xaa Xaa Xaa Xaa Xaa  Xaa Xaa Xaa Xaa  Xaa Xaa Xaa
    1055             1060                 1065

Xaa Xaa  Xaa Xaa Xaa Xaa Xaa  Xaa Xaa Xaa Xaa  Xaa Xaa Xaa
    1070             1075                 1080

Xaa Xaa  Xaa Xaa Xaa Xaa Xaa
    1085             1090

<210> SEQ ID NO 20
<211> LENGTH: 1090
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (1)..(23)
<223> OTHER INFORMATION: X is any amino acid or absent
<220> FEATURE:
<221> NAME/KEY: MISC_FEATURE
<222> LOCATION: (25)..(25)
<223> OTHER INFORMATION: X is any amino acid or absent
<220> FEATURE:
<221> NAME/KEY: MISC_FEATURE
<222> LOCATION: (28)..(29)
<223> OTHER INFORMATION: X is any amino acid or absent
<220> FEATURE:
<221> NAME/KEY: MISC_FEATURE
<222> LOCATION: (31)..(31)
<223> OTHER INFORMATION: X is any amino acid or absent
<220> FEATURE:
<221> NAME/KEY: MISC_FEATURE
<222> LOCATION: (35)..(36)
<223> OTHER INFORMATION: X is any amino acid or absent
<220> FEATURE:
<221> NAME/KEY: MISC_FEATURE
<222> LOCATION: (39)..(41)
<223> OTHER INFORMATION: X is any amino acid or absent
<220> FEATURE:
<221> NAME/KEY: MISC_FEATURE
<222> LOCATION: (43)..(43)
<223> OTHER INFORMATION: X is any amino acid or absent
<220> FEATURE:
<221> NAME/KEY: MISC_FEATURE
<222> LOCATION: (46)..(46)
<223> OTHER INFORMATION: X is any amino acid or absent
<220> FEATURE:
<221> NAME/KEY: MISC_FEATURE
<222> LOCATION: (48)..(49)
<223> OTHER INFORMATION: X is any amino acid or absent
<220> FEATURE:
<221> NAME/KEY: MISC_FEATURE
<222> LOCATION: (53)..(53)
<223> OTHER INFORMATION: X is any amino acid or absent
<220> FEATURE:
<221> NAME/KEY: MISC_FEATURE
```

-continued

```
<222> LOCATION: (57)..(58)
<223> OTHER INFORMATION: X is any amino acid or absent
<220> FEATURE:
<221> NAME/KEY: MISC_FEATURE
<222> LOCATION: (61)..(61)
<223> OTHER INFORMATION: X is any amino acid or absent
<220> FEATURE:
<221> NAME/KEY: MISC_FEATURE
<222> LOCATION: (63)..(76)
<223> OTHER INFORMATION: X is any amino acid or absent
<220> FEATURE:
<221> NAME/KEY: MISC_FEATURE
<222> LOCATION: (78)..(78)
<223> OTHER INFORMATION: X is any amino acid or absent
<220> FEATURE:
<221> NAME/KEY: MISC_FEATURE
<222> LOCATION: (81)..(81)
<223> OTHER INFORMATION: X is any amino acid or absent
<220> FEATURE:
<221> NAME/KEY: MISC_FEATURE
<222> LOCATION: (83)..(84)
<223> OTHER INFORMATION: X is any amino acid or absent
<220> FEATURE:
<221> NAME/KEY: MISC_FEATURE
<222> LOCATION: (87)..(87)
<223> OTHER INFORMATION: X is any amino acid or absent
<220> FEATURE:
<221> NAME/KEY: MISC_FEATURE
<222> LOCATION: (90)..(94)
<223> OTHER INFORMATION: X is any amino acid or absent
<220> FEATURE:
<221> NAME/KEY: MISC_FEATURE
<222> LOCATION: (97)..(98)
<223> OTHER INFORMATION: X is any amino acid or absent
<220> FEATURE:
<221> NAME/KEY: MISC_FEATURE
<222> LOCATION: (100)..(102)
<223> OTHER INFORMATION: X is any amino acid or absent
<220> FEATURE:
<221> NAME/KEY: MISC_FEATURE
<222> LOCATION: (104)..(108)
<223> OTHER INFORMATION: X is any amino acid or absent
<220> FEATURE:
<221> NAME/KEY: MISC_FEATURE
<222> LOCATION: (110)..(124)
<223> OTHER INFORMATION: X is any amino acid or absent
<220> FEATURE:
<221> NAME/KEY: MISC_FEATURE
<222> LOCATION: (127)..(128)
<223> OTHER INFORMATION: X is any amino acid or absent
<220> FEATURE:
<221> NAME/KEY: MISC_FEATURE
<222> LOCATION: (137)..(137)
<223> OTHER INFORMATION: X is any amino acid or absent
<220> FEATURE:
<221> NAME/KEY: MISC_FEATURE
<222> LOCATION: (139)..(152)
<223> OTHER INFORMATION: X is any amino acid or absent
<220> FEATURE:
<221> NAME/KEY: MISC_FEATURE
<222> LOCATION: (154)..(155)
<223> OTHER INFORMATION: X is any amino acid or absent
<220> FEATURE:
<221> NAME/KEY: MISC_FEATURE
<222> LOCATION: (158)..(158)
<223> OTHER INFORMATION: X is any amino acid or absent
<220> FEATURE:
<221> NAME/KEY: MISC_FEATURE
<222> LOCATION: (160)..(161)
<223> OTHER INFORMATION: X is any amino acid or absent
<220> FEATURE:
<221> NAME/KEY: MISC_FEATURE
<222> LOCATION: (165)..(166)
<223> OTHER INFORMATION: X is any amino acid or absent
<220> FEATURE:
<221> NAME/KEY: MISC_FEATURE
<222> LOCATION: (168)..(174)
<223> OTHER INFORMATION: X is any amino acid or absent
<220> FEATURE:
```

```
<221> NAME/KEY: MISC_FEATURE
<222> LOCATION: (176)..(176)
<223> OTHER INFORMATION: X is any amino acid or absent
<220> FEATURE:
<221> NAME/KEY: MISC_FEATURE
<222> LOCATION: (179)..(187)
<223> OTHER INFORMATION: X is any amino acid or absent
<220> FEATURE:
<221> NAME/KEY: MISC_FEATURE
<222> LOCATION: (189)..(189)
<223> OTHER INFORMATION: X is any amino acid or absent
<220> FEATURE:
<221> NAME/KEY: MISC_FEATURE
<222> LOCATION: (195)..(195)
<223> OTHER INFORMATION: X is any amino acid or absent
<220> FEATURE:
<221> NAME/KEY: MISC_FEATURE
<222> LOCATION: (197)..(200)
<223> OTHER INFORMATION: X is any amino acid or absent
<220> FEATURE:
<221> NAME/KEY: MISC_FEATURE
<222> LOCATION: (202)..(204)
<223> OTHER INFORMATION: X is any amino acid or absent
<220> FEATURE:
<221> NAME/KEY: MISC_FEATURE
<222> LOCATION: (206)..(206)
<223> OTHER INFORMATION: X is any amino acid or absent
<220> FEATURE:
<221> NAME/KEY: MISC_FEATURE
<222> LOCATION: (208)..(209)
<223> OTHER INFORMATION: X is any amino acid or absent
<220> FEATURE:
<221> NAME/KEY: MISC_FEATURE
<222> LOCATION: (217)..(217)
<223> OTHER INFORMATION: X is any amino acid or absent
<220> FEATURE:
<221> NAME/KEY: MISC_FEATURE
<222> LOCATION: (225)..(226)
<223> OTHER INFORMATION: X is any amino acid or absent
<220> FEATURE:
<221> NAME/KEY: MISC_FEATURE
<222> LOCATION: (229)..(231)
<223> OTHER INFORMATION: X is any amino acid or absent
<220> FEATURE:
<221> NAME/KEY: MISC_FEATURE
<222> LOCATION: (233)..(234)
<223> OTHER INFORMATION: X is any amino acid or absent
<220> FEATURE:
<221> NAME/KEY: MISC_FEATURE
<222> LOCATION: (236)..(258)
<223> OTHER INFORMATION: X is any amino acid or absent
<220> FEATURE:
<221> NAME/KEY: MISC_FEATURE
<222> LOCATION: (260)..(263)
<223> OTHER INFORMATION: X is any amino acid or absent
<220> FEATURE:
<221> NAME/KEY: MISC_FEATURE
<222> LOCATION: (265)..(267)
<223> OTHER INFORMATION: X is any amino acid or absent
<220> FEATURE:
<221> NAME/KEY: MISC_FEATURE
<222> LOCATION: (270)..(271)
<223> OTHER INFORMATION: X is any amino acid or absent
<220> FEATURE:
<221> NAME/KEY: MISC_FEATURE
<222> LOCATION: (273)..(279)
<223> OTHER INFORMATION: X is any amino acid or absent
<220> FEATURE:
<221> NAME/KEY: MISC_FEATURE
<222> LOCATION: (281)..(283)
<223> OTHER INFORMATION: X is any amino acid or absent
<220> FEATURE:
<221> NAME/KEY: MISC_FEATURE
<222> LOCATION: (285)..(289)
<223> OTHER INFORMATION: X is any amino acid or absent
<220> FEATURE:
<221> NAME/KEY: MISC_FEATURE
<222> LOCATION: (291)..(297)
<223> OTHER INFORMATION: X is any amino acid or absent
```

```
<220> FEATURE:
<221> NAME/KEY: MISC_FEATURE
<222> LOCATION: (301)..(306)
<223> OTHER INFORMATION: X is any amino acid or absent
<220> FEATURE:
<221> NAME/KEY: MISC_FEATURE
<222> LOCATION: (310)..(310)
<223> OTHER INFORMATION: X is any amino acid or absent
<220> FEATURE:
<221> NAME/KEY: MISC_FEATURE
<222> LOCATION: (312)..(363)
<223> OTHER INFORMATION: X is any amino acid or absent
<220> FEATURE:
<221> NAME/KEY: MISC_FEATURE
<222> LOCATION: (365)..(433)
<223> OTHER INFORMATION: X is any amino acid or absent
<220> FEATURE:
<221> NAME/KEY: MISC_FEATURE
<222> LOCATION: (435)..(452)
<223> OTHER INFORMATION: X is any amino acid or absent
<220> FEATURE:
<221> NAME/KEY: MISC_FEATURE
<222> LOCATION: (454)..(456)
<223> OTHER INFORMATION: X is any amino acid or absent
<220> FEATURE:
<221> NAME/KEY: MISC_FEATURE
<222> LOCATION: (458)..(459)
<223> OTHER INFORMATION: X is any amino acid or absent
<220> FEATURE:
<221> NAME/KEY: MISC_FEATURE
<222> LOCATION: (461)..(464)
<223> OTHER INFORMATION: X is any amino acid or absent
<220> FEATURE:
<221> NAME/KEY: MISC_FEATURE
<222> LOCATION: (466)..(467)
<223> OTHER INFORMATION: X is any amino acid or absent
<220> FEATURE:
<221> NAME/KEY: MISC_FEATURE
<222> LOCATION: (469)..(472)
<223> OTHER INFORMATION: X is any amino acid or absent
<220> FEATURE:
<221> NAME/KEY: MISC_FEATURE
<222> LOCATION: (477)..(477)
<223> OTHER INFORMATION: X is any amino acid or absent
<220> FEATURE:
<221> NAME/KEY: MISC_FEATURE
<222> LOCATION: (479)..(485)
<223> OTHER INFORMATION: X is any amino acid or absent
<220> FEATURE:
<221> NAME/KEY: MISC_FEATURE
<222> LOCATION: (487)..(488)
<223> OTHER INFORMATION: X is any amino acid or absent
<220> FEATURE:
<221> NAME/KEY: MISC_FEATURE
<222> LOCATION: (490)..(491)
<223> OTHER INFORMATION: X is any amino acid or absent
<220> FEATURE:
<221> NAME/KEY: MISC_FEATURE
<222> LOCATION: (494)..(527)
<223> OTHER INFORMATION: X is any amino acid or absent
<220> FEATURE:
<221> NAME/KEY: MISC_FEATURE
<222> LOCATION: (529)..(531)
<223> OTHER INFORMATION: X is any amino acid or absent
<220> FEATURE:
<221> NAME/KEY: MISC_FEATURE
<222> LOCATION: (533)..(537)
<223> OTHER INFORMATION: X is any amino acid or absent
<220> FEATURE:
<221> NAME/KEY: MISC_FEATURE
<222> LOCATION: (539)..(548)
<223> OTHER INFORMATION: X is any amino acid or absent
<220> FEATURE:
<221> NAME/KEY: MISC_FEATURE
<222> LOCATION: (550)..(551)
<223> OTHER INFORMATION: X is any amino acid or absent
<220> FEATURE:
<221> NAME/KEY: MISC_FEATURE
<222> LOCATION: (553)..(554)
```

```
<223> OTHER INFORMATION: X is any amino acid or absent
<220> FEATURE:
<221> NAME/KEY: MISC_FEATURE
<222> LOCATION: (556)..(558)
<223> OTHER INFORMATION: X is any amino acid or absent
<220> FEATURE:
<221> NAME/KEY: MISC_FEATURE
<222> LOCATION: (561)..(561)
<223> OTHER INFORMATION: X is any amino acid or absent
<220> FEATURE:
<221> NAME/KEY: MISC_FEATURE
<222> LOCATION: (564)..(565)
<223> OTHER INFORMATION: X is any amino acid or absent
<220> FEATURE:
<221> NAME/KEY: MISC_FEATURE
<222> LOCATION: (568)..(569)
<223> OTHER INFORMATION: X is any amino acid or absent
<220> FEATURE:
<221> NAME/KEY: MISC_FEATURE
<222> LOCATION: (572)..(573)
<223> OTHER INFORMATION: X is any amino acid or absent
<220> FEATURE:
<221> NAME/KEY: MISC_FEATURE
<222> LOCATION: (575)..(577)
<223> OTHER INFORMATION: X is any amino acid or absent
<220> FEATURE:
<221> NAME/KEY: MISC_FEATURE
<222> LOCATION: (579)..(581)
<223> OTHER INFORMATION: X is any amino acid or absent
<220> FEATURE:
<221> NAME/KEY: MISC_FEATURE
<222> LOCATION: (584)..(584)
<223> OTHER INFORMATION: X is any amino acid or absent
<220> FEATURE:
<221> NAME/KEY: MISC_FEATURE
<222> LOCATION: (587)..(595)
<223> OTHER INFORMATION: X is any amino acid or absent
<220> FEATURE:
<221> NAME/KEY: MISC_FEATURE
<222> LOCATION: (597)..(599)
<223> OTHER INFORMATION: X is any amino acid or absent
<220> FEATURE:
<221> NAME/KEY: MISC_FEATURE
<222> LOCATION: (601)..(612)
<223> OTHER INFORMATION: X is any amino acid or absent
<220> FEATURE:
<221> NAME/KEY: MISC_FEATURE
<222> LOCATION: (615)..(616)
<223> OTHER INFORMATION: X is any amino acid or absent
<220> FEATURE:
<221> NAME/KEY: MISC_FEATURE
<222> LOCATION: (619)..(619)
<223> OTHER INFORMATION: X is any amino acid or absent
<220> FEATURE:
<221> NAME/KEY: MISC_FEATURE
<222> LOCATION: (622)..(622)
<223> OTHER INFORMATION: X is any amino acid or absent
<220> FEATURE:
<221> NAME/KEY: MISC_FEATURE
<222> LOCATION: (626)..(628)
<223> OTHER INFORMATION: X is any amino acid or absent
<220> FEATURE:
<221> NAME/KEY: MISC_FEATURE
<222> LOCATION: (631)..(632)
<223> OTHER INFORMATION: X is any amino acid or absent
<220> FEATURE:
<221> NAME/KEY: MISC_FEATURE
<222> LOCATION: (634)..(634)
<223> OTHER INFORMATION: X is any amino acid or absent
<220> FEATURE:
<221> NAME/KEY: MISC_FEATURE
<222> LOCATION: (637)..(639)
<223> OTHER INFORMATION: X is any amino acid or absent
<220> FEATURE:
<221> NAME/KEY: MISC_FEATURE
<222> LOCATION: (642)..(643)
<223> OTHER INFORMATION: X is any amino acid or absent
<220> FEATURE:
<221> NAME/KEY: MISC_FEATURE
```

```
<222> LOCATION: (646)..(647)
<223> OTHER INFORMATION: X is any amino acid or absent
<220> FEATURE:
<221> NAME/KEY: MISC_FEATURE
<222> LOCATION: (650)..(651)
<223> OTHER INFORMATION: X is any amino acid or absent
<220> FEATURE:
<221> NAME/KEY: MISC_FEATURE
<222> LOCATION: (655)..(656)
<223> OTHER INFORMATION: X is any amino acid or absent
<220> FEATURE:
<221> NAME/KEY: MISC_FEATURE
<222> LOCATION: (658)..(660)
<223> OTHER INFORMATION: X is any amino acid or absent
<220> FEATURE:
<221> NAME/KEY: MISC_FEATURE
<222> LOCATION: (663)..(665)
<223> OTHER INFORMATION: X is any amino acid or absent
<220> FEATURE:
<221> NAME/KEY: MISC_FEATURE
<222> LOCATION: (667)..(669)
<223> OTHER INFORMATION: X is any amino acid or absent
<220> FEATURE:
<221> NAME/KEY: MISC_FEATURE
<222> LOCATION: (672)..(673)
<223> OTHER INFORMATION: X is any amino acid or absent
<220> FEATURE:
<221> NAME/KEY: MISC_FEATURE
<222> LOCATION: (676)..(676)
<223> OTHER INFORMATION: X is any amino acid or absent
<220> FEATURE:
<221> NAME/KEY: MISC_FEATURE
<222> LOCATION: (678)..(678)
<223> OTHER INFORMATION: X is any amino acid or absent
<220> FEATURE:
<221> NAME/KEY: MISC_FEATURE
<222> LOCATION: (685)..(685)
<223> OTHER INFORMATION: X is any amino acid or absent
<220> FEATURE:
<221> NAME/KEY: MISC_FEATURE
<222> LOCATION: (687)..(687)
<223> OTHER INFORMATION: X is any amino acid or absent
<220> FEATURE:
<221> NAME/KEY: MISC_FEATURE
<222> LOCATION: (689)..(695)
<223> OTHER INFORMATION: X is any amino acid or absent
<220> FEATURE:
<221> NAME/KEY: MISC_FEATURE
<222> LOCATION: (697)..(697)
<223> OTHER INFORMATION: X is any amino acid or absent
<220> FEATURE:
<221> NAME/KEY: MISC_FEATURE
<222> LOCATION: (701)..(701)
<223> OTHER INFORMATION: X is any amino acid or absent
<220> FEATURE:
<221> NAME/KEY: MISC_FEATURE
<222> LOCATION: (704)..(704)
<223> OTHER INFORMATION: X is any amino acid or absent
<220> FEATURE:
<221> NAME/KEY: MISC_FEATURE
<222> LOCATION: (709)..(709)
<223> OTHER INFORMATION: X is any amino acid or absent
<220> FEATURE:
<221> NAME/KEY: MISC_FEATURE
<222> LOCATION: (719)..(719)
<223> OTHER INFORMATION: X is any amino acid or absent
<220> FEATURE:
<221> NAME/KEY: MISC_FEATURE
<222> LOCATION: (721)..(721)
<223> OTHER INFORMATION: X is any amino acid or absent
<220> FEATURE:
<221> NAME/KEY: MISC_FEATURE
<222> LOCATION: (725)..(725)
<223> OTHER INFORMATION: X is any amino acid or absent
<220> FEATURE:
<221> NAME/KEY: MISC_FEATURE
<222> LOCATION: (728)..(729)
<223> OTHER INFORMATION: X is any amino acid or absent
<220> FEATURE:
```

-continued

```
<221> NAME/KEY: MISC_FEATURE
<222> LOCATION: (731)..(731)
<223> OTHER INFORMATION: X is any amino acid or absent
<220> FEATURE:
<221> NAME/KEY: MISC_FEATURE
<222> LOCATION: (733)..(733)
<223> OTHER INFORMATION: X is any amino acid or absent
<220> FEATURE:
<221> NAME/KEY: MISC_FEATURE
<222> LOCATION: (735)..(736)
<223> OTHER INFORMATION: X is any amino acid or absent
<220> FEATURE:
<221> NAME/KEY: MISC_FEATURE
<222> LOCATION: (739)..(739)
<223> OTHER INFORMATION: X is any amino acid or absent
<220> FEATURE:
<221> NAME/KEY: MISC_FEATURE
<222> LOCATION: (743)..(749)
<223> OTHER INFORMATION: X is any amino acid or absent
<220> FEATURE:
<221> NAME/KEY: MISC_FEATURE
<222> LOCATION: (751)..(752)
<223> OTHER INFORMATION: X is any amino acid or absent
<220> FEATURE:
<221> NAME/KEY: MISC_FEATURE
<222> LOCATION: (762)..(762)
<223> OTHER INFORMATION: X is any amino acid or absent
<220> FEATURE:
<221> NAME/KEY: MISC_FEATURE
<222> LOCATION: (765)..(765)
<223> OTHER INFORMATION: X is any amino acid or absent
<220> FEATURE:
<221> NAME/KEY: MISC_FEATURE
<222> LOCATION: (769)..(769)
<223> OTHER INFORMATION: X is any amino acid or absent
<220> FEATURE:
<221> NAME/KEY: MISC_FEATURE
<222> LOCATION: (771)..(771)
<223> OTHER INFORMATION: X is any amino acid or absent
<220> FEATURE:
<221> NAME/KEY: MISC_FEATURE
<222> LOCATION: (775)..(775)
<223> OTHER INFORMATION: X is any amino acid or absent
<220> FEATURE:
<221> NAME/KEY: MISC_FEATURE
<222> LOCATION: (778)..(779)
<223> OTHER INFORMATION: X is any amino acid or absent
<220> FEATURE:
<221> NAME/KEY: MISC_FEATURE
<222> LOCATION: (781)..(788)
<223> OTHER INFORMATION: X is any amino acid or absent
<220> FEATURE:
<221> NAME/KEY: MISC_FEATURE
<222> LOCATION: (793)..(793)
<223> OTHER INFORMATION: X is any amino acid or absent
<220> FEATURE:
<221> NAME/KEY: MISC_FEATURE
<222> LOCATION: (797)..(797)
<223> OTHER INFORMATION: X is any amino acid or absent
<220> FEATURE:
<221> NAME/KEY: MISC_FEATURE
<222> LOCATION: (800)..(800)
<223> OTHER INFORMATION: X is any amino acid or absent
<220> FEATURE:
<221> NAME/KEY: MISC_FEATURE
<222> LOCATION: (802)..(803)
<223> OTHER INFORMATION: X is any amino acid or absent
<220> FEATURE:
<221> NAME/KEY: MISC_FEATURE
<222> LOCATION: (805)..(810)
<223> OTHER INFORMATION: X is any amino acid or absent
<220> FEATURE:
<221> NAME/KEY: MISC_FEATURE
<222> LOCATION: (813)..(814)
<223> OTHER INFORMATION: X is any amino acid or absent
<220> FEATURE:
<221> NAME/KEY: MISC_FEATURE
<222> LOCATION: (818)..(818)
<223> OTHER INFORMATION: X is any amino acid or absent
```

```
-continued

<220> FEATURE:
<221> NAME/KEY: MISC_FEATURE
<222> LOCATION: (821)..(821)
<223> OTHER INFORMATION: X is any amino acid or absent
<220> FEATURE:
<221> NAME/KEY: MISC_FEATURE
<222> LOCATION: (824)..(824)
<223> OTHER INFORMATION: X is any amino acid or absent
<220> FEATURE:
<221> NAME/KEY: MISC_FEATURE
<222> LOCATION: (827)..(827)
<223> OTHER INFORMATION: X is any amino acid or absent
<220> FEATURE:
<221> NAME/KEY: MISC_FEATURE
<222> LOCATION: (830)..(830)
<223> OTHER INFORMATION: X is any amino acid or absent
<220> FEATURE:
<221> NAME/KEY: MISC_FEATURE
<222> LOCATION: (832)..(833)
<223> OTHER INFORMATION: X is any amino acid or absent
<220> FEATURE:
<221> NAME/KEY: MISC_FEATURE
<222> LOCATION: (837)..(838)
<223> OTHER INFORMATION: X is any amino acid or absent
<220> FEATURE:
<221> NAME/KEY: MISC_FEATURE
<222> LOCATION: (840)..(856)
<223> OTHER INFORMATION: X is any amino acid or absent
<220> FEATURE:
<221> NAME/KEY: MISC_FEATURE
<222> LOCATION: (858)..(860)
<223> OTHER INFORMATION: X is any amino acid or absent
<220> FEATURE:
<221> NAME/KEY: MISC_FEATURE
<222> LOCATION: (863)..(865)
<223> OTHER INFORMATION: X is any amino acid or absent
<220> FEATURE:
<221> NAME/KEY: MISC_FEATURE
<222> LOCATION: (868)..(868)
<223> OTHER INFORMATION: X is any amino acid or absent
<220> FEATURE:
<221> NAME/KEY: MISC_FEATURE
<222> LOCATION: (871)..(873)
<223> OTHER INFORMATION: X is any amino acid or absent
<220> FEATURE:
<221> NAME/KEY: MISC_FEATURE
<222> LOCATION: (875)..(875)
<223> OTHER INFORMATION: X is any amino acid or absent
<220> FEATURE:
<221> NAME/KEY: MISC_FEATURE
<222> LOCATION: (877)..(879)
<223> OTHER INFORMATION: X is any amino acid or absent
<220> FEATURE:
<221> NAME/KEY: MISC_FEATURE
<222> LOCATION: (881)..(886)
<223> OTHER INFORMATION: X is any amino acid or absent
<220> FEATURE:
<221> NAME/KEY: MISC_FEATURE
<222> LOCATION: (889)..(890)
<223> OTHER INFORMATION: X is any amino acid or absent
<220> FEATURE:
<221> NAME/KEY: MISC_FEATURE
<222> LOCATION: (894)..(894)
<223> OTHER INFORMATION: X is any amino acid or absent
<220> FEATURE:
<221> NAME/KEY: MISC_FEATURE
<222> LOCATION: (902)..(903)
<223> OTHER INFORMATION: X is any amino acid or absent
<220> FEATURE:
<221> NAME/KEY: MISC_FEATURE
<222> LOCATION: (905)..(905)
<223> OTHER INFORMATION: X is any amino acid or absent
<220> FEATURE:
<221> NAME/KEY: MISC_FEATURE
<222> LOCATION: (907)..(907)
<223> OTHER INFORMATION: X is any amino acid or absent
<220> FEATURE:
<221> NAME/KEY: MISC_FEATURE
<222> LOCATION: (911)..(912)
```

```
<223> OTHER INFORMATION: X is any amino acid or absent
<220> FEATURE:
<221> NAME/KEY: MISC_FEATURE
<222> LOCATION: (915)..(917)
<223> OTHER INFORMATION: X is any amino acid or absent
<220> FEATURE:
<221> NAME/KEY: MISC_FEATURE
<222> LOCATION: (920)..(920)
<223> OTHER INFORMATION: X is any amino acid or absent
<220> FEATURE:
<221> NAME/KEY: MISC_FEATURE
<222> LOCATION: (922)..(922)
<223> OTHER INFORMATION: X is any amino acid or absent
<220> FEATURE:
<221> NAME/KEY: MISC_FEATURE
<222> LOCATION: (924)..(924)
<223> OTHER INFORMATION: X is any amino acid or absent
<220> FEATURE:
<221> NAME/KEY: MISC_FEATURE
<222> LOCATION: (939)..(944)
<223> OTHER INFORMATION: X is any amino acid or absent
<220> FEATURE:
<221> NAME/KEY: MISC_FEATURE
<222> LOCATION: (946)..(961)
<223> OTHER INFORMATION: X is any amino acid or absent
<220> FEATURE:
<221> NAME/KEY: MISC_FEATURE
<222> LOCATION: (964)..(964)
<223> OTHER INFORMATION: X is any amino acid or absent
<220> FEATURE:
<221> NAME/KEY: MISC_FEATURE
<222> LOCATION: (970)..(970)
<223> OTHER INFORMATION: X is any amino acid or absent
<220> FEATURE:
<221> NAME/KEY: MISC_FEATURE
<222> LOCATION: (973)..(974)
<223> OTHER INFORMATION: X is any amino acid or absent
<220> FEATURE:
<221> NAME/KEY: MISC_FEATURE
<222> LOCATION: (977)..(979)
<223> OTHER INFORMATION: X is any amino acid or absent
<220> FEATURE:
<221> NAME/KEY: MISC_FEATURE
<222> LOCATION: (981)..(984)
<223> OTHER INFORMATION: X is any amino acid or absent
<220> FEATURE:
<221> NAME/KEY: MISC_FEATURE
<222> LOCATION: (986)..(987)
<223> OTHER INFORMATION: X is any amino acid or absent
<220> FEATURE:
<221> NAME/KEY: MISC_FEATURE
<222> LOCATION: (990)..(991)
<223> OTHER INFORMATION: X is any amino acid or absent
<220> FEATURE:
<221> NAME/KEY: MISC_FEATURE
<222> LOCATION: (993)..(993)
<223> OTHER INFORMATION: X is any amino acid or absent
<220> FEATURE:
<221> NAME/KEY: MISC_FEATURE
<222> LOCATION: (995)..(995)
<223> OTHER INFORMATION: X is any amino acid or absent
<220> FEATURE:
<221> NAME/KEY: MISC_FEATURE
<222> LOCATION: (998)..(1001)
<223> OTHER INFORMATION: X is any amino acid or absent
<220> FEATURE:
<221> NAME/KEY: MISC_FEATURE
<222> LOCATION: (1003)..(1003)
<223> OTHER INFORMATION: X is any amino acid or absent
<220> FEATURE:
<221> NAME/KEY: MISC_FEATURE
<222> LOCATION: (1005)..(1008)
<223> OTHER INFORMATION: X is any amino acid or absent
<220> FEATURE:
<221> NAME/KEY: MISC_FEATURE
<222> LOCATION: (1010)..(1011)
<223> OTHER INFORMATION: X is any amino acid or absent
<220> FEATURE:
<221> NAME/KEY: MISC_FEATURE
```

<222> LOCATION: (1013)..(1090)
<223> OTHER INFORMATION: X is any amino acid or absent

<400> SEQUENCE: 20

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Leu Xaa Asp Gly Xaa Xaa Leu Xaa Tyr
            20                  25                  30

Arg Ala Xaa Xaa Ala Leu Xaa Xaa Xaa Leu Xaa Thr Ser Xaa Gly Xaa
        35                  40                  45

Xaa Thr Asn Ala Xaa Tyr Gly Phe Xaa Xaa Met Leu Xaa Lys Xaa Xaa
    50                  55                  60

Xaa Xaa Xaa Xaa Xaa Xaa Xaa Xaa Xaa Xaa Val Xaa Phe Asp
65                  70                  75              80

Xaa Lys Xaa Xaa Thr Phe Xaa Arg His Xaa Xaa Xaa Xaa Tyr Lys
            85                  90                  95

Xaa Xaa Arg Xaa Xaa Xaa Pro Xaa Xaa Xaa Xaa Gln Xaa Xaa Xaa
        100                 105                 110

Xaa Xaa Xaa Xaa Xaa Xaa Xaa Xaa Xaa Xaa Leu Glu Xaa Xaa
            115                 120                 125

Gly Tyr Glu Ala Asp Asp Ile Ile Xaa Thr Xaa Xaa Xaa Xaa Xaa
130                 135                 140

Xaa Xaa Xaa Xaa Xaa Xaa Xaa Ile Xaa Xaa Gly Asp Xaa Asp Xaa
145                 150                 155                 160

Xaa Gln Leu Val Xaa Xaa Lys Xaa Xaa Xaa Xaa Xaa Xaa Lys Xaa
        165                 170                 175

Ile Thr Xaa Xaa Xaa Xaa Xaa Xaa Xaa Val Xaa Glu Lys Tyr
        180                 185                 190

Gly Val Xaa Pro Xaa Xaa Xaa Xaa Asp Xaa Xaa Xaa Leu Xaa Gly Xaa
            195                 200                 205

Xaa Ser Asp Asn Ile Pro Gly Val Xaa Gly Ile Gly Glu Lys Thr Ala
210                 215                 220

Xaa Xaa Leu Leu Xaa Xaa Xaa Gly Xaa Xaa Glu Xaa Xaa Xaa Xaa
225                 230                 235                 240

Xaa Xaa Xaa Xaa Xaa Xaa Xaa Xaa Xaa Xaa Xaa Xaa Xaa Xaa Xaa
            245                 250                 255

Xaa Xaa Leu Xaa Xaa Xaa Glu Xaa Xaa Xaa Leu Ser Xaa Xaa Leu
        260                 265                 270

Xaa Xaa Xaa Xaa Xaa Xaa Pro Xaa Xaa Xaa Glu Xaa Xaa Xaa Xaa
        275                 280                 285

Xaa Leu Xaa Xaa Xaa Xaa Xaa Xaa Glu Lys Leu Xaa Xaa Xaa Xaa
290                 295                 300

Xaa Xaa Leu Glu Phe Xaa Ser Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Leu Xaa Xaa Xaa Xaa
            355                 360                 365

Xaa Xaa Xaa Xaa Xaa Xaa Xaa Xaa Xaa Xaa Xaa Xaa Xaa Xaa Xaa
            370                 375                 380

Xaa Xaa Xaa Xaa Xaa Xaa Xaa Xaa Xaa Xaa Xaa Xaa Xaa Xaa Xaa
385                 390                 395                 400
```

```
Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
            420                 425                 430

Xaa Leu Xaa Xaa Xaa Xaa Xaa Xaa Xaa Xaa Xaa Xaa Xaa Xaa Xaa
        435                 440                 445

Xaa Xaa Xaa Xaa Leu Xaa Xaa Xaa Gly Xaa Xaa Leu Xaa Xaa Xaa Xaa
450                 455                 460

Phe Xaa Xaa Asp Xaa Xaa Xaa Xaa Ala Tyr Leu Leu Xaa Pro Xaa Xaa
465                 470                 475                 480

Xaa Xaa Xaa Xaa Xaa Asp Xaa Xaa Ala Xaa Xaa Tyr Leu Xaa Xaa
                485                 490                 495

Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Ala
        515                 520                 525

Xaa Xaa Xaa Ala Xaa Xaa Xaa Xaa Leu Xaa Xaa Xaa Xaa Xaa Xaa
530                 535                 540

Xaa Xaa Xaa Xaa Glu Xaa Xaa Leu Xaa Xaa Leu Xaa Xaa Xaa Ile Glu
545                 550                 555                 560

Xaa Pro Leu Xaa Xaa Val Leu Xaa Xaa Met Glu Xaa Xaa Gly Xaa Xaa
                565                 570                 575

Xaa Asp Xaa Xaa Xaa Leu Lys Xaa Leu Ser Xaa Xaa Xaa Xaa Xaa
            580                 585                 590

Xaa Xaa Xaa Leu Xaa Xaa Xaa Ile Xaa Xaa Xaa Xaa Xaa Xaa Xaa
        595                 600                 605

Xaa Xaa Xaa Xaa Ala Gly Xaa Xaa Phe Asn Xaa Asn Ser Xaa Lys Gln
610                 615                 620

Leu Xaa Xaa Xaa Leu Phe Xaa Xaa Leu Xaa Leu Pro Xaa Xaa Xaa Lys
625                 630                 635                 640

Thr Xaa Xaa Thr Gly Xaa Xaa Ser Thr Xaa Xaa Glu Val Leu Xaa Xaa
            645                 650                 655

Leu Xaa Xaa Xaa His Pro Xaa Xaa Xaa Ile Xaa Xaa Xaa Ile Leu Xaa
            660                 665                 670

Xaa Tyr Arg Xaa Leu Xaa Lys Leu Lys Ser Thr Tyr Xaa Asp Xaa Leu
        675                 680                 685

Xaa Xaa Xaa Xaa Xaa Xaa Pro Xaa Thr Gly Arg Xaa His Thr Xaa
        690                 695                 700

Phe Asn Gln Thr Xaa Thr Ala Thr Gly Arg Leu Ser Ser Ser Xaa Pro
705                 710                 715                 720

Xaa Asn Leu Gln Xaa Ile Pro Xaa Xaa Arg Xaa Glu Xaa Gly Xaa Xaa
            725                 730                 735

Ile Arg Xaa Ala Phe Val Xaa Xaa Xaa Xaa Xaa Xaa Ile Xaa Xaa
            740                 745                 750

Ala Asp Tyr Ser Gln Ile Glu Leu Arg Xaa Leu Ala Xaa His Leu Ser
            755                 760                 765

Xaa Asp Xaa Asn Leu Ile Xaa Ala Phe Xaa Xaa Gly Xaa Xaa Xaa Xaa
770                 775                 780

Xaa Xaa Xaa Xaa Asp Ile His Thr Xaa Thr Ala Ser Xaa Ile Phe Xaa
785                 790                 795                 800

Val Xaa Xaa Glu Xaa Xaa Xaa Xaa Xaa Val Thr Xaa Xaa Met Arg
            805                 810                 815
```

-continued

```
Arg Xaa Ala Lys Xaa Val Asn Xaa Gly Ile Xaa Tyr Gly Xaa Ser Xaa
        820             825             830

Xaa Gly Leu Ser Xaa Xaa Leu Xaa Xaa Xaa Xaa Xaa Xaa Xaa Xaa Xaa
    835             840             845

Xaa Xaa Xaa Xaa Xaa Xaa Xaa Ile Xaa Xaa Xaa Glu Ala Xaa Xaa
850             855             860

Xaa Ile Glu Xaa Tyr Phe Xaa Xaa Pro Xaa Val Xaa Xaa Xaa Ile
865             870             875             880

Xaa Xaa Xaa Xaa Xaa Xaa Ala Lys Xaa Xaa Gly Tyr Val Xaa Thr Leu
            885             890             895

Phe Gly Arg Arg Arg Xaa Xaa Pro Xaa Ile Xaa Ser Arg Asn Xaa Xaa
        900             905             910

Val Arg Xaa Xaa Xaa Glu Arg Xaa Ala Xaa Asn Xaa Pro Ile Gln Gly
        915             920             925

Thr Ala Ala Asp Ile Ile Lys Leu Ala Met Xaa Xaa Xaa Xaa Xaa
        930             935             940

Leu Xaa Xaa Xaa Xaa Xaa Xaa Xaa Xaa Xaa Xaa Xaa Xaa Xaa Xaa
945             950             955             960

Xaa Leu Gln Xaa His Asp Glu Leu Val Xaa Glu Val Xaa Xaa Glu Glu
            965             970             975

Xaa Xaa Xaa Val Xaa Xaa Xaa Xaa Lys Xaa Xaa Met Glu Xaa Xaa Val
        980             985             990

Xaa Leu Xaa Val Pro Xaa Xaa  Xaa Leu Xaa Val Xaa  Xaa Xaa Xaa
        995             1000            1005

Gly Xaa  Xaa Trp Xaa Xaa Xaa  Xaa Xaa Xaa Xaa Xaa  Xaa Xaa Xaa
    1010            1015            1020

Xaa Xaa  Xaa Xaa Xaa Xaa Xaa  Xaa Xaa Xaa Xaa Xaa  Xaa Xaa Xaa
    1025            1030            1035

Xaa Xaa  Xaa Xaa Xaa Xaa Xaa  Xaa Xaa Xaa Xaa Xaa  Xaa Xaa Xaa
    1040            1045            1050

Xaa Xaa  Xaa Xaa Xaa Xaa Xaa  Xaa Xaa Xaa Xaa Xaa  Xaa Xaa Xaa
    1055            1060            1065

Xaa Xaa  Xaa Xaa Xaa Xaa Xaa  Xaa Xaa Xaa Xaa Xaa  Xaa Xaa Xaa
    1070            1075            1080

Xaa Xaa  Xaa Xaa Xaa Xaa Xaa
    1085            1090

<210> SEQ ID NO 21
<211> LENGTH: 989
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (2)..(2)
<223> OTHER INFORMATION: X is any amino acid or absent
<220> FEATURE:
<221> NAME/KEY: MISC_FEATURE
<222> LOCATION: (5)..(6)
<223> OTHER INFORMATION: X is any amino acid or absent
<220> FEATURE:
<221> NAME/KEY: MISC_FEATURE
<222> LOCATION: (8)..(8)
<223> OTHER INFORMATION: X is any amino acid or absent
<220> FEATURE:
<221> NAME/KEY: MISC_FEATURE
<222> LOCATION: (12)..(13)
<223> OTHER INFORMATION: X is any amino acid or absent
<220> FEATURE:
<221> NAME/KEY: MISC_FEATURE
```

-continued

```
<222> LOCATION: (16)..(18)
<223> OTHER INFORMATION: X is any amino acid or absent
<220> FEATURE:
<221> NAME/KEY: MISC_FEATURE
<222> LOCATION: (20)..(20)
<223> OTHER INFORMATION: X is any amino acid or absent
<220> FEATURE:
<221> NAME/KEY: MISC_FEATURE
<222> LOCATION: (23)..(23)
<223> OTHER INFORMATION: X is any amino acid or absent
<220> FEATURE:
<221> NAME/KEY: MISC_FEATURE
<222> LOCATION: (25)..(26)
<223> OTHER INFORMATION: X is any amino acid or absent
<220> FEATURE:
<221> NAME/KEY: MISC_FEATURE
<222> LOCATION: (30)..(30)
<223> OTHER INFORMATION: X is any amino acid or absent
<220> FEATURE:
<221> NAME/KEY: MISC_FEATURE
<222> LOCATION: (34)..(35)
<223> OTHER INFORMATION: X is any amino acid or absent
<220> FEATURE:
<221> NAME/KEY: MISC_FEATURE
<222> LOCATION: (38)..(38)
<223> OTHER INFORMATION: X is any amino acid or absent
<220> FEATURE:
<221> NAME/KEY: MISC_FEATURE
<222> LOCATION: (40)..(53)
<223> OTHER INFORMATION: X is any amino acid or absent
<220> FEATURE:
<221> NAME/KEY: MISC_FEATURE
<222> LOCATION: (55)..(55)
<223> OTHER INFORMATION: X is any amino acid or absent
<220> FEATURE:
<221> NAME/KEY: MISC_FEATURE
<222> LOCATION: (58)..(58)
<223> OTHER INFORMATION: X is any amino acid or absent
<220> FEATURE:
<221> NAME/KEY: MISC_FEATURE
<222> LOCATION: (60)..(61)
<223> OTHER INFORMATION: X is any amino acid or absent
<220> FEATURE:
<221> NAME/KEY: MISC_FEATURE
<222> LOCATION: (64)..(64)
<223> OTHER INFORMATION: X is any amino acid or absent
<220> FEATURE:
<221> NAME/KEY: MISC_FEATURE
<222> LOCATION: (67)..(71)
<223> OTHER INFORMATION: X is any amino acid or absent
<220> FEATURE:
<221> NAME/KEY: MISC_FEATURE
<222> LOCATION: (74)..(75)
<223> OTHER INFORMATION: X is any amino acid or absent
<220> FEATURE:
<221> NAME/KEY: MISC_FEATURE
<222> LOCATION: (77)..(79)
<223> OTHER INFORMATION: X is any amino acid or absent
<220> FEATURE:
<221> NAME/KEY: MISC_FEATURE
<222> LOCATION: (81)..(85)
<223> OTHER INFORMATION: X is any amino acid or absent
<220> FEATURE:
<221> NAME/KEY: MISC_FEATURE
<222> LOCATION: (87)..(101)
<223> OTHER INFORMATION: X is any amino acid or absent
<220> FEATURE:
<221> NAME/KEY: MISC_FEATURE
<222> LOCATION: (104)..(105)
<223> OTHER INFORMATION: X is any amino acid or absent
<220> FEATURE:
<221> NAME/KEY: MISC_FEATURE
<222> LOCATION: (114)..(114)
<223> OTHER INFORMATION: X is any amino acid or absent
<220> FEATURE:
<221> NAME/KEY: MISC_FEATURE
<222> LOCATION: (116)..(129)
<223> OTHER INFORMATION: X is any amino acid or absent
<220> FEATURE:
```

```
<221> NAME/KEY: MISC_FEATURE
<222> LOCATION: (131)..(132)
<223> OTHER INFORMATION: X is any amino acid or absent
<220> FEATURE:
<221> NAME/KEY: MISC_FEATURE
<222> LOCATION: (135)..(135)
<223> OTHER INFORMATION: X is any amino acid or absent
<220> FEATURE:
<221> NAME/KEY: MISC_FEATURE
<222> LOCATION: (137)..(138)
<223> OTHER INFORMATION: X is any amino acid or absent
<220> FEATURE:
<221> NAME/KEY: MISC_FEATURE
<222> LOCATION: (142)..(143)
<223> OTHER INFORMATION: X is any amino acid or absent
<220> FEATURE:
<221> NAME/KEY: MISC_FEATURE
<222> LOCATION: (145)..(151)
<223> OTHER INFORMATION: X is any amino acid or absent
<220> FEATURE:
<221> NAME/KEY: MISC_FEATURE
<222> LOCATION: (153)..(153)
<223> OTHER INFORMATION: X is any amino acid or absent
<220> FEATURE:
<221> NAME/KEY: MISC_FEATURE
<222> LOCATION: (156)..(164)
<223> OTHER INFORMATION: X is any amino acid or absent
<220> FEATURE:
<221> NAME/KEY: MISC_FEATURE
<222> LOCATION: (166)..(166)
<223> OTHER INFORMATION: X is any amino acid or absent
<220> FEATURE:
<221> NAME/KEY: MISC_FEATURE
<222> LOCATION: (172)..(172)
<223> OTHER INFORMATION: X is any amino acid or absent
<220> FEATURE:
<221> NAME/KEY: MISC_FEATURE
<222> LOCATION: (174)..(177)
<223> OTHER INFORMATION: X is any amino acid or absent
<220> FEATURE:
<221> NAME/KEY: MISC_FEATURE
<222> LOCATION: (179)..(181)
<223> OTHER INFORMATION: X is any amino acid or absent
<220> FEATURE:
<221> NAME/KEY: MISC_FEATURE
<222> LOCATION: (183)..(183)
<223> OTHER INFORMATION: X is any amino acid or absent
<220> FEATURE:
<221> NAME/KEY: MISC_FEATURE
<222> LOCATION: (185)..(186)
<223> OTHER INFORMATION: X is any amino acid or absent
<220> FEATURE:
<221> NAME/KEY: MISC_FEATURE
<222> LOCATION: (194)..(194)
<223> OTHER INFORMATION: X is any amino acid or absent
<220> FEATURE:
<221> NAME/KEY: MISC_FEATURE
<222> LOCATION: (202)..(203)
<223> OTHER INFORMATION: X is any amino acid or absent
<220> FEATURE:
<221> NAME/KEY: MISC_FEATURE
<222> LOCATION: (206)..(208)
<223> OTHER INFORMATION: X is any amino acid or absent
<220> FEATURE:
<221> NAME/KEY: MISC_FEATURE
<222> LOCATION: (210)..(211)
<223> OTHER INFORMATION: X is any amino acid or absent
<220> FEATURE:
<221> NAME/KEY: MISC_FEATURE
<222> LOCATION: (213)..(235)
<223> OTHER INFORMATION: X is any amino acid or absent
<220> FEATURE:
<221> NAME/KEY: MISC_FEATURE
<222> LOCATION: (237)..(240)
<223> OTHER INFORMATION: X is any amino acid or absent
<220> FEATURE:
<221> NAME/KEY: MISC_FEATURE
<222> LOCATION: (242)..(244)
<223> OTHER INFORMATION: X is any amino acid or absent
```

```
-continued

<220> FEATURE:
<221> NAME/KEY: MISC_FEATURE
<222> LOCATION: (247)..(248)
<223> OTHER INFORMATION: X is any amino acid or absent
<220> FEATURE:
<221> NAME/KEY: MISC_FEATURE
<222> LOCATION: (250)..(256)
<223> OTHER INFORMATION: X is any amino acid or absent
<220> FEATURE:
<221> NAME/KEY: MISC_FEATURE
<222> LOCATION: (258)..(260)
<223> OTHER INFORMATION: X is any amino acid or absent
<220> FEATURE:
<221> NAME/KEY: MISC_FEATURE
<222> LOCATION: (262)..(266)
<223> OTHER INFORMATION: X is any amino acid or absent
<220> FEATURE:
<221> NAME/KEY: MISC_FEATURE
<222> LOCATION: (268)..(274)
<223> OTHER INFORMATION: X is any amino acid or absent
<220> FEATURE:
<221> NAME/KEY: MISC_FEATURE
<222> LOCATION: (278)..(283)
<223> OTHER INFORMATION: X is any amino acid or absent
<220> FEATURE:
<221> NAME/KEY: MISC_FEATURE
<222> LOCATION: (287)..(287)
<223> OTHER INFORMATION: X is any amino acid or absent
<220> FEATURE:
<221> NAME/KEY: MISC_FEATURE
<222> LOCATION: (289)..(340)
<223> OTHER INFORMATION: X is any amino acid or absent
<220> FEATURE:
<221> NAME/KEY: MISC_FEATURE
<222> LOCATION: (342)..(410)
<223> OTHER INFORMATION: X is any amino acid or absent
<220> FEATURE:
<221> NAME/KEY: MISC_FEATURE
<222> LOCATION: (412)..(429)
<223> OTHER INFORMATION: X is any amino acid or absent
<220> FEATURE:
<221> NAME/KEY: MISC_FEATURE
<222> LOCATION: (431)..(433)
<223> OTHER INFORMATION: X is any amino acid or absent
<220> FEATURE:
<221> NAME/KEY: MISC_FEATURE
<222> LOCATION: (435)..(436)
<223> OTHER INFORMATION: X is any amino acid or absent
<220> FEATURE:
<221> NAME/KEY: MISC_FEATURE
<222> LOCATION: (438)..(441)
<223> OTHER INFORMATION: X is any amino acid or absent
<220> FEATURE:
<221> NAME/KEY: MISC_FEATURE
<222> LOCATION: (443)..(444)
<223> OTHER INFORMATION: X is any amino acid or absent
<220> FEATURE:
<221> NAME/KEY: MISC_FEATURE
<222> LOCATION: (446)..(449)
<223> OTHER INFORMATION: X is any amino acid or absent
<220> FEATURE:
<221> NAME/KEY: MISC_FEATURE
<222> LOCATION: (454)..(454)
<223> OTHER INFORMATION: X is any amino acid or absent
<220> FEATURE:
<221> NAME/KEY: MISC_FEATURE
<222> LOCATION: (456)..(462)
<223> OTHER INFORMATION: X is any amino acid or absent
<220> FEATURE:
<221> NAME/KEY: MISC_FEATURE
<222> LOCATION: (464)..(465)
<223> OTHER INFORMATION: X is any amino acid or absent
<220> FEATURE:
<221> NAME/KEY: MISC_FEATURE
<222> LOCATION: (467)..(468)
<223> OTHER INFORMATION: X is any amino acid or absent
<220> FEATURE:
<221> NAME/KEY: MISC_FEATURE
<222> LOCATION: (471)..(504)
```

```
<223> OTHER INFORMATION: X is any amino acid or absent
<220> FEATURE:
<221> NAME/KEY: MISC_FEATURE
<222> LOCATION: (506)..(508)
<223> OTHER INFORMATION: X is any amino acid or absent
<220> FEATURE:
<221> NAME/KEY: MISC_FEATURE
<222> LOCATION: (510)..(514)
<223> OTHER INFORMATION: X is any amino acid or absent
<220> FEATURE:
<221> NAME/KEY: MISC_FEATURE
<222> LOCATION: (516)..(525)
<223> OTHER INFORMATION: X is any amino acid or absent
<220> FEATURE:
<221> NAME/KEY: MISC_FEATURE
<222> LOCATION: (527)..(528)
<223> OTHER INFORMATION: X is any amino acid or absent
<220> FEATURE:
<221> NAME/KEY: MISC_FEATURE
<222> LOCATION: (530)..(531)
<223> OTHER INFORMATION: X is any amino acid or absent
<220> FEATURE:
<221> NAME/KEY: MISC_FEATURE
<222> LOCATION: (533)..(535)
<223> OTHER INFORMATION: X is any amino acid or absent
<220> FEATURE:
<221> NAME/KEY: MISC_FEATURE
<222> LOCATION: (538)..(538)
<223> OTHER INFORMATION: X is any amino acid or absent
<220> FEATURE:
<221> NAME/KEY: MISC_FEATURE
<222> LOCATION: (541)..(542)
<223> OTHER INFORMATION: X is any amino acid or absent
<220> FEATURE:
<221> NAME/KEY: MISC_FEATURE
<222> LOCATION: (545)..(546)
<223> OTHER INFORMATION: X is any amino acid or absent
<220> FEATURE:
<221> NAME/KEY: MISC_FEATURE
<222> LOCATION: (549)..(550)
<223> OTHER INFORMATION: X is any amino acid or absent
<220> FEATURE:
<221> NAME/KEY: MISC_FEATURE
<222> LOCATION: (552)..(554)
<223> OTHER INFORMATION: X is any amino acid or absent
<220> FEATURE:
<221> NAME/KEY: MISC_FEATURE
<222> LOCATION: (556)..(558)
<223> OTHER INFORMATION: X is any amino acid or absent
<220> FEATURE:
<221> NAME/KEY: MISC_FEATURE
<222> LOCATION: (561)..(561)
<223> OTHER INFORMATION: X is any amino acid or absent
<220> FEATURE:
<221> NAME/KEY: MISC_FEATURE
<222> LOCATION: (564)..(572)
<223> OTHER INFORMATION: X is any amino acid or absent
<220> FEATURE:
<221> NAME/KEY: MISC_FEATURE
<222> LOCATION: (574)..(576)
<223> OTHER INFORMATION: X is any amino acid or absent
<220> FEATURE:
<221> NAME/KEY: MISC_FEATURE
<222> LOCATION: (578)..(589)
<223> OTHER INFORMATION: X is any amino acid or absent
<220> FEATURE:
<221> NAME/KEY: MISC_FEATURE
<222> LOCATION: (592)..(593)
<223> OTHER INFORMATION: X is any amino acid or absent
<220> FEATURE:
<221> NAME/KEY: MISC_FEATURE
<222> LOCATION: (596)..(596)
<223> OTHER INFORMATION: X is any amino acid or absent
<220> FEATURE:
<221> NAME/KEY: MISC_FEATURE
<222> LOCATION: (599)..(599)
<223> OTHER INFORMATION: X is any amino acid or absent
<220> FEATURE:
<221> NAME/KEY: MISC_FEATURE
```

-continued

```
<222> LOCATION: (603)..(605)
<223> OTHER INFORMATION: X is any amino acid or absent
<220> FEATURE:
<221> NAME/KEY: MISC_FEATURE
<222> LOCATION: (608)..(609)
<223> OTHER INFORMATION: X is any amino acid or absent
<220> FEATURE:
<221> NAME/KEY: MISC_FEATURE
<222> LOCATION: (611)..(611)
<223> OTHER INFORMATION: X is any amino acid or absent
<220> FEATURE:
<221> NAME/KEY: MISC_FEATURE
<222> LOCATION: (614)..(616)
<223> OTHER INFORMATION: X is any amino acid or absent
<220> FEATURE:
<221> NAME/KEY: MISC_FEATURE
<222> LOCATION: (619)..(620)
<223> OTHER INFORMATION: X is any amino acid or absent
<220> FEATURE:
<221> NAME/KEY: MISC_FEATURE
<222> LOCATION: (623)..(624)
<223> OTHER INFORMATION: X is any amino acid or absent
<220> FEATURE:
<221> NAME/KEY: MISC_FEATURE
<222> LOCATION: (627)..(628)
<223> OTHER INFORMATION: X is any amino acid or absent
<220> FEATURE:
<221> NAME/KEY: MISC_FEATURE
<222> LOCATION: (632)..(633)
<223> OTHER INFORMATION: X is any amino acid or absent
<220> FEATURE:
<221> NAME/KEY: MISC_FEATURE
<222> LOCATION: (635)..(637)
<223> OTHER INFORMATION: X is any amino acid or absent
<220> FEATURE:
<221> NAME/KEY: MISC_FEATURE
<222> LOCATION: (640)..(642)
<223> OTHER INFORMATION: X is any amino acid or absent
<220> FEATURE:
<221> NAME/KEY: MISC_FEATURE
<222> LOCATION: (644)..(646)
<223> OTHER INFORMATION: X is any amino acid or absent
<220> FEATURE:
<221> NAME/KEY: MISC_FEATURE
<222> LOCATION: (649)..(650)
<223> OTHER INFORMATION: X is any amino acid or absent
<220> FEATURE:
<221> NAME/KEY: MISC_FEATURE
<222> LOCATION: (653)..(653)
<223> OTHER INFORMATION: X is any amino acid or absent
<220> FEATURE:
<221> NAME/KEY: MISC_FEATURE
<222> LOCATION: (655)..(655)
<223> OTHER INFORMATION: X is any amino acid or absent
<220> FEATURE:
<221> NAME/KEY: MISC_FEATURE
<222> LOCATION: (662)..(662)
<223> OTHER INFORMATION: X is any amino acid or absent
<220> FEATURE:
<221> NAME/KEY: MISC_FEATURE
<222> LOCATION: (664)..(664)
<223> OTHER INFORMATION: X is any amino acid or absent
<220> FEATURE:
<221> NAME/KEY: MISC_FEATURE
<222> LOCATION: (666)..(672)
<223> OTHER INFORMATION: X is any amino acid or absent
<220> FEATURE:
<221> NAME/KEY: MISC_FEATURE
<222> LOCATION: (674)..(674)
<223> OTHER INFORMATION: X is any amino acid or absent
<220> FEATURE:
<221> NAME/KEY: MISC_FEATURE
<222> LOCATION: (678)..(678)
<223> OTHER INFORMATION: X is any amino acid or absent
<220> FEATURE:
<221> NAME/KEY: MISC_FEATURE
<222> LOCATION: (681)..(681)
<223> OTHER INFORMATION: X is any amino acid or absent
<220> FEATURE:
```

```
<221> NAME/KEY: MISC_FEATURE
<222> LOCATION: (686)..(686)
<223> OTHER INFORMATION: X is any amino acid or absent
<220> FEATURE:
<221> NAME/KEY: MISC_FEATURE
<222> LOCATION: (696)..(696)
<223> OTHER INFORMATION: X is any amino acid or absent
<220> FEATURE:
<221> NAME/KEY: MISC_FEATURE
<222> LOCATION: (698)..(698)
<223> OTHER INFORMATION: X is any amino acid or absent
<220> FEATURE:
<221> NAME/KEY: MISC_FEATURE
<222> LOCATION: (702)..(702)
<223> OTHER INFORMATION: X is any amino acid or absent
<220> FEATURE:
<221> NAME/KEY: MISC_FEATURE
<222> LOCATION: (705)..(706)
<223> OTHER INFORMATION: X is any amino acid or absent
<220> FEATURE:
<221> NAME/KEY: MISC_FEATURE
<222> LOCATION: (708)..(708)
<223> OTHER INFORMATION: X is any amino acid or absent
<220> FEATURE:
<221> NAME/KEY: MISC_FEATURE
<222> LOCATION: (710)..(710)
<223> OTHER INFORMATION: X is any amino acid or absent
<220> FEATURE:
<221> NAME/KEY: MISC_FEATURE
<222> LOCATION: (712)..(713)
<223> OTHER INFORMATION: X is any amino acid or absent
<220> FEATURE:
<221> NAME/KEY: MISC_FEATURE
<222> LOCATION: (716)..(716)
<223> OTHER INFORMATION: X is any amino acid or absent
<220> FEATURE:
<221> NAME/KEY: MISC_FEATURE
<222> LOCATION: (720)..(726)
<223> OTHER INFORMATION: X is any amino acid or absent
<220> FEATURE:
<221> NAME/KEY: MISC_FEATURE
<222> LOCATION: (728)..(729)
<223> OTHER INFORMATION: X is any amino acid or absent
<220> FEATURE:
<221> NAME/KEY: MISC_FEATURE
<222> LOCATION: (739)..(739)
<223> OTHER INFORMATION: X is any amino acid or absent
<220> FEATURE:
<221> NAME/KEY: MISC_FEATURE
<222> LOCATION: (742)..(742)
<223> OTHER INFORMATION: X is any amino acid or absent
<220> FEATURE:
<221> NAME/KEY: MISC_FEATURE
<222> LOCATION: (746)..(746)
<223> OTHER INFORMATION: X is any amino acid or absent
<220> FEATURE:
<221> NAME/KEY: MISC_FEATURE
<222> LOCATION: (748)..(748)
<223> OTHER INFORMATION: X is any amino acid or absent
<220> FEATURE:
<221> NAME/KEY: MISC_FEATURE
<222> LOCATION: (752)..(752)
<223> OTHER INFORMATION: X is any amino acid or absent
<220> FEATURE:
<221> NAME/KEY: MISC_FEATURE
<222> LOCATION: (755)..(756)
<223> OTHER INFORMATION: X is any amino acid or absent
<220> FEATURE:
<221> NAME/KEY: MISC_FEATURE
<222> LOCATION: (758)..(765)
<223> OTHER INFORMATION: X is any amino acid or absent
<220> FEATURE:
<221> NAME/KEY: MISC_FEATURE
<222> LOCATION: (770)..(770)
<223> OTHER INFORMATION: X is any amino acid or absent
<220> FEATURE:
<221> NAME/KEY: MISC_FEATURE
<222> LOCATION: (774)..(774)
<223> OTHER INFORMATION: X is any amino acid or absent
```

-continued

```
<220> FEATURE:
<221> NAME/KEY: MISC_FEATURE
<222> LOCATION: (777)..(777)
<223> OTHER INFORMATION: X is any amino acid or absent
<220> FEATURE:
<221> NAME/KEY: MISC_FEATURE
<222> LOCATION: (779)..(780)
<223> OTHER INFORMATION: X is any amino acid or absent
<220> FEATURE:
<221> NAME/KEY: MISC_FEATURE
<222> LOCATION: (782)..(787)
<223> OTHER INFORMATION: X is any amino acid or absent
<220> FEATURE:
<221> NAME/KEY: MISC_FEATURE
<222> LOCATION: (790)..(791)
<223> OTHER INFORMATION: X is any amino acid or absent
<220> FEATURE:
<221> NAME/KEY: MISC_FEATURE
<222> LOCATION: (795)..(795)
<223> OTHER INFORMATION: X is any amino acid or absent
<220> FEATURE:
<221> NAME/KEY: MISC_FEATURE
<222> LOCATION: (798)..(798)
<223> OTHER INFORMATION: X is any amino acid or absent
<220> FEATURE:
<221> NAME/KEY: MISC_FEATURE
<222> LOCATION: (801)..(801)
<223> OTHER INFORMATION: X is any amino acid or absent
<220> FEATURE:
<221> NAME/KEY: MISC_FEATURE
<222> LOCATION: (804)..(804)
<223> OTHER INFORMATION: X is any amino acid or absent
<220> FEATURE:
<221> NAME/KEY: MISC_FEATURE
<222> LOCATION: (807)..(807)
<223> OTHER INFORMATION: X is any amino acid or absent
<220> FEATURE:
<221> NAME/KEY: MISC_FEATURE
<222> LOCATION: (809)..(810)
<223> OTHER INFORMATION: X is any amino acid or absent
<220> FEATURE:
<221> NAME/KEY: MISC_FEATURE
<222> LOCATION: (814)..(815)
<223> OTHER INFORMATION: X is any amino acid or absent
<220> FEATURE:
<221> NAME/KEY: MISC_FEATURE
<222> LOCATION: (817)..(833)
<223> OTHER INFORMATION: X is any amino acid or absent
<220> FEATURE:
<221> NAME/KEY: MISC_FEATURE
<222> LOCATION: (835)..(837)
<223> OTHER INFORMATION: X is any amino acid or absent
<220> FEATURE:
<221> NAME/KEY: MISC_FEATURE
<222> LOCATION: (840)..(842)
<223> OTHER INFORMATION: X is any amino acid or absent
<220> FEATURE:
<221> NAME/KEY: MISC_FEATURE
<222> LOCATION: (845)..(845)
<223> OTHER INFORMATION: X is any amino acid or absent
<220> FEATURE:
<221> NAME/KEY: MISC_FEATURE
<222> LOCATION: (848)..(850)
<223> OTHER INFORMATION: X is any amino acid or absent
<220> FEATURE:
<221> NAME/KEY: MISC_FEATURE
<222> LOCATION: (852)..(852)
<223> OTHER INFORMATION: X is any amino acid or absent
<220> FEATURE:
<221> NAME/KEY: MISC_FEATURE
<222> LOCATION: (854)..(856)
<223> OTHER INFORMATION: X is any amino acid or absent
<220> FEATURE:
<221> NAME/KEY: MISC_FEATURE
<222> LOCATION: (858)..(863)
<223> OTHER INFORMATION: X is any amino acid or absent
<220> FEATURE:
<221> NAME/KEY: MISC_FEATURE
<222> LOCATION: (866)..(867)
```

```
<223> OTHER INFORMATION: X is any amino acid or absent
<220> FEATURE:
<221> NAME/KEY: MISC_FEATURE
<222> LOCATION: (871)..(871)
<223> OTHER INFORMATION: X is any amino acid or absent
<220> FEATURE:
<221> NAME/KEY: MISC_FEATURE
<222> LOCATION: (879)..(880)
<223> OTHER INFORMATION: X is any amino acid or absent
<220> FEATURE:
<221> NAME/KEY: MISC_FEATURE
<222> LOCATION: (882)..(882)
<223> OTHER INFORMATION: X is any amino acid or absent
<220> FEATURE:
<221> NAME/KEY: MISC_FEATURE
<222> LOCATION: (884)..(884)
<223> OTHER INFORMATION: X is any amino acid or absent
<220> FEATURE:
<221> NAME/KEY: MISC_FEATURE
<222> LOCATION: (888)..(889)
<223> OTHER INFORMATION: X is any amino acid or absent
<220> FEATURE:
<221> NAME/KEY: MISC_FEATURE
<222> LOCATION: (892)..(894)
<223> OTHER INFORMATION: X is any amino acid or absent
<220> FEATURE:
<221> NAME/KEY: MISC_FEATURE
<222> LOCATION: (897)..(897)
<223> OTHER INFORMATION: X is any amino acid or absent
<220> FEATURE:
<221> NAME/KEY: MISC_FEATURE
<222> LOCATION: (899)..(899)
<223> OTHER INFORMATION: X is any amino acid or absent
<220> FEATURE:
<221> NAME/KEY: MISC_FEATURE
<222> LOCATION: (901)..(901)
<223> OTHER INFORMATION: X is any amino acid or absent
<220> FEATURE:
<221> NAME/KEY: MISC_FEATURE
<222> LOCATION: (916)..(921)
<223> OTHER INFORMATION: X is any amino acid or absent
<220> FEATURE:
<221> NAME/KEY: MISC_FEATURE
<222> LOCATION: (923)..(938)
<223> OTHER INFORMATION: X is any amino acid or absent
<220> FEATURE:
<221> NAME/KEY: MISC_FEATURE
<222> LOCATION: (941)..(941)
<223> OTHER INFORMATION: X is any amino acid or absent
<220> FEATURE:
<221> NAME/KEY: MISC_FEATURE
<222> LOCATION: (947)..(947)
<223> OTHER INFORMATION: X is any amino acid or absent
<220> FEATURE:
<221> NAME/KEY: MISC_FEATURE
<222> LOCATION: (950)..(951)
<223> OTHER INFORMATION: X is any amino acid or absent
<220> FEATURE:
<221> NAME/KEY: MISC_FEATURE
<222> LOCATION: (954)..(956)
<223> OTHER INFORMATION: X is any amino acid or absent
<220> FEATURE:
<221> NAME/KEY: MISC_FEATURE
<222> LOCATION: (958)..(961)
<223> OTHER INFORMATION: X is any amino acid or absent
<220> FEATURE:
<221> NAME/KEY: MISC_FEATURE
<222> LOCATION: (963)..(964)
<223> OTHER INFORMATION: X is any amino acid or absent
<220> FEATURE:
<221> NAME/KEY: MISC_FEATURE
<222> LOCATION: (967)..(968)
<223> OTHER INFORMATION: X is any amino acid or absent
<220> FEATURE:
<221> NAME/KEY: MISC_FEATURE
<222> LOCATION: (970)..(970)
<223> OTHER INFORMATION: X is any amino acid or absent
<220> FEATURE:
<221> NAME/KEY: MISC_FEATURE
```

```
<222> LOCATION: (972)..(972)
<223> OTHER INFORMATION: X is any amino acid or absent
<220> FEATURE:
<221> NAME/KEY: MISC_FEATURE
<222> LOCATION: (975)..(978)
<223> OTHER INFORMATION: X is any amino acid or absent
<220> FEATURE:
<221> NAME/KEY: MISC_FEATURE
<222> LOCATION: (980)..(980)
<223> OTHER INFORMATION: X is any amino acid or absent
<220> FEATURE:
<221> NAME/KEY: MISC_FEATURE
<222> LOCATION: (982)..(985)
<223> OTHER INFORMATION: X is any amino acid or absent
<220> FEATURE:
<221> NAME/KEY: MISC_FEATURE
<222> LOCATION: (987)..(988)
<223> OTHER INFORMATION: X is any amino acid or absent

<400> SEQUENCE: 21

Leu Xaa Asp Gly Xaa Xaa Leu Xaa Tyr Arg Ala Xaa Xaa Ala Leu Xaa
 1               5                  10                  15

Xaa Xaa Leu Xaa Thr Ser Xaa Gly Xaa Xaa Thr Asn Ala Xaa Tyr Gly
            20                  25                  30

Phe Xaa Xaa Met Leu Xaa Lys Xaa Xaa Xaa Xaa Xaa Xaa Xaa Xaa Xaa
        35                  40                  45

Xaa Xaa Xaa Xaa Xaa Val Xaa Phe Asp Xaa Lys Xaa Xaa Thr Phe Xaa
 50                  55                  60

Arg His Xaa Xaa Xaa Xaa Xaa Tyr Lys Xaa Xaa Arg Xaa Xaa Xaa Pro
 65                  70                  75                  80

Xaa Xaa Xaa Xaa Xaa Gln Xaa Xaa Xaa Xaa Xaa Xaa Xaa Xaa Xaa Xaa
                85                  90                  95

Xaa Xaa Xaa Xaa Xaa Leu Glu Xaa Xaa Gly Tyr Glu Ala Asp Asp Ile
            100                 105                 110

Ile Xaa Thr Xaa Xaa Xaa Xaa Xaa Xaa Xaa Xaa Xaa Xaa Xaa Xaa Xaa
        115                 120                 125

Xaa Ile Xaa Xaa Gly Asp Xaa Asp Xaa Xaa Gln Leu Val Xaa Xaa Lys
130                 135                 140

Xaa Xaa Xaa Xaa Xaa Xaa Xaa Lys Xaa Ile Thr Xaa Xaa Xaa Xaa Xaa
145                 150                 155                 160

Xaa Xaa Xaa Xaa Val Xaa Glu Lys Tyr Gly Val Xaa Pro Xaa Xaa Xaa
                165                 170                 175

Xaa Asp Xaa Xaa Xaa Leu Xaa Gly Xaa Xaa Ser Asp Asn Ile Pro Gly
            180                 185                 190

Val Xaa Gly Ile Gly Glu Lys Thr Ala Xaa Xaa Leu Leu Xaa Xaa Xaa
        195                 200                 205

Gly Xaa Xaa Glu Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Leu Xaa Xaa Xaa Xaa Xaa
225                 230                 235                 240

Glu Xaa Xaa Xaa Leu Ser Xaa Xaa Leu Xaa Xaa Xaa Xaa Xaa Xaa Xaa
                245                 250                 255

Pro Xaa Xaa Xaa Glu Xaa Xaa Xaa Xaa Xaa Leu Xaa Xaa Xaa Xaa Xaa
            260                 265                 270

Xaa Xaa Glu Lys Leu Xaa Xaa Xaa Xaa Xaa Leu Glu Phe Xaa Ser
        275                 280                 285

Xaa Xaa Xaa Xaa Xaa Xaa Xaa Xaa Xaa Xaa Xaa Xaa Xaa Xaa Xaa Xaa
290                 295                 300

Xaa Xaa Xaa Xaa Xaa Xaa Xaa Xaa Xaa Xaa Xaa Xaa Xaa Xaa Xaa Xaa
```

```
                305                 310                 315                 320
Xaa Xaa Xaa Xaa Xaa Xaa Xaa Xaa Xaa Xaa Xaa Xaa Xaa Xaa Xaa Xaa
                    325                 330                 335

Xaa Xaa Xaa Xaa Leu Xaa Xaa Xaa Xaa Xaa Xaa Xaa Xaa Xaa Xaa Xaa
                    340                 345                 350

Xaa Xaa Xaa Xaa Xaa Xaa Xaa Xaa Xaa Xaa Xaa Xaa Xaa Xaa Xaa Xaa
                    355                 360                 365

Xaa Xaa Xaa Xaa Xaa Xaa Xaa Xaa Xaa Xaa Xaa Xaa Xaa Xaa Xaa
            370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Leu Xaa Xaa Xaa Xaa Xaa
                    405                 410                 415

Xaa Xaa Xaa Xaa Xaa Xaa Xaa Xaa Xaa Xaa Xaa Xaa Leu Xaa Xaa
                    420                 425                 430

Xaa Gly Xaa Xaa Leu Xaa Xaa Xaa Xaa Phe Xaa Xaa Asp Xaa Xaa Xaa
                    435                 440                 445

Xaa Ala Tyr Leu Leu Xaa Pro Xaa Xaa Xaa Xaa Xaa Xaa Xaa Asp Xaa
            450                 455                 460

Xaa Ala Xaa Xaa Tyr Leu Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
                    485                 490                 495

Xaa Xaa Xaa Xaa Xaa Xaa Xaa Ala Xaa Xaa Xaa Ala Xaa Xaa Xaa
                    500                 505                 510

Xaa Xaa Leu Xaa Xaa Xaa Xaa Xaa Xaa Xaa Xaa Xaa Glu Xaa Xaa
                    515                 520                 525

Leu Xaa Xaa Leu Xaa Xaa Xaa Ile Glu Xaa Pro Leu Xaa Xaa Val Leu
            530                 535                 540

Xaa Xaa Met Glu Xaa Xaa Gly Xaa Xaa Xaa Asp Xaa Xaa Xaa Leu Lys
545                 550                 555                 560

Xaa Leu Ser Xaa Xaa Xaa Xaa Xaa Xaa Xaa Xaa Leu Xaa Xaa Xaa
                    565                 570                 575

Ile Xaa Xaa Xaa Xaa Xaa Xaa Xaa Xaa Xaa Xaa Xaa Ala Gly Xaa
            580                 585                 590

Xaa Phe Asn Xaa Asn Ser Xaa Lys Gln Leu Xaa Xaa Xaa Leu Phe Xaa
                    595                 600                 605

Xaa Leu Xaa Leu Pro Xaa Xaa Xaa Lys Thr Xaa Xaa Thr Gly Xaa Xaa
            610                 615                 620

Ser Thr Xaa Xaa Glu Val Leu Xaa Xaa Leu Xaa Xaa Xaa His Pro Xaa
625                 630                 635                 640

Xaa Xaa Ile Xaa Xaa Xaa Ile Leu Xaa Xaa Tyr Arg Xaa Leu Xaa Lys
            645                 650                 655

Leu Lys Ser Thr Tyr Xaa Asp Xaa Leu Xaa Xaa Xaa Xaa Xaa Xaa
            660                 665                 670

Pro Xaa Thr Gly Arg Xaa His Thr Xaa Phe Asn Gln Thr Xaa Thr Ala
    675                 680                 685

Thr Gly Arg Leu Ser Ser Xaa Pro Xaa Asn Leu Gln Xaa Ile Pro
            690                 695                 700

Xaa Xaa Arg Xaa Glu Xaa Gly Xaa Xaa Ile Arg Xaa Ala Phe Val Xaa
705                 710                 715                 720

Xaa Xaa Xaa Xaa Xaa Xaa Ile Xaa Xaa Ala Asp Tyr Ser Gln Ile Glu
                    725                 730                 735
```

-continued

```
Leu Arg Xaa Leu Ala Xaa His Leu Ser Xaa Asp Xaa Asn Leu Ile Xaa
            740                 745                 750

Ala Phe Xaa Xaa Gly Xaa Xaa Xaa Xaa Xaa Xaa Xaa Asp Ile His
            755                 760                 765

Thr Xaa Thr Ala Ser Xaa Ile Phe Xaa Val Xaa Xaa Glu Xaa Xaa Xaa
    770                 775                 780

Xaa Xaa Xaa Val Thr Xaa Xaa Met Arg Arg Xaa Ala Lys Xaa Val Asn
785                 790                 795                 800

Xaa Gly Ile Xaa Tyr Gly Xaa Ser Xaa Xaa Gly Leu Ser Xaa Xaa Leu
                805                 810                 815

Xaa Xaa Xaa Xaa Xaa Xaa Xaa Xaa Xaa Xaa Xaa Xaa Xaa Xaa Xaa Xaa
            820                 825                 830

Xaa Ile Xaa Xaa Xaa Glu Ala Xaa Xaa Xaa Ile Glu Xaa Tyr Phe Xaa
            835                 840                 845

Xaa Xaa Pro Xaa Val Xaa Xaa Xaa Ile Xaa Xaa Xaa Xaa Xaa Xaa Ala
        850                 855                 860

Lys Xaa Xaa Gly Tyr Val Xaa Thr Leu Phe Gly Arg Arg Xaa Xaa
865                 870                 875                 880

Pro Xaa Ile Xaa Ser Arg Asn Xaa Xaa Val Arg Xaa Xaa Xaa Glu Arg
                885                 890                 895

Xaa Ala Xaa Asn Xaa Pro Ile Gln Gly Thr Ala Ala Asp Ile Ile Lys
            900                 905                 910

Leu Ala Met Xaa Xaa Xaa Xaa Xaa Leu Xaa Xaa Xaa Xaa Xaa Xaa
            915                 920                 925

Xaa Xaa Xaa Xaa Xaa Xaa Xaa Xaa Leu Gln Xaa His Asp Glu
    930                 935                 940

Leu Val Xaa Glu Val Xaa Xaa Glu Glu Xaa Xaa Xaa Val Xaa Xaa Xaa
945                 950                 955                 960

Xaa Lys Xaa Xaa Met Glu Xaa Xaa Val Xaa Leu Xaa Val Pro Xaa Xaa
                965                 970                 975

Xaa Xaa Leu Xaa Val Xaa Xaa Xaa Gly Xaa Xaa Trp
            980                 985

<210> SEQ ID NO 22
<211> LENGTH: 144
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (2)..(2)
<223> OTHER INFORMATION: X is any amino acid or absent
<220> FEATURE:
<221> NAME/KEY: MISC_FEATURE
<222> LOCATION: (5)..(6)
<223> OTHER INFORMATION: X is any amino acid or absent
<220> FEATURE:
<221> NAME/KEY: MISC_FEATURE
<222> LOCATION: (8)..(8)
<223> OTHER INFORMATION: X is any amino acid or absent
<220> FEATURE:
<221> NAME/KEY: MISC_FEATURE
<222> LOCATION: (12)..(13)
<223> OTHER INFORMATION: X is any amino acid or absent
<220> FEATURE:
<221> NAME/KEY: MISC_FEATURE
<222> LOCATION: (16)..(18)
<223> OTHER INFORMATION: X is any amino acid or absent
<220> FEATURE:
<221> NAME/KEY: MISC_FEATURE
<222> LOCATION: (20)..(20)
```

```
<223> OTHER INFORMATION: X is any amino acid or absent
<220> FEATURE:
<221> NAME/KEY: MISC_FEATURE
<222> LOCATION: (23)..(23)
<223> OTHER INFORMATION: X is any amino acid or absent
<220> FEATURE:
<221> NAME/KEY: MISC_FEATURE
<222> LOCATION: (25)..(26)
<223> OTHER INFORMATION: X is any amino acid or absent
<220> FEATURE:
<221> NAME/KEY: MISC_FEATURE
<222> LOCATION: (30)..(30)
<223> OTHER INFORMATION: X is any amino acid or absent
<220> FEATURE:
<221> NAME/KEY: MISC_FEATURE
<222> LOCATION: (34)..(35)
<223> OTHER INFORMATION: X is any amino acid or absent
<220> FEATURE:
<221> NAME/KEY: MISC_FEATURE
<222> LOCATION: (38)..(38)
<223> OTHER INFORMATION: X is any amino acid or absent
<220> FEATURE:
<221> NAME/KEY: MISC_FEATURE
<222> LOCATION: (40)..(53)
<223> OTHER INFORMATION: X is any amino acid or absent
<220> FEATURE:
<221> NAME/KEY: MISC_FEATURE
<222> LOCATION: (55)..(55)
<223> OTHER INFORMATION: X is any amino acid or absent
<220> FEATURE:
<221> NAME/KEY: MISC_FEATURE
<222> LOCATION: (58)..(58)
<223> OTHER INFORMATION: X is any amino acid or absent
<220> FEATURE:
<221> NAME/KEY: MISC_FEATURE
<222> LOCATION: (60)..(61)
<223> OTHER INFORMATION: X is any amino acid or absent
<220> FEATURE:
<221> NAME/KEY: MISC_FEATURE
<222> LOCATION: (64)..(64)
<223> OTHER INFORMATION: X is any amino acid or absent
<220> FEATURE:
<221> NAME/KEY: MISC_FEATURE
<222> LOCATION: (67)..(71)
<223> OTHER INFORMATION: X is any amino acid or absent
<220> FEATURE:
<221> NAME/KEY: MISC_FEATURE
<222> LOCATION: (74)..(75)
<223> OTHER INFORMATION: X is any amino acid or absent
<220> FEATURE:
<221> NAME/KEY: MISC_FEATURE
<222> LOCATION: (77)..(79)
<223> OTHER INFORMATION: X is any amino acid or absent
<220> FEATURE:
<221> NAME/KEY: MISC_FEATURE
<222> LOCATION: (81)..(85)
<223> OTHER INFORMATION: X is any amino acid or absent
<220> FEATURE:
<221> NAME/KEY: MISC_FEATURE
<222> LOCATION: (87)..(101)
<223> OTHER INFORMATION: X is any amino acid or absent
<220> FEATURE:
<221> NAME/KEY: MISC_FEATURE
<222> LOCATION: (104)..(105)
<223> OTHER INFORMATION: X is any amino acid or absent
<220> FEATURE:
<221> NAME/KEY: MISC_FEATURE
<222> LOCATION: (114)..(114)
<223> OTHER INFORMATION: X is any amino acid or absent
<220> FEATURE:
<221> NAME/KEY: MISC_FEATURE
<222> LOCATION: (116)..(129)
<223> OTHER INFORMATION: X is any amino acid or absent
<220> FEATURE:
<221> NAME/KEY: MISC_FEATURE
<222> LOCATION: (131)..(132)
<223> OTHER INFORMATION: X is any amino acid or absent
<220> FEATURE:
<221> NAME/KEY: MISC_FEATURE
```

<222> LOCATION: (135)..(135)
<223> OTHER INFORMATION: X is any amino acid or absent
<220> FEATURE:
<221> NAME/KEY: MISC_FEATURE
<222> LOCATION: (137)..(138)
<223> OTHER INFORMATION: X is any amino acid or absent
<220> FEATURE:
<221> NAME/KEY: MISC_FEATURE
<222> LOCATION: (142)..(143)
<223> OTHER INFORMATION: X is any amino acid or absent

<400> SEQUENCE: 22

```
Leu Xaa Asp Gly Xaa Xaa Leu Xaa Tyr Arg Ala Xaa Xaa Ala Leu Xaa
1               5                   10                  15

Xaa Xaa Leu Xaa Thr Ser Xaa Gly Xaa Xaa Thr Asn Ala Xaa Tyr Gly
            20                  25                  30

Phe Xaa Xaa Met Leu Xaa Lys Xaa Xaa Xaa Xaa Xaa Xaa Xaa Xaa Xaa
        35                  40                  45

Xaa Xaa Xaa Xaa Xaa Val Xaa Phe Asp Xaa Lys Xaa Xaa Thr Phe Xaa
    50                  55                  60

Arg His Xaa Xaa Xaa Xaa Xaa Tyr Lys Xaa Xaa Arg Xaa Xaa Xaa Pro
65                  70                  75                  80

Xaa Xaa Xaa Xaa Xaa Gln Xaa Xaa Xaa Xaa Xaa Xaa Xaa Xaa Xaa Xaa
                85                  90                  95

Xaa Xaa Xaa Xaa Xaa Leu Glu Xaa Xaa Gly Tyr Glu Ala Asp Asp Ile
            100                 105                 110

Ile Xaa Thr Xaa Xaa Xaa Xaa Xaa Xaa Xaa Xaa Xaa Xaa Xaa Xaa Xaa
        115                 120                 125

Xaa Ile Xaa Xaa Gly Asp Xaa Asp Xaa Xaa Gln Leu Val Xaa Xaa Lys
    130                 135                 140
```

<210> SEQ ID NO 23
<211> LENGTH: 464
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (2)..(3)
<223> OTHER INFORMATION: X is any amino acid or absent
<220> FEATURE:
<221> NAME/KEY: MISC_FEATURE
<222> LOCATION: (5)..(6)
<223> OTHER INFORMATION: X is any amino acid or absent
<220> FEATURE:
<221> NAME/KEY: MISC_FEATURE
<222> LOCATION: (8)..(10)
<223> OTHER INFORMATION: X is any amino acid or absent
<220> FEATURE:
<221> NAME/KEY: MISC_FEATURE
<222> LOCATION: (13)..(13)
<223> OTHER INFORMATION: X is any amino acid or absent
<220> FEATURE:
<221> NAME/KEY: MISC_FEATURE
<222> LOCATION: (16)..(17)
<223> OTHER INFORMATION: X is any amino acid or absent
<220> FEATURE:
<221> NAME/KEY: MISC_FEATURE
<222> LOCATION: (20)..(21)
<223> OTHER INFORMATION: X is any amino acid or absent
<220> FEATURE:
<221> NAME/KEY: MISC_FEATURE
<222> LOCATION: (24)..(25)
<223> OTHER INFORMATION: X is any amino acid or absent
<220> FEATURE:
<221> NAME/KEY: MISC_FEATURE
<222> LOCATION: (27)..(29)
<223> OTHER INFORMATION: X is any amino acid or absent

```
<220> FEATURE:
<221> NAME/KEY: MISC_FEATURE
<222> LOCATION: (31)..(33)
<223> OTHER INFORMATION: X is any amino acid or absent
<220> FEATURE:
<221> NAME/KEY: MISC_FEATURE
<222> LOCATION: (36)..(36)
<223> OTHER INFORMATION: X is any amino acid or absent
<220> FEATURE:
<221> NAME/KEY: MISC_FEATURE
<222> LOCATION: (39)..(47)
<223> OTHER INFORMATION: X is any amino acid or absent
<220> FEATURE:
<221> NAME/KEY: MISC_FEATURE
<222> LOCATION: (49)..(51)
<223> OTHER INFORMATION: X is any amino acid or absent
<220> FEATURE:
<221> NAME/KEY: MISC_FEATURE
<222> LOCATION: (53)..(64)
<223> OTHER INFORMATION: X is any amino acid or absent
<220> FEATURE:
<221> NAME/KEY: MISC_FEATURE
<222> LOCATION: (67)..(68)
<223> OTHER INFORMATION: X is any amino acid or absent
<220> FEATURE:
<221> NAME/KEY: MISC_FEATURE
<222> LOCATION: (71)..(71)
<223> OTHER INFORMATION: X is any amino acid or absent
<220> FEATURE:
<221> NAME/KEY: MISC_FEATURE
<222> LOCATION: (74)..(74)
<223> OTHER INFORMATION: X is any amino acid or absent
<220> FEATURE:
<221> NAME/KEY: MISC_FEATURE
<222> LOCATION: (78)..(80)
<223> OTHER INFORMATION: X is any amino acid or absent
<220> FEATURE:
<221> NAME/KEY: MISC_FEATURE
<222> LOCATION: (83)..(84)
<223> OTHER INFORMATION: X is any amino acid or absent
<220> FEATURE:
<221> NAME/KEY: MISC_FEATURE
<222> LOCATION: (86)..(86)
<223> OTHER INFORMATION: X is any amino acid or absent
<220> FEATURE:
<221> NAME/KEY: MISC_FEATURE
<222> LOCATION: (89)..(91)
<223> OTHER INFORMATION: X is any amino acid or absent
<220> FEATURE:
<221> NAME/KEY: MISC_FEATURE
<222> LOCATION: (94)..(95)
<223> OTHER INFORMATION: X is any amino acid or absent
<220> FEATURE:
<221> NAME/KEY: MISC_FEATURE
<222> LOCATION: (98)..(99)
<223> OTHER INFORMATION: X is any amino acid or absent
<220> FEATURE:
<221> NAME/KEY: MISC_FEATURE
<222> LOCATION: (102)..(103)
<223> OTHER INFORMATION: X is any amino acid or absent
<220> FEATURE:
<221> NAME/KEY: MISC_FEATURE
<222> LOCATION: (107)..(108)
<223> OTHER INFORMATION: X is any amino acid or absent
<220> FEATURE:
<221> NAME/KEY: MISC_FEATURE
<222> LOCATION: (110)..(112)
<223> OTHER INFORMATION: X is any amino acid or absent
<220> FEATURE:
<221> NAME/KEY: MISC_FEATURE
<222> LOCATION: (115)..(117)
<223> OTHER INFORMATION: X is any amino acid or absent
<220> FEATURE:
<221> NAME/KEY: MISC_FEATURE
<222> LOCATION: (119)..(121)
<223> OTHER INFORMATION: X is any amino acid or absent
<220> FEATURE:
<221> NAME/KEY: MISC_FEATURE
<222> LOCATION: (124)..(125)
```

```
<223> OTHER INFORMATION: X is any amino acid or absent
<220> FEATURE:
<221> NAME/KEY: MISC_FEATURE
<222> LOCATION: (128)..(128)
<223> OTHER INFORMATION: X is any amino acid or absent
<220> FEATURE:
<221> NAME/KEY: MISC_FEATURE
<222> LOCATION: (130)..(130)
<223> OTHER INFORMATION: X is any amino acid or absent
<220> FEATURE:
<221> NAME/KEY: MISC_FEATURE
<222> LOCATION: (137)..(137)
<223> OTHER INFORMATION: X is any amino acid or absent
<220> FEATURE:
<221> NAME/KEY: MISC_FEATURE
<222> LOCATION: (139)..(139)
<223> OTHER INFORMATION: X is any amino acid or absent
<220> FEATURE:
<221> NAME/KEY: MISC_FEATURE
<222> LOCATION: (141)..(147)
<223> OTHER INFORMATION: X is any amino acid or absent
<220> FEATURE:
<221> NAME/KEY: MISC_FEATURE
<222> LOCATION: (149)..(149)
<223> OTHER INFORMATION: X is any amino acid or absent
<220> FEATURE:
<221> NAME/KEY: MISC_FEATURE
<222> LOCATION: (153)..(153)
<223> OTHER INFORMATION: X is any amino acid or absent
<220> FEATURE:
<221> NAME/KEY: MISC_FEATURE
<222> LOCATION: (156)..(156)
<223> OTHER INFORMATION: X is any amino acid or absent
<220> FEATURE:
<221> NAME/KEY: MISC_FEATURE
<222> LOCATION: (161)..(161)
<223> OTHER INFORMATION: X is any amino acid or absent
<220> FEATURE:
<221> NAME/KEY: MISC_FEATURE
<222> LOCATION: (171)..(171)
<223> OTHER INFORMATION: X is any amino acid or absent
<220> FEATURE:
<221> NAME/KEY: MISC_FEATURE
<222> LOCATION: (173)..(173)
<223> OTHER INFORMATION: X is any amino acid or absent
<220> FEATURE:
<221> NAME/KEY: MISC_FEATURE
<222> LOCATION: (177)..(177)
<223> OTHER INFORMATION: X is any amino acid or absent
<220> FEATURE:
<221> NAME/KEY: MISC_FEATURE
<222> LOCATION: (180)..(181)
<223> OTHER INFORMATION: X is any amino acid or absent
<220> FEATURE:
<221> NAME/KEY: MISC_FEATURE
<222> LOCATION: (183)..(183)
<223> OTHER INFORMATION: X is any amino acid or absent
<220> FEATURE:
<221> NAME/KEY: MISC_FEATURE
<222> LOCATION: (185)..(185)
<223> OTHER INFORMATION: X is any amino acid or absent
<220> FEATURE:
<221> NAME/KEY: MISC_FEATURE
<222> LOCATION: (187)..(187)
<223> OTHER INFORMATION: X is any amino acid or absent
<220> FEATURE:
<221> NAME/KEY: MISC_FEATURE
<222> LOCATION: (188)..(188)
<223> OTHER INFORMATION: Xaa can be any naturally occurring amino acid
<220> FEATURE:
<221> NAME/KEY: MISC_FEATURE
<222> LOCATION: (191)..(191)
<223> OTHER INFORMATION: X is any amino acid or absent
<220> FEATURE:
<221> NAME/KEY: MISC_FEATURE
<222> LOCATION: (195)..(201)
<223> OTHER INFORMATION: X is any amino acid or absent
<220> FEATURE:
<221> NAME/KEY: MISC_FEATURE
```

```
<222> LOCATION: (203)..(204)
<223> OTHER INFORMATION: X is any amino acid or absent
<220> FEATURE:
<221> NAME/KEY: MISC_FEATURE
<222> LOCATION: (214)..(214)
<223> OTHER INFORMATION: X is any amino acid or absent
<220> FEATURE:
<221> NAME/KEY: MISC_FEATURE
<222> LOCATION: (217)..(217)
<223> OTHER INFORMATION: X is any amino acid or absent
<220> FEATURE:
<221> NAME/KEY: MISC_FEATURE
<222> LOCATION: (221)..(221)
<223> OTHER INFORMATION: X is any amino acid or absent
<220> FEATURE:
<221> NAME/KEY: MISC_FEATURE
<222> LOCATION: (223)..(223)
<223> OTHER INFORMATION: X is any amino acid or absent
<220> FEATURE:
<221> NAME/KEY: MISC_FEATURE
<222> LOCATION: (227)..(227)
<223> OTHER INFORMATION: X is any amino acid or absent
<220> FEATURE:
<221> NAME/KEY: MISC_FEATURE
<222> LOCATION: (230)..(231)
<223> OTHER INFORMATION: X is any amino acid or absent
<220> FEATURE:
<221> NAME/KEY: MISC_FEATURE
<222> LOCATION: (233)..(240)
<223> OTHER INFORMATION: X is any amino acid or absent
<220> FEATURE:
<221> NAME/KEY: MISC_FEATURE
<222> LOCATION: (245)..(245)
<223> OTHER INFORMATION: X is any amino acid or absent
<220> FEATURE:
<221> NAME/KEY: MISC_FEATURE
<222> LOCATION: (249)..(249)
<223> OTHER INFORMATION: X is any amino acid or absent
<220> FEATURE:
<221> NAME/KEY: MISC_FEATURE
<222> LOCATION: (252)..(252)
<223> OTHER INFORMATION: X is any amino acid or absent
<220> FEATURE:
<221> NAME/KEY: MISC_FEATURE
<222> LOCATION: (254)..(255)
<223> OTHER INFORMATION: X is any amino acid or absent
<220> FEATURE:
<221> NAME/KEY: MISC_FEATURE
<222> LOCATION: (257)..(262)
<223> OTHER INFORMATION: X is any amino acid or absent
<220> FEATURE:
<221> NAME/KEY: MISC_FEATURE
<222> LOCATION: (265)..(266)
<223> OTHER INFORMATION: X is any amino acid or absent
<220> FEATURE:
<221> NAME/KEY: MISC_FEATURE
<222> LOCATION: (270)..(270)
<223> OTHER INFORMATION: X is any amino acid or absent
<220> FEATURE:
<221> NAME/KEY: MISC_FEATURE
<222> LOCATION: (273)..(273)
<223> OTHER INFORMATION: X is any amino acid or absent
<220> FEATURE:
<221> NAME/KEY: MISC_FEATURE
<222> LOCATION: (276)..(276)
<223> OTHER INFORMATION: X is any amino acid or absent
<220> FEATURE:
<221> NAME/KEY: MISC_FEATURE
<222> LOCATION: (279)..(279)
<223> OTHER INFORMATION: X is any amino acid or absent
<220> FEATURE:
<221> NAME/KEY: MISC_FEATURE
<222> LOCATION: (282)..(282)
<223> OTHER INFORMATION: X is any amino acid or absent
<220> FEATURE:
<221> NAME/KEY: MISC_FEATURE
<222> LOCATION: (284)..(285)
<223> OTHER INFORMATION: X is any amino acid or absent
<220> FEATURE:
```

```
<221> NAME/KEY: MISC_FEATURE
<222> LOCATION: (289)..(290)
<223> OTHER INFORMATION: X is any amino acid or absent
<220> FEATURE:
<221> NAME/KEY: MISC_FEATURE
<222> LOCATION: (292)..(308)
<223> OTHER INFORMATION: X is any amino acid or absent
<220> FEATURE:
<221> NAME/KEY: MISC_FEATURE
<222> LOCATION: (310)..(312)
<223> OTHER INFORMATION: X is any amino acid or absent
<220> FEATURE:
<221> NAME/KEY: MISC_FEATURE
<222> LOCATION: (315)..(317)
<223> OTHER INFORMATION: X is any amino acid or absent
<220> FEATURE:
<221> NAME/KEY: MISC_FEATURE
<222> LOCATION: (320)..(320)
<223> OTHER INFORMATION: X is any amino acid or absent
<220> FEATURE:
<221> NAME/KEY: MISC_FEATURE
<222> LOCATION: (323)..(325)
<223> OTHER INFORMATION: X is any amino acid or absent
<220> FEATURE:
<221> NAME/KEY: MISC_FEATURE
<222> LOCATION: (327)..(327)
<223> OTHER INFORMATION: X is any amino acid or absent
<220> FEATURE:
<221> NAME/KEY: MISC_FEATURE
<222> LOCATION: (329)..(331)
<223> OTHER INFORMATION: X is any amino acid or absent
<220> FEATURE:
<221> NAME/KEY: MISC_FEATURE
<222> LOCATION: (333)..(338)
<223> OTHER INFORMATION: X is any amino acid or absent
<220> FEATURE:
<221> NAME/KEY: MISC_FEATURE
<222> LOCATION: (341)..(342)
<223> OTHER INFORMATION: X is any amino acid or absent
<220> FEATURE:
<221> NAME/KEY: MISC_FEATURE
<222> LOCATION: (346)..(346)
<223> OTHER INFORMATION: X is any amino acid or absent
<220> FEATURE:
<221> NAME/KEY: MISC_FEATURE
<222> LOCATION: (354)..(355)
<223> OTHER INFORMATION: X is any amino acid or absent
<220> FEATURE:
<221> NAME/KEY: MISC_FEATURE
<222> LOCATION: (357)..(357)
<223> OTHER INFORMATION: X is any amino acid or absent
<220> FEATURE:
<221> NAME/KEY: MISC_FEATURE
<222> LOCATION: (359)..(359)
<223> OTHER INFORMATION: X is any amino acid or absent
<220> FEATURE:
<221> NAME/KEY: MISC_FEATURE
<222> LOCATION: (363)..(364)
<223> OTHER INFORMATION: X is any amino acid or absent
<220> FEATURE:
<221> NAME/KEY: MISC_FEATURE
<222> LOCATION: (367)..(369)
<223> OTHER INFORMATION: X is any amino acid or absent
<220> FEATURE:
<221> NAME/KEY: MISC_FEATURE
<222> LOCATION: (372)..(372)
<223> OTHER INFORMATION: X is any amino acid or absent
<220> FEATURE:
<221> NAME/KEY: MISC_FEATURE
<222> LOCATION: (374)..(374)
<223> OTHER INFORMATION: X is any amino acid or absent
<220> FEATURE:
<221> NAME/KEY: MISC_FEATURE
<222> LOCATION: (376)..(376)
<223> OTHER INFORMATION: X is any amino acid or absent
<220> FEATURE:
<221> NAME/KEY: MISC_FEATURE
<222> LOCATION: (391)..(396)
<223> OTHER INFORMATION: X is any amino acid or absent
```

```
<220> FEATURE:
<221> NAME/KEY: MISC_FEATURE
<222> LOCATION: (398)..(413)
<223> OTHER INFORMATION: X is any amino acid or absent
<220> FEATURE:
<221> NAME/KEY: MISC_FEATURE
<222> LOCATION: (416)..(416)
<223> OTHER INFORMATION: X is any amino acid or absent
<220> FEATURE:
<221> NAME/KEY: MISC_FEATURE
<222> LOCATION: (422)..(422)
<223> OTHER INFORMATION: X is any amino acid or absent
<220> FEATURE:
<221> NAME/KEY: MISC_FEATURE
<222> LOCATION: (425)..(426)
<223> OTHER INFORMATION: X is any amino acid or absent
<220> FEATURE:
<221> NAME/KEY: MISC_FEATURE
<222> LOCATION: (429)..(431)
<223> OTHER INFORMATION: X is any amino acid or absent
<220> FEATURE:
<221> NAME/KEY: MISC_FEATURE
<222> LOCATION: (433)..(436)
<223> OTHER INFORMATION: X is any amino acid or absent
<220> FEATURE:
<221> NAME/KEY: MISC_FEATURE
<222> LOCATION: (438)..(439)
<223> OTHER INFORMATION: X is any amino acid or absent
<220> FEATURE:
<221> NAME/KEY: MISC_FEATURE
<222> LOCATION: (442)..(443)
<223> OTHER INFORMATION: X is any amino acid or absent
<220> FEATURE:
<221> NAME/KEY: MISC_FEATURE
<222> LOCATION: (445)..(445)
<223> OTHER INFORMATION: X is any amino acid or absent
<220> FEATURE:
<221> NAME/KEY: MISC_FEATURE
<222> LOCATION: (447)..(447)
<223> OTHER INFORMATION: X is any amino acid or absent
<220> FEATURE:
<221> NAME/KEY: MISC_FEATURE
<222> LOCATION: (450)..(453)
<223> OTHER INFORMATION: X is any amino acid or absent
<220> FEATURE:
<221> NAME/KEY: MISC_FEATURE
<222> LOCATION: (455)..(455)
<223> OTHER INFORMATION: X is any amino acid or absent
<220> FEATURE:
<221> NAME/KEY: MISC_FEATURE
<222> LOCATION: (457)..(460)
<223> OTHER INFORMATION: X is any amino acid or absent
<220> FEATURE:
<221> NAME/KEY: MISC_FEATURE
<222> LOCATION: (462)..(463)
<223> OTHER INFORMATION: X is any amino acid or absent

<400> SEQUENCE: 23

Glu Xaa Xaa Leu Xaa Xaa Leu Xaa Xaa Xaa Ile Glu Xaa Pro Leu Xaa
1               5                   10                  15

Xaa Val Leu Xaa Xaa Met Glu Xaa Xaa Gly Xaa Xaa Xaa Asp Xaa Xaa
            20                  25                  30

Xaa Leu Lys Xaa Leu Ser Xaa Xaa Xaa Xaa Xaa Xaa Xaa Xaa Xaa Leu
        35                  40                  45

Xaa Xaa Xaa Ile Xaa Xaa Xaa Xaa Xaa Xaa Xaa Xaa Xaa Xaa Xaa Xaa
    50                  55                  60

Ala Gly Xaa Xaa Phe Asn Xaa Asn Ser Xaa Lys Gln Leu Xaa Xaa Xaa
65                  70                  75                  80

Leu Phe Xaa Xaa Leu Xaa Leu Pro Xaa Xaa Xaa Lys Thr Xaa Xaa Thr
                85                  90                  95

Gly Xaa Xaa Ser Thr Xaa Xaa Glu Val Leu Xaa Xaa Leu Xaa Xaa Xaa
            100                 105                 110
```

```
His Pro Xaa Xaa Xaa Ile Xaa Xaa Xaa Ile Leu Xaa Xaa Tyr Arg Xaa
        115                 120                 125

Leu Xaa Lys Leu Lys Ser Thr Tyr Xaa Asp Xaa Leu Xaa Xaa Xaa Xaa
    130                 135                 140

Xaa Xaa Xaa Pro Xaa Thr Gly Arg Xaa His Thr Xaa Phe Asn Gln Thr
145                 150                 155                 160

Xaa Thr Ala Thr Gly Arg Leu Ser Ser Ser Xaa Pro Xaa Asn Leu Gln
                165                 170                 175

Xaa Ile Pro Xaa Xaa Arg Xaa Glu Xaa Gly Xaa Xaa Ile Arg Xaa Ala
            180                 185                 190

Phe Val Xaa Xaa Xaa Xaa Xaa Xaa Xaa Ile Xaa Xaa Ala Asp Tyr Ser
        195                 200                 205

Gln Ile Glu Leu Arg Xaa Leu Ala Xaa His Leu Ser Xaa Asp Xaa Asn
    210                 215                 220

Leu Ile Xaa Ala Phe Xaa Xaa Gly Xaa Xaa Xaa Xaa Xaa Xaa Xaa Xaa
225                 230                 235                 240

Asp Ile His Thr Xaa Thr Ala Ser Xaa Ile Phe Xaa Val Xaa Xaa Glu
                245                 250                 255

Xaa Xaa Xaa Xaa Xaa Xaa Val Thr Xaa Xaa Met Arg Arg Xaa Ala Lys
            260                 265                 270

Xaa Val Asn Xaa Gly Ile Xaa Tyr Gly Xaa Ser Xaa Xaa Gly Leu Ser
        275                 280                 285

Xaa Xaa Leu Xaa Xaa Xaa Xaa Xaa Xaa Xaa Xaa Xaa Xaa Xaa Xaa Xaa
    290                 295                 300

Xaa Xaa Xaa Xaa Ile Xaa Xaa Xaa Glu Ala Xaa Xaa Xaa Ile Glu Xaa
305                 310                 315                 320

Tyr Phe Xaa Xaa Xaa Pro Xaa Val Xaa Xaa Xaa Ile Xaa Xaa Xaa Xaa
                325                 330                 335

Xaa Xaa Ala Lys Xaa Xaa Gly Tyr Val Xaa Thr Leu Phe Gly Arg Arg
            340                 345                 350

Arg Xaa Xaa Pro Xaa Ile Xaa Ser Arg Asn Xaa Xaa Val Arg Xaa Xaa
        355                 360                 365

Xaa Glu Arg Xaa Ala Xaa Asn Xaa Pro Ile Gln Gly Thr Ala Ala Asp
    370                 375                 380

Ile Ile Lys Leu Ala Met Xaa Xaa Xaa Xaa Xaa Xaa Leu Xaa Xaa Xaa
385                 390                 395                 400

Xaa Xaa Xaa Xaa Xaa Xaa Xaa Xaa Xaa Xaa Xaa Xaa Xaa Leu Gln Xaa
                405                 410                 415

His Asp Glu Leu Val Xaa Glu Val Xaa Xaa Glu Glu Xaa Xaa Xaa Val
            420                 425                 430

Xaa Xaa Xaa Xaa Lys Xaa Xaa Met Glu Xaa Xaa Val Xaa Leu Xaa Val
        435                 440                 445

Pro Xaa Xaa Xaa Xaa Leu Xaa Val Xaa Xaa Xaa Xaa Gly Xaa Xaa Trp
    450                 455                 460
```

```
<210> SEQ ID NO 24
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 24
gatcaacccc gctgccccac                                                   20
```

```
<210> SEQ ID NO 25
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 25
cgaagcccat ccccgctcag                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 26
gcgcatgcaa gctgacctgg                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 27
tcacgctcca aggcgggaac                                                    20

<210> SEQ ID NO 28
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 28
cctgctctgc cgcttcacgc                                                    20

<210> SEQ ID NO 29
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 29
gatgacgcat cctcacgata atatccgg                                           28

<210> SEQ ID NO 30
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 30
cctgctctgc cgcttcacgc                                                    20

<210> SEQ ID NO 31
<211> LENGTH: 28
<212> TYPE: DNA
<213> ORGANISM: Artificial Sequence
<220> FEATURE:
<223> OTHER INFORMATION: Synthetic Sequence
```

```
<400> SEQUENCE: 31
gatgacgcat cctcacgata atatccgg                                          28

<210> SEQ ID NO 32
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 32
atgtcaccac aaacagagac taaag                                             25

<210> SEQ ID NO 33
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 33
tgcattacga tcggaacgcc ca                                                22

<210> SEQ ID NO 34
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 34
atgtcaccac aaacagagac taaag                                             25

<210> SEQ ID NO 35
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 35
tgcattacga tcggaacgcc ca                                                22

<210> SEQ ID NO 36
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 36
gatcaacccc gctgccccac                                                   20

<210> SEQ ID NO 37
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 37
cgaagcccat ccccgctcag                                                   20

<210> SEQ ID NO 38
```

<211> LENGTH: 832
<212> TYPE: PRT
<213> ORGANISM: Thermus aquaticus

<400> SEQUENCE: 38

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
```

-continued

```
            385                 390                 395                 400
        Glu Ala Gly Glu Arg Ala Ala Leu Ser Glu Arg Leu Phe Ala Asn Leu
                        405                 410                 415

Trp Gly Arg Leu Glu Gly Glu Arg Leu Leu Trp Leu Tyr Arg Glu
                        420                 425                 430

Val Glu Arg Pro Leu Ser Ala Val Leu Ala His Met Glu Ala Thr Gly
                        435                 440                 445

Val Arg Leu Asp Val Ala Tyr Leu Arg Ala Leu Ser Leu Glu Val Ala
                450                 455                 460

Glu Glu Ile Ala Arg Leu Glu Ala Glu Val Phe Arg Leu Ala Gly His
        465                 470                 475                 480

Pro Phe Asn Leu Asn Ser Arg Asp Gln Leu Glu Arg Val Leu Phe Asp
                        485                 490                 495

Glu Leu Gly Leu Pro Ala Ile Gly Lys Thr Glu Lys Thr Gly Lys Arg
                        500                 505                 510

Ser Thr Ser Ala Ala Val Leu Glu Ala Leu Arg Glu Ala His Pro Ile
                        515                 520                 525

Val Glu Lys Ile Leu Gln Tyr Arg Glu Leu Thr Lys Leu Lys Ser Thr
                530                 535                 540

Tyr Ile Asp Pro Leu Pro Asp Leu Ile His Pro Arg Thr Gly Arg Leu
        545                 550                 555                 560

His Thr Arg Phe Asn Gln Thr Ala Thr Ala Thr Gly Arg Leu Ser Ser
                        565                 570                 575

Ser Asp Pro Asn Leu Gln Asn Ile Pro Val Arg Thr Pro Leu Gly Gln
                        580                 585                 590

Arg Ile Arg Arg Ala Phe Ile Ala Glu Glu Gly Trp Leu Leu Val Ala
                        595                 600                 605

Leu Asp Tyr Ser Gln Ile Glu Leu Arg Val Leu Ala His Leu Ser Gly
                        610                 615                 620

Asp Glu Asn Leu Ile Arg Val Phe Gln Glu Gly Arg Asp Ile His Thr
        625                 630                 635                 640

Glu Thr Ala Ser Trp Met Phe Gly Val Pro Arg Glu Ala Val Asp Pro
                        645                 650                 655

Leu Met Arg Arg Ala Ala Lys Thr Ile Asn Phe Gly Val Leu Tyr Gly
                        660                 665                 670

Met Ser Ala His Arg Leu Ser Gln Glu Leu Ala Ile Pro Tyr Glu Glu
                        675                 680                 685

Ala Gln Ala Phe Ile Glu Arg Tyr Phe Gln Ser Phe Pro Lys Val Arg
                        690                 695                 700

Ala Trp Ile Glu Lys Thr Leu Glu Glu Gly Arg Arg Arg Gly Tyr Val
        705                 710                 715                 720

Glu Thr Leu Phe Gly Arg Arg Tyr Val Pro Asp Leu Glu Ala Arg
                        725                 730                 735

Val Lys Ser Val Arg Glu Ala Ala Glu Arg Met Ala Phe Asn Met Pro
                        740                 745                 750

Val Gln Gly Thr Ala Ala Asp Leu Met Lys Leu Ala Met Val Lys Leu
                        755                 760                 765

Phe Pro Arg Leu Glu Glu Met Gly Ala Arg Met Leu Leu Gln Val His
                        770                 775                 780

Asp Glu Leu Val Leu Glu Ala Pro Lys Glu Arg Ala Glu Ala Val Ala
        785                 790                 795                 800

Arg Leu Ala Lys Glu Val Met Glu Gly Val Tyr Pro Leu Ala Val Pro
                        805                 810                 815
```

Leu Glu Val Glu Val Gly Ile Gly Glu Asp Trp Leu Ser Ala Lys Glu
            820                 825                 830

<210> SEQ ID NO 39
<211> LENGTH: 832
<212> TYPE: PRT
<213> ORGANISM: Thermus aquaticus

<400> SEQUENCE: 39

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro

```
              355                 360                 365
Pro Gly Asp Asp Pro Met Leu Leu Ala Tyr Leu Leu Asp Pro Ser Asn
        370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Lys Thr Gly Lys Arg
                500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
        660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
        740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780
```

```
Asp Glu Leu Val Leu Glu Ala Pro Lys Glu Arg Ala Glu Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
        820                 825                 830

<210> SEQ ID NO 40
<211> LENGTH: 832
<212> TYPE: PRT
<213> ORGANISM: Thermus aquaticus

<400> SEQUENCE: 40

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Asn Ala Leu Gln Asp Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
```

-continued

```
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
                370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
                450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Lys Lys Thr Gly Lys Arg
                500                 505                 510
Ser Thr Ser Ala Ala Val Leu Glu Ala Leu Arg Glu Ala His Pro Ile
                515                 520                 525
Val Glu Lys Ile Leu Gln Tyr Arg Glu Leu Thr Lys Leu Lys Ser Thr
                530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
                580                 585                 590
Arg Ile Arg Arg Ala Phe Ile Ala Glu Glu Gly Trp Leu Leu Val Ala
                595                 600                 605
Leu Asp Tyr Ser Gln Ile Glu Leu Arg Val Leu Ala His Leu Ser Gly
                610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
                675                 680                 685
Ala Gln Ala Phe Ile Glu Arg Tyr Phe Gln Ser Phe Pro Lys Val Arg
                690                 695                 700
Ala Trp Ile Glu Lys Thr Leu Glu Glu Gly Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
                740                 745                 750
```

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
        820                 825                 830

<210> SEQ ID NO 41
<211> LENGTH: 834
<212> TYPE: PRT
<213> ORGANISM: Thermus thermophilus

<400> SEQUENCE: 41

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
            85                  90                  95

Leu Ala Leu Ile Lys Glu Leu Val Asp Leu Leu Gly Phe Thr Arg Leu
        100                 105                 110

Glu Val Pro Gly Tyr Glu Ala Asp Asp Val Leu Ala Thr Leu Ala Lys
    115                 120                 125

Lys Ala Glu Lys Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
            165                 170                 175

Pro Glu Gln Trp Val Asp Phe Arg Ala Leu Val Gly Asp Pro Ser Asp
        180                 185                 190

Asn Leu Pro Gly Val Lys Gly Ile Gly Glu Lys Thr Ala Leu Lys Leu
    195                 200                 205

Leu Lys Glu Trp Gly Ser Leu Glu Asn Leu Leu Lys Asn Leu Asp Arg
210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
            245                 250                 255

Glu Val Asp Leu Ala Gln Gly Arg Glu Pro Asp Arg Glu Gly Leu Arg
        260                 265                 270

Ala Phe Leu Glu Arg Leu Glu Phe Gly Ser Leu Leu His Glu Phe Gly
    275                 280                 285

Leu Leu Glu Ala Pro Ala Pro Leu Glu Glu Ala Pro Trp Pro Pro Pro

```
            290                 295                 300
Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Lys Leu Leu Trp Leu Tyr
            420                 425                 430

His Glu Val Glu Lys Pro Leu Ser Arg Val Leu Ala His Met Glu Ala
        435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720
```

```
Tyr Val Glu Thr Leu Phe Gly Arg Arg Tyr Val Pro Asp Leu Asn
                    725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
                755                 760                 765

Lys Leu Phe Pro Arg Leu Arg Glu Met Gly Ala Arg Met Leu Leu Gln
        770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                    805                 810                 815

Val Pro Leu Glu Val Glu Val Gly Met Gly Glu Asp Trp Leu Ser Ala
                    820                 825                 830

Lys Gly

<210> SEQ ID NO 42
<211> LENGTH: 834
<212> TYPE: PRT
<213> ORGANISM: Thermus thermophilus

<400> SEQUENCE: 42

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Thr Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
                100                 105                 110

Glu Val Pro Gly Tyr Glu Ala Asp Asp Val Leu Ala Thr Leu Ala Lys
            115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255
```

-continued

```
Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Glu Glu Val Arg Gly
            340                 345                 350

Leu Leu Ala Lys Asp Leu Cys Val Leu Ala Ser Arg Glu Gly Leu Asp
        355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
        435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Lys Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670
```

Tyr Gly Met Ser Ala His Arg Leu Ser Gln Glu Leu Ala Ile Pro Tyr
            675                 680                 685

Glu Glu Ala Val Ala Phe Ile Glu Arg Tyr Phe Gln Ser Phe Pro Lys
690                 695                 700

Val Arg Ala Trp Met Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Ile Asn
                740                 745                 750

Met Pro Val Gln Gly Thr Ala Ala Asp Leu Met Lys Leu Ala Met Val
                755                 760                 765

Lys Leu Phe Pro Arg Leu Arg Glu Met Gly Ala Arg Met Leu Leu Gln
                770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
                820                 825                 830

Lys Gly

<210> SEQ ID NO 43
<211> LENGTH: 877
<212> TYPE: PRT
<213> ORGANISM: Geobacillus stearothermophilus

<400> SEQUENCE: 43

Met Arg Leu Lys Lys Lys Leu Val Leu Ile Asp Gly Asn Ser Val Ala
1               5                   10                  15

Tyr Arg Ala Phe Phe Ala Leu Pro Leu Leu His Asn Asp Lys Gly Ile
                20                  25                  30

His Thr Asn Ala Val Tyr Gly Phe Thr Met Met Leu Asn Lys Ile Leu
            35                  40                  45

Ala Glu Glu Gln Pro Thr His Leu Leu Val Ala Phe Asp Ala Gly Lys
        50                  55                  60

Thr Thr Phe Arg His Glu Thr Phe Gln Glu Tyr Lys Gly Gly Arg Gln
65              70                  75                  80

Gln Thr Pro Pro Glu Leu Ser Glu Gln Phe Pro Leu Leu Arg Glu Leu
                85                  90                  95

Leu Lys Thr Tyr Arg Ile Pro Ala Tyr Glu Leu Tyr Ile Tyr Glu Ala
            100                 105                 110

Asp Asp Ile Ile Gly Thr Leu Ala Ala Arg Ala Glu Gln Glu Gly Phe
        115                 120                 125

Glu Val Lys Ile Ile Ser Gly Asp Arg Asp Leu Thr Gln Leu Ala Ser
130                 135                 140

Arg His Val Thr Val Asp Ile Thr Lys Lys Gly Ile Thr Asp Ile Glu
145                 150                 155                 160

Pro Tyr Thr Pro Glu Thr Val Arg Glu Lys Tyr Gly Leu Thr Pro Glu
                165                 170                 175

Gln Ile Val Asp Leu Lys Gly Leu Met Gly Asp Lys Ser Asp Asn Ile
            180                 185                 190

Pro Gly Val Pro Gly Ile Gly Glu Lys Thr Ala Val Lys Leu Leu Lys
        195                 200                 205

```
Gln Phe Gly Thr Val Glu Asn Val Leu Ala Ser Ile Asp Glu Val Lys
    210                 215                 220

Gly Glu Lys Val Lys Glu Lys Leu Arg Gln His Arg Asp Leu Ala Leu
225                 230                 235                 240

Leu Ser Lys Gln Leu Ala Ser Ile Cys Arg Asp Ala Pro Val Glu Leu
            245                 250                 255

Ser Leu Asp Ala Leu Val Tyr Glu Gly Gln Asp Arg Glu Lys Val Ile
        260                 265                 270

Ala Leu Phe Lys Glu Leu Gly Phe Gln Ser Phe Leu Glu Lys Met Ala
    275                 280                 285

Ala Pro Ala Ala Glu Gly Arg Lys Pro Leu Glu Glu Met Glu Phe Ala
290                 295                 300

Ile Val Asp Val Ile Thr Glu Glu Met Leu Ala Asp Lys Ala Ala Leu
305                 310                 315                 320

Val Val Glu Val Met Glu Glu Asn Tyr His Asp Ala Pro Ile Val Gly
                325                 330                 335

Ile Ala Leu Val Asn Glu His Gly Arg Phe Phe Met Arg Pro Glu Thr
            340                 345                 350

Ala Leu Ala Asp Ser Gln Phe Leu Ala Trp Leu Ala Asp Glu Thr Lys
        355                 360                 365

Lys Lys Ser Met Phe Asp Ala Lys Arg Ala Val Val Ala Leu Lys Trp
    370                 375                 380

Lys Gly Ile Asp Val Arg Gly Val Ala Phe Asp Leu Leu Leu Ala Ala
385                 390                 395                 400

Tyr Leu Leu Asn Pro Ala Gln Asp Ala Gly Asp Ile Ala Ala Val Ala
                405                 410                 415

Lys Met Lys Gln Tyr Glu Ala Val Arg Ser Asp Glu Ala Val Tyr Gly
            420                 425                 430

Lys Gly Val Lys Arg Ser Leu Pro Asp Glu Gln Thr Leu Ala Glu His
        435                 440                 445

Leu Val Arg Lys Ala Ala Ile Trp Ala Leu Glu Gln Pro Phe Met
    450                 455                 460

Asp Asp Leu Arg Asn Asn Glu Gln Asp Gln Leu Leu Thr Lys Leu Glu
465                 470                 475                 480

Gln Pro Leu Ala Ala Ile Leu Ala Glu Met Glu Phe Thr Gly Val Asn
                485                 490                 495

Val Asp Thr Lys Arg Leu Glu Gln Met Gly Ser Glu Leu Ala Glu Gln
            500                 505                 510

Leu Arg Ala Ile Glu Gln Arg Ile Tyr Glu His Ala Gly Gln Glu Phe
        515                 520                 525

Asn Ile Asn Ser Pro Lys Gln Leu Gly Val Ile Leu Phe Glu Lys Leu
    530                 535                 540

Gln Leu Pro Val Leu Lys Lys Thr Lys Thr Gly Tyr Ser Thr Ser Ala
545                 550                 555                 560

Asp Val Leu Glu Lys Leu Ala Pro His His Glu Ile Val Glu Asn Ile
                565                 570                 575

Leu His Tyr Arg Gln Leu Gly Lys Leu Gln Ser Thr Tyr Ile Glu Gly
            580                 585                 590

Leu Leu Lys Val Val Arg Pro Asp Thr Gly Lys Val His Thr Met Phe
        595                 600                 605

Asn Gln Thr Leu Thr Gln Thr Gly Arg Leu Ser Ser Ala Glu Pro Asn
    610                 615                 620

Leu Gln Asn Ile Pro Ile Arg Leu Glu Glu Gly Arg Lys Ile Arg Gln
```

```
625                 630                 635                 640
Ala Phe Val Pro Ser Glu Pro Asp Trp Leu Ile Phe Ala Ala Asp Tyr
                645                 650                 655

Ser Gln Ile Glu Leu Arg Val Leu Ala His Ile Ala Asp Asp Asn
            660                 665                 670

Leu Ile Glu Ala Phe Gln Arg Asp Leu Asp Ile His Thr Lys Thr Ala
        675                 680                 685

Met Asp Ile Phe His Val Ser Glu Glu Val Thr Ala Asn Met Arg
    690                 695                 700

Arg Gln Ala Lys Ala Val Asn Phe Gly Ile Val Tyr Gly Ile Ser Asp
705                 710                 715                 720

Tyr Gly Leu Ala Gln Asn Leu Asn Ile Thr Arg Lys Glu Ala Ala Glu
                725                 730                 735

Phe Ile Glu Arg Tyr Phe Ala Ser Phe Pro Gly Val Arg Arg Tyr Met
            740                 745                 750

Glu Asn Ile Val Gln Glu Ala Lys Gln Lys Gly Tyr Val Thr Thr Leu
        755                 760                 765

Leu His Arg Arg Arg Tyr Leu Pro Asp Ile Thr Ser Arg Asn Phe Asn
    770                 775                 780

Val Arg Ser Phe Ala Glu Arg Thr Ala Met Asn Thr Pro Ile Gln Gly
785                 790                 795                 800

Ser Ala Ala Asp Ile Ile Lys Lys Ala Met Ile Asp Leu Ala Ala Arg
                805                 810                 815

Leu Lys Glu Glu Gln Leu Gln Ala Arg Leu Leu Leu Gln Val His Asp
            820                 825                 830

Glu Leu Ile Leu Glu Ala Pro Lys Glu Glu Ile Glu Arg Leu Cys Glu
        835                 840                 845

Leu Val Pro Glu Val Met Glu Gln Ala Val Ser Ser Val Pro Leu Lys
    850                 855                 860

Val Asp Tyr His Tyr Gly Pro Thr Trp Tyr Asp Ala Lys
865                 870                 875

<210> SEQ ID NO 44
<211> LENGTH: 877
<212> TYPE: PRT
<213> ORGANISM: Bacillus stearothermophilus

<400> SEQUENCE: 44

Met Arg Leu Lys Lys Lys Leu Val Leu Ile Asp Gly Asn Ser Val Ala
1               5                   10                  15

Tyr Arg Ala Phe Phe Ala Leu Pro Leu Leu His Asn Asp Lys Gly Ile
            20                  25                  30

His Thr Asn Ala Val Tyr Gly Phe Thr Met Met Leu Asn Lys Ile Leu
        35                  40                  45

Ala Glu Glu Gln Pro Thr Thr Leu Leu Val Ala Phe Asp Ala Gly Lys
    50                  55                  60

Thr Thr Phe Arg His Glu Thr Phe Gln Glu Tyr Lys Gly Gly Arg Gln
65                  70                  75                  80

Gln Thr Pro Pro Glu Leu Ser Glu Gln Phe Pro Leu Leu Arg Glu Leu
                85                  90                  95

Leu Lys Thr Tyr Arg Ile Pro Ala Tyr Glu Leu Tyr Ile Tyr Glu Ala
            100                 105                 110

Asp Asp Ile Ile Gly Thr Leu Ala Ala Arg Ala Glu Gln Glu Gly Phe
        115                 120                 125
```

-continued

```
Glu Val Lys Ile Ile Ser Gly Asp Arg Asp Leu Thr Gln Leu Ala Ser
130                 135                 140

Arg His Val Thr Val Asp Ile Thr Lys Lys Gly Ile Thr Asp Ile Glu
145                 150                 155                 160

Pro Tyr Thr Pro Glu Thr Val Arg Glu Lys Tyr Gly Leu Thr Pro Glu
                165                 170                 175

Gln Ile Val Asp Leu Lys Gly Leu Met Gly Asp Lys Ser Asp Asn Ile
            180                 185                 190

Pro Gly Val Pro Gly Ile Gly Glu Lys Thr Ala Val Lys Leu Leu Lys
        195                 200                 205

Gln Phe Gly Thr Val Glu Asn Val Leu Ala Ser Ile Asp Glu Val Lys
210                 215                 220

Gly Glu Lys Val Lys Glu Lys Leu Arg Gln His Arg Asp Leu Ala Leu
225                 230                 235                 240

Leu Ser Lys Gln Leu Ala Ser Ile Cys Arg Asp Ala Pro Val Glu Leu
                245                 250                 255

Ser Leu Asp Ala Leu Val Tyr Glu Gly Gln Asp Arg Glu Lys Val Ile
            260                 265                 270

Ala Leu Phe Lys Glu Leu Gly Phe Gln Ser Phe Leu Glu Lys Met Ala
        275                 280                 285

Ala Pro Ala Ala Glu Gly Arg Lys Pro Leu Glu Glu Met Glu Phe Ala
290                 295                 300

Ile Val Asp Val Ile Thr Glu Glu Met Leu Ala Asp Lys Ala Ala Leu
305                 310                 315                 320

Val Val Glu Val Met Glu Glu Asn Tyr His Asp Ala Pro Ile Val Gly
                325                 330                 335

Ile Ala Leu Val Asn Glu His Gly Arg Phe Phe Met Arg Pro Glu Thr
            340                 345                 350

Ala Leu Ala Asp Ser Gln Phe Leu Ala Trp Leu Ala Asp Glu Glu Lys
        355                 360                 365

Lys Lys Ser Met Phe Asp Ala Lys Arg Cys Val Ala Leu Lys Trp
370                 375                 380

Lys Gly Ile Asp Val Arg Gly Val Ala Phe Asp Leu Leu Ala Ala
385                 390                 395                 400

Tyr Leu Leu Asn Pro Ala Gln Asp Ala Gly Asp Ile Ala Ala Val Ala
                405                 410                 415

Lys Met Lys Gln Tyr Glu Ala Val Arg Ser Asp Glu Ala Val Tyr Gly
            420                 425                 430

Lys Gly Val Lys Arg Ser Leu Pro Asp Glu Gln Thr Leu Ala Glu His
        435                 440                 445

Leu Val Arg Lys Ala Ala Ala Ile Trp Ala Leu Glu Gln Pro Phe Met
450                 455                 460

Asp Asp Leu Arg Asn Asn Glu Gln Asp Gln Leu Leu Thr Lys Leu Glu
465                 470                 475                 480

Gln Pro Leu Ala Ala Ile Leu Ala Glu Met Glu Phe Thr Gly Val Asn
                485                 490                 495

Val Asp Thr Lys Arg Leu Glu Gln Met Gly Ser Glu Leu Ala Glu Gln
            500                 505                 510

Leu Arg Ala Ile Glu Gln Arg Ile Tyr Glu His Ala Gly Gln Glu Phe
        515                 520                 525

Asn Ile Asn Ser Pro Lys Gln Leu Gly Val Ile Leu Phe Glu Lys Leu
530                 535                 540

Gln Leu Pro Val Leu Lys Lys Thr Lys Thr Gly Tyr Ser Thr Ser Ala
```

```
                545                 550                 555                 560
Asp Val Leu Glu Lys Leu Ala Pro His His Glu Ile Val Glu Asn Ile
                565                 570                 575

Leu His Tyr Arg Gln Leu Gly Lys Leu Gln Ser Thr Tyr Ile Glu Gly
                580                 585                 590

Leu Leu Lys Val Val Arg Pro Asp Thr Gly Lys Val His Thr Met Phe
            595                 600                 605

Asn Gln Thr Leu Thr Gln Thr Gly Arg Leu Ser Ser Ala Glu Pro Asn
        610                 615                 620

Leu Gln Asn Ile Pro Ile Arg Leu Glu Glu Gly Arg Lys Ile Arg Gln
625                 630                 635                 640

Ala Phe Val Pro Ser Glu Pro Asp Trp Leu Ile Phe Ala Ala Asp Tyr
                645                 650                 655

Ser Gln Ile Glu Leu Arg Val Leu Ala His Ile Ala Asp Asp Asp Asn
                660                 665                 670

Leu Ile Glu Ala Phe Gln Arg Asp Leu Asp Ile His Thr Lys Thr Ala
            675                 680                 685

Met Asp Ile Phe His Val Ser Glu Glu Glu Val Thr Ala Asn Met Arg
        690                 695                 700

Arg Gln Ala Lys Ala Val Asn Phe Gly Ile Val Tyr Gly Ile Ser Asp
705                 710                 715                 720

Tyr Gly Leu Ala Gln Asn Leu Asn Ile Thr Arg Lys Glu Ala Ala Glu
                725                 730                 735

Phe Ile Glu Arg Tyr Phe Ala Ser Phe Pro Gly Val Arg Arg Tyr Met
                740                 745                 750

Glu Asn Ile Val Gln Glu Ala Lys Gln Lys Gly Tyr Val Thr Thr Leu
            755                 760                 765

Leu His Arg Arg Arg Tyr Leu Pro Asp Ile Thr Ser Arg Asn Phe Asn
        770                 775                 780

Val Arg Ser Phe Ala Glu Arg Thr Ala Ile Asn Thr Pro Ile Gln Gly
785                 790                 795                 800

Ser Ala Ala Asp Ile Ile Lys Lys Ala Met Ile Asp Leu Ala Ala Arg
                805                 810                 815

Leu Lys Glu Glu Gln Leu Gln Ala Arg Leu Leu Leu Gln Val His Asp
                820                 825                 830

Glu Leu Ile Leu Glu Ala Pro Lys Glu Glu Ile Glu Arg Leu Cys Glu
            835                 840                 845

Leu Val Pro Glu Val Met Glu Gln Ala Val Ser Ser Val Pro Leu Lys
        850                 855                 860

Val Asp Tyr His Tyr Gly Pro Thr Trp Tyr Asp Ala Lys
865                 870                 875

<210> SEQ ID NO 45
<211> LENGTH: 928
<212> TYPE: PRT
<213> ORGANISM: Escherichia coli

<400> SEQUENCE: 45

Met Val Gln Ile Pro Gln Asn Pro Leu Ile Leu Val Asp Gly Ser Ser
1               5                   10                  15

Tyr Leu Tyr Arg Ala Tyr His Ala Phe Pro Pro Leu Thr Asn Ser Ala
                20                  25                  30

Gly Glu Pro Thr Gly Ala Met Tyr Gly Val Leu Asn Met Leu Arg Ser
            35                  40                  45
```

-continued

```
Leu Ile Met Gln Tyr Lys Pro Thr His Ala Ala Val Val Phe Asp Ala
 50                  55                  60

Lys Gly Lys Thr Phe Arg Asp Glu Leu Phe Glu His Tyr Lys Ser His
 65                  70                  75                  80

Arg Pro Pro Met Pro Asp Asp Leu Arg Ala Gln Ile Glu Pro Leu His
                 85                  90                  95

Ala Met Val Lys Ala Met Gly Leu Pro Leu Leu Ala Val Ser Gly Val
            100                 105                 110

Glu Ala Asp Asp Val Ile Gly Thr Leu Ala Arg Glu Ala Glu Lys Ala
            115                 120                 125

Gly Arg Pro Val Leu Ile Ser Thr Gly Asp Lys Asp Met Ala Gln Leu
130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                165                 170                 175

Ile Asp Phe Leu Ala Leu Met Gly Asp Ser Ser Asp Asn Ile Pro Gly
            180                 185                 190

Val Pro Gly Val Gly Glu Lys Thr Ala Gln Ala Leu Leu Gln Gly Leu
        195                 200                 205

Gly Gly Leu Asp Thr Leu Tyr Ala Glu Pro Glu Lys Ile Ala Gly Leu
210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                245                 250                 255

Glu Leu Glu Leu Thr Cys Glu Gln Leu Glu Val Gln Gln Pro Ala Ala
            260                 265                 270

Glu Glu Leu Leu Gly Leu Phe Lys Lys Tyr Glu Phe Lys Arg Trp Thr
        275                 280                 285

Ala Asp Val Glu Ala Gly Lys Trp Leu Gln Ala Lys Gly Ala Lys Pro
290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
                325                 330                 335

Glu Thr Leu Lys Ala Trp Ile Ala Lys Leu Glu Lys Ala Pro Val Phe
            340                 345                 350

Ala Phe Asp Thr Glu Thr Asp Ser Leu Asp Asn Ile Ser Ala Asn Leu
        355                 360                 365

Val Gly Leu Ser Phe Ala Ile Glu Pro Gly Val Ala Ala Tyr Ile Pro
370                 375                 380

Val Ala His Asp Tyr Leu Asp Ala Pro Asp Gln Ile Ser Arg Glu Arg
385                 390                 395                 400

Ala Leu Glu Leu Leu Lys Pro Leu Leu Glu Asp Glu Lys Ala Leu Lys
                405                 410                 415

Val Gly Gln Asn Leu Lys Tyr Asp Arg Gly Ile Leu Ala Asn Tyr Gly
            420                 425                 430

Ile Glu Leu Arg Gly Ile Ala Phe Asp Thr Met Leu Glu Ser Tyr Ile
        435                 440                 445

Leu Asn Ser Val Ala Gly Arg His Asp Met Asp Ser Leu Ala Glu Arg
450                 455                 460

Trp Leu Lys His Lys Thr Ile Thr Phe Glu Glu Ile Ala Gly Lys Gly
```

```
                465                 470                 475                 480
Lys Asn Gln Leu Thr Phe Asn Gln Ile Ala Leu Glu Glu Ala Gly Arg
                    485                 490                 495

Tyr Ala Ala Glu Asp Ala Asp Val Thr Leu Gln Leu His Leu Lys Met
            500                 505                 510

Trp Pro Asp Leu Gln Lys His Lys Gly Pro Leu Asn Val Phe Glu Asn
            515                 520                 525

Ile Glu Met Pro Leu Val Pro Val Leu Ser Arg Ile Glu Arg Asn Gly
        530                 535                 540

Val Lys Ile Asp Pro Lys Val Leu His Asn His Ser Glu Glu Leu Thr
545                 550                 555                 560

Leu Arg Leu Ala Glu Leu Glu Lys Lys Ala His Glu Ile Ala Gly Glu
                565                 570                 575

Glu Phe Asn Leu Ser Ser Thr Lys Gln Leu Gln Thr Ile Leu Phe Glu
            580                 585                 590

Lys Gln Gly Ile Lys Pro Leu Lys Lys Thr Pro Gly Gly Ala Pro Ser
            595                 600                 605

Thr Ser Glu Glu Val Leu Glu Glu Leu Ala Leu Asp Tyr Pro Leu Pro
        610                 615                 620

Lys Val Ile Leu Glu Tyr Arg Gly Leu Ala Lys Leu Lys Ser Thr Tyr
625                 630                 635                 640

Thr Asp Lys Leu Pro Leu Met Ile Asn Pro Lys Thr Gly Arg Val His
                645                 650                 655

Thr Ser Tyr His Gln Ala Val Thr Ala Thr Gly Arg Leu Ser Ser Thr
            660                 665                 670

Asp Pro Asn Leu Gln Asn Ile Pro Val Arg Asn Glu Glu Gly Arg Arg
        675                 680                 685

Ile Arg Gln Ala Phe Ile Ala Pro Glu Asp Tyr Val Ile Val Ser Ala
            690                 695                 700

Asp Tyr Ser Gln Ile Glu Leu Arg Ile Met Ala His Leu Ser Arg Asp
705                 710                 715                 720

Lys Gly Leu Leu Thr Ala Phe Ala Glu Gly Lys Asp Ile His Arg Ala
                725                 730                 735

Thr Ala Ala Glu Val Phe Gly Leu Pro Leu Glu Thr Val Thr Ser Glu
            740                 745                 750

Gln Arg Arg Ser Ala Lys Ala Ile Asn Phe Gly Leu Ile Tyr Gly Met
            755                 760                 765

Ser Ala Phe Gly Leu Ala Arg Gln Leu Asn Ile Pro Arg Lys Glu Ala
        770                 775                 780

Gln Lys Tyr Met Asp Leu Tyr Phe Glu Arg Tyr Pro Gly Val Leu Gln
785                 790                 795                 800

Tyr Met Glu Arg Thr Arg Ala Gln Ala Lys Glu Gln Gly Tyr Val Glu
                805                 810                 815

Thr Leu Asp Gly Arg Arg Leu Tyr Leu Pro Asp Ile Lys Ser Ser Asn
            820                 825                 830

Gly Ala Arg Arg Ala Ala Ala Glu Arg Ala Ala Ile Asn Ala Pro Met
            835                 840                 845

Gln Gly Thr Ala Ala Asp Ile Ile Lys Arg Ala Met Ile Ala Val Asp
        850                 855                 860

Ala Trp Leu Gln Ala Glu Gln Pro Arg Val Arg Met Ile Met Gln Val
865                 870                 875                 880

His Asp Glu Leu Val Phe Glu Val His Lys Asp Val Asp Ala Val
                885                 890                 895
```

```
Ala Lys Gln Ile His Gln Leu Met Glu Asn Cys Thr Arg Leu Asp Val
                900                 905                 910

Pro Leu Leu Val Glu Val Gly Ser Gly Glu Asn Trp Asp Gln Ala His
            915                 920                 925
```

<210> SEQ ID NO 46
<211> LENGTH: 928
<212> TYPE: PRT
<213> ORGANISM: Escherichia coli

<400> SEQUENCE: 46

```
Met Val Gln Ile Pro Gln Asn Pro Leu Ile Leu Val Asp Gly Ser Ser
1               5                   10                  15

Tyr Leu Tyr Arg Ala Tyr His Ala Phe Pro Pro Leu Thr Asn Ser Ala
                20                  25                  30

Gly Glu Pro Thr Gly Ala Met Tyr Gly Val Leu Asn Met Leu Arg Ser
            35                  40                  45

Leu Ile Met Gln Tyr Lys Pro Thr Thr Ala Ala Val Val Phe Asp Ala
    50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95

Ala Met Val Lys Ala Met Gly Leu Pro Leu Leu Ala Val Ser Gly Val
                100                 105                 110

Glu Ala Asp Asp Val Ile Gly Thr Leu Ala Arg Glu Ala Glu Lys Ala
            115                 120                 125

Gly Arg Pro Val Leu Ile Ser Thr Gly Asp Lys Asp Met Ala Gln Leu
    130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                165                 170                 175

Ile Asp Phe Leu Ala Leu Met Gly Asp Ser Ser Asp Asn Ile Pro Gly
            180                 185                 190

Val Pro Gly Val Gly Glu Lys Thr Ala Gln Ala Leu Leu Gln Gly Leu
    195                 200                 205

Gly Gly Leu Asp Thr Leu Tyr Ala Glu Pro Glu Lys Ile Ala Gly Leu
210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                245                 250                 255

Glu Leu Glu Leu Thr Cys Glu Gln Leu Glu Val Gln Gln Pro Ala Ala
            260                 265                 270

Glu Glu Leu Leu Gly Leu Phe Lys Lys Tyr Glu Phe Lys Arg Trp Thr
    275                 280                 285

Ala Asp Val Glu Ala Gly Lys Trp Leu Gln Ala Lys Gly Ala Lys Pro
290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
                325                 330                 335

Glu Thr Leu Lys Ala Trp Ile Ala Lys Leu Glu Lys Ala Pro Val Phe
```

```
              340                 345                 350
Ala Phe Asp Thr Glu Thr Asp Ser Leu Asp Asn Ile Ser Ala Asn Leu
            355                 360                 365

Val Gly Leu Ser Phe Ala Ile Glu Pro Gly Val Ala Ala Tyr Ile Pro
            370                 375                 380

Val Ala His Asp Tyr Leu Asp Ala Pro Asp Gln Ile Ser Arg Glu Arg
385                 390                 395                 400

Ala Leu Glu Leu Lys Pro Leu Leu Glu Asp Glu Lys Cys Leu Lys
                405                 410                 415

Val Gly Gln Asn Leu Lys Tyr Asp Arg Gly Ile Leu Ala Asn Tyr Gly
            420                 425                 430

Ile Glu Leu Arg Gly Ile Ala Phe Asp Thr Met Leu Glu Ser Tyr Ile
            435                 440                 445

Leu Asn Ser Val Ala Gly Arg His Asp Met Asp Ser Leu Ala Glu Arg
            450                 455                 460

Trp Leu Lys His Lys Thr Ile Thr Phe Glu Glu Ile Ala Gly Lys Gly
465                 470                 475                 480

Lys Asn Gln Leu Thr Phe Asn Gln Ile Ala Leu Glu Glu Ala Gly Arg
                485                 490                 495

Tyr Ala Ala Glu Asp Ala Asp Val Thr Leu Gln Leu His Leu Lys Met
                500                 505                 510

Trp Pro Asp Leu Gln Lys His Lys Gly Pro Leu Asn Val Phe Glu Asn
                515                 520                 525

Ile Glu Met Pro Leu Val Pro Val Leu Ser Arg Ile Glu Arg Asn Gly
            530                 535                 540

Val Lys Ile Asp Pro Lys Val Leu His Asn His Ser Glu Glu Leu Thr
545                 550                 555                 560

Leu Arg Leu Ala Glu Leu Glu Lys Lys Ala His Glu Ile Ala Gly Glu
                565                 570                 575

Glu Phe Asn Leu Ser Ser Thr Lys Gln Leu Gln Thr Ile Leu Phe Glu
                580                 585                 590

Lys Gln Gly Ile Lys Pro Leu Lys Lys Thr Lys Gly Gly Ala Pro Ser
                595                 600                 605

Thr Ser Glu Glu Val Leu Glu Glu Leu Ala Leu Asp Tyr Pro Leu Pro
            610                 615                 620

Lys Val Ile Leu Glu Tyr Arg Gly Leu Ala Lys Leu Lys Ser Thr Tyr
625                 630                 635                 640

Thr Asp Lys Leu Pro Leu Met Ile Asn Pro Lys Thr Gly Arg Val His
                645                 650                 655

Thr Ser Tyr His Gln Ala Val Thr Ala Thr Gly Arg Leu Ser Ser Thr
                660                 665                 670

Asp Pro Asn Leu Gln Asn Ile Pro Val Arg Asn Glu Glu Gly Arg Arg
                675                 680                 685

Ile Arg Gln Ala Phe Ile Ala Pro Glu Asp Tyr Val Ile Val Ser Ala
            690                 695                 700

Asp Tyr Ser Gln Ile Glu Leu Arg Ile Met Ala His Leu Ser Arg Asp
705                 710                 715                 720

Lys Gly Leu Leu Thr Ala Phe Ala Glu Gly Lys Asp Ile His Arg Ala
                725                 730                 735

Thr Ala Ala Glu Val Phe Gly Leu Pro Leu Glu Thr Val Thr Ser Glu
            740                 745                 750

Gln Arg Arg Ser Ala Lys Ala Ile Asn Phe Gly Leu Ile Tyr Gly Met
            755                 760                 765
```

-continued

Ser Ala Phe Gly Leu Ala Arg Gln Leu Asn Ile Pro Arg Lys Glu Ala
    770                 775                 780

Gln Lys Tyr Met Asp Leu Tyr Phe Glu Arg Tyr Pro Gly Val Leu Gln
785                 790                 795                 800

Tyr Met Glu Arg Thr Arg Ala Gln Ala Lys Glu Gln Gly Tyr Val Glu
                805                 810                 815

Thr Leu Asp Gly Arg Arg Leu Tyr Leu Pro Asp Ile Lys Ser Ser Asn
            820                 825                 830

Gly Ala Arg Arg Ala Ala Glu Arg Ala Ala Ile Asn Ala Pro Met
        835                 840                 845

Gln Gly Thr Ala Ala Asp Ile Ile Lys Arg Ala Met Ile Ala Val Asp
850                 855                 860

Ala Trp Leu Gln Ala Glu Gln Pro Arg Val Arg Met Ile Met Gln Val
865                 870                 875                 880

His Asp Glu Leu Val Phe Glu Val His Lys Asp Val Asp Ala Val
                885                 890                 895

Ala Lys Gln Ile His Gln Leu Met Glu Asn Cys Thr Arg Leu Asp Val
        900                 905                 910

Pro Leu Leu Val Glu Val Gly Ser Gly Glu Asn Trp Asp Gln Ala His
    915                 920                 925

<210> SEQ ID NO 47
<211> LENGTH: 832
<212> TYPE: PRT
<213> ORGANISM: Artificial Sequence
<220> FEATURE:
<223> OTHER INFORMATION: Clone 15 mutated bacterial DNA polymerase

<400> SEQUENCE: 47

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Thr Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

-continued

```
Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Glu Glu Ala Arg Gly Leu Leu
                340                 345                 350

Ala Lys Asp Leu Cys Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Lys Thr Gly Lys Arg
            500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620
```

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
        660                 665                 670

Met Ser Ala His Arg Leu Ser Gln Glu Leu Ala Ile Pro Tyr Glu Glu
    675                 680                 685

Ala Gln Ala Phe Ile Glu Arg Tyr Phe Gln Ser Phe Pro Lys Val Arg
690                 695                 700

Ala Trp Met Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
            725                 730                 735

Val Lys Ser Val Arg Glu Ala Ala Glu Arg Met Ala Ile Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 48
<211> LENGTH: 832
<212> TYPE: PRT
<213> ORGANISM: Artificial Sequence
<220> FEATURE:
<223> OTHER INFORMATION: Clone 15 mutated bacterial DNA polymerase

<400> SEQUENCE: 48

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Thr Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
            85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

-continued

```
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
        195                 200                 205
Glu Glu Trp Gly Ser Leu Glu Ala Leu Leu Lys Asn Leu Asp Arg Leu
    210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
        275                 280                 285
Glu Ser Pro Lys Ala Leu Glu Glu Ala Pro Trp Pro Pro Glu Gly
    290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Glu Glu Ala Arg Gly Leu Leu
            340                 345                 350
Ala Lys Asp Leu Cys Val Leu Ala Leu Arg Glu Gly Leu Gly Leu Pro
        355                 360                 365
Pro Gly Asp Asp Pro Met Leu Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
            420                 425                 430
Val Glu Arg Pro Leu Ser Ala Val Leu Ala His Met Glu Ala Thr Gly
        435                 440                 445
Val Arg Leu Asp Val Ala Tyr Leu Arg Ala Leu Ser Leu Glu Val Ala
    450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Lys Thr Gly Lys Arg
            500                 505                 510
Ser Thr Ser Ala Ala Val Leu Glu Ala Leu Arg Glu Ala His Pro Ile
        515                 520                 525
Val Glu Lys Ile Leu Gln Tyr Arg Glu Leu Thr Lys Leu Lys Ser Thr
    530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
```

```
                   580                 585                 590
Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Met Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Leu Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 49
<211> LENGTH: 832
<212> TYPE: PRT
<213> ORGANISM: Thermus aquaticus

<400> SEQUENCE: 49

Met Arg Gly Met Leu Pro Leu Phe Glu Pro Lys Gly Arg Val Leu Leu
1               5                  10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125
```

```
Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
    275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
    355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
    435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
```

His Thr Arg Phe Asn Gln Thr Ala Thr Ala Thr Gly Arg Leu Ser Ser
            545                 550                 555                 560

Ser Asp Pro Asn Leu Gln Asn Ile Pro Val Arg Thr Pro Leu Gly Gln
            565                 570                 575

Arg Ile Arg Ala Phe Ile Ala Glu Glu Gly Trp Leu Val Ala
580                 585                 590

Leu Asp Tyr Ser Gln Ile Glu Leu Arg Val Leu Ala His Leu Ser Gly
            595                 600                 605

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 50
<211> LENGTH: 834
<212> TYPE: PRT
<213> ORGANISM: Thermus thermophilus

<400> SEQUENCE: 50

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
            85                  90                  95

```
Leu Ala Leu Ile Lys Glu Leu Val Asp Leu Gly Phe Thr Arg Leu
            100                 105                 110

Glu Val Pro Gly Tyr Glu Ala Asp Val Leu Ala Thr Leu Ala Lys
            115                 120                 125

Lys Ala Glu Lys Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                    165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Leu Leu Lys Asn Leu Asp Arg
210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                    245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro
290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                    325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
            355                 360                 365

Leu Val Pro Gly Asp Asp Pro Met Leu Leu Ala Tyr Leu Leu Asp Pro
370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                    405                 410                 415

Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
            450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                    485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
```

```
            515                 520                 525
Pro Ile Val Glu Lys Ile Leu Gln His Arg Glu Leu Thr Lys Leu Lys
530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly

<210> SEQ ID NO 51
<211> LENGTH: 832
<212> TYPE: PRT
<213> ORGANISM: Thermus aquaticus

<400> SEQUENCE: 51

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
```

-continued

```
            50                  55                  60
Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
            100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
            130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
                195                 200                 205

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480
```

```
Pro Phe Asn Leu Asn Ser Arg Asp Gln Leu Glu Arg Val Leu Phe Asp
            485                 490                 495
Glu Leu Gly Leu Pro Ala Ile Gly Lys Thr Glu Lys Thr Gly Lys Arg
        500                 505                 510
Ser Thr Ser Ala Ala Val Leu Glu Ala Leu Arg Glu Ala His Pro Ile
    515                 520                 525
Val Glu Lys Ile Leu Gln Tyr Arg Glu Leu Thr Lys Leu Lys Ser Thr
530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
        595                 600                 605
Leu Asp Tyr Ser Gln Ile Glu Leu Arg Val Leu Ala His Leu Ser Gly
    610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
        675                 680                 685
Ala Gln Ala Phe Ile Glu Arg Tyr Phe Gln Ser Phe Pro Lys Val Arg
    690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
Val Gln Gly Thr Ala Ala Asp Leu Met Lys Leu Ala Met Val Lys Leu
        755                 760                 765
Phe Pro Arg Leu Glu Glu Met Gly Ala Arg Met Leu Leu Gln Val His
    770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
            820                 825                 830

<210> SEQ ID NO 52
<211> LENGTH: 877
<212> TYPE: PRT
<213> ORGANISM: Bacillus stearothermophilus

<400> SEQUENCE: 52

Met Arg Leu Lys Lys Lys Leu Val Leu Ile Asp Gly Asn Ser Val Ala
1               5                   10                  15
Tyr Arg Ala Phe Phe Ala Leu Pro Leu Leu His Asn Asp Lys Gly Ile
```

```
                 20                  25                  30
His Thr Asn Ala Val Tyr Gly Phe Thr Met Met Leu Asn Lys Ile Leu
             35                  40                  45
Ala Glu Glu Gln Pro Thr His Leu Leu Val Ala Phe Asp Ala Gly Lys
         50                  55                  60
Thr Thr Phe Arg His Glu Thr Phe Gln Glu Tyr Lys Gly Gly Arg Gln
 65                  70                  75                  80
Gln Thr Pro Pro Glu Leu Ser Glu Gln Phe Pro Leu Leu Arg Glu Leu
                 85                  90                  95
Leu Lys Thr Tyr Arg Ile Pro Ala Tyr Glu Leu Tyr Ile Tyr Glu Ala
             100                 105                 110
Asp Asp Ile Ile Gly Thr Leu Ala Ala Arg Ala Glu Gln Glu Gly Phe
         115                 120                 125
Glu Val Lys Ile Ile Ser Gly Asp Arg Asp Leu Thr Gln Leu Ala Ser
             130                 135                 140
Arg His Val Thr Val Asp Ile Thr Lys Lys Gly Ile Thr Asp Ile Glu
145                 150                 155                 160
Pro Tyr Thr Pro Glu Thr Val Arg Glu Lys Tyr Gly Leu Thr Pro Glu
                 165                 170                 175
Gln Ile Val Asp Leu Lys Gly Leu Met Gly Asp Lys Ser Asp Asn Ile
             180                 185                 190
Pro Gly Val Pro Gly Ile Gly Glu Lys Thr Ala Val Lys Leu Leu Lys
         195                 200                 205
Gln Phe Gly Thr Val Glu Asn Val Leu Ala Ser Ile Asp Glu Val Lys
             210                 215                 220
Gly Glu Lys Val Lys Glu Lys Leu Arg Gln His Arg Asp Leu Ala Leu
225                 230                 235                 240
Leu Ser Lys Gln Leu Ala Ser Ile Cys Arg Asp Ala Pro Val Glu Leu
                 245                 250                 255
Ser Leu Asp Ala Leu Val Tyr Glu Gly Gln Asp Arg Glu Lys Val Ile
             260                 265                 270
Ala Leu Phe Lys Glu Leu Gly Phe Gln Ser Phe Leu Glu Lys Met Ala
         275                 280                 285
Ala Pro Ala Ala Glu Gly Arg Lys Pro Leu Glu Glu Met Glu Phe Ala
         290                 295                 300
Ile Val Asp Val Ile Thr Glu Glu Met Leu Ala Asp Lys Ala Ala Leu
305                 310                 315                 320
Val Val Glu Val Met Glu Glu Asn Tyr His Asp Ala Pro Ile Val Gly
                 325                 330                 335
Ile Ala Leu Val Asn Glu His Gly Arg Phe Phe Met Arg Pro Glu Thr
             340                 345                 350
Ala Leu Ala Asp Ser Gln Phe Leu Ala Trp Leu Ala Asp Glu Thr Lys
         355                 360                 365
Lys Lys Ser Met Phe Asp Ala Lys Arg Ala Val Val Ala Leu Lys Trp
         370                 375                 380
Lys Gly Ile Asp Val Arg Gly Val Ala Phe Asp Leu Leu Leu Ala Ala
385                 390                 395                 400
Tyr Leu Leu Asn Pro Ala Gln Asp Ala Gly Asp Ile Ala Ala Val Ala
                 405                 410                 415
Lys Met Lys Gln Tyr Glu Ala Val Arg Ser Asp Glu Ala Val Tyr Gly
             420                 425                 430
Lys Gly Val Lys Arg Ser Leu Pro Asp Glu Gln Thr Leu Ala Glu His
         435                 440                 445
```

-continued

```
Leu Val Arg Lys Ala Ala Ile Trp Ala Leu Glu Gln Pro Phe Met
    450             455                 460
Asp Asp Leu Arg Asn Asn Glu Gln Asp Gln Leu Leu Thr Lys Leu Glu
465             470                 475                 480
Gln Pro Leu Ala Ala Ile Leu Ala Glu Met Glu Phe Thr Gly Val Asn
                485                 490                 495
Val Asp Thr Lys Arg Leu Glu Gln Met Gly Ser Glu Leu Ala Glu Gln
            500                 505                 510
Leu Arg Ala Ile Glu Gln Arg Ile Tyr Glu His Ala Gly Gln Glu Phe
            515                 520                 525
Asn Ile Asn Ser Pro Lys Gln Leu Gly Val Ile Leu Phe Glu Lys Leu
            530                 535                 540
Gln Leu Pro Val Leu Lys Lys Thr Lys Thr Gly Tyr Ser Thr Ser Ala
545                 550                 555                 560
Asp Val Leu Glu Lys Leu Ala Pro His His Glu Ile Val Glu Asn Ile
                565                 570                 575
Leu His Tyr Arg Gln Leu Gly Lys Leu Gln Ser Thr Tyr Ile Glu Gly
                580                 585                 590
Leu Leu Lys Val Val Arg Pro Asp Thr Gly Lys Val His Thr Met Phe
            595                 600                 605
Asn Gln Thr Leu Thr Gln Thr Gly Arg Leu Ser Ser Ala Glu Pro Asn
            610                 615                 620
Leu Gln Asn Ile Pro Ile Arg Leu Glu Glu Gly Arg Lys Ile Arg Gln
625                 630                 635                 640
Ala Phe Val Pro Ser Glu Pro Asp Trp Leu Ile Phe Ala Ala Asp Tyr
                645                 650                 655
Ser Gln Ile Glu Leu Arg Val Leu Ala His Ile Ala Asp Asp Asp Asn
            660                 665                 670
Leu Ile Glu Ala Phe Gln Arg Asp Leu Asp Ile His Thr Lys Thr Ala
            675                 680                 685
Met Asp Ile Phe His Val Ser Glu Glu Val Thr Ala Asn Met Arg
690                 695                 700
Arg Gln Ala Lys Ala Val Asn Phe Gly Ile Val Tyr Gly Ile Ser Asp
705                 710                 715                 720
Tyr Gly Leu Ala Gln Asn Leu Asn Ile Thr Arg Lys Glu Ala Ala Glu
                725                 730                 735
Phe Ile Glu Arg Tyr Phe Ala Ser Phe Pro Gly Val Arg Arg Tyr Met
                740                 745                 750
Glu Asn Ile Val Gln Glu Ala Lys Gln Lys Gly Tyr Val Thr Thr Leu
            755                 760                 765
Leu His Arg Arg Arg Tyr Leu Pro Asp Ile Thr Ser Arg Asn Phe Asn
            770                 775                 780
Val Arg Ser Phe Ala Glu Arg Thr Ala Met Asn Thr Pro Ile Gln Gly
785                 790                 795                 800
Ser Ala Ala Asp Ile Ile Lys Lys Ala Met Ile Asp Leu Ala Ala Arg
                805                 810                 815
Leu Lys Glu Glu Gln Leu Gln Ala Arg Leu Leu Leu Gln Val His Asp
            820                 825                 830
Glu Leu Ile Leu Glu Ala Pro Lys Glu Glu Ile Glu Arg Leu Cys Glu
            835                 840                 845
Leu Val Pro Glu Val Met Glu Gln Ala Val Ser Ser Val Pro Leu Lys
    850                 855                 860
```

```
Val Asp Tyr His Tyr Gly Pro Thr Trp Tyr Asp Ala Lys
865                 870                 875

<210> SEQ ID NO 53
<211> LENGTH: 832
<212> TYPE: PRT
<213> ORGANISM: Thermus aquaticus

<400> SEQUENCE: 53

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365
```

```
Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
    675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
    755                 760                 765

Phe Pro Arg Leu Glu Glu Met Gly Ala Arg Met Leu Leu Gln Val His
770                 775                 780
```

```
Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
        820                 825                 830

<210> SEQ ID NO 54
<211> LENGTH: 928
<212> TYPE: PRT
<213> ORGANISM: Escherichia coli

<400> SEQUENCE: 54

Met Val Gln Ile Pro Gln Asn Pro Leu Ile Leu Val Asp Gly Ser Ser
1               5                   10                  15

Tyr Leu Tyr Arg Ala Tyr His Ala Phe Pro Pro Leu Thr Asn Ser Ala
            20                  25                  30

Gly Glu Pro Thr Gly Ala Met Tyr Gly Val Leu Asn Met Leu Arg Ser
        35                  40                  45

Leu Ile Met Gln Tyr Lys Pro Thr His Ala Ala Val Val Phe Asp Ala
    50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95

Ala Met Val Lys Ala Met Gly Leu Pro Leu Leu Ala Val Ser Gly Val
            100                 105                 110

Glu Ala Asp Asp Val Ile Gly Thr Leu Ala Arg Glu Ala Glu Lys Ala
        115                 120                 125

Gly Arg Pro Val Leu Ile Ser Thr Gly Asp Lys Asp Met Ala Gln Leu
    130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                165                 170                 175

Ile Asp Phe Leu Ala Leu Met Gly Asp Ser Ser Asp Asn Ile Pro Gly
            180                 185                 190

Val Pro Gly Val Gly Lys Thr Ala Gln Ala Leu Leu Gln Gly Leu
    195                 200                 205

Gly Gly Leu Asp Thr Leu Tyr Ala Glu Pro Glu Lys Ile Ala Gly Leu
210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
            245                 250                 255

Glu Leu Glu Leu Thr Cys Glu Gln Leu Glu Val Gln Gln Pro Ala Ala
        260                 265                 270

Glu Glu Leu Leu Gly Leu Phe Lys Lys Tyr Glu Phe Lys Arg Trp Thr
    275                 280                 285

Ala Asp Val Glu Ala Gly Lys Trp Leu Gln Ala Lys Gly Ala Lys Pro
290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
            325                 330                 335
```

```
Glu Thr Leu Lys Ala Trp Ile Ala Lys Leu Glu Lys Ala Pro Val Phe
                340                 345                 350

Ala Phe Asp Thr Glu Thr Asp Ser Leu Asp Asn Ile Ser Ala Asn Leu
            355                 360                 365

Val Gly Leu Ser Phe Ala Ile Glu Pro Gly Val Ala Ala Tyr Ile Pro
        370                 375                 380

Val Ala His Asp Tyr Leu Asp Ala Pro Asp Gln Ile Ser Arg Glu Arg
385                 390                 395                 400

Ala Leu Glu Leu Leu Lys Pro Leu Leu Glu Asp Lys Ala Leu Lys
                405                 410                 415

Val Gly Gln Asn Leu Lys Tyr Asp Arg Gly Ile Leu Ala Asn Tyr Gly
                420                 425                 430

Ile Glu Leu Arg Gly Ile Ala Phe Asp Thr Met Leu Glu Ser Tyr Ile
            435                 440                 445

Leu Asn Ser Val Ala Gly Arg His Asp Met Asp Ser Leu Ala Glu Arg
        450                 455                 460

Trp Leu Lys His Lys Thr Ile Thr Phe Glu Glu Ile Ala Gly Lys Gly
465                 470                 475                 480

Lys Asn Gln Leu Thr Phe Asn Gln Ile Ala Leu Glu Glu Ala Gly Arg
                485                 490                 495

Tyr Ala Ala Glu Asp Ala Asp Val Thr Leu Gln Leu His Leu Lys Met
            500                 505                 510

Trp Pro Asp Leu Gln Lys His Lys Gly Pro Leu Asn Val Phe Glu Asn
        515                 520                 525

Ile Glu Met Pro Leu Val Pro Val Leu Ser Arg Ile Glu Arg Asn Gly
            530                 535                 540

Val Lys Ile Asp Pro Lys Val Leu His Asn His Ser Glu Glu Leu Thr
545                 550                 555                 560

Leu Arg Leu Ala Glu Leu Glu Lys Lys Ala His Glu Ile Ala Gly Glu
                565                 570                 575

Glu Phe Asn Leu Ser Ser Thr Lys Gln Leu Gln Thr Ile Leu Phe Glu
            580                 585                 590

Lys Gln Gly Ile Lys Pro Leu Lys Lys Thr Pro Gly Gly Ala Pro Ser
        595                 600                 605

Thr Ser Glu Glu Val Leu Glu Glu Leu Ala Leu Asp Tyr Pro Leu Pro
        610                 615                 620

Lys Val Ile Leu Glu Tyr Arg Gly Leu Ala Lys Leu Lys Ser Thr Tyr
625                 630                 635                 640

Thr Asp Lys Leu Pro Leu Met Ile Asn Pro Lys Thr Gly Arg Val His
                645                 650                 655

Thr Ser Tyr His Gln Ala Val Thr Ala Thr Gly Arg Leu Ser Ser Thr
            660                 665                 670

Asp Pro Asn Leu Gln Asn Ile Pro Val Arg Asn Glu Glu Gly Arg Arg
        675                 680                 685

Ile Arg Gln Ala Phe Ile Ala Pro Glu Asp Tyr Val Ile Val Ser Ala
            690                 695                 700

Asp Tyr Ser Gln Ile Glu Leu Arg Ile Met Ala His Leu Ser Arg Asp
705                 710                 715                 720

Lys Gly Leu Leu Thr Ala Phe Ala Glu Gly Lys Asp Ile His Arg Ala
                725                 730                 735

Thr Ala Ala Glu Val Phe Gly Leu Pro Leu Glu Thr Val Thr Ser Glu
            740                 745                 750
```

-continued

```
Gln Arg Arg Ser Ala Lys Ala Ile Asn Phe Gly Leu Ile Tyr Gly Met
        755                 760                 765

Ser Ala Phe Gly Leu Ala Arg Gln Leu Asn Ile Pro Arg Lys Glu Ala
    770                 775                 780

Gln Lys Tyr Met Asp Leu Tyr Phe Glu Arg Tyr Pro Gly Val Leu Gln
785                 790                 795                 800

Tyr Met Glu Arg Thr Arg Ala Gln Ala Lys Glu Gln Gly Tyr Val Glu
            805                 810                 815

Thr Leu Asp Gly Arg Arg Leu Tyr Leu Pro Asp Ile Lys Ser Ser Asn
            820                 825                 830

Gly Ala Arg Arg Ala Ala Ala Glu Arg Ala Ala Ile Asn Ala Pro Met
            835                 840                 845

Gln Gly Thr Ala Ala Asp Ile Ile Lys Arg Ala Met Ile Ala Val Asp
    850                 855                 860

Ala Trp Leu Gln Ala Glu Gln Pro Arg Val Arg Met Ile Met Gln Val
865                 870                 875                 880

His Asp Glu Leu Val Phe Glu Val His Lys Asp Val Asp Ala Val
                885                 890                 895

Ala Lys Gln Ile His Gln Leu Met Glu Asn Cys Thr Arg Leu Asp Val
            900                 905                 910

Pro Leu Leu Val Glu Val Gly Ser Gly Glu Asn Trp Asp Gln Ala His
        915                 920                 925
```

MODIFIED DNA POLYMERASES FOR IMPROVED AMPLIFICATION

CROSS REFERENCE TO RELATED APPLICATIONS

This application is a national phase entry of international application serial number PCT/US2012/021348, filed Jan. 13, 2012 which claims priority to U.S. Provisional Patent Application Ser. No. 61/432,936, filed Jan. 14, 2011, the entire disclosure of which is hereby incorporated by reference.

BACKGROUND OF THE INVENTION

DNA polymerases are a family of enzymes that use single-stranded DNA as a template to synthesize the complementary DNA strand. In particular, DNA polymerases can add free nucleotides to the 3' end of a newly-forming strand resulting in elongation of the new strand in a 5'-3' direction. Most DNA polymerases are multifunctional proteins that possess both polymerizing and exonucleolytic activities (e.g., 3'→5' exonuclease or 5'→3' exonuclease activity).

DNA polymerases, like other natural enzymes, have evolved over millions of years to be efficient in their natural cellular environment. Many of them are almost perfectly adapted to work in that environment. In such an environment, the way that the protein can evolve is constrained by a number of requirements; the protein has to interact with other cellular components, it has to function in the cytoplasm (i.e., particular pH, ionic strength, in the presence of particular compounds, etc.) and it cannot cause lethal or disadvantageous side effects that detract from the fitness of the parent organism as a whole.

When DNA polymerases are removed from their natural environment and used in industrial or research applications, the environment and conditions under which the enzyme is operating is inevitably vastly different than those in which it evolved. Many of the constraints that limited the evolutionary direction the protein could take fall away. Therefore, there is vast potential for improvement of DNA polymerases for use in industrial or research applications.

SUMMARY OF THE INVENTION

The present invention provides improved DNA polymerases that may be better suited for applications in recombinant DNA technologies, in particular technologies involving plant-derived samples. Among other things, the present invention provides modified DNA polymerases derived from directed evolution experiments designed to select mutations that confer advantageous phenotypes under conditions used in industrial or research applications. In particular, the present invention provides modified DNA polymerases that can effectively amplify biological samples containing various PCR inhibitors, especially plant-derived inhibitors. Thus, the present invention represents a significant improvement in recombinant DNA technology.

Accordingly, in one aspect, the present invention provides a modified DNA polymerase comprising an amino acid alteration (e.g., an amino acid substitution, deletion, and/or insertion) at a position corresponding to F749 of Taq polymerase (SEQ ID NO: 38) and at least one additional amino acid alteration at a position corresponding to A61, K346, S357, or I707 of Taq polymerase (SEQ ID NO: 38) relative to the corresponding wild-type enzyme. In some embodiments, a modified DNA polymerase according to the present invention contains amino acid alterations (e.g., amino acid substitution(s), deletion(s), and/or insertion(s)) at positions corresponding to A61, K346, S357, I707 and F749 of Taq polymerase (SEQ ID NO: 38) relative to the corresponding wild-type enzyme. In some embodiments, a modified DNA polymerase further contains an amino acid alteration at a position corresponding to E507 of Taq polymerase (SEQ ID NO: 38).

In some embodiments, the amino acid alteration at position 749 is an amino acid substitution. In some embodiments, the amino acid substitution at position 749 is selected from the group consisting of F749L, F749I, F749V, F749T, F749Y, and F749M. In some embodiments, the amino acid substitution at position 749 is F749L. In some embodiments, the amino acid substitution at position 749 is F749V.

In another aspect, the present invention provides a modified DNA polymerase comprising one or more amino acid alterations (e.g., amino acid substitution(s), deletion(s), and/or insertion(s)) at one or more positions corresponding to A61, K346 and/or S357 of Taq polymerase (SEQ ID NO: 38) relative to the corresponding wild-type enzyme. In some embodiments, a modified DNA polymerase further comprises one or more additional alterations at one or more additional positions corresponding to E507, I707, and/or F749 of Taq polymerase (SEQ ID NO: 38). In some embodiments, suitable amino acid substitutions are selected from the group consisting of A61T, K346E, S357C, I707M, F749I, E507K and combinations thereof. In some embodiments, a modified DNA polymerase according to the invention contains amino acid substitutions of A61T, K346E, S357C, I707M, F749I, and E507K. In some embodiments, suitable amino acid substitutions are selected from the group consisting of A61T, K346E, S357C, I707M, F749L, E507K and combinations thereof. In some embodiments, a modified DNA polymerase according to the invention contains amino acid substitutions of A61T, K346E, S357C, I707M, F749L, and E507K.

In a further aspect, the present invention provides modified DNA polymerases containing one or more amino acid alterations (e.g., one or more substitutions, deletions, or insertions) corresponding to one or more positions selected from A61, K346, S357, I707, and/or F749 of Taq polymerase (SEQ ID NO: 38) relative to the corresponding wild-type enzyme. In certain embodiments, an amino acid alteration at I707 is not I707L. In certain embodiments, an amino acid alteration at F749 is not F749Y or F749S. In some embodiments, the modified DNA polymerases contain an additional alteration at a position corresponding to E507 of Taq polymerase (SEQ ID NO: 38).

In some embodiments, the DNA polymerase is modified from a naturally-occurring polymerase, e.g., a naturally-occurring polymerase isolated from any species of the genus *Thermus*, any species of the genus *Meiothermus*, any species of the genus *Thermotoga*, and/or any species of the genus *Thermomicrobium*. In some embodiments, the naturally-occurring polymerase is isolated from *Bacillus stearothermophilus, Sphaerobacter thermophilus, Dictoglomus thermophilum,* and/or *Escherichia coli*. In some embodiments, the naturally-occurring polymerase is isolated from *Thermus aquaticus, Thermus thermophilus, Thermus caldophilus,* or *Thermus filiformis*. In some embodiments, the naturally-occurring polymerase is isolated from *Thermus aquaticus*.

In some embodiments, the modified DNA polymerase has increased enzyme activity, processivity, resistance to nucleic acid intercalating dyes, and/or salt resistance as compared to the corresponding wild-type enzyme. In some embodiments, the modified DNA polymerase has increased resistance to plant-derived PCR inhibitors as compared to the corresponding wild-type enzyme.

In another aspect, the present invention provides formulations of DNA polymerases containing modified DNA polymerases described herein and at least one DNA polymerase exhibiting 3'-exonuclease activity. In some embodiments, the modified DNA polymerase and the at least one DNA polymerase exhibiting 3'-exonuclease activity are present in a ratio of about 1:1 to about 1:2000 relative units of enzyme. In some embodiments, the modified DNA polymerase and the at least one DNA polymerase exhibiting 3'-exonuclease activity are present in a ratio of about 1:4 to about 1:100 relative units of enzyme. In some embodiments, the at least one DNA polymerase exhibiting 3'-exonuclease activity is selected from the group consisting of *Thermococcus litoralis* (Vent™, GenBank: AAA72101), *Pyrococcus furiosus* (Pfu, GenBank: D12983, BAA02362), *Pyrococcus woesii, Pyrococcus* GB-D (Deep Vent™, GenBank: AAA67131), *Thermococcus kodakaraensis* KOD1 (KOD, GenBank: BD175553, BAA06142; *Thermococcus* sp. strain KOD (Pfx, GenBank: AAE68738)), *Thermococcus gorgonarius* (Tgo, Pdb: 4699806), *Sulfolobus solataricus* (GenBank: NC002754, P26811), *Aeropyrum pernix* (GenBank: BAA81109), *Archaeglobus fulgidus* (GenBank: Q29753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366), *Thermococcus fumicolans* (GenBank: CAA93738, P74918), *Thermococcus hydrothermalis* (GenBank: CAC18555), *Thermococcus* spp. GE8 (GenBank: CAC12850), *Thermococcus* spp. JDF-3 (GenBank: AX135456; WO0132887), *Thermococcus* spp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* spp. GE23 (GenBank: CAA90887), *Pyrococcus* spp. ST700 (GenBank: CAC12847), *Thermococcus pacificus* (GenBank: AX411312.1), *Thermococcus zilligii* (GenBank: DQ3366890), *Thermococcus aggregans, Thermococcus barossii, Thermococcus celer* (GenBank: DD259850.1), *Thermococcus profundus* (GenBank: E14137), *Thermococcus siculi* (GenBank: DD259857.1), *Thermococcus thioreducens, Thermococcus onnurineus* NA1, *Sulfolobus acidocaldarium, Sulfolobus tokodaii, Pyrobaculum calidifontis, Pyrobaculum islandicum* (GenBank: AAF27815), *Methanococcus jannaschii* (GenBank: Q58295), *Desulforococcus* species TOK, *Desulfurococcus, Pyrolobus, Pyrodictium, Staphylothermus, Vulcanisaetta, Methanococcus* (GenBank: P52025), GenBank AAC62712, GenBank P956901, and GenBank BAAA07579.

In other, related aspects, the present invention provides modified Taq polymerases containing one or more, two or more, three or more, four or more, or each of the amino acid substitutions selected from the group consisting of A61T, K346E, S357C, I707M, E507K and F749I or F749L.

In yet another aspect, the present invention provides modified Taq polymerases containing amino acid substitutions of E507K and F749 I and at least one additional amino acid substitution selected from the group consisting of A61T, K346E, S357C, and I707M.

In another aspect, the present invention provides formulations of DNA polymerases containing modified Taq polymerases described herein and at least one DNA polymerase exhibiting 3'-exonuclease activity. In some embodiments, the modified Taq polymerase and the at least one DNA polymerase exhibiting 3'-exonuclease activity are present in a ratio of about 1:1 to about 1:2000 relative units of enzyme. In some embodiments, the modified DNA polymerase and the at least one DNA polymerase exhibiting 3'-exonuclease activity are present in a ratio of about 1:4 to about 1:100 relative units of enzyme. In some embodiments, the at least one DNA polymerase exhibiting 3'-exonuclease activity is selected from the group consisting of *Thermococcus litoralis* (Vent™, GenBank: AAA72101), *Pyrococcus furiosus* (Pfu, GenBank: D12983, BAA02362), *Pyrococcus woesii, Pyrococcus* GB-D (Deep Vent™, GenBank: AAA67131), *Thermococcus kodakaraensis* KOD1 (KOD, GenBank: BD175553, BAA06142; *Thermococcus* sp. strain KOD (Pfx, GenBank: AAE68738)), *Thermococcus gorgonarius* (Tgo, Pdb: 4699806), *Sulfolobus solataricus* (GenBank: NC002754, P26811), *Aeropyrum pernix* (GenBank: BAA81109), *Archaeglobus fulgidus* (GenBank: O29753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366), *Thermococcus fumicolans* (GenBank: CAA93738, P74918), *Thermococcus hydrothermalis* (GenBank: CAC18555), *Thermococcus* spp. GE8 (GenBank: CAC12850), *Thermococcus* spp. JDF-3 (GenBank: AX135456; WO0132887), *Thermococcus* spp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* spp. GE23 (GenBank: CAA90887), *Pyrococcus* spp. ST700 (GenBank: CAC12847), *Thermococcus pacificus* (GenBank: AX411312.1), *Thermococcus zilligii* (GenBank: DQ3366890), *Thermococcus aggregans, Thermococcus barossii, Thermococcus celer* (GenBank: DD259850.1), *Thermococcus profundus* (GenBank: E14137), *Thermococcus siculi* (GenBank: DD259857.1), *Thermococcus thioreducens, Thermococcus onnurineus* NA1, *Sulfolobus acidocaldarium, Sulfolobus tokodaii, Pyrobaculum calidifontis, Pyrobaculum islandicum* (GenBank: AAF27815), *Methanococcus jannaschii* (GenBank: Q58295), *Desulforococcus* species TOK, *Desulfurococcus, Pyrolobus, Pyrodictium, Staphylothermus, Vulcanisaetta, Methanococcus* (GenBank: P52025), GenBank AAC62712, GenBank P956901, and GenBank BAAA07579.

The present invention also features kits containing a modified DNA polymerase described herein and uses thereof. In addition, the present invention provides nucleotide sequences encoding modified DNA polymerases described herein, and vectors and/or cells that include the nucleotide sequences.

The invention further provides methods including amplifying nucleic acids in a biological sample, including purified DNA and crude DNA extractions, using a modified DNA polymerase (e.g., Taq polymerase) as described herein.

In some embodiments, the biological sample is a plant sample (e.g., a crude plant sample such as leaf tissue, seed tissue, plant tissue, organ tissue, and/or crude plant DNA extracts). In some embodiments, the plant sample is a stored plant sample. In some embodiments, the biological sample is nucleic acid (e.g., DNA) purified from a plant sample.

In some embodiments, the biological sample is a crude non-plant sample (e.g., a sample such as mammalian tissue sample, buccal swabs, forensic samples, blood spots, cell culture samples, stabilized blood samples, microbiological samples, FFPE tissue, Guthrie card blood samples, FTA card blood samples. In some embodiments, the non-plant sample is a stored sample. In some embodiments, the biological sample is nucleic acid (e.g., DNA) purified from a non-plant sample.

In this application, the use of "or" means "and/or" unless stated otherwise. As used in this application, the term "comprise" and variations of the term, such as "comprising" and "comprises," are not intended to exclude other additives, components, integers or steps. As used herein, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWINGS

The drawings are for illustration purposes only not for limitation.

DEFINITIONS

Figure 1:
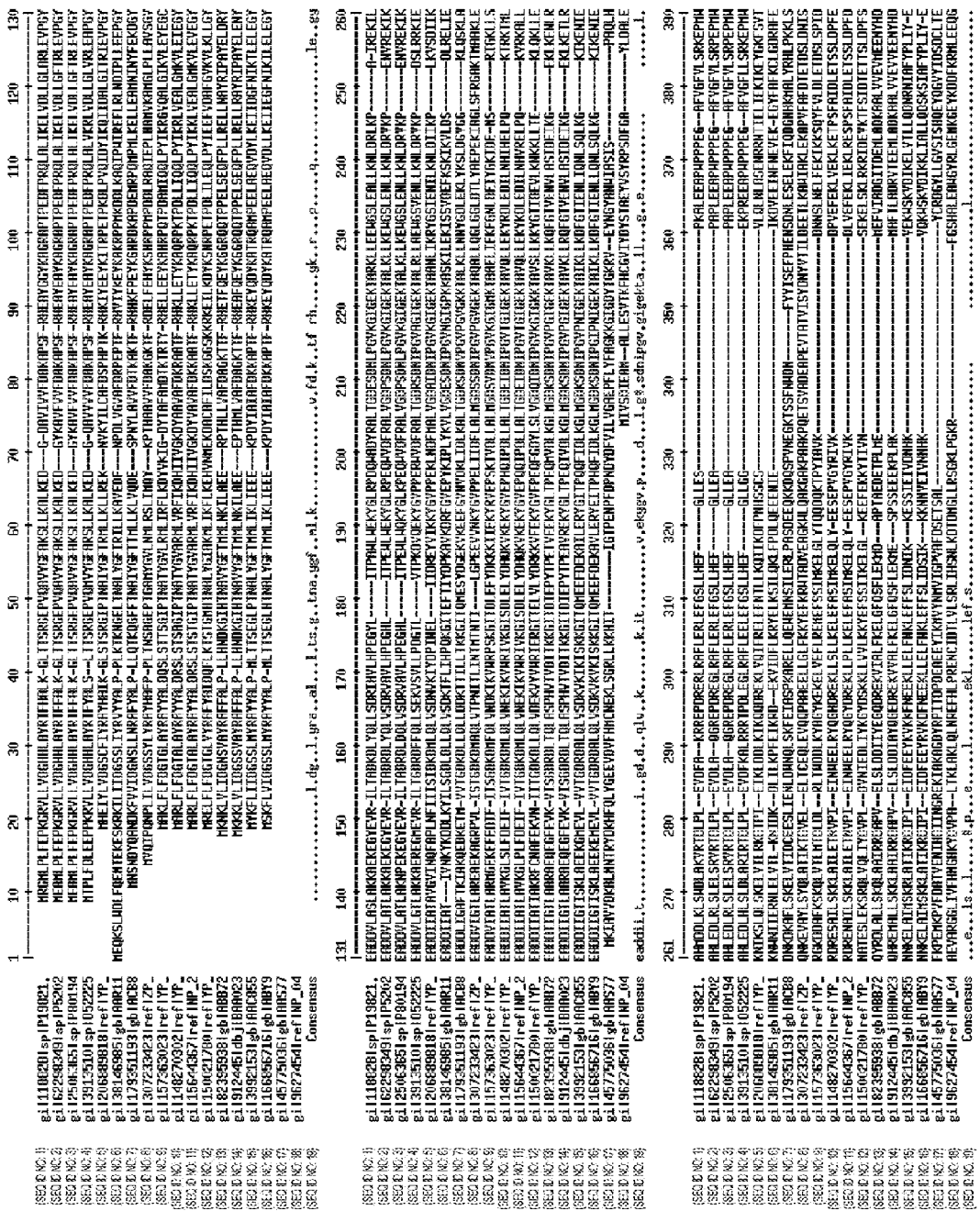
FIG. 1 depicts an alignment of amino acid sequences of naturally-occurring DNA polymerases from bacterial species. Exemplary amino acid alterations discovered by directed evolution experiments are shown above each alignment. gi|118828|sp|P19821. (SEQ ID NO: 1); gi|62298349|sp|P5202 (SEQ ID NO: 2); gi|2506365|sp|P80194 (SEQ ID NO: 3); gi|3913510|sp|O52225 (SEQ ID NO: 4); gi|206889818|ref|YP_ (SEQ ID NO: 5); gi|38146985|gb|AAR11 (SEQ ID NO: 6); gi|179351193|gb|ACB8 (SEQ ID NO: 7); gi|307233423|ref|ZP_ (SEQ ID NO: 8); gi|157363023|ref|YP_ (SEQ ID NO: 9); gi|148270302|ref|YP_ (SEQ ID NO: 10); gi|15644367|ref|NP_2 (SEQ ID NO: 11); gi|150021780|ref|YP_ (SEQ ID NO: 12); gi|82395938|gb|ABB72 (SEQ ID NO: 13); gi|912445|dbj|BAA023 (SEQ ID NO: 14); gi|3992153|gb|AAC855 (SEQ ID NO: 15); gi|166856716|gb|ABY9 (SEQ ID NO: 16); gi|45775036|gb|AAS77 (SEQ ID NO: 17); gi|9627454|ref|NP_04 (SEQ ID NO:18); Consensus (SEQ ID NO: 19).

In order for the present invention to be more readily understood, certain terms are first defined below. Additional definitions for the following terms and other terms are set forth throughout the specification.

Amino acid: As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

Base Pair (bp): As used herein, base pair refers to a partnership of adenine (A) with thymine (T), or of cytosine (C) with guanine (G) in a double stranded DNA molecule.

Chimeric polymerase: As used herein, the term "chimeric polymerase" (also referred to as "chimera") refers to any recombinant polymerase containing at least a first amino acid sequence derived from a first DNA polymerase and a second amino acid sequence derived from a second DNA polymerase. Typically, the first and second DNA polymerases are characterized with at least one distinct functional characteristics (e.g., processivity, elongation rate, fidelity). As used herein, a sequence derived from a DNA polymerase of interest refers to any sequence found in the DNA polymerase of interest, or any sequence having at least 70% (e.g., at least 75%, 80%, 85%, 90%, 91%, 92%, 93%, 94%, 95%, 96%, 97%, 98%, 99%) identical to an amino acid sequence found in the DNA polymerase of interest. A "chimeric polymerase" according to the invention may contain two or more amino acid sequences from related or similar polymerases (e.g., proteins sharing similar sequences and/or structures), joined to form a new functional protein. A "chimeric polymerase" according to the invention may contain two or more amino acid sequences from unrelated polymerases, joined to form a new functional protein. For example, a chimeric polymerase of the invention may be an "interspecies" or "intergenic" fusion of protein structures expressed by different kinds of organisms.

Complementary: As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

Corresponding to: As used herein, the term "corresponding to" is often used to designate the position/identity of an amino acid residue in a DNA polymerase or a nucleotide in a polynucleotide encoding a DNA polymerase. Those of ordinary skill will appreciate that, for purposes of simplicity, a canonical numbering system (based on wild type Taq polymerase) is utilized herein (as illustrated, for example, in FIG. 1, so that an amino acid "corresponding to" a residue at position 190, for example, need not actually be the 190$^{th}$ amino acid in a particular amino acid chain but rather a residue that plays the same role, structurally or functionally, as the residue found at 190 in wild type Taq polymerase; those of ordinary skill in the art readily appreciate how to identify corresponding amino acids. Exemplary methods for identifying corresponding residues include, but are not limited to, sequence alignment, molecular modeling, and mutagenesis studies.

DNA binding affinity: As used herein, the term "DNA-binding affinity" typically refers to the activity of a DNA polymerase in binding DNA nucleic acid. In some embodiments, DNA binding activity can be measured in a two bandshift assay. For example, in some embodiments (based on the assay of Guagliardi et al. (1997) *J. Mol. Biol.* 267:841-848), double-stranded nucleic acid (the 452-bp HindIII-EcoRV fragment from the *S. solfataricus* lacS gene) is labeled with $^{32}$P to a specific activity of at least about $2.5 \times 10^7$ cpm/µg (or at least about 4000 cpm/fmol) using standard methods. See, e.g., Sambrook et al. (2001) Molecular Cloning: A Laboratory Manual ($3^{rd}$ ed., Cold Spring Harbor Laboratory Press, NY) at 9.63-9.75 (describing end-labeling of nucleic acids). A reaction mixture is prepared containing at least about 0.5 µg of the polypeptide in about 10 µl of binding buffer (50 mM sodium phosphate buffer (pH 8.0), 10% glycerol, 25 mM KCl, 25 mM MgCl$_2$). The reaction mixture is heated to 37° C. for 10 min About $1 \times 10^4$ to $5 \times 10^4$ cpm (or about 0.5-2 ng) of the labeled double-stranded nucleic acid is added to the reaction mixture and incubated for an additional 10 min. The reaction mixture is loaded onto a native polyacrylamide gel in 0.5× Tris-borate buffer. The reaction mixture is subjected to electrophoresis at room temperature. The gel is dried and subjected to autoradiography using standard methods. Any detectable decrease in the mobility of the labeled double-stranded nucleic acid indicates formation of a binding complex between the polypeptide and the double-stranded nucleic acid. Such nucleic acid binding activity may be quantified using standard densitometric methods to measure the amount of radioactivity in the binding complex relative to the total amount of radioactivity in the initial reaction mixture.

Elongation rate: As used herein, the term "elongation rate" refers to the average speed at which a DNA polymerase extends a polymer chain. As used herein, a high elongation rate refers to an elongation rate higher than 50 nt/s (e.g., higher than 50, 55, 60, 65, 70, 75, 80, 85, 90, 95, 100, 105, 110, 115, 120, 125, 130, 135, 140 nt/s). As used in this application, the terms "elongation rate" and "speed" are used inter-changeably.

Enzyme activity: As used herein, the term "enzyme activity" refers to the specificity and efficiency of a DNA polymerase. Enzyme activity of a DNA polymerase is also referred to as "polymerase activity," which typically refers to the activity of a DNA polymerase in catalyzing the template-directed synthesis of a polynucleotide. Enzyme activity of a polymerase can be measured using various techniques and methods known in the art. For example, serial dilutions of polymerase can be prepared in dilution buffer (e.g., 20 mM Tris.Cl, pH 8.0, 50 mM KCl, 0.5% NP 40, and 0.5% Tween-20). For each dilution, 5 µl can be removed and added to 45 µl of a reaction mixture containing 25 mM TAPS (pH 9.25), 50 mM KCl, 2 mM MgCl$_2$, 0.2 mM dATP, 0.2 mM dGTP, 0.2 mM dTTP, 0.1 mM dCTP, 12.5 µg activated DNA, 100 µM [α-$^{32}$P]dCTP (0.05 µCi/nmol) and sterile deionized water. The reaction mixtures can be incubated at 37° C. (or 74° C. for thermostable DNA polymerases) for 10 minutes and then stopped by immediately cooling the reaction to 4° C. and adding 10 µl of ice-cold 60 mM EDTA. A 25 µl aliquot can be removed from each reaction mixture. Unincorporated radioactively labeled dCTP can be removed from each aliquot by gel filtration (Centri-Sep, Princeton Separations, Adelphia, N.J.). The column eluate can be mixed with scintillation fluid (1 ml). Radioactivity in the column eluate is quantified with a scintillation counter to determine the amount of product synthesized by the polymerase. One unit of polymerase activity can be defined as the amount of polymerase necessary to synthesize 10 nmole of product in 30 minutes (Lawyer et al. (1989) *J. Biol. Chem.* 264:6427-647). Other methods of measuring polymerase activity are known in the art (see, e.g. Sambrook et al. (2001) Molecular Cloning: A Laboratory Manual (3.sup.rd ed., Cold Spring Harbor Laboratory Press, NY)).

Fidelity: As used herein, the term "fidelity" refers to the accuracy of DNA polymerization by template-dependent DNA polymerase. The fidelity of a DNA polymerase is typically measured by the error rate (the frequency of incorporating an inaccurate nucleotide, i.e., a nucleotide that is not incorporated at a template-dependent manner). The accuracy or fidelity of DNA polymerization is maintained by both the polymerase activity and the exonuclease activity of a DNA polymerase. The term "high fidelity" refers to an error rate less than $4.45 \times 10^{-6}$ (e.g., less than $4.0 \times 10^{-6}$, $3.5 \times 10^{-6}$, $3.0 \times 10^{-6}$, $2.5 \times 10^{-6}$, $2.0 \times 10^{-6}$, $1.5 \times 10^{-6}$, $1.0 \times 10^{-6}$, $0.5 \times 10^{-6}$) mutations/nt/doubling. The fidelity or error rate of a DNA polymerase may be measured using assays known to the art. For example, the error rates of DNA polymerases can be tested using the lacI PCR fidelity assay described in Cline, J. et al. (96) NAR 24: 3546-3551. Briefly, a 1.9 kb fragment encoding the lacIOlacZα target gene is amplified from pPRIAZ plasmid DNA using 2.5 U DNA polymerase (i.e. amount of enzyme necessary to incorporate 25 nmoles of total dNTPs in 30 min. at 72° C.) in the appropriate PCR buffer. The lad-containing PCR products are then cloned into lambda GT10 arms, and the percentage of lacI mutants (MF, mutation frequency) is determined in a color screening assay, as described (Lundberg, K. S., Shoemaker, D. D., Adams, M. W. W., Short, J. M., Sorge, J. A., and Mathur, E. J. (1991) Gene 180:1-8). Error rates are expressed as mutation frequency per by per duplication (MF/bp/d), where by is the number of detectable sites in the lad gene sequence (349) and d is the number of effective target doublings. Similar to the above, any plasmid containing the lacIOlacZα target gene can be used as template for the PCR. The PCR product may be cloned into a vector different from lambda GT (e.g., plasmid) that allows for blue/white color screening.

Fusion DNA polymerase: As used herein, the term "fusion DNA polymerase" refers to any DNA polymerase that is combined (e.g., covalently or non-covalently) with one or more protein domains having a desired activity (e.g., DNA-binding, stabilizing template-primer complexes, hydrolyzing dUTP). In some embodiments, the one or more protein domains are derived from a non-polymerase protein. Typically, fusion DNA polymerases are generated to improve certain functional characteristics (e.g., processivity, elongation rate, fidelity, salt-resistance, etc.) of a DNA polymerase.

Joined: As used herein, "joined" refers to any method known in the art for functionally connecting polypeptide domains, including without limitation recombinant fusion with or without intervening domains, inter-mediated fusion, non-covalent association, and covalent bonding, including disulfide bonding, hydrogen bonding, electrostatic bonding, and conformational bonding.

Modified DNA polymerase: As used herein, the term "modified DNA polymerase" refers to a DNA polymerase originated from another (i.e., parental) DNA polymerase and contains one or more amino acid alterations (e.g., amino acid substitution, deletion, or insertion) compared to the parental DNA polymerase. In some embodiments, a modified DNA polymerases of the invention is originated or modified from a naturally-occurring or wild-type DNA polymerase. In some embodiments, a modified DNA polymerase of the invention is originated or modified from a recombinant or engineered DNA polymerase including, but not limited to, chimeric DNA polymerase, fusion DNA polymerase or another modified DNA polymerase. Typically, a modified DNA polymerase has at least one changed phenotype compared to the parental polymerase.

Mutant: As used herein, the term "mutant" refers to a modified protein which displays altered characteristics when compared to the parental protein.

Mutation: As used herein, the term "mutation" refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence. Herein, the term "mutation" is used interchangeably with "alteration."

Nucleotide: As used herein, a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence," and is represented herein by a formula whose left to right orientation is in the conventional direction of 5'-terminus to 3'-terminus.

Nucleic acid intercalating dyes: As used herein, the term "nucleic acid intercalating dyes" refers to any molecules that bind to nucleic acids in a reversible, non-covalent fashion, by insertion between the base pairs of the double helix, thereby indicating the presence and amount of nucleic acids. Generally, nucleic acid intercalating dyes are planar, aromatic, ring-shaped chromophore molecules. In some embodiments, intercalating dyes include fluorescent dyes. Numerous intercalating dyes are known in the art. Some non-limiting examples include PICO GREEN (P-7581, Molecular Probes), EB (E-8751, Sigma), propidium iodide (P-4170, Sigma), Acridine orange (A-6014, Sigma), 7-aminoactinomycin D (A-1310, Molecular Probes), cyanine dyes (e.g., TOTO, YOYO, BOBO, and POPO), SYTO, SYBR Green I, SYBR Green II, SYBR DX, OliGreen, CyQuant GR, SYTOX Green, SYTO9, SYTO10, SYTO17, SYBR14, FUN-1, DEAD Red, Hexidium Iodide, Dihydroethidium, Ethidium Homodimer, 9-Amino-6-Chloro-2-Methoxyacridine, DAPI, DIPI, Indole dye, Imidazole dye, Actinomycin D, Hydroxystilbamidine, and LDS 751 (U.S. Pat. No. 6,210,885), BOXTO, LC Green, Evagreen, Bebo.

Oligonucleotide or Polynucleotide: As used herein, the term "oligonucleotide" is defined as a molecule including two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning. As used herein, the term "polynucleotide" refers to a polymer molecule composed of nucleotide monomers covalently bonded in a chain. DNA (deoxyribonucleic acid) and RNA (ribonucleic acid) are examples of polynucleotides.

Polymerase: As used herein, a "polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed toward the 5' end of the template strand. A "DNA polymerase" catalyzes the polymerization of deoxynucleotides.

Primer: As used herein, the term "primer" refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and thermostable enzyme in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

Processivity: As used herein, "processivity" refers to the ability of a polymerase to remain attached to the template and perform multiple modification reactions. "Modification reactions" include but are not limited to polymerization, and exonucleolytic cleavage. In some embodiments, "processivity" refers to the ability of a DNA polymerase to perform a sequence of polymerization steps without intervening dissociation of the enzyme from the growing DNA chains. Typically, "processivity" of a DNA polymerase is measured by the length of nucleotides (for example 20 nts, 300 nts, 0.5-1 kb, or more) that are polymerized or modified without intervening dissociation of the DNA polymerase from the growing DNA chain. "Processivity" can depend on the nature of the polymerase, the sequence of a DNA template, and reaction conditions, for example, salt concentration, temperature or the presence of specific proteins. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 nts, 380 nts, 400 nts, or higher) per association/disassociation with the template. Processivity can be measured according the methods defined herein and in WO 01/92501 A1.

Synthesis: As used herein, the term "synthesis" refers to any in vitro method for making new strand of polynucleotide or elongating existing polynucleotide (i.e., DNA or RNA) in a template dependent manner. Synthesis, according to the invention, includes amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, PCR, the labeling of polynucleotide (i.e., for probes and oligonucleotide primers), polynucleotide sequencing.

Template DNA molecule: As used herein, the term "template DNA molecule" refers to a strand of a nucleic acid from which a complementary nucleic acid strand is synthesized by a DNA polymerase, for example, in a primer extension reaction.

Template dependent manner: As used herein, the term "template dependent manner" refers to a process that involves the template dependent extension of a primer molecule (e.g., DNA synthesis by DNA polymerase). The term "template dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: Molecular Biology of the Gene, 4th Ed., W. A. Benjamin, Inc., Menlo Park, Calif. (1987)).

Thermostable enzyme: As used herein, the term "thermostable enzyme" refers to an enzyme which is stable to heat (also referred to as heat-resistant) and catalyzes (facilitates) polymerization of nucleotides to form primer extension products that are complementary to a polynucleotide template sequence. Typically, thermostable stable polymerases are preferred in a thermocycling process wherein double stranded nucleic acids are denatured by exposure to a high temperature (e.g., about 95° C.) during the PCR cycle. A thermostable enzyme described herein effective for a PCR amplification reaction satisfies at least one criteria, i.e., the enzyme does not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90° C. to about 96° C. for a time depending mainly on the temperature and the nucleic acid length, typically about 0.5 to ten minutes. Higher temperatures may be tolerated as the buffer salt concentration and/or GC composition of the nucleic acid is increased. In some embodiments, thermostable enzymes will not become irreversibly denatured at about 90° C.-100° C. Typically, a thermostable enzyme suitable for the invention has an optimum temperature at which it functions that is higher than about 40° C., which is the temperature below which hybridization of primer to template is promoted, although, depending on (1) magnesium and salt, concentrations and (2) composition and length of primer, hybridization can occur at higher temperature (e.g., 45° C.-70° C.). The higher the temperature optimum for the enzyme, the greater the specificity and/or selectivity of the primer-directed extension process. However, enzymes that are active below 40° C. (e.g., at 37° C.) are also with the scope of this invention provided they are heat-stable. In some embodiments, the optimum temperature ranges from about 50° C. to 90° C. (e.g., 60° C.-80° C.).

Wild-type: As used herein, the term "wild-type" refers to a gene or gene product which has the characteristics of that gene or gene product when isolated from a naturally-occurring source.

DETAILED DESCRIPTION OF THE INVENTION

The present invention provides, among other things, modified DNA polymerases containing amino acid alterations based on mutations identified in directed evolution experiments designed to select enzymes that are better suited for applications in recombinant DNA technologies. In particular, the present invention provides modified DNA polymerases that have superior activity in amplifying biological samples containing various PCR inhibitors (e.g., plant-derived inhibitors).

Traditionally, inhibitors are a major obstacle for efficient amplification in PCR, for example in PCR reactions containing plant-derived samples. It was known that polysaccharides, secondary metabolites, polyphenolics and the like co-isolate with nucleic acids from plant tissues resulting in inhibition of amplification. See, Koonjul P. K. et al. "Inclusion of polyvinylpyrrolidone in the polymerase chain reaction reverses the inhibitory effects of polyphenolic contamination of RNA," Nucleic Acids Research, 1999, 27(3):915-916; Demeke T. and Jenkins G. R., "Influence of DNA extraction methods, PCR inhibitors and quantification methods on real-time PCR assay of biotechnology-derived traits," Anal Bioanal Chem, 2010, 396:1977-1990. As described in the Examples section, the present inventors have, through directed DNA polymerase evolution screening, successfully discovered mutations (see e.g., Table 2) that renders a modified DNA polymerase containing such mutations able to effectively amplify inhibitor-containing samples with higher yield and sensitivity as compared to a wild-type or unmodified parental polymerase control. In some cases, a modified DNA polymerase provided by the present invention may amplify inhibitor-containing samples where a wild-type or unmodified parental polymerase control fails completely. Thus, the present invention provides an effective solution to overcome this major obstacle for efficient PCR amplification.

As can be appreciated by one skilled in the art, Taq polymerase was used as an exemplary polymerase. One or more modifications described herein may be introduced to various DNA polymerases to achieve the same effects.

Various aspects of the invention are described in detail in the following sections. The use of sections is not meant to limit the invention. Each section can apply to any aspect of the invention. In this application, the use of "or" means "and/or" unless stated otherwise.

Directed DNA Polymerase Evolution Screening

As described in the Examples section, the present inventors have successfully developed directed DNA polymerase evolution experiments by mimicking the typical or less-than typical environments and conditions under which an enzyme is usually used or expected to be used in real-life industrial or research applications.

Various mutations have been observed during the selection process. Many mutations confer advantages relating to enzyme characteristics including, but not limited to, expression efficiency, solubility and folding robustness, thermostability, polymerization activity, processivity, speed (elongation rate), concentration robustness, resistance to impurities, resistance to chemical additives, fidelity, avoidance of primer-dimers, strand-displacement activity, altered nuclease activity, nucleotide selectivity, and other properties and characteristics involved in the process of DNA polymerization.

It is contemplated that the mutations identified herein confer a variety of phenotypes that can make DNA polymerases better suited for applications in recombinant DNA technologies. For example, mutations identified in accordance with the present invention may render modified DNA polymerases containing one or more of such mutations that are resistant to PCR inhibitors (e.g., plant-derived PCR inhibitors), salt, PCR additives (e.g., PCR enhancers). In some embodiments, a modified DNA polymerase is resistant to a PCR inhibitor (e.g., a plant-derived inhibitor) if the modified DNA polymerase amplifies a sample containing the PCR inhibitor (e.g., a plant-derived inhibitor) with higher yield (e.g., with more than 1.2-fold, 1.5-fold, 2-fold, 2.5-fold, 3-fold, 3.5-fold, 4-fold, 4.5-fold, 5-fold or more in yield) as compared to a wild-type or an unmodified parental polymerase control under otherwise identical conditions. In some embodiments, a modified DNA polymerase is resistant to a PCR inhibitor (e.g., a plant-derived inhibitor) if the modified DNA polymerase amplifies a sample containing the PCR inhibitor (e.g., a plant-derived inhibitor) where a wild-type or an unmodified parental polymerase control fails to amplify the sample under otherwise identical conditions. As used herein, an unmodified parental polymerase control refers to a polymerase from which a modified DNA polymerase of the invention is derived. An unmodified parental polymerase control may have a sequence of a wild-type polymerase. In some embodiments, an unmodified parental polymerase control may also contain one or more mutations as compared to a wild-type polymerase, or a chimeric polymerase, fusion polymerase or any type of DNA polymerases described in the DNA polymerases section below. As used herein, PCR inhibitors include, but are not limited to, polysaccharides, secondary metabolites, polyphenolics, ionic detergents, organic solvents, heavy metals, salts, pigments, alcohols, urea, DMSO, betaine, heparin, fluorescent dyes, humic acid, heme, immunoglobulins. Typical plant-derived PCR inhibitors include, but are not limited to, polysaccharides, secondary metabolites, polyphenolics, phytic acid, tannins, dextran sulfate, pigments, plant oils, plant waxes.

Mutations identified in accordance with the present invention may also confer enzymatic phenotypes related to the selective advantages described herein. Indeed, the present inventors have identified or expect to identify mutant polymerases that express well, are more soluble, that display higher activity, processivity and/or speed, that are active over a wide range of concentrations, that have a higher fidelity, and other phenotypes that may not be immediately measurable. Since many of these phenotypes may depend on the manner in which the DNA and polymerase interact, it is contemplated that many of the mutations identified in accordance with the present invention may affect DNA-polymerase binding characteristics.

In addition, it is contemplated that mutations identified according to the present invention may confer enzymatic phenotypes not directly related to the selective advantages described herein. For example, some phenotypes may confer no advantage, but merely be a side effect of the advantageous mutation. In addition, some mutants may display phenotypes that could be considered disadvantageous. For example, some mutations confer an advantage (for example, high activity), but this advantage comes at a cost (for example, high error-rate). If the advantage outweighs the disadvantage, the mutation will still be selected for. Such mutations may have commercial uses. For example, a low fidelity enzyme could be used in error prone PCR (e.g., for mutagenesis).

Exemplary mutations and mutant clones containing combinations of mutations associated with specific phenotypes are discussed in the Examples section and are shown at least in Tables 3, 4, 5, 8, 12, and 15.

It is further contemplated that, since many DNA polymerases have similar sequences, structures and functional domains, mutations and/or the positions where mutations occur identified herein can serve as bases for modification of DNA polymerases in general. For example, same or similar mutations, as well as other alterations, may be introduced at the corresponding positions in various DNA polymerases to generate modified enzymes that are better adapted for recombinant use.

DNA Polymerases

Modified DNA polymerases in accordance with the present invention may be modified from any types of DNA polymerases including, but not limited to, naturally-occurring wild-type DNA polymerases, recombinant DNA polymerase or engineered DNA polymerases such as chimeric DNA polymerases, fusion DNA polymerases, or other modified DNA polymerases. In particular embodiments, DNA polymerases suitable for the invention are thermostable DNA polymerases (PCR-able).

Naturally-Occurring DNA Polymerases

In some embodiments, naturally-occurring DNA polymerases suitable for the invention are type A DNA polymerases (also known as family A DNA polymerases). Type A DNA polymerases are classified based on amino acid sequence homology to *E. coli* polymerase I (Braithwaite and Ito, *Nuc. Acids. Res.* 21:787-802, 1993), and include *E. coli* pol I, *Thermus aquaticus* DNA pol I (Taq polymerase), *Thermus flavus* DNA pol I, *Streptococcus pneumoniae* DNA pol I, *Bacillus stearothermophilus* pol I, phage polymerase T5, phage polymerase T7, mitochondrial DNA polymerase pol gamma, as well as additional polymerases discussed below.

Family A DNA polymerases are commercially available, including Taq polymerase (New England BioLabs), *E. coli* pol I (New England BioLabs), *E. coli* pol I Klenow fragment (New England BioLabs), and T7 DNA polymerase (New England BioLabs), and *Bacillus stearothermophilus* (Bst) DNA polymerase (New England BioLabs).

Suitable DNA polymerases can also be derived from bacteria or other organisms with optimal growth temperatures that are similar to the desired assay temperatures. For example, such suitable bacteria or other organisms may exhibit maximal growth temperatures of >80-85° C. or optimal growth temperatures of >70-80° C.

Sequence information of many type A DNA polymerases are publicly available. Table 1 provides a list of GenBank Accession numbers and other GenBank Accession information for exemplary type A DNA polymerases, including species from which they are derived.

TABLE 1

Sequence Accession Information for Certain Type A DNA Polymerases
*Geobacillus stearothermophilus*

| ACCESSION | 3BDP_A |
|---|---|
| VERSION | 3BDP_AGI: 4389065 |
| DBSOURCE | pdb: molecule 3BDP, chain 65, release Aug. 27, 2007. |

*Natranaerobius thermophiles* JW/NM-WN-LF

| ACCESSION | ACB85463 |
|---|---|
| VERSION | ACB 85463.1 GI: 179351193 |
| DBSOURCE | accession CP001034.1 |

*Thermus thermophiles* HB8

| ACCESSION | P52028 |
|---|---|
| VERSION | P52028.2 GI: 62298349 |
| DBSOURCE | swissprot: locus DPO1T_THET8, accession P52028 |

*Thermus thermophilus*

| ACCESSION | P30313 |
|---|---|
| VERSION | P30313.1 GI: 232010 |
| DBSOURCE | swissprot: locus DPO1F_THETH, accession P30313 |

*Thermus caldophilus*

| ACCESSION | P80194 |
|---|---|
| VERSION | P80194.2 GI: 2506365 |
| DBSOURCE | swissprot: locus DPO1_THECA, accession P80194 |

*Thermus filiformis*

| ACCESSION | O52225 |
|---|---|
| VERSION | O52225.1 GI: 3913510 |
| DBSOURCE | swissprot: locus DPO1_THEFI, accession O52225 |

*Thermus filiformis*

| ACCESSION | AAR11876 |
|---|---|
| VERSION | AAR11876.1 GI: 38146983 |
| DBSOURCE | accession AY247645.1 |

*Thermus aquaticus*

| ACCESSION | P19821 |
|---|---|
| VERSION | P19821.1 GI: 118828 |
| DBSOURCE | swissprot: locus DPO1_THEAQ, accession P19821 |

*Thermotoga lettingae* TMO

| ACCESSION | YP_001469790 |
|---|---|
| VERSION | YP_001469790.1 GI: 157363023 |
| DBSOURCE | REFSEQ: accession NC_009828.1 |

*Thermosipho melanesiensis* BI429

| ACCESSION | YP_001307134 |
|---|---|
| VERSION | YP_001307134.1 GI: 150021780 |
| DBSOURCE | REFSEQ: accession NC_009616.1 |

*Thermotoga petrophila* RKU-1

| ACCESSION | YP_001244762 |
|---|---|
| VERSION | YP_001244762.1 GI: 148270302 |
| DBSOURCE | REFSEQ: accession NC_009486.1 |

*Thermotoga maritima* MSB8

| ACCESSION | NP_229419 |
|---|---|
| VERSION | NP_229419.1 GI: 15644367 |
| DBSOURCE | REFSEQ: accession NC_000853.1 |

*Thermodesulfovibrio yellowstonii* DSM 11347

| ACCESSION | YP_002249284 |
|---|---|
| VERSION | YP_002249284.1 GI: 206889818 |
| DBSOURCE | REFSEQ: accession NC_011296.1 |

*Dictyoglomus thermophilum*

| ACCESSION | AAR11877 |
|---|---|
| VERSION | AAR11877.1 GI: 38146985 |
| DBSOURCE | accession AY247646.1 |

TABLE 1-continued

Sequence Accession Information for Certain Type A DNA Polymerases
*Geobacillus stearothermophilus*

*Geobacillus* sp. MKK-2005

| ACCESSION | ABB72056 |
|---|---|
| VERSION | ABB72056.1 GI: 82395938 |
| DBSOURCE | accession DQ244056.1 |

*Bacillus caldotenax*

| ACCESSION | BAA02361 |
|---|---|
| VERSION | BAA02361.1 GI: 912445 |
| DBSOURCE | locus BACPOLYTG accession D12982.1 |

*Thermoanaerobacter thermohydrosulfuricus*

| ACCESSION | AAC85580 |
|---|---|
| VERSION | AAC85580.1 GI: 3992153 |
| DBSOURCE | locus AR003995 accession AAC85580.1 |

*Thermoanaerobacter pseudethanolicus* ATCC 33223

| ACCESSION | ABY95124 |
|---|---|
| VERSION | ABY95124.1 GI: 166856716 |
| DBSOURCE | accession CP000924.1 |

*Enterobacteria phage* T5

| ACCESSION | AAS77168 CAA04580 |
|---|---|
| VERSION | AAS77168.1 GI: 45775036 |
| DBSOURCE | accession AY543070.1 |

*Enterobacteria phage* T7 (T7)

| ACCESSION | NP_041982 |
|---|---|
| VERSION | NP_041982.1 GI: 9627454 |
| DBSOURCE | REFSEQ: accession NC_001604.1 |

*Escherichia coli* str. K-12 substr. MG1655

| ACCESSION | AAB02998 |
|---|---|
| VERSION | AAB02998.1 GI: 304969 |
| DBSOURCE | locus ECOUW87 accession L19201.1 |

Additional DNA polymerases are shown in FIG. 1. DNA polymerases suitable for the present invention include DNA polymerases that have not yet been isolated.

In some embodiments, a naturally-occurring DNA polymerase suitable for the present invention is isolated from any species of the genus *Thermus*, any species of the genus *Meiothermus*, any species of the genus *Thermotoga*, and/or any species of the genus *Thermomicrobium*. In some embodiments, a naturally-occurring polymerase suitable for the present invention is isolated from *Bacillus stearothermophilus*, *Sphaerobacter thermophilus*, *Dictoglomus thermophilum*, and/or *Escherichia coli*. In some embodiments, a naturally-occurring polymerase suitable for the present invention is isolated from *Thermus aquaticus*, *Thermus thermophilus*, *Thermus caldophilus*, or *Thermus filiformis*. In some embodiments, the naturally-occurring polymerase is isolated from *Thermus aquaticus*.

Truncated DNA Polymerases

In some embodiments, DNA polymerases suitable for the present invention include truncated versions of naturally-occurring polymerases (e.g., a fragment of a DNA polymerase resulted from an N-terminal, C-terminal or internal deletion that retains polymerase activity). One exemplary truncated DNA polymerase suitable for the invention is KlenTaq which contains a deletion of a portion of the 5' to 3' exonuclease domain (see, Barnes W. M. (1992) *Gene* 112:29-35; and Lawyer F. C. et al. (1993) *PCR Methods and Applications*, 2:275-287).

In some embodiments, DNA polymerases in accordance with the present invention are defined by or comprise the consensus sequence XXXXXXXXXXXXXXXXXXXX-XXXLXDGXXLXYRAXXALXXXLXTSXGXXTN- AXYG FXXMLXKXXXXXXXXXXXXXXXVXFDXKX-
XTFXRHXXXXXYKXXRXXXPXXXXXQX XXXXX-
XXXXXXXXXLEXXGYEADDIIXTXXXXX-
XXXXXXXXXXIXXGDXDXXQLVXX KXXXXXXXKX-
ITXXXXXXXXXXVXEKYGVXPXXXXDXXXLXG-
XXSDNIPGVXGIGEKT AXXLLXXXGXXEXXXXX-
XXXXXXXXXXXXXXXXXLXXXXEXXXLSXX-
LXXXXXX XPXXXEXXXXXLXXXXXXXEKLXX-
XXXXLEFXSXXXXXXXXXXXXXXXXXXXXX XX-
XXXXXXXXXXXXXXXXXXXXXXXXXXLXXX-
XXXXXXXXXXXXXXXXXXX XXXXXXXXX-
XXXXXXXXXXXXXXXXXXXXXXXXXXXXX-
XXXXXXLXXXXXXX XXXXXXXXXXXLXXXGXX-
LXXXXFXXDXXXXAYLLXPXXXXXXXDXAXX-
YLXXX XXXXXXXXXXXXXXXXXXXXXXXXX-
XXXXAXXXAXXXXXLXXXXXXXXXXEX XLXX-
LXXXIEXPLXXVLXXMEXXGXXXDXXXLKX-
LSXXXXXXXXXXLXXXIXXXXXX XXXXXX-
AGXXFNXNSXKQLXXXLFXXLXLPXXXK-
TXXTGXXSTXXEVLXXLXXXHP XXXIXXXILXX-
YRXLXKLKSTYXDXLXXXXXXXPXTGRXHTXFN-
QTXTATGRLSSSXP XNLQXIPXXRXEXGXXIRX-
AFVXXXXXXXIXXADYSQIELRXLAXHLSXDXNLI-
XAFXX GXXXXXXXXDIHTXTASXIFXVXX-
EXXXXXXXVTXXMRRXAKXVNXGIXYGXSXXGLS
XXLXXXXXXXXXXXXXXXXXIXXX-
EAXXXIEXYFXXXPXVXXXIXXXXXXAKXXGY
VXTLFGRRRXXPXIXSRNXXVRXXXERX-
AXNXPIQGTAADIIKLAMXXXXXXLXXXXX
XXXXXXXX Bedford et al. *Proc. Natl. Acad. Sci. USA* 94: 479-484 (1997). Fusion of the archaeal PCNA binding domain to Taq DNA polymerase results in a DNA polymerase fusion that has enhanced processivity and produces higher yields of PCR amplified DNA in the presence, of PCNA (Motz, M., et al., *J. Biol. Chem.* May 3, 2002; 277 (18); 16179-88). Also, fusion of the sequence non-specific DNA binding protein Sso7d or Sac7d from *Sulfolobus sulfataricus* to a DNA polymerase, such as Pfu or Taq DNA polymerase, was shown to greatly increase the processivity of these DNA polymerases as disclosed in WO 01/92501 A1, which is hereby incorporated by reference. Additional fusion polymerases are described in US Publication No. 20070190538A1, which is incorporated herein by reference.

Commercially available exemplary fusion polymerases include, but are not limited to, TopoTaq™ (Fidelity Systems) which is a hybrid of Taq polymerase fused to a sequence non-specific Helix-hairpin-helix (HhH) motif from DNA topoisomerase V (Topo V) (see, U.S. Pat. Nos. 5,427,928; 5,656,463; 5,902,879; 6,548,251; Pavlov et al., 2002, *Proc. Natl. Acad. Sci. USA*, 99:13510-13515, all of which are incorporated herein by references); Phusion™ (Finnzymes and NEB, sold by BioRad as iProof) which is a chimeric Deep Vent™/Pfu DNA polymerase fused to a small basic chromatin-like Sso7d protein (see, U.S. Pat. No. 6,627,424, U.S. Application Publication Nos. 20040191825, 20040081963, 20040002076, 20030162173, 20030148330, and Wang et al. 2004, Nucleic Acids Research, 32(3), 1197-1207, all of which are hereby incorporated by reference); PfuUltra™ II Fusion (Agilent) which is a Pfu-based DNA polymerase fused to a double stranded DNA binding protein (U.S. Application No. 20070148671, which is incorporated by reference); Herculase II Fusion (Agilent) which is a Herculase II enzyme fused to a DNA-binding domain; and Pfx50 (Invitrogen) which is a DNA polymerase from *T. zilligii* fused to an accessory protein that stabilizes primer-template complexes.

Generation of Modified DNA Polymerases of the Invention

Modified DNA polymerases can be generated by introducing one or more amino acid alterations into a DNA polymerase at the positions corresponding to the positions described herein (e.g., positions identified in Table 2).

TABLE 2

Mutations in Taq polymerase.

| Position | Mutation |
|---|---|
| 61 | A61T |
| 346 | K346E |
| 357 | S357C |
| 507 | E507K |
| 707 | I707M |
| 749 | F749I |

Typically, corresponding positions in various DNA polymerases can be determined by alignment of amino acid sequences. Alignment of amino acid sequences can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology* 266, 460-480 (1996); URL: //blast.wustl/edu/blast/README.html). WU-BLAST-2 uses several search parameters, most of which are set to the default values. The adjustable parameters are set with the following values: overlap span=1, overlap fraction=0.125, word threshold (T)=11. HSP score (S) and HSP S2 parameters are dynamic values and are established by the program itself, depending upon the composition of the particular sequence, however, the minimum values may be adjusted and are set as indicated above. An example of an alignment is shown in FIG. 1. Exemplary amino acid alterations (e.g., corresponding to those alterations in Taq polymerase described above) in DNA polymerases from various organisms are shown in Table. 3.

TABLE 3

Exemplary Amino Acid Alterations in DNA Polymerases (pairwise alignments were performed to the Taq DNA polymerase protein sequence using the ClustalW algorithm, with default settings).

| Position | Residue in Taq Polymerase (Examplary Mutation) | Corresponding Residue in *Thermus thermophilus* DNA Polymerase I (Examplary Mutation) | Corresponding Residue in *Geobacilis staerothermophilus* DNA Polymerase I (Exemplary Mutation) | Corresponding Residue in *E. coli* DNA Polymerase I (Exemplary Mutation) |
|---|---|---|---|---|
| 61 | DAVIVVFDA (A61T) | KAVFVVFDA (A62T) | THLLVAFDA (H55T) | THAAVVFDA (H57T) |
| 346 | LKEARGLLA (K346E) | LKEVRGLLA (K348E) | ETKKKSMFD (T367E) | LELLKPLLE (E403) |
| 357 | LSVLALREG (S357C) | LAVLASREG (A359C) | RAVVALKWK (A378C) | KALKVGQNL (A414C) |
| 507 | TEKTGKRST (E507K) | TQKTGKRST Q509K | TKTGYSTSA K553 | TPGGAPSTS P603K |
| 707 | WIEKTLEEG (I707M) | WIEKTLEEG (I709M) | YMENIVQEA (M752) | YMERTRAQA (M802) |
| 749 | AFNMPVQGT (F749I) | AFNMPVQGT (F751I) | AMNTPIQGS (M794I) | AINAPMQGT (I844) |

Alterations may be a substitution, deletion or insertion of one or more amino acid residues. Appropriate alteration for each position can be determined by examining the nature and the range of mutations at the corresponding position described herein. In some embodiments, appropriate amino acid alterations can be determined by evaluating a three-dimensional structure of a DNA polymerase of interest (e.g., parental DNA polymerase). For example, amino acid substitutions identical or similar to those described in Table 2 can be introduced to a DNA polymerase. Alternative amino acid substitutions can be made using any of the techniques and guidelines for conservative and non-conservative amino acids as set forth, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (H is, Arg, Lys); Class V (Ile, Leu, Val, Met); and Class VI (Phe, Tyr, Trp). For example, substitution of an Asp for another class III residue such as Asn, Gln, or Glu, is a conservative substitution. As used herein, "non-conservative substitution" refers to the substitution of an amino acid in one class with an amino acid from another class; for example, substitution of an Ala, a class II residue, with a class III residue such as Asp, Asn, Glu, or Gln. Insertions or deletions may optionally be in the range of 1 to 5 amino acids.

Appropriate amino acid alterations allowed in relevant positions may be confirmed by testing the resulting modified DNA polymerases for activity in the in vitro assays known in the art or as described in the Examples below.

The variations can be made using methods known in the art such as oligonucleotide-mediated (site-directed) mutagenesis, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., *Gene*, 34:315 (1985)), restriction selection mutagenesis (Wells et al., *Philos. Trans. R. Soc.* London SerA, 317:415 (1986)), inverse PCR with mutations included in the primer sequence, or other known techniques can be performed on the cloned DNA to produce desired modified DNA polymerases.

In some embodiments, alterations suitable for the invention also include chemical modification including acetylation, acylation, amidation, ADP-ribosylation, glycosylation, GPI anchor formation, covalent attachment of a lipid or lipid derivative, methylation, myristlyation, pegylation, prenylation, phosphorylation, ubiquitination, or any similar process.

Modified DNA polymerases according to the invention may contain one or more (e.g., one, two, three, four, or five) of the amino acid alterations at one or more (e.g., one, two, three, four, or five) positions corresponding to those described in Table 2. Modified DNA polymerases according to the invention may also contain additional substitutions, insertions and/or deletions independent of the mutations observed or selected in the directed evolution experiments. Thus, in some embodiments, a modified DNA polymerase according to the invention has an amino acid sequence at least 70%, e.g., at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99%, identical to a corresponding wild-type (or naturally-occurring) DNA polymerase. In some embodiments, a modified DNA polymerase has 1, 2, 3, 4, 5, 6, 7, 8, 9, 10, 11, 12, 13, 14, or 15 amino acid substitutions, deletions, insertions, or a combination thereof, relative to a wild type form of the polymerase.

"Percent (%) amino acid sequence identity" is defined as the percentage of amino acid residues in a modified sequence that are identical with the amino acid residues in the corresponding parental sequence, after aligning the sequences and introducing gaps, if necessary, to achieve the maximum percent sequence identity, and not considering any conservative substitutions as part of the sequence identity. Alignment for purposes of determining percent amino acid sequence identity are similar to the alignment for purposes of determining corresponding positions as described above.

Methods well known in the art may be applied to express and isolate modified DNA polymerases. Many bacterial expression vectors contain sequence elements or combinations of sequence elements allowing high level inducible expression of the protein encoded by a foreign sequence. For example, expression vectors are commercially available from, for example, Novagen (accessible at the hypertext transfer protocol on the world wide web at emdbiosciences.com/html/NVG/All Tables.html#).

As an example, bacteria expressing an integrated inducible form of the T7 RNA polymerase gene may be transformed with an expression vector bearing a modified DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the chimeric gene from the T7 promoter.

Appropriate host strains of bacteria may be selected from those available in the art by one of skill in the art. As a non-limiting example, *E. coli* strain BL-21 is commonly used for expression of exogenous proteins since it is protease deficient relative to other strains of *E. coli*. For situations in which codon usage for the particular polymerase gene differs from that normally seen in *E. coli* genes, there are strains of BL-21 that are modified to carry tRNA genes encoding tRNAs with rarer anticodons (for example, argU, ileY, leuW, and proL tRNA genes), allowing high efficiency expression of cloned genes (several BL21-CODON PLUS™ cell strains carrying rare-codon tRNAs are available from Agilent, for example). Additionally or alternatively, genes encoding DNA polymerases may be codon optimized to facilitate expression in *E. coli*. Codon optimized sequences can be chemically synthesized.

There are many methods known to those of skill in the art that are suitable for the purification of a modified DNA polymerase of the invention. For example, the method of Lawyer et al. (1993, *PCR Meth. & App.* 2: 275) is well suited for the isolation of DNA polymerases expressed in *E. coli*, as it was designed originally for the isolation of Taq polymerase. Alternatively, the method of Kong et al. (1993, *J. Biol. Chem.* 268: 1965, incorporated herein by reference) may be used, which employs a heat denaturation step to destroy host proteins, and two column purification steps (over DEAE-Sepharose and heparin-Sepharose columns) to isolate highly active and approximately 80% pure DNA polymerase.

Further, modified DNA polymerase may be isolated by an ammonium sulfate fractionation, followed by Q Sepharose and DNA cellulose columns, or by adsorption of contaminants on a HiTrap Q column, followed by gradient elution from a HiTrap heparin column.

Applications of Modified DNA Polymerases of the Invention

Modified DNA polymerases of the present invention may be used for any methods involving polynucleotide synthesis. Polynucleotide synthesis methods are well known to a person of ordinary skill in the art and can be found, for example, in Molecular Cloning second edition, Sambrook et al., Cold Spring Harbor Laboratory Press, Cold Spring Harbor, N.Y. (1989). For example, modified DNA polymerases of the present invention have a variety of uses in recombinant DNA technology including, but not limited to, labeling of DNA by nick translation, second-strand cDNA synthesis in cDNA cloning, DNA sequencing, whole-genome amplification and amplifying, detecting, and/or cloning nucleic acid sequences using polymerase chain reaction (PCR).

In some embodiments, the invention provides enzymes that are better suited for PCR used in industrial or research applications. PCR refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

In some embodiments, the invention provides enzymes that are better suited for PCR amplification of plant-derived samples Inhibitors, such as polysaccharides, secondary metabolites, and polyphenolics, among others, can co-isolate with nucleic acids from plant tissues, leading to an inhibition of downstream molecular manipulations, such as PCR (see, for example, Koonjul, 1998, *Nucleic Acids Research.*, 27(3): 915. Such inhibitors may act in a variety of ways, such as by causing precipitation of DNA, denaturation of DNA, decreasing the ability of a polymerase enzyme to bind to magnesium ions (e.g., kinetically modifying the PCR reaction by chelating cofactors such as magnesium), binding to target DNA or DNA polymerase, etc. (see, for example, Demeke, 2010, *Anal Bioanal Chem.*, 396:1977. PCR inhibitors may originate from plant tissue (e.g., leaves, bark, fruit, etc.) or from reagents used for DNA isolation. Modified DNA polymerases in accordance with the present invention may be more resistant to PCR inhibitors, in particular PCR inhibitors present in plant-derived samples, as compared to their wild-type counterparts or unmodified parental polymerases.

Modified DNA polymerases with higher processivity, elongation rate, salt resistance, and/or fidelity are expected to improve efficiency and success rate of long-range amplification (higher yield, longer targets amplified) and reduce the amount of required DNA template.

Various specific PCR amplification applications are available in the art (for reviews, see for example, Erlich, 1999, *Rev Immunogenet.*, 1: 127-34; Prediger 2001, *Methods Mol. Biol.* 160: 49-63; Jurecic et al., 2000, *Curr. Opin. Microbiol.* 3: 316-21; Triglia, 2000, *Methods Mol. Biol.* 130: 79-83; MaClelland et al., 1994, *PCR Methods Appl.* 4: S66-81; Abramson and Myers, 1993, *Current Opinion in Biotechnology* 4: 41-47; each of which is incorporated herein by references).

As non-limiting examples, modified DNA polymerases described herein can be used in PCR applications including, but are not limited to, i) hot-start PCR which reduces non-specific amplification; ii) touch-down PCR which starts at high annealing temperature, then decreases annealing temperature in steps to reduce non-specific PCR product; iii) nested PCR which synthesizes more reliable product using an outer set of primers and an inner set of primers; iv) inverse PCR for amplification of regions flanking a known sequence. In this method, DNA is digested, the desired fragment is circularized by ligation, then PCR using primer complementary to the known sequence extending outwards; v) AP-PCR (arbitrary primed)/RAPD (random amplified polymorphic DNA). These methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cells. It may also be used to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. A first step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be use as control to verify the quality of PCR; x) Q/C-PCR (Quantitative comparative) which uses an internal control DNA sequence (but of different size) which compete with the target DNA (competitive PCR) for the same set of primers; xi) Recursive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis; xv) DOP-PCR that uses partially degenerate primers for whole-genome amplification; xvi) quantitative PCR using SYBR green or oligonucleotide probes to detect amplification; and xvii) error-prone PCR in which conditions are optimized to give an increased number of mutations in the PCR product.

It should be understood that this invention is not limited to any particular amplification system. As other systems are developed, those systems may benefit by practice of this invention.

In some embodiments, modified DNA polymerases are blended with other DNA polymerases in order to further increase processivity, elongation rate, salt resistance, and/or fidelity and reduce the amount of required DNA for PCR applications. For examples, in some embodiments, modified DNA polymerases in accordance with the present invention may be used with DNA polymerases exhibiting 3'-exonuclease activity (e.g., proofreading activity). In some embodiments, DNA polymerases exhibiting 3'-exonuclease activity are type B DNA polymerases (also known as family B DNA polymerases). Family B polymerases include, but are not limited to, *E. coli* pol II, archaeal polymerases, PRD1, phi29, M2, T4 bacteriophage DNA polymerases, eukaryotic polymerases a, A, c, and many viral polymerases. In some embodiments, DNA polymerases suitable for the invention are archaeal polymerases (e.g., euryarchaeal polymerases). Suitable exemplary archaeal polymerases include, but are not limited to, DNA polymerases from archaea (e.g., *Thermococcus litoralis* (Vent™, GenBank: AAA72101), *Pyrococcus furiosus* (Pfu, GenBank: D12983, BAA02362), *Pyrococcus woesii*, *Pyrococcus* GB-D (Deep Vent™, GenBank: AAA67131), *Thermococcus kodakaraensis* KODI (KOD, GenBank: BD175553, BAA06142; *Thermococcus* sp. strain KOD (Pfx, GenBank: AAE68738)), *Thermococcus gorgonarius* (Tgo, Pdb: 4699806), *Sulfolobus solataricus* (GenBank: NC002754, P26811), *Aeropyrum pernix* (GenBank: BAA81109), *Archaeglobus fulgidus* (GenBank: O29753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366),

*Thermococcus fumicolans* (GenBank: CAA93738, P74918), *Thermococcus hydrothermalis* (GenBank: CAC18555), *Thermococcus* spp. GE8 (GenBank: CAC12850), *Thermococcus* spp. JDF-3 (GenBank: AX135456; WO0132887), *Thermococcus* spp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* spp. GE23 (GenBank: CAA90887), *Pyrococcus* spp. ST700 (GenBank: CAC12847), *Thermococcus pacificus* (GenBank: AX411312.1), *Thermococcus zilligii* (GenBank: DQ3366890), *Thermococcus aggregans*, *Thermococcus barossii*, *Thermococcus celer* (GenBank: DD259850.1), *Thermococcus profundus* (GenBank: E14137), *Thermococcus siculi* (GenBank: DD259857.1), *Thermococcus thioreducens*, *Thermococcus onnurineus* NA1, *Sulfolobus acidocaldarium*, *Sulfolobus tokodaii*, *Pyrobaculum calidifontis*, *Pyrobaculum islandicum* (GenBank: AAF27815), *Methanococcus jannaschii* (GenBank: Q58295), *Desulforococcus* species TOK, *Desulfurococcus*, *Pyrolobus*, *Pyrodictium*, *Staphylothermus*, *Vulcanisaetta*, *Methanococcus* (GenBank: P52025) and other archaeal B polymerases, such as GenBank AAC62712, P956901, BAAA07579)). See, for example, International Patent Application PCT/US09/063,166 (WO2010/062776), entitled "CHIMERIC DNA POLYMERASES", the entire contents of which is incorporated herein by reference. Type B DNA polymerases suitable for the present invention also include modified type B DNA polymerases such as those described in International Patent Application PCT/US2009/063169 (WO2010/062779), entitled "MODIFIED DNA POLYMERASES", the entire contents of which is herein incorporated by reference.

It will be appreciated that polymerase blends in accordance with the present disclosure may contain a ratio of modified DNA polymerases to other types of DNA polymerases exhibiting 3'-exonuclease activity (e.g., Type B polymerases) in any appropriate range, for example, from about 1:1 to about 1:2000 relative units of modified DNA polymerase to DNA polymerases exhibiting 3'-exonuclease activity; 1:2 to about 1:1000 relative units of modified DNA polymerase to DNA polymerases exhibiting 3'-exonuclease activity; 1:4 to about 1:500 relative units of modified DNA polymerase to DNA polymerases exhibiting 3'-exonuclease activity; and from about 1:1 to about 1:100 relative units of modified DNA polymerase to DNA polymerases exhibiting 3'-exonuclease activity. See, for example, suitable exemplary ratios between various polymerases and methods and formulations for making polymerase blends are described in U.S. Pat. No. 5,436,149, the entire contents of which are herein incorporated by reference.

In some embodiments, modified DNA polymerases are used with PCR additives in order to further increase processivity, elongation rate, salt resistance, and/or fidelity and reduce the amount of required DNA for PCR applications. In some embodiments, additives provide improved enzyme thermostability, modified primer annealing characteristics, improved melting characteristics of DNA, sequestration of PCR inhibitors. Exemplary additives that may be used in accordance with the present disclosure include, but are not limited to, bovine serum albumin, tetramethyl ammonium chloride, dimethylsulfoxide, beta-mercaptoethanol, tris(2-carboxyethyl) phosphine, sodium metabisulfite, povidone, Tween 20, Triton X-100, Nonidet P-40, polyethylene glycol, betaine, formamide, 7-deaza dGTP, spermidine, thermostable RecA, glycerol, gelatin, low-fat milk powder, and combinations thereof.

Kits

The invention also contemplates kit formats which include a package unit having one or more containers containing modified DNA polymerases of the invention and compositions thereof. In some embodiments, the present invention provides kits further including containers of various reagents used for polynucleotide synthesis, including synthesis in PCR.

Inventive kits in accordance with the present invention may also contain one or more of the following items: polynucleotide precursors, primers, buffers, instructions, PCR additives and controls. Kits may include containers of reagents mixed together in suitable proportions for performing the methods in accordance with the invention. Reagent containers preferably contain reagents in unit quantities that obviate measuring steps when performing the subject methods.

EXAMPLES

Example 1

Directed Evolution Experiments Using Taq Polymerase

To select mutated enzymes that would better be suited for recombinant DNA technologies, a directed evolution experiment is designed by simply mimicking the normal conditions under which the enzyme is usually used, or possibly under less than perfect conditions such as are expected in real-life applications. After conducting enough rounds of selection, an enzyme (or multiple enzymes) that is better suited for typical applications in recombinant DNA technologies should appear. Details of directed evolution experiments and exemplary advantages of associated with selected mutations are described in the co-pending application entitled "Modified DNA Polymerases (WO2010/062779), which is incorporated by reference herein.

In particular, we have performed directed evolution experiments using a mutant type A DNA polymerase, Taq-E507K. Directed evolution experiments were conducted on Taq-E507K mutant libraries created by error-prone PCR.

Several rounds of selection were conducted. During the course of the ongoing selection, it is likely that many different mutations will confer different types of advantage, to different degrees, either alone or in combination. Typically, during the first rounds of selection, there are no obvious dominant clones, while the huge numbers of neutral or disadvantageous mutants are likely to be eliminated. Thereafter, a number of particular mutations typically appear in higher than expected numbers. These mutations are there because they have some advantages.

Typically, the selections are considered to have worked when the vast pool of mutants that are in the starting material have been eliminated and the pool is dominated by a remaining few types or families of mutants that have out-competed the other mutants and the wild type. At this stage, it is not necessary to define exactly the nature of the improvement that the mutations confer. The fact that it was selected for is sufficient proof, especially if the same mutation becomes dominant in independently run selections.

Further selection results in the number of some of these mutations increasing in the pool, while others may be eliminated possibly because they have some advantages but they are not sufficient to compete with better-adapted clones. At the same time, some previously unnoticed mutants may appear. The late appearance of these mutants might be due to the fact that these specific mutations were low in number in the starting pool, or that the mutation required another (or more than one) mutation in the same clone for the advantage to manifest. If selections continue even further, eventually, a few clones will likely to dominate substantially. Typically, it is important to isolate clones before this final point if it is desirable to isolate a wide range of beneficial mutations.

Figure 2:
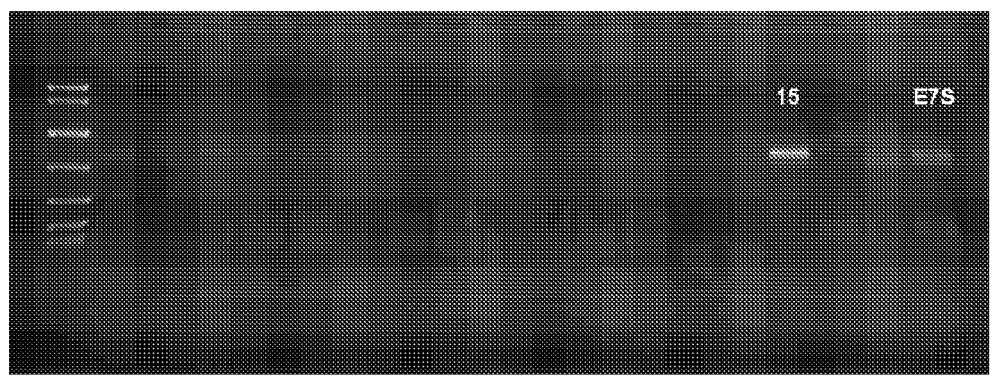
FIG. 2 depicts an exemplary PCR screening using a mixed plant extract to poison a PCR reaction producing a 1 kb Lambda fragment. Unlabeled lanes are various clones from the selection. Clone 15 (labeled) gave the highest yield compared to test samples and a control sample (Taq-E7S; labeled).

In particular experiments, DNA polymerase mutants of Taq-E507K were generated and screened for resistance to plant-derived PCR inhibitors. Several rounds of selection were conducted on Taq-E507K. During the course of the ongoing selections, many different mutations were observed either alone or in combination at various positions. Clones that exhibited higher tolerance than wild-type or its parental clone Taq-E507K to plant-derived PCR inhibitors were selected and sequenced. Clone 15 is an exemplary clone which demonstrated high yield amplification of samples containing plant-derived PCR inhibitors (FIG. 2). Sequence analysis of Clone 15 revealed mutations shown in Table 4. A general phenotype of Clone 15 is higher resistance to plant-derived PCR inhibitors than wild-type Taq or parental clone Taq-E507K. Clone 15 is further characterized for a variety of phenotypes, as described in further Examples below.

TABLE 4

Mutations Observed in Taq Mutant Clone 15 Selected for Resistance to Plant-derived PCR Inhibitors

| Position | Mutation |
| --- | --- |
| 61 | A61T |
| 346 | K346E |
| 357 | S357C |
| 707 | I707M |
| 749 | F749I |

It was contemplated a subset (e.g., one, two, three, four) of the five mutations shown in Table 4 may be sufficient to render the beneficial phenotypes of clone 15. Taq-E507K DNA polymerase and other mutant Taq-E507K polymerases were used as an example in the screen. It was contemplated that one or more mutations similar to those described in Table 4 may be introduced to various other DNA polymerases, in particular Type A DNA polymerases including those described herein.

Example 2

Types of Selective Advantage

There are a wide range of advantages that may have been selected for, some of which are listed and discussed below:
1) Expression Efficiency:
The clones that express higher levels of the enzyme will have an advantage over those that express less. The specific activity of the mutated enzyme may not have been improved but the total activity will have. This characteristics is particularly valuable to a manufacture of enzymes because this will allow increased production levels and/or reduced production costs.
2) Solubility and Folding Robustness:
When solubility increases, the probability of inclusion bodies forming decreases. Therefore, in these clones, a higher proportion of useful, correctly folded enzyme product is expressed.
3) Thermostability:
It is well known that, during the thermocycling required for PCR, a certain fraction of the enzyme is inactivated due to the heating. An enzyme that is resistant to heat-inactivation will maintain activity longer. Therefore, less enzyme can be used and/or more cycles can be conducted.
4) Activity:
Mutants with increased enzymatic activity provide more efficient polymerization.
5) Processivity:
Mutants with increased processivity are able to synthesize long PCR products and synthesize sequences with complexed secondary structure. Mutant enzymes that can incorporate more nucleotides/extension step are likely to operate efficiently at lower concentrations.
6) Speed:
Mutants with increased elongation rate provide more efficient polymerization. Enzymes that are fast can also be used with shorter extension times. This is particularly valuable for a high-throughput system.
7) Concentration Robustness:
It is known that PCR reactions may not be carried out appropriately if too much or too little enzyme is used. Under the selection conditions we used, a polymerase that can generate appropriate products whether it is supplied in excess or at low levels will have an advantage.
8) Resistance to Salts, PCR Additives and Other Inhibitors:
The selection was conducted in the presence of salts, PCR additives (e.g., intercalating dyes), and other impurities (e.g., plant derived inhibitors). The presence of salts may reduce the DNA binding affinity of polymerases. The presence of impurities may interfere with formation of a desired PCR product. A polymerase that is resistant to salts and inhibitors and can synthesize desired products is advantageous and will be selected for. The characteristic is particularly suited for applications in which PCR is used in crude samples.
9) Fidelity:
All polymerases make mistakes during replication, either by incorporating the wrong dNTP or by stuttering which causes deletions and insertions. Such mistakes can eliminate functional genes during selection, so there is a pressure for mistakes not to be made. A polymerase with higher fidelity is advantageous and will be selected for.
10) Strand-Displacement Activity:
Secondary structure in the DNA due to intramolecular self annealing may inhibit DNA strand-elongation catalyzed by the polymerase. Similarly, partial re-annealing of the complementary DNA in addition to the primer will inhibit PCR. Any enzyme with improved strand-displacement activity will have an advantage in the selection.
11) Pyrophosphate Tolerance:
Pyrophosphate is released during incorporation of nucleotides into the nascent strand by polymerases. Accumulation of pyrophosphate may lead to inhibition of the polymerase activity. Polymerases that were selected for in the Directed evolution example may have evolved to become less affected by pyrophosphate inhibition.
12) Unknown:
There many other factors involved in the process of PCR. Enzymes that are better adapted to PCR for any reason may be selected under our selection conditions.
Clone 15 is further characterized for a variety of phenotypes. So far, we have conducted tests for a few different phenotypes: tolerance to inhibitors, tolerance to salt, performance in various buffers, and speed. The tests to examine phenotypes are described in the following examples.

Example 3

Tolerance to Plant Inhibitors and High Salt

Clone 15 was tested for the ability to amplify a 1.2 kb PCR amplicon using a 0.5 mm diameter grapevine leaf discs directly in PCR reactions in the absence or presence of high salt. Reactions were performed in a buffer containing 150 mM Tris-H$_2$SO$_4$ (pH 8.5) and optionally 50 mM KCl. Exemplary reaction components are shown in Table 5 and Table 6. Exemplary cycling profile for this assay is shown in Table 7.

Exemplary primers include:

```
                                  (SEQ ID NO: 24)
Forward primer:     GATCAACCCCGCTGCCCCAC (SEQ ID NO: 25)
Reverse primer:     CGAAGCCCATCCCCGCTCAG
```

TABLE 5

Exemplary Reaction Components for Assays without KCl

| Reaction component | Concentration | | Reaction volume = 50 In 50 uL |
|---|---|---|---|
| PCR water | — | — | 29.3 |
| Tris- H$_2$SO$_4$ (pH 8.5) | 2 | M | 3.8 |
| MgCl2 (supplement to 2.0 mM) | 25 | mM | 4.0 |
| Povidone | 20% | m/v | 7.5 |
| dNTPs | 10 | mM each | 1.0 |
| Primer | 10 | uM | 1.5 |
| Primer | 10 | uM | 1.5 |
| 0.5 mm dia grapevine leaf disc | — | ng/uL | — |
| Taq DNA polymerase | 20 | ng/uL | 1.5 |
| TOTAL | | | 50.0 |

TABLE 6

Exemplary Reaction Components for Assays with 50 mM KCl

| Reaction component | Concentration | | Reaction volume = 50 In 50 uL |
|---|---|---|---|
| PCR water | — | — | 26.8 |
| Tris- H$_2$SO$_4$ (pH 8.5) | 2 | M | 3.8 |
| MgCl2 (supplement to 2.0 mM) | 25 | mM | 4.0 |
| KCl | 50 | mM | 2.5 |
| Povidone | 20% | m/v | 7.5 |
| dNTPs | 10 | mM each | 1.0 |
| Primer | 10 | uM | 1.5 |
| Primer | 10 | uM | 1.5 |
| 0.5 mm dia grapevine leaf disc | — | ng/uL | — |
| Taq DNA polymerase | 20 | ng/uL | 1.5 |
| TOTAL | | | 50.0 |

TABLE 7

Exemplary Cycling Profile

| Cycling profile: Cycle | No. | Temp (° C.) | Time | |
|---|---|---|---|---|
| Initial denaturation | 1 | 95 | 10 | min |
| Denaturation | 45 | 95 | 20 | sec |
| Annealing/Extension | 45 | 72 | 40 | sec |
| Final elongation | 1 | 72 | 1 | min |
| HOLD | 1 | 4 | Indefinite | |

Figure 3:
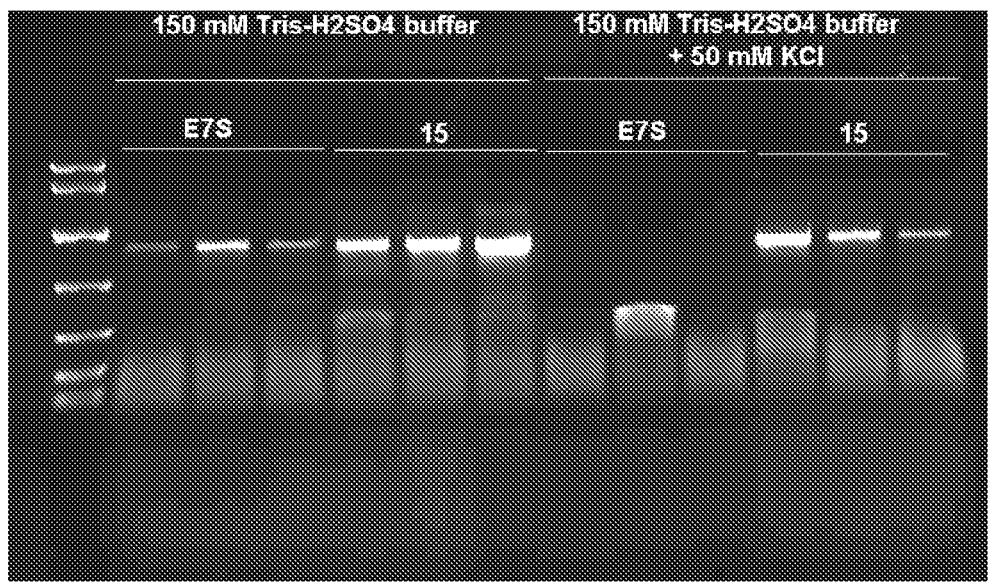
FIG. 3 depicts an exemplary PCR reaction using a control polymerase (Taq-E7S) or Clone 15 to amplify a 1.2 kb amplicon using 0.5 mm diameter grapevine leaf discs under varying KCl conditions. Reactions were performed in triplicate.

Reaction products were run on an agarose gel and scored for a presence or absence, as well as intensity of a band at the appropriate fragment size. Exemplary results are shown in Table 8 and FIG. 3. Clone 15 gave a higher yield than control polymerase Taq-E7S. Furthermore, Taq-E7S failed when an additional 50 mM KCl was added to the buffer, indicating that Clone 15 is more salt-tolerant than Taq-E7S. Taq-E7S was previously shown to be tolerant to a host of PCR inhibitors compared to wild-type Taq (See, for example, WO2010/062777, the entire contents of which is herein incorporated by reference).

TABLE 8

Fragments Produced by Clone 15

| Clone Name: | −50 mM KCl | +50 mM KCl |
|---|---|---|
| Taq-E7S | + | − |
| Clone 15 | ++ | + |

Example 4

Tolerance to Plant Inhibitors

Clone 15 was tested for the ability to amplify a 1.45 kb PCR amplicon using 0.5 mm diameter potato leaf discs directly in PCR reactions. Reactions were performed in a buffer containing 150 mM Tris-H$_2$SO$_4$ (pH 8.5). Exemplary reaction components are shown in Table 9. Exemplary cycling profile for this assay is shown in Table 10.

Exemplary Primers:

```
                                  (SEQ ID NO: 26)
Forward primer:     GCGCATGCAAGCTGACCTGG (SEQ ID NO: 27)
Reverse primer:     TCACGCTCCAAGGCGGGAAC
```

TABLE 9

Exemplary Reaction Components for Assays

| Reaction component | Concentration | | Reaction volume = 50 In 50 uL |
|---|---|---|---|
| PCR water | — | — | 29.3 |
| Tris- H$_2$SO$_4$ (pH 8.5) | 2 | M | 3.8 |
| MgCl2 (supplement to 2.0 mM) | 25 | mM | 4.0 |
| Povidone | 20% | m/v | 7.5 |
| dNTPs | 10 | mM each | 1.0 |
| Primer | 10 | uM | 1.5 |
| Primer | 10 | uM | 1.5 |
| 0.5 mm dia potato leaf disc | — | ng/uL | — |
| Taq DNA polymerase | 20 | ng/uL | 1.5 |
| TOTAL | | | 50.0 |

TABLE 10

Exemplary Cycling Profile

| Cycling profile: Cycle | No. | Temp (' C.) | Time | |
|---|---|---|---|---|
| Initial denaturation | 1 | 95 | 3 | min |
| Denaturation | 40 | 95 | 20 | sec |
| Annealing/Extension | 40 | 72 | 45 | sec |
| Final elongation | 1 | 72 | 1 | min |
| HOLD | 1 | 4 | Indefinite | |

Figure 4:
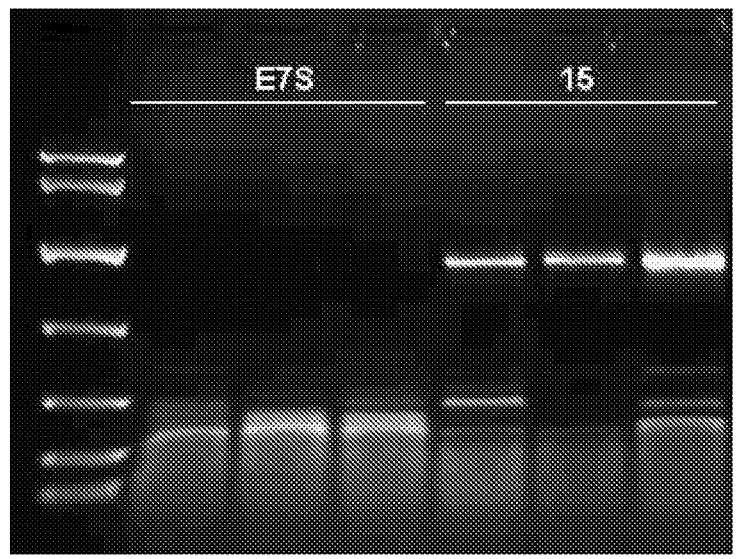
FIG. 4 depicts an exemplary PCR reaction using a control polymerase (Taq-E7S) or Clone 15 to amplify a 1.45 kb amplicon using 0.5 mm diameter potato leaf discs. Reactions were performed in triplicate.

Reaction products were run on an agarose gel and scored for either a presence or absence of a band at the appropriate fragment size. Exemplary results are shown in Table 11 and FIG. 4. Clone 15 exhibited positive amplification from the leaf discs whereas clone Taq-E7S did not exhibit positive amplification.

TABLE 11

Fragments Produced by Clone 15

| Clone Name: | Amplicon |
|---|---|
| Taq-E7S | − |
| Clone 15 | + |

Example 5

Tolerance to Buffer Conditions

Taq, Taq-E7S, and Clone 15 were tested for the ability to amplify a 1 kb PCR amplicon using λ DNA in PCR reactions. Reactions were performed in a buffer containing 150 mM Tris-H₂SO₄ (pH 8.5; with and without 50 mM KCl) or 10 mM Tris-HCl (pH 8.3; with either 50 mM or 100 mM KCl). Exemplary reaction components are shown in Table 12. Exemplary cycling profile for this assay is shown in Table 13.

Exemplary Primers:

```
                          (SEQ ID NO: 28)
Forward primer:   CCTGCTCTGCCGCTTCACGC (SEQ ID NO: 29)
Reverse primer:   GATGACGCATCCTCACGATAATATCCGG
```

TABLE 12

Exemplary Reaction Components for Assays

| Reaction component | Concentration |
|---|---|
| Buffer (150 mM Tris-H₂SO₄ (pH 8.5) or 10 mM Tris-HCl (pH 8.3)) | 1X |
| KCl | 0 mM, 50 mM, or 100 mM |
| MgCl₂ | 1.5 mM |
| dNTPs | 0.2 mM each |
| Primer | 0.3 uM |
| Primer | 0.3 uM |
| Template (λ DNA) | 5 ng, 1 ng, 200 pg, 40 pg, 8 pg or 0 pg |
| DNA polymerase | 1 unit |

TABLE 13

Exemplary Cycling Profile

| Cycling profile: Cycle | No. | Temp (° C.) | Time |
|---|---|---|---|
| Initial denaturation | 1 | 95 | 3 min |
| Denaturation | 30 | 95 | 20 sec |
| Annealing/Extension | 30 | 72 | 30 sec |
| Final elongation | 1 | 72 | 1 min |
| HOLD | 1 | 4 | Indefinite |

Figure 5:
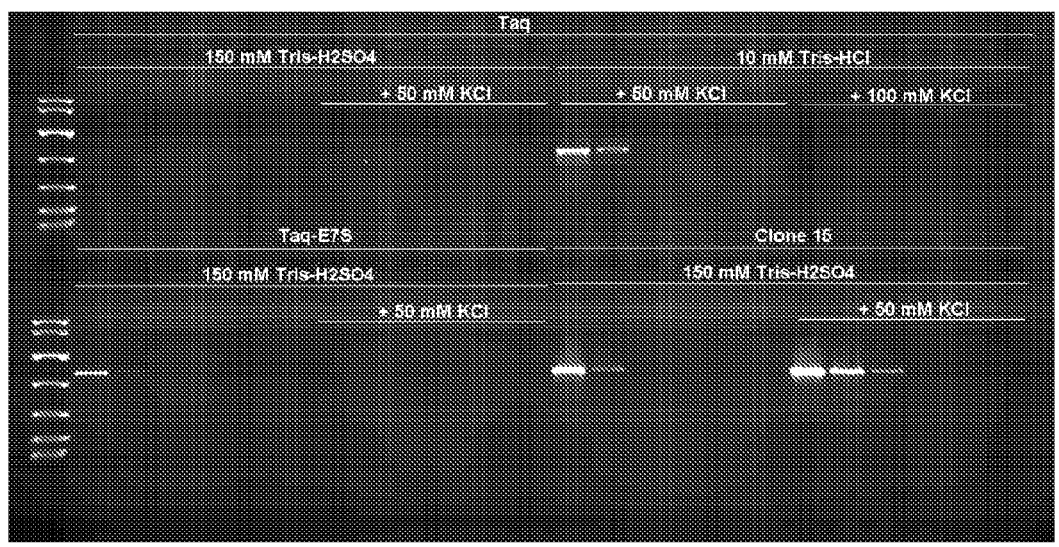
FIG. 5 depicts an exemplary PCR reaction using a control polymerase (Taq or Taq-E7S) or Clone 15 to amplify a 1 kb amplicon from various amounts of Lambda template DNA (5 ng, 1 ng, 200 pg, 40 pg, 8 pg, no-template control) in PCR buffer with and without KCl.

Reaction products were run on an agarose gel and scored for either a presence or absence of a band at the appropriate fragment size. Exemplary results are shown in Table 14 and FIG. 5. Taq did not amplify in 150 mM Tris-H₂SO₄ buffer, whereas both Taq-E7S and Clone 15 did. Taq-E7S did not amplify when 50 mM KCl was added, whereas the performance of Clone 15 actually improved upon addition of 50 mM KCl. Taq amplified in 10 mM Tris-HCl buffer with 50 mM KCl, but not with 100 mM KCl.

TABLE 14

Fragments Produced by Taq, Taq-E7S and Clone 15

| | | Amount of Template DNA | | | | |
|---|---|---|---|---|---|---|
| | | 5 ng | 1 ng | 200 pg | 40 pg | 8 pg |
| | 150 mM Tris H₂SO₄ | | | | | |
| Taq | −50 mM KCl | no | no | no | no | no |
| | +50 mM KCl | no | no | no | no | no |
| | 10 mM Tris HCl | | | | | |
| | +50 mM KCl | yes | yes | no | no | no |
| | +100 mM KCl | no | no | no | no | no |
| | 150 mM Tris H₂SO₄ | | | | | |
| Taq-E7S | −50 mM KCl | yes | yes | no | no | no |
| | +50 mM KCl | no | no | no | no | no |
| | 150 mM Tris H₂SO₄ | | | | | |
| Clone 5 | −50 mM KCl | yes | yes | no | no | no |
| | +50 mM KCl | yes | yes | yes | no | no |

Example 6

Tolerance to Buffer Conditions and Annealing/Extension Times

Taq, Taq-E7S, and Clone 15 were tested for the ability to amplify a 1 kb PCR amplicon using λ DNA in PCR reactions. Reactions were performed in a buffer containing 10 mM Tris-HCl (pH 8.3; with either 50 mM or 100 mM KCl). Exemplary reaction components are shown in Table 15. Exemplary cycling profile for this assay is shown in Tables 16 and 17.

Exemplary Primers:

```
                          (SEQ ID NO: 30)
Forward primer:   CCTGCTCTGCCGCTTCACGC (SEQ ID NO: 31)
Reverse primer:   GATGACGCATCCTCACGATAATATCCGG
```

TABLE 15

Exemplary Reaction Components for Assays

| Reaction component | Concentration |
|---|---|
| Buffer (10 mM Tris-HCl (pH 8.3)) | 1X |
| KCl | 50 mM or 100 mM |
| MgCl₂ | 1.5 mM |
| dNTPs | 0.2 mM each |
| Primer | 0.3 uM |
| Primer | 0.3 uM |
| Template (λ DNA) | 5 ng, 1 ng, 200 pg, 40 pg, 8 pg or 0 pg |
| DNA polymerase | 1 unit |

TABLE 16

Exemplary Cycling Profile

| Cycling profile: Cycle | No. | Temp (° C.) | Time |
|---|---|---|---|
| Initial denaturation | 1 | 95 | 3 min |
| Denaturation | 30 | 95 | 20 sec |
| Annealing/Extension | 30 | 72 | 30 sec |

TABLE 16-continued

Exemplary Cycling Profile

Cycling profile:

| Cycle | No. | Temp (° C.) | Time |
|---|---|---|---|
| Final elongation | 1 | 72 | 1 min |
| HOLD | 1 | 4 | Indefinite |

TABLE 17

Exemplary Cycling Profile

Cycling profile:

| Cycle | No. | Temp (° C.) | Time |
|---|---|---|---|
| Initial denaturation | 1 | 95 | 3 min |
| Denaturation | 30 | 95 | 20 sec |
| Annealing/Extension | 30 | 72 | 20 sec |
| Final elongation | 1 | 72 | 1 min |
| HOLD | 1 | 4 | Indefinite |

Figure 6:
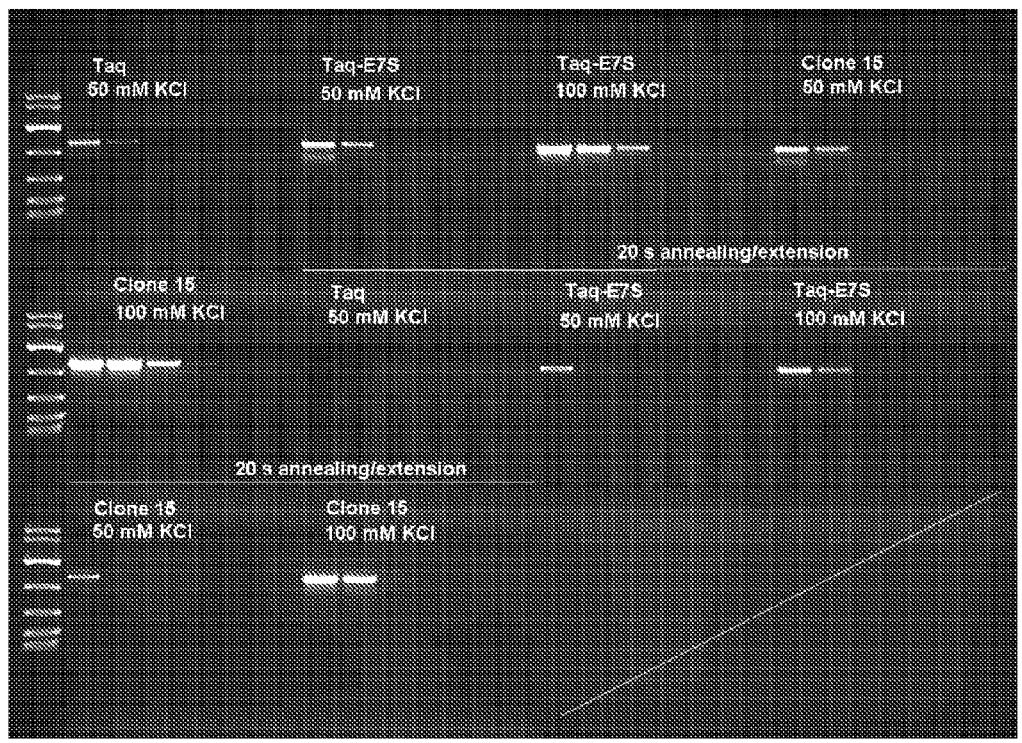
FIG. 6 depicts an exemplary PCR reaction using a control polymerase (Taq or Taq-E7S) or Clone 15 to amplify a 1 kb amplicon from various amounts of Lambda template DNA (5 ng, 1 ng, 200 pg, 40 pg, 8 pg, no-template control) in PCR buffer with and without KCl Two PCR programs, one with a 30 s annealing/extension time and one with a 20 s annealing/extension time were used.

Reaction products were run on an agarose gel and scored for either a presence or absence of a band at the appropriate fragment size. Exemplary results are shown in Table 18 and FIG. 6. Clone 15 outperforms both Taq and Taq-E7S, including when KCl is added to 100 mM. The annealing/extension time can be decreased to 20 s, with a concomitant decrease in sensitivity, but the advantage of Clone 15 over Taq and Taq-E7S is nonetheless maintained. Clone 15 is able to tolerate higher-salt buffer environments compared to Taq and Taq-E7S polymerases, which may translate, for example, into better performance with crude sample types.

TABLE 18

Fragments Produced by Taq, Taq-E7S and Clone 15

| | | Amount of Template DNA | | | | |
|---|---|---|---|---|---|---|
| | | 5 ng | 1 ng | 200 pg | 40 pg | 8 pg |
| | 30 s | | | | | |
| Taq | 50 mM KCl | yes | yes | no | no | no |
| | 20 s | | | | | |
| | +50 mM KCl | yes/no | no | no | no | no |
| | | Amount of Template DNA | | | | |
| | | 5 ng | 1 ng | 200 pg | 40 pg | 8 pg |
| | 30 s | | | | | |
| Taq-E7S | +50 mM KCl | yes | yes | no | no | no |
| | +100 mM KCl | yes | yes | yes | no | no |
| | 20 s | | | | | |
| | +50 mM KCl | yes | yes/no | no | no | no |
| | +100 mM KCl | yes | yes | no | no | no |
| | | Amount of Template DNA | | | | |
| | | 5 ng | 1 ng | 200 pg | 40 pg | 8 pg |
| | 30 s | | | | | |
| Clone 15 | +50 mM KCl | yes | yes | no | no | no |
| | +100 mM KCl | yes | yes | yes | yes/no | no |
| | 20 s | | | | | |
| | +50 mM KCl | yes | yes/no | no | no | no |
| | +100 mM KCl | yes | yes | yes | no | no |

Example 7

Tolerance to Sample and Buffer Conditions

Taq, Taq-E7S, and Clone 15 were tested for the ability to amplify an 800 bp fragment using 0.5 mm diameter grapevine leaf discs as template in PCR reactions. Reactions were performed in a buffer containing 10 mM Tris-HCl (pH 8.3; with either 50 mM or 100 mM KCl). Exemplary reaction components are shown in Table 19. Exemplary cycling profile for this assay is shown in Tables 20 and 21.

Exemplary Primers:

```
                                      (SEQ ID NO: 32)
Forward primer:   ATGTCACCACAAACAGAGACTAAAG (SEQ ID NO: 33)
Reverse primer:   TGCATTACGATCGGAACGCCCA
```

TABLE 19

Exemplary Reaction Components for Assays

| Reaction component | Concentration |
|---|---|
| Buffer (10 mM Tris-HCl (pH 8.3)) | 1X |
| KCl | 50 mM or 100 mM |
| MgCl₂ | 2.0 mM |
| dNTPs | 0.2 mM each |
| Primer | 0.3 uM |
| Primer | 0.3 uM |
| Template (grapevine leaf disc) | 0.5 mm diameter |
| DNA polymerase | 1 unit |
| Additive (povidone) | 3% m/v |

TABLE 20

Exemplary Cycling Profile for Taq polymerase

Cycling profile:

| Cycle | No. | Temp (° C.) | Time |
|---|---|---|---|
| Initial denaturation | 1 | 95 | 10 min |
| Denaturation | 30 | 95 | 20 sec |
| | 30 | 55 | 15 sec |
| Annealing/Extension | 30 | 72 | 50 sec |
| Final elongation | 1 | 72 | 1 min |
| HOLD | 1 | 4 | Indefinite |

TABLE 21

Exemplary Cycling Profile for Taq-E7S and Clone 15

Cycling profile:

| Cycle | No. | Temp (° C.) | Time |
|---|---|---|---|
| Initial denaturation | 1 | 95 | 10 min |
| Denaturation | 30 | 95 | 20 sec |
| | 30 | 55 | 15 sec |
| Annealing/Extension | 30 | 72 | 25 sec |
| Final elongation | 1 | 72 | 1 min |
| HOLD | 1 | 4 | Indefinite |

Figure 7:
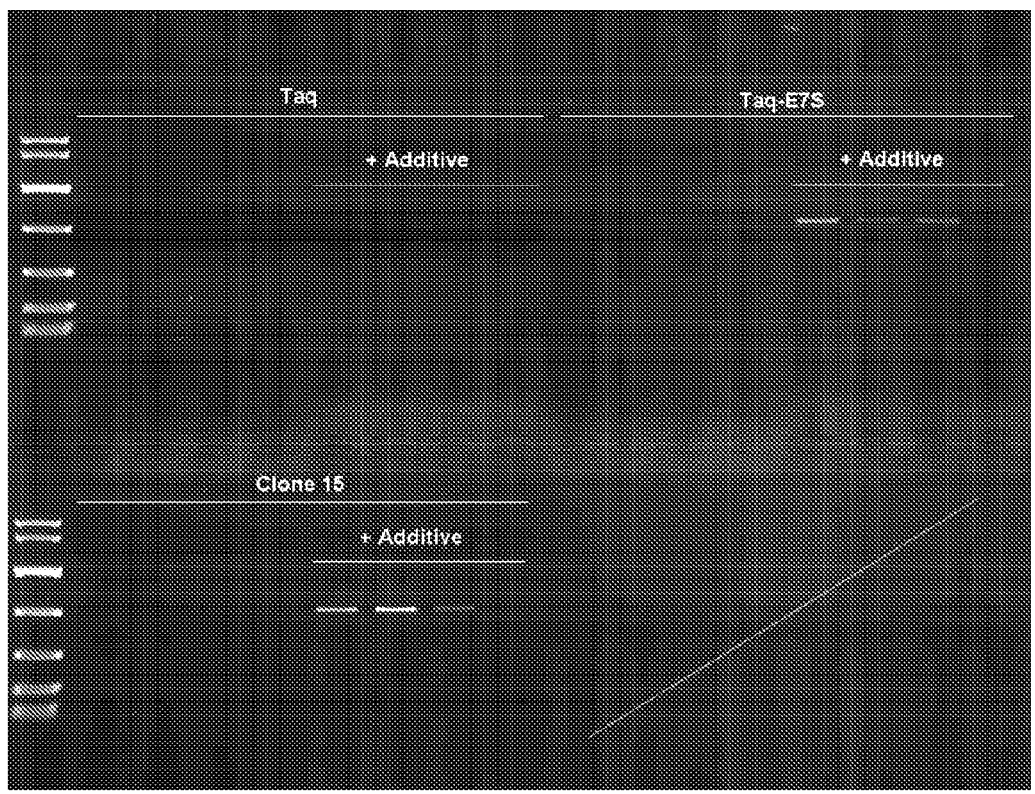
FIG. 7 depicts an exemplary PCR reaction using a control polymerase (Taq or Taq-E7S) or Clone 15 to amplify a 800 bp amplicon using 0.5 mm diameter grapevine leaf discs in the presence or absence of an exemplary additive. Reactions were performed in triplicate.

Reaction products were run on an agarose gel and scored for either a presence or absence of a band at the appropriate fragment size. Exemplary results are shown in FIG. 7. None of the enzymes are capable of amplifying from this difficult sample without povidone additive, but Clone 15 provides higher average yield than Taq-E7S in the presence of the additive. Taq failed to amplify. Exemplary additives that may be used in accordance with the present disclosure include, but are not limited to, bovine serum albumin, tetramethyl ammonium chloride, dimethylsulfoxide, beta-mercaptoethanol, sodium metabisulfite, povidone, Tween 20, Triton X-100, Nonidet P-40, polyethylene glycol, betaine, formamide, 7-deaza dGTP, spermidine, thermostable RecA, glycerol, gelatin, low-fat milk powder, and combinations thereof.

Example 8

Alternative Substitutions at Position 749 in Clone 15

Clone 15 polymerase, and altered versions of Clone 15 polymerases, containing alternative substitutions at position 749 (e.g., F749L, F749V, F749T, F749Y, F749P, F749M), were tested for their ability to amplify an 800 bp amplicon from the plant chloroplast genome using crude extract or purified genomic DNA. Reactions were performed in a buffer containing reaction components as shown in Table 22. Exemplary cycling profile for this assay is shown in Table 23.

Exemplary Primers Include:

```
                      (SEQ ID NO: 34)
Forward primer:  ATGTCACCACAAACAGAGACTAAAG (SEQ ID NO: 35)
Reverse primer:  TGCATTACGATCGGAACGCCCA
```

TABLE 22

Exemplary Reaction Components

| Reaction component | Concentration | | Reaction volume = 50 In 50 uL |
|---|---|---|---|
| PCR water | — | — | 21.3-25.8 |
| Tris- HCl (pH 8.5) | 1 | M | 6.75 |
| MgCl2 (supplement to 2.0 mM) | 25 | mM | 4.0 |
| Povidone | 20% | m/v | 7.5 |
| dNTPs | 10 | mM each | 1.0 |
| Primer F | 10 | uM | 1.5 |
| Primer R | 10 | uM | 1.5 |
| Gapevine leaf extract or purified DNA | — | — | 0.5-5 |
| DNA polymerase | 20 | ng/uL | 1.5 |
| TOTAL | | | 50.0 |

TABLE 23

Exemplary Cycling Profile

| Cycling profile: Cycle | No. | Temp (° C.) | Time |
|---|---|---|---|
| Initial denaturation | 1 | 95 | 10 min |
| Denaturation | 35 | 95 | 20 sec |
| Annealing | 35 | 55 | 15 sec |
| Extension | 35 | 72 | 30 sec |
| Final elongation | 1 | 72 | 1 min |
| HOLD | 1 | 4 | Indefinite |

Figure 8:
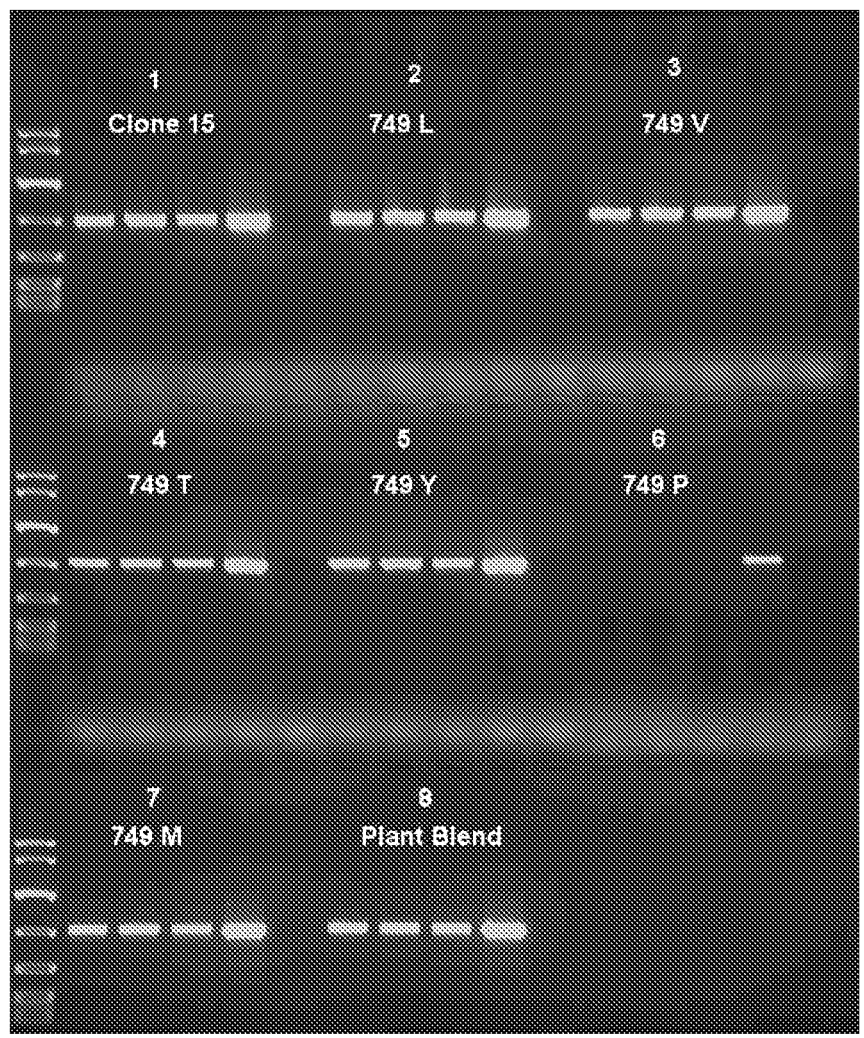
FIG. 8 depicts an exemplary PCR reaction using Clone 15 polymerase and altered versions of Clone 15 polymerases containing alternative substitutions at position 749, to amplify an 800 bp amplicon from crude extract or purified grapevine leaf DNA extracts.

Reaction products were run on an agarose gel and scored for a presence or absence, as well as intensity of a band at the appropriate fragment size. Exemplary results are shown in Table 24 and FIG. 8. As shown in FIG. 8, from left to right for each series, results were obtained from crude template in the form of 0.5 mm diameter grapevine leaf disc, 0.5 μl, 1.0 μl, and 5.0 μl of a crude grapevine leaf extract, followed by a reaction with 2.5 ng purified grapevine genomic DNA and a no-template control. "Plant Blend" indicates a blend of Clone 15 with a proofreading DNA polymerase. A substitution of a P at position 749 resulted in a detrimental effect on the performance of the enzyme, producing a lower yield of PCR product from purified DNA, and no product from crude extract. All other substitutions generated an 800 bp PCR product from both the crude extract and purified DNA, with substitutions of L or V at position 749 seemed to be most promising.

TABLE 24

| | Fragments Produced | | | | |
|---|---|---|---|---|---|
| | Crude Extract | | | Purified DNA | Neg. Control |
| | 0.5 μl | 1.0 μl | 5.0 μl | 2.5 ng | — |
| Clone 15 | yes | yes | yes | yes | no |
| 749 L | yes | yes | yes | yes | no |
| 749 V | yes | yes | yes | yes | no |
| 749 T | yes | yes | yes | yes | no |
| 749 Y | yes | yes | yes | yes | no |
| 749 P | no | no | no | yes | no |
| 749 M | yes | yes | yes | yes | no |
| Plant Blend | yes | yes | yes | yes | no |

Example 9

Amplification of Long PCR Fragment from Plant Extract

For this experiment, some the altered versions of Clone 15 polymerases from Example 7, blended with a small percentage of proofreading DNA Polymerase, were used to amplify a 1221 bp fragment of the grapevine chromosomal genome. The following primer set was used, at 50 PCR cycles (other conditions the same as in Example 7 above):

Exemplary Primers Include:

```
                      (SEQ ID NO: 36)
Forward primer:  GATCAACCCCGCTGCCCCAC (SEQ ID NO: 37)
Reverse primer:  CGAAGCCCATCCCCGCTCAG
```

Figure 9:
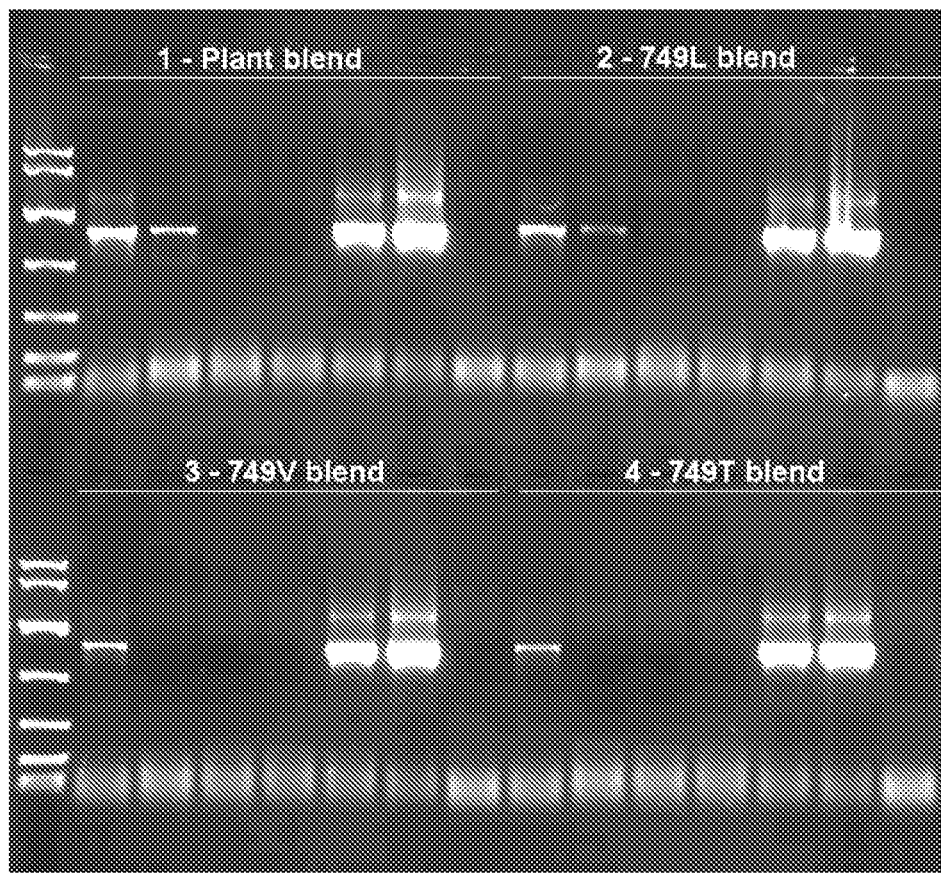
FIG. 9 depicts an exemplary PCR reaction using blend versions of certain altered versions of Clone 15 from FIG. 8, to amplify a 1221 bp amplicon from crude extract or purified grapevine leaf DNA extracts.

Reaction products were run on an agarose gel and scored for a presence or absence, as well as intensity of a band at the appropriate fragment size. Exemplary results are shown in Table 25 and FIG. 9. As shown in FIG. 9, from left to right for each series, results were obtained from crude template in the form of a 0.5 mm diameter grapevine leaf disc, 0.5 μl, 1.0 μl, and 5.0 μl of a crude grapevine leaf extract, followed by a reaction with 7 ng purified grapevine genomic DNA spiked with 1.0 μl crude extract, 7 ng purified grapevine genomic DNA alone and a no-template control. "Plant Blend" indicates a blend of Clone 15 with a proofreading DNA polymerase. "Blend" versions of altered Clone 15, for example, those containing substitutions of Leucine, Valine and Threonine, indicates a blend of altered Clone 15 with a proofreading DNA polymerase.

These results indicate that blend versions of altered Clone 15, for example, those containing substitutions of Leucine, Valine and Threonine at position 749, are capable of amplifying long PCR fragments from plant materials (e.g., leaf disc or crude extract). In particular, modified Clone 15 containing a leucine residue at position 749 provides similar performance as a modified Clone 15 containing an isoleucine residue at position 749.

TABLE 25

| | Fragments Produced | | | | | |
|---|---|---|---|---|---|---|
| | Crude Template 0.5 mm leaf disk | Crude Extract 0.5 ul | Crude Extract 1.0 ul | Crude Extract 5.0 ul | Purified DNA spiked with Crude Extract 7 ng DNA + 1.0 ul Extract | Purified DNA 7 ng | Neg. Control — |
| Plant Blend | yes | yes | no | no | yes | yes | no |
| 749 L Blend | yes | yes | yes | no | yes | yes | no |
| 749 V Blend | yes | no | no | no | yes | yes | no |
| 749 T Blend | yes | no | no | no | yes | yes | no |

TABLE 26

Amino acid sequences of wildtype and modified DNA polymerases

>Wild-type Taq(SEQ ID NO: 38)

MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVHDELVLEAPKERAEAVARLAKEVMEGVYPLAVPLEVEVGIGEDWLSAKE*

Taq-E507K (SEQ ID NO: 39)

MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTKKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVHDELVLEAPKERAEAVARLAKEVMEGVYPLAVPLEVEVGIGEDWLSAKE*

Taq-E7S (SEQ ID NO: 40)

MRGMLPLFEPKGRVLLVDGHHLAYRTFHALKGLTTSRGEPVQAVYGFAKSLLNALQDDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTKKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVHDELVLEAPKERAEAVARLAKEVMEGVYPLAVPLEVEVGIGEDWLSAKE*

>gi|55981023|ref|YP_144320.1| DNA polymerase I [*Thermus thermophilus* HB8]
(SEQ ID NO: 41)

MEAMLPLFEPKGRVLLVDGHHLAYRTFFALKGLTTSRGEPVQAVYGFAKSLLKALKEDGYKAVFVVFDAKAPSFRHE
AYEAYKAGRAPTPEDFPRQLALIKELVDLLGFTRLEVPGYEADDVLATLAKKAEKEGYEVRILTADRDLYQLVSDRV
AVLHPEGHLITPEWLWEKYGLRPEQWVDFRALVGDPSDNLPGVKGIGEKTALKLLKEWGSLENLLKNLDRVKPENVR
EKIKAHLEDLRLSLELSRVRTDLPLEVDLAQGREPDREGLRAFLERLEFGSLLHEFGLLEAPAPLEEAPWPPPEGAF
VGFVLSRPEPMWAELKALAACRDGRVHRAADPLAGLKDLKEVRGLLAKDLAVLASREGLDLVPGDDPMLLAYLLDPS
NTTPEGVARRYGGEWTEDAAHRALLSERLHRNLLKRLEGEEKLLWLYHEVEKPLSRVLAHMEATGVRLDVAYLQALS
LELAEEEIRRLEEEVFRLAGHPFNLNSRDQLERVLFDELRLPALGKTQKTGKRSTSAAVLEALREAHPIVEKILQHRE
LTKLKNTYVDPLPSLVHPRTGRLHTRFNQTATATGRLSSSDPNLQNIPVRTPLGQRIRRAFVAEAGWALVALDYSQI
ELRVLAHLSGDENLIRVFQEGKDIHTQTASWMFGVPPEAVDPLMRRAAKTVNFGVLYGMSAHRLSQELAIPYEEAVA

TABLE 26-continued

Amino acid sequences of wildtype and modified DNA polymerases

FIERYFQSFPKVRAWIEKTLEEGRKRGYVETLFGRRRYVPDLNARVKSVREAAERMAFNMPVQGTAADLMKLAMVKL
FPRLREMGARMLLQVHDELLLEAPQARAEEVAALAKEAMEKAYPLAVPLEVEVGMGEDWLSAKG

*Thermus thermophilus* HB8 with Clone 15 mutations in corresponding positions
(SEQ ID NO: 42)

MEAMLPLFEPKGRVLLVDGHHLAYRTFFALKGLTTSRGEPVQAVYGFAKSLLKALKEDGYKTVFVVFDAKAPSFRHE
AYEAYKAGRAPTPEDFPRQLALIKELVDLLGFTRLEVPGYEADDVLATLAKKAEKEGYEVRILTADRDLYQLVSDRV
AVLHPEGHLITPEWLWEKYGLRPEQWVDFRALVGDPSDNLPGVKGIGEKTALKLLKEWGSLENLLKNLDRVKPENVR
EKIKAHLEDLRLSLELSRVRTDLPLEVDLAQGREPDREGLRAFLERLEFGSLLHEFGLLEAPAPLEEAPWPPPEGAF
VGFVLSRPEPMWAELKALAACRDGRVHRAADPLAGLKDLEEVRGLLAKDLCVLASREGLDLVPGDDPMLLAYLLDPS
NTTPEGVARRYGGEWTEDAAHRALLSERLHRNLLKRLEGEEKLLWLYHEVEKPLSRVLAHMEATGVRLDVAYLQALS
LELAEEIRRLEEEVFRLAGHPFNLNSRDQLERVLFDELRLPALGKTKKTGKRSTSAAVLEALREAHPIVEKILQHRE
LTKLKNTYVDPLPSLVHPRTGRLHTRFNQTATATGRLSSSDPNLQNIPVRTPLGQRIRRAFVAEAGWALVALDYSQI
ELRVLAHLSGDENLIRVFQEGKDIHTQTASWMFGVPPEAVDPLMRRAAKTVNFGVLYGMSAHRLSQELAIPYEEAVA
FIERYFQSFPKVRAWMEKTLEEGRKRGYVETLFGRRRYVPDLNARVKSVREAAERMAI**NMPVQGTAADLMKLAMVKL
FPRLREMGARMLLQVHDELLLEAPQARAEEVAALAKEAMEKAYPLAVPLEVEVGMGEDWLSAKG

>gi|2231821|gb|AAB62092.1| DNA polymerase I [*Geobacillus stearothermophilus*]
(SEQ ID NO: 43)

MRLKKKLVLIDGNSVAYRAFFALPLLHNDKGIHTNAVYGFTMMLNKILAEEQPTHLLVAFDAGKTTFRHETFQEYKG
GRQQTPPELSEQFPLLRELLKTYRIPAYELYIYEADDIIGTLAARAEQEGFEVKIISGDRDLTQLASRHVTVDITKK
GITDIEPYTPETVREKYGLTPEQIVDLKGLMGDKSDNIPGVPGIGEKTAVKLLKQFGTVENVLASIDEVKGEKVKEK
LRQHRDLALLSKQLASICRDAPVELSLDALVYEGQDREKVIALFKELGFQSFLEKMAAPAAEGRKPLEEMEFAIVDV
ITEEMLADKAALVVEVMEENYHDAPIVGIALVNEHGRFFMRPETALADSQFLAWLADETKKKSMFDAKRAVVALKWK
GIDVRGVAFDLLLAAYLLNPAQDAGDIAAVAKMKQYEAVRSDEAVYGKGVKRSLPDEQTLAEHLVRKAAAIWALEQP
FMDDLRNNEQDQLLTKLEQPLAAILAEMEFTGVNVDTKRLEQMGSELAEQLRAIEQRIYEHAGQEFNINSPKQLGVI
LFEKLQLPVLKKTKTGYSTSADVLEKLAPHHEIVENILHYRQLGKLQSTYIEGLLKVVRPDTGKVHTMFNQTLTQTG
RLSSAEPNLQNIPIRLEEGRKIRQAFVPSEPDWLIFAADYSQIELRVLAHIADDDNLIEAFQRDLDIHTKTAMDIFH
VSEEEVTANMRRQAKAVNFGIVYGISDYGLAQNLNITRKEAAEFIERYFASPFPGVRRYMENIVQEAKQKGYVTTLLH
RRRYLPDITSRNFNVRSFAERTAMNTPIQGSAADIIKKAMIDLAARLKEEQLQARLLLQVHDELILEAPKEEIERLC
ELVPEVMEQAVSSVPLKVDYHYGPTWYDAK

*Bacillus stearothermophilus* with Clone 15 mutations in corresponding
positions (SEQ ID NO: 44)

MRLKKKLVLIDGNSVAYRAFFALPLLHNDKGIHTNAVYGFTMMLNKILAEEQPTTLLVAFDAGKTTFRHETFQEYKG
GRQQTPPELSEQFPLLRELLKTYRIPAYELYIYEADDIIGTLAARAEQEGFEVKIISGDRDLTQLASRHVTVDITKK
GITDIEPYTPETVREKYGLTPEQIVDLKGLMGDKSDNIPGVPGIGEKTAVKLLKQFGTVENVLASIDEVKGEKVKEK
LRQHRDLALLSKQLASICRDAPVELSLDALVYEGQDREKVIALFKELGFQSFLEKMAAPAAEGRKPLEEMEFAIVDV
ITEEMLADKAALVVEVMEENYHDAPIVGIALVNEHGRFFMRPETALADSQFLAWLADEEKKKSMFDAKRCVALKWK
GIDVRGVAFDLLLAAYLLNPAQDAGDIAAVAKMKQYEAVRSDEAVYGKGVKRSLPDEQTLAEHLVRKAAAIWALEQP
FMDDLRNNEQDQLLTKLEQPLAAILAEMEFTGVNVDTKRLEQMGSELAEQLRAIEQRIYEHAGQEFNINSPKQLGVI
LFEKLQLPVLKKTKTGYSTSADVLEKLAPHHEIVENILHYRQLGKLQSTYIEGLLKVVRPDTGKVHTMFNQTLTQTG
RLSSAEPNLQNIPIRLEEGRKIRQAFVPSEPDWLIFAADYSQIELRVLAHIADDDNLIEAFQRDLDIHTKTAMDIFH
VSEEEVTANMRRQAKAVNFGIVYGISDYGLAQNLNITRKEAAEFIERYFASPFPGVRRYMENIVQEAKQKGYVTTLLH
RRRYLPDITSRNFNVRSFAERTAINTPIQGSAADIIKKAMIDLAARLKEEQLQARLLLQVHDELILEAPKEEIERLC
ELVPEVMEQAVSSVPLKVDYHYGPTWYDAK

>gi|307233423|ref|ZP_07519834.1| DNA polymerase I [*Escherichia coli* TA143]
(SEQ ID NO: 45)

MVQIPQNPLILVDGSSYLYRAYHAFPPLTNSAGEPTGAMYGVLNMLRSLIMQYKPTHAAVVFDAKGKTFRDELFEHY
KSHRPPMPDDLRAQIEPLHAMVKAMGLPLLAVSGVEADDVIGTLAREAEKAGRPVLISTGDKDMAQLVTPNITLINT
MTNTILGPEEVVNKYGVPPELIIDFLALMGDSSDNIPGVPGVGEKTAQALLQGLGGLDTLYAEPEKIAGLSFRGAKT
MAAKLEQNKEVAYLSYQLATIKTDVELELTCEQLEVQQPAAEELLGLFKKYEFKRWTADVEAGKWLQAKGAKPAAKP
QETSVADEAPEVTATVISYDNYVTILDEETLKAWIAKLEKAPVFAFDTETDSLDNISANLVGLSFAIEPGVAAYIPV
AHDYLDAPDQISRERALELLKPLLEDEKALKVGQNLKYDRGILANYGIELRGIAFDTMLESYILNSVAGRHDMDSLA
ERWLKHKTITFEEIAGKGKNQLTFNQIALEEAGRYAAEDADVTLQLHLKMWPDLQKHKGPLNVFENIEMPLVPVLSR
IERNGVKIDPKVLHNHSEELTLRLAELEKKAHEIAGEEFNLSSTKQLQTILFEKQGIKPLKKTPGGAPSTSEEVLEE
LALDYPLPKVILEYRGLAKLKSTYTDKLPLMINPKTGRVHTSYHQAVTATGRLSSTDPNLQNIPVRNEEGRRIRQAF
IAPEDYVIVSADYSQIELRIMAHLSRDKGLLTAFAEGKDIHRATAAEVFGLPLETVTSEQRRSAKAINFGLIYGMSA
FGLARQLNIPRKEAQKYMDLYFERYPGVLQYMERTRAQAKEQGYVETLDGRRLYLPDIKSSNGARRAAAERAAINAP
MQGTAADIIKRAMIAVDAWLQAEQPRVRMIMQVHDELVFEVHKDDVDAVAKQIHQLMENCTRLDVPLLVEVGSGENW
DQAH

*Escherichia coli* with Clone 15 mutations in corresponding positions
(SEQ ID NO: 46)

MVQIPQNPLILVDGSSYLYRAYHAFPPLTNSAGEPTGAMYGVLNMLRSLIMQYKPTTAAVVFDAKGKTFRDELFEHY
KSHRPPMPDDLRAQIEPLHAMVKAMGLPLLAVSGVEADDVIGTLAREAEKAGRPVLISTGDKDMAQLVTPNITLINT
MTNTILGPEEVVNKYGVPPELIIDFLALMGDSSDNIPGVPGVGEKTAQALLQGLGGLDTLYAEPEKIAGLSFRGAKT
MAAKLEQNKEVAYLSYQLATIKTDVELELTCEQLEVQQPAAEELLGLFKKYEFKRWTADVEAGKWLQAKGAKPAAKP
QETSVADEAPEVTATVISYDNYVTILDEETLKAWIAKLEKAPVFAFDTETDSLDNISANLVGLSFAIEPGVAAYIPV
AHDYLDAPDQISRERALELLKPLLEDEKCLKVGQNLKYDRGILANYGIELRGIAFDTMLESYILNSVAGRHDMDSLA
ERWLKHKTITFEEIAGKGKNQLTFNQIALEEAGRYAAEDADVTLQLHLKMWPDLQKHKGPLNVFENIEMPLVPVLSR
IERNGVKIDPKVLHNHSEELTLRLAELEKKAHEIAGEEFNLSSTKQLQTILFEKQGIKPLKKTEGGAPSTSEEVLEE

TABLE 26-continued

Amino acid sequences of wildtype and modified DNA polymerases

LALDYPLPKVILEYRGLAKLKSTYTDKLPLMINPKTGRVHTSYHQAVTATGRLSSTDPNLQNIPVRNEEGRRIRQAF
IAPEDYVIVSADYSQIELRIMAHLSRDKGLLTAFAEGKDIHRATAAEVFGLPLETVTSEQRRSAKAINFGLIYGMSA
FGLARQLNIPRKEAQKYMDLYFERYPGVLQYMERTRAQAKEQGYVETLDGRRLYLPDIKSSNGARRAAAERAAINAP
MQGTAADIIKRAMIAVDAWLQAEQPRVRMIMQVHDELVFEVHKDDVDAVAKQIHQLMENCTRLDVPLLVEVGSGENW
DQAH

>Clone 15 (SEQ ID NO: 47)

MRGMLPLFEPKGRVLLVDGHHLAYRTFHALKGLTTSRGEPVQAVYGFAKSLLKALKEDGDTVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLEEARGLLAKDLCVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVERLAGHPFNLNSRDQLERVLFDELGLPAIGKTKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWMEKTLEEGRRRGYVETLFGRRRYVPDLEARVKSVREAAERMAINMPVQGTAADLMKLAMVKLFP
RLEEMGARMLLQVHDELVLEAPKERAEAVARLAKEVMEGVYPLAVPLEVEVGIGEDWLSAKE*

>Clone 15(F749L) (SEQ ID NO: 48)

MRGMLPLFEPKGRVLLVDGHHLAYRTFHALKGLTTSRGEPVQAVYGFAKSLLKALKEDGDTVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLEEARGLLAKDLCVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVERLAGHPFNLNSRDQLERVLFDELGLPAIGKTKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWMEKTLEEGRRRGYVETLFGRRRYVPDLEARVKSVREAAERMALNMPVQGTAADLMKLAMVKLFP
RLEEMGARMLLQVHDELVLEAPKERAEAVARLAKEVMEGVYPLAVPLEVEVGIGEDWLSAKE

TABLE 27

Exemplary alignments of DNA polymerase amino acid sequences

*Thermus aquaticus/Thermus thermophilus* alignment

```
  1 MRGMLPLFEPKGRVLLVDGHHLAYRTFHALKGLTTSRGEPVQAVYGFAKSLLKALKEDG-

1 MEAMLPLFEPKGRVLLVDGHHLAYRTFFALKGLTTSRGEPVQAVYGFAKSLLKALKEDGY

60 DAVIVVFDAKAPSFRHEAYGGYKAGRAPTPEDFPRQLALIKELVDLLGLARLEVPGYEAD

61 KAVFVVFDAKAPSFRHEAYEAYKAGRAPTPEDFPRQLALIKELVDLLGFTRLEVPGYEAD

120 DVLASLAKKAEKEGYEVRILTADKDLYQLLSDRIHVLHPEGYLITPAWLWEKYGLRPDQW

121 DVLATLAKKAEKEGYEVRILTADRDLYQLVSDRVAVLHPEGHLITPEWLWEKYGLRPEQW

180 ADYRALTGDESDNLPGVKGIGEKTARKLLEEWGSLEALLKNLDRLKP-AIREKILAHMDD

181 VDFRALVGDPSDNLPGVKGIGEKTALKLLKEWGSLENLLKNLDRVKPENVREKIKAHLED

239 LKLSWDLAKVRTDLPLEVDFAKRREPDRERLRAFLERLEFGSLLHEFGLLESPKALEEAP

241 LRLSLELSRVRTDLPLEVDLAQGREPDREGLRAFLERLEFGSLLHEFGLLEAPAPLEEAP

299 WPPPEGAFVGFVLSRKEPMWADLLALAAARGGRVHRAPEPYKALRDLKEARGLLAKDLSV

301 WPPPEGAFVGFVLSRPEPMWAELKALAACRDGRVHRAADPLAGLKDLKEVRGLLAKDLAV

359 LALREGLGLPPGDDPMLLAYLLDPSNTTPEGVARRYGGEWTEEAGERAALSERLFANLWG

361 LASREGLDLVPGDDPMLLAYLLDPSNTTPEGVARRYGGEWTEDAAHRALLSERLHRNLLK

419 RLEGEERLLWLYREVERPLSAVLAHMEATGVRLDVAYLRALSLEVAEEIARLEAEVFRLA

421 RLEGEEKLLWLYHEVEKPLSRVLAHMEATGVRLDVAYLQALSLELAEEIRRLEEEVFRLA

479 GHPFNLNSRDQLERVLFDELGLPAIGKTEKTGKRSTSAAVLEALREAHPIVEKILQYREL

481 GHPFNLNSRDQLERVLFDELRLPALGKTQKTGKRSTSAAVLEALREAHPIVEKILQHREL
```

TABLE 27-continued

Exemplary alignments of DNA polymerase amino acid sequences

```
539 TKLKSTYIDPLPDLIHPRTGRLHTRFNQTATATGRLSSSDPNLQNIPVRTPLGQRIRRAF

541 TKLKNTYVDPLPSLVHPRTGRLHTRFNQTATATGRLSSSDPNLQNIPVRTPLGQRIRRAF

599 IAEEGWLLVALDYSQIELRVLAHLSGDENLIRVFQEGRDIHTETASWMFGVPREAVDPLM

601 VAEAGWALVALDYSQIELRVLAHLSGDENLIRVFQEGKDIHTQTASWMFGVPPEAVDPLM

659 RRAAKTINFGVLYGMSAHRLSQELAIPYEEAQAFIERYFQSFPKVRAWIEKTLEEGRRRG

661 RRAAKTVNFGVLYGMSAHRLSQELAIPYEEAVAFIERYFQSFPKVRAWIEKTLEEGRKRG

719 YVETLFGRRRYVPDLEARVKSVREAAERMAFNMPVQGTAADLMKLAMVKLFPRLEEMGAR

721 YVETLFGRRRYVPDLNARVKSVREAAERMAFNMPVQGTAADLMKLAMVKLFPRLREMGAR

779 MLLQVHDELVLEAPKERAEAVARLAKEVMEGVYPLAVPLEVEVGIGEDWLSAKE
    (SEQ ID NO: 49)

781 MLLQVHDELLLEAPQARAEEVAALAKEAMEKAYPLAVPLEVEVGMGEDWLSAKG
    (SEQ ID NO: 50)
```

*Thermus aquaticus/Bacillus stearothermophilus* alignment

```
  1 MRGMLPLFEPKGRVLLVDGHHLAYRTFHALKGLTTSRGEPVQAVYGFAKSLLKALKEDG-

1 MR------LKKKLVLIDGNSVAYRAFFALPLLHNDKGIHTNAVYGFTMMLNKILAEEQP

60 DAVIVVFDAKAPSFRHEAYGGYKAGRAPTPEDFPRQLALIKELVDLLGLARLEVPGYEAD

54 THLLVAFDAGKTTFRHETFQEYKGGRQQTPPELSEQFPLLRELLKTYRIPAYELYIYEAD

120 DVLASLAKKAEKEGYEVRILTADKDLYQLLSDRIHVLHPEG-----YLITPAWLWEKYGL

114 DIIGTLAARAEQEGFEVKIISGDRDLTQLASRHVTVDITKKGITDIEPYTPETVREKYGL

175 RPDQWADYRALTGDESDNLPGVKGIGEKTARKLLEEWGSLEALLKNLDRLKP-AIREKIL

174 TPEQIVDLKGLMGDKSDNIPGVPGIGEKTAVKLLKQFGTVENVLASIDEVKGEKVKEKLR

234 AHMDDLKLSWDLAKVRTDLPLEVDFAKRRE--PDRERLRAFLERLEFGSLLHEFG--LLE

234 QHRDLALLSKQLASICRDAPVELSLDALVYEGQDREKVIALFKELGFQSFLEKMAAPAAE

290 SPKALEEAPWPPPE-------GAFVGFVLSRKEPMWADLLALAAARG---GRVHRAPEPY

294 GRKPLEEMEFAIVDVITEEMLADKAALVVEVMEENYHDAPIVGIALVNEHGRFFMRPETA

340 KA-------LRDLKEARGLLAKDLSVLALR-EGLGLP-PGDDPMLLAYLLDPSNTT----

354 LADSQFLAWLADETKKKSMFDAKRAVVALKWKGIDVRGVAFDLLLAAYLLNPAQDAGDIA

387 PEGVARRYGGEWTEEAG----------ERAALSERLF---ANLWGRLE------GEERLL

414 AVAKMKQYEAVRSDEAVYGKGVKRSLPDEQTLAEHLVRKAAAIWALEQPFMDDLRNNEQD

428 WLYREVERPLSAVLAHMEATGVRLDVAYLRALSLEVAEEIARLEAEVFRLAGHPFNLNSR

474 QLLTKLEQPLAAILAEMEFTGVNVDTKRLEQMGSELAEQLRAIEQRIYEHAGQEFNINSP

488 DQLERVLFDELGLPAIGKTEKTGKRSTSAAVLEALREAHPIVEKILQYRELTKLKSTYID

534 KQLGVILFEKLQLPVLKKTKTG--YSTSADVLEKLAPHHEIVENILHYRQLGKLQSTYIE

548 PLPDLIHPRTGRLHTRFNQTATATGRLSSSDPNLQNIPVRTPLGQRIRRAFIAEEG-WLL

592 GLLKVVRPDTGKVHTMFNQTLTQTGRLSSAEPNLQNIPIRLEEGRKIRQAFVPSEPDWLI

607 VALDYSQIELRVLAHLSGDENLIRVFQEGRDIHTETASWMFGVPREAVDPLMRRAAKTIN

652 FAADYSQIELRVLAHIADDDNLIEAFQRDLDIHTKTAMDIFHVSEEEVTANMRRQAKAVN

667 FGVLYGMSAHRLSQELAIPYEEAQAFIERYFQSFPKVRAWIEKTLEEGRRRGYVETLFGR

712 FGIVYGISDYGLAQNLNITRKEAAEFIERYFASFPGVRRYMENIVQEAKQKGYVTTLLHR

727 RRYVPDLEARVKSVREAAERMAFNMPVQGTAADLMKLAMVKLFPRL--EEMGARMLLQVH
```

TABLE 27-continued

Exemplary alignments of DNA polymerase amino acid sequences

```
772 RRYLPDITSRNFNVRSFAERTAMNTPIQGSAADIIKKAMIDLAARLKEEQLQARLLLQVH

785 DELVLEAPKERAEAVARLAKEVMEGVYPLAVPLEVEVGIGEDWLSAKE
    (SEQ ID NO: 51)

832 DELILEAPKEEIERLCELVPEVMEQAVS-SVPLKVDYHYGPTWYDAK-
    (SEQ ID NO: 52)
```

*Thermus aquaticus/Escherichia coli* alignment

```
  1 MRGMLPLFEPKGRVLLVDGHHLAYRTFHALKGLTTSRGEPVQAVYGFAKSLLKALKEDG-

1 -----MVQIPQNPLILVDGSSYLYRAYHAFPPLTNSAGEPTGAMYGVLNMLRSLIMQYKP

60 DAVIVVFDAKAPSFRHEAYGGYKAGRAPTPEDFPRQLALIKELVDLLGLARLEVPGYEAD

56 THAAVVFDAKGKTFRDELFEHYKSHRPPMPDDLRAQIEPLHAMVKAMGLPLLAVSGVEAD

120 DVLASLAKKAEKEGYEVRILTADKDLYQLLSDRIHVLHPEG-YLITPAWLWEKYGLRPDQ

116 DVIGTLAREAEKAGRPVLISTGDKDMAQLVTPNITLINTMTNTILGPEEVVNKYGVPPEL

179 WADYRALTGDESDNLPGVKGIGEKTARKLLEEWGSLEALLKNLDRLK-------PAIREK

176 IIDFLALMGDSSDNIPGVPGVGEKTAQALLQGLGGLDTLYAEPEKIAGLSFRGAKTMAAK

232 ILAHMDDLKLSWDLAKVRTDLPLEVDFAK--RREPDRERLRAFLERLEFG---------S

236 LEQNKEVAYLSYQLATIKTDVELELTCEQLEVQQPAAEELLGLFKKYEFKRWTADVEAGK

281 LLHEFGLLESPK-----ALEEAPWPPP-------------EGAFVGFVLSRKEP------

296 WLQAKGAKPAAKPQETSVADEAPEVTATVISYDNYVTILDEETLKAWIAKLEKAPVFAFD

316 --------MWADLLALAAARGGRVHR----------APEPYKALRDLKEARGLLAKDLSV

356 TETDSLDNISANLVGLSFAIEPGVAAYIPVAHDYLDAPDQISRERALELLKPLLEDEKAL

359 LA---LREGLGLPPGD---------DPMLLAYLLDPSN-----------------TTPEG

416 KVGQNLKYDRGILANYGIELRGIAFDTMLESYILNSVAGRHDMDSLAERWLKHKTITFEE

390 VARR------YGGEWTEEAG----ERAALSERLFANLWGRLEGEERLLWLYREVERPLSA

476 IAGKGKNQLTFNQIALEEAGRYAAEDADVTLQLHLKMWPDLQKHKGPLNVFENIEMPLVP

440 VLAHMEATGVRLDVAYLRALSLEVAEEIARLEAEVFRLAGHPFNLNSRDQLERVLFDELG

536 VLSRIERNGVKIDPKVLHNHSEELTLRLAELEKKAHEIAGEEFNLSSTKQLQTILFEKQG

500 LPAIGKTEKTGKRSTSAAVLEALREAHPIVEKILQYRELTKLKSTYIDPLPDLIHPRTGR

596 IKPLKKTPG-GAPSTSEEVLEELALDYPLPKVILEYRGLAKLKSTYTDKLPLMINPKTGR

560 LHTRFNQTATATGRLSSSDPNLQNIPVRTPLGQRIRRAFIAEEGWLLVALDYSQIELRVL

655 VHTSYHQAVTATGRLSSTDPNLQNIPVRNEEGRRIRQAFIAPEDYVIVSADYSQIELRIM

620 AHLSGDENLIRVFQEGRDIHTETASWMFGVPREAVDPLMRRAAKTINFGVLYGMSAHRLS

715 AHLSRDKGLLTAFAEGKDIHRATAAEVFGLPLETVISEQRRSAKAINFGLIYGMSAFGLA

680 QELAIPYEEAQAFIERYFQSFPKVRAWIEKTLEEGRRRGYVETLFGRRRYVPDLEARVKS

775 RQLNIPRKEAQKYMDLYFERYPGVLQYMERTRAQAKEQGYVETLDGRRLYLPDIKSSNGA

740 VREAAERMAFNMPVQGTAADLMKLAMVKLFPRLEEMG--ARMLLQVHDELVLEAPKERAE

835 RRAAAERAAINAPMQGTAADIIKRAMIAVDAWLQAEQPRVRMIMQVHDELVFEVHKDDVD

798 AVARLAKEVMEGVYPLAVPLEVEVGIGEDWLSAKE
    (SEQ ID NO: 53)

895 AVAKQIHQLMENCTRLDVPLLVEVGSGENWDQAH-
    (SEQ ID NO: 54)
```

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

INCORPORATION OF REFERENCES

All publications and patent documents cited in this application are incorporated by reference in their entirety to the same extent as if the contents of each individual publication or patent document were incorporated herein. All sequence information associated with sequence accession numbers publically available as of the filing date of the present application is hereby incorporated by reference.

We claim:

1. A DNA polymerase whose amino acid sequence is at least 95% identical to that of SEQ ID NO:38, but differs from SEQ ID NO:38 at a position corresponding to F749 of SEQ ID NO:38 and furthermore differs from SEQ ID NO:38 by at least two additional amino acids at positions corresponding to at least two of A61, K346, S357, E507 or I707 of SEQ ID NO:38.

2. The DNA polymerase of claim 1, wherein the amino acid at a position corresponding to F749 of SEQ ID NO: 38, is selected from the group consisting of L, I, V, T, Y, and M.

3. The DNA polymerase of claim 1, wherein the amino acid at a position corresponding to 749 of SEQ ID NO: 38 is L, and the at least two additional amino acids correspond to amino acids in SEQ ID NO: 38, but are substitutions relative to SEQ ID NO: 38 and are selected from the group consisting of: A61T, K346E, S357C, E507K, I707M and combinations thereof.

4. The DNA polymerase of claim 3, wherein the DNA polymerase has increased resistance to a plant-derived PCR inhibitor as compared to that of SEQ ID NO: 38.

5. A formulation of DNA polymerases comprising:
 (i) a DNA polymerase whose amino acid sequence is at least 95% identical to that of SEQ ID NO: 38, but differs from SEQ ID NO: 38 by an amino acid at a position corresponding to F749 of SEQ ID NO:38; and furthermore differs from SEQ ID NO: 38 by at least two additional amino acids at positions corresponding to at least two of A61, K346, S357, E507 or I707 of SEQ ID NO:38; and
 (ii) at least one DNA polymerase exhibiting 3'-exonuclease activity.

6. The formulation of claim 5, wherein the DNA polymerase and the at least one DNA polymerase exhibiting 3'-exonuclease activity are present in a ratio of about 1:1 to about 1:2000 relative units of enzyme.

7. A method comprising a step of amplifying nucleic acids in a biological sample using:
 (i) a DNA polymerase whose amino acid sequence is at least 95% identical to that of SEQ ID NO: 38, but differs from SEQ ID NO: 38 by an amino acid at a position corresponding to F749 of SEQ ID NO:38; and furthermore differs from SEQ ID NO: 38 by at least two additional amino acids at positions corresponding to at least two of A61, K346, S357, E507, or I707 of SEQ ID NO:38; and
 (ii) at least one additional DNA polymerase, wherein the least one additional DNA polymerase has 3'-exonuclease activity.

8. The method of claim 7, wherein the biological sample includes purified DNA or a crude DNA extract.

9. The method of claim 7, wherein the biological sample is a plant sample.

10. The method of claim 9, wherein the plant sample is selected from the group consisting of: leaf tissue, seed tissue, plant tissue, organ tissue, stored plant sample, crude plant DNA extract, and combinations thereof.

11. The method of claim 7, wherein the DNA polymerase and the at least one additional DNA polymerase are present in a ratio of about 1:1 to about 1:2000 relative units of enzyme.

12. The DNA polymerase of claim 1, whose amino acid sequence is at least 96% identical to that of SEQ ID NO: 38.

13. The DNA polymerase of claim 1, whose amino acid sequence is at least 97% identical to that of SEQ ID NO: 38.

14. The DNA polymerase of claim 1, whose amino acid sequence is at least 98% identical to that of SEQ ID NO: 38.

15. The DNA polymerase of claim 3, wherein the DNA polymerase has increased resistance to salt relative to that of SEQ ID NO: 38.

16. A DNA polymerase whose amino acid sequence is that of SEQ ID NO: 47.

17. A DNA polymerase whose amino acid sequence is that of SEQ ID NO: 48.

18. A DNA polymerase whose amino acid sequence is at least 98% identical to that of SEQ ID NO: 47, including in that it has I at a position corresponding to F749 of SEQ ID NO: 38, and in that it has at least two other amino acid substitutions at positions relative to wild type DNA polymerase of SEQ ID NO: 38, which positions are selected from the group consisting of 61, 346, 357, 507, 707, and combinations thereof.

19. A DNA polymerase whose amino acid sequence is at least 98% identical to that of SEQ ID NO: 48, including in that it has L at a position corresponding to F749 of SEQ ID NO: 38 and in that it has at least two other amino acid substitutions at positions relative to wild type DNA polymerase of SEQ ID NO: 38, which positions are selected from the group consisting of 61, 346, 357, 507, 707 and combinations thereof.

\* \* \* \* \*